US007662557B2

(12) United States Patent
McCafferty et al.

(10) Patent No.: US 7,662,557 B2
(45) Date of Patent: Feb. 16, 2010

(54) METHODS FOR PRODUCING MEMBERS OF SPECIFIC BINDING PAIRS

(75) Inventors: John McCafferty, Sawston (GB); Anthony Richard Pope, Cambridge (GB); Kevin Stuart Johnson, Cambridge (GB); Henricus Renerus Jacobus Mattheus Hoogenboom, Little Shalford (GB); Andrew David Griffiths, Cambridge (GB); Ronald Henry Jackson, Cambridge (GB); Kaspar Philipp Holliger, Cambridge (GB); James David Marks, Cherry Hinton (GB); Timothy Piers Clackson, Palo Alto, CA (US); David John Chiswell, Middle Claydon (GB); Gregory Paul Winter, Cambridge (GB); Timothy Peter Bonnert, Cambridge (GB)

(73) Assignees: Medical Research Council, London (GB); Medimmune Limited, Cambridge (GB)

( * ) Notice: Subject to any disclaimer, the term of this patent is extended or adjusted under 35 U.S.C. 154(b) by 150 days.

(21) Appl. No.: 10/803,653

(22) Filed: Mar. 18, 2004

(65) Prior Publication Data
US 2004/0157215 A1 Aug. 12, 2004

Related U.S. Application Data

(60) Division of application No. 09/726,219, filed on Nov. 28, 2000, now Pat. No. 6,806,079, which is a continuation of application No. 08/484,893, filed on Jun. 7, 1995, now Pat. No. 6,172,197, which is a continuation of application No. 07/971,857, filed as application No. PCT/GB91/01134 on Jul. 10, 1991, now Pat. No. 5,969,108.

(30) Foreign Application Priority Data

| Jul. 10, 1990 | (GB) | ................................ 9015198.6 |
| Oct. 19, 1990 | (GB) | ................................ 9022845.3 |
| Nov. 12, 1990 | (GB) | ................................ 9024503.6 |
| Mar. 6, 1991 | (GB) | ................................ 9104744.9 |
| May 15, 1991 | (GB) | ................................ 9110549.4 |

(51) Int. Cl.
C12Q 1/68 (2006.01)
G01N 33/53 (2006.01)
C12P 21/04 (2006.01)
C40B 30/04 (2006.01)
C40B 50/06 (2006.01)

(52) U.S. Cl. .......................... 435/6; 435/7.1; 435/69.7; 506/9; 506/26

(58) Field of Classification Search .................. 435/6, 435/7.1, 69.7; 506/9, 26
See application file for complete search history.

(56) References Cited

U.S. PATENT DOCUMENTS

| 4,593,002 A | 6/1986 | Dulbecco .................. 435/172.3 |
| 4,704,692 A | 11/1987 | Ladner |
| 4,816,397 A | 3/1989 | Boss et al. .................... 435/68 |
| 4,946,778 A | 8/1990 | Ladner et al. ............. 435/69.6 |
| 5,091,513 A | 2/1992 | Huston et al. ............... 530/387 |
| 5,223,409 A * | 6/1993 | Ladner et al. ............. 435/69.7 |
| 5,258,289 A | 11/1993 | Davis et al. |
| 5,260,203 A | 11/1993 | Ladner et al. |
| 5,403,484 A | 4/1995 | Ladner et al. ............ 435/235.1 |
| 5,427,908 A | 6/1995 | Dower et al. .................... 435/5 |
| 5,534,617 A * | 7/1996 | Cunningham et al. ....... 530/399 |
| 5,567,610 A | 10/1996 | Borrebaeck et al. |
| 5,580,717 A | 12/1996 | Dower et al. |
| 5,658,727 A | 8/1997 | Barbas et al. .................. 435/6 |
| 5,688,666 A * | 11/1997 | Bass et al. ................. 435/69.4 |
| 5,698,426 A | 12/1997 | Huse |
| 5,750,373 A | 5/1998 | Garrard et al. ............. 435/69.4 |
| 5,759,817 A | 6/1998 | Barbas ....................... 435/69.7 |
| 5,770,356 A | 6/1998 | Light et al. .................... 435/5 |
| 5,780,225 A | 7/1998 | Wigler et al. |
| 5,780,279 A | 7/1998 | Matthews et al. ......... 435/172.3 |
| 5,814,476 A | 9/1998 | Kauffman et al. |
| 5,821,047 A | 10/1998 | Garrard et al. .................. 435/5 |

(Continued)

FOREIGN PATENT DOCUMENTS

AU B-27617/88 7/1989

(Continued)

OTHER PUBLICATIONS

Promega Technical Bulletin, printed Jan. 11, 2008, revised Dec. 2006, pGEM-3ZF(+) Vector, 9 pages.*

(Continued)

*Primary Examiner*—Amber D. Steele
(74) *Attorney, Agent, or Firm*—Howrey LLP

(57) ABSTRACT

A member of a specific binding pair (sbp) is identified by expressing DNA encoding a genetically diverse population of such sbp members in recombinant host cells in which the sbp members are displayed in functional form at the surface of a secreted recombinant genetic display package (rgdp) containing DNA encoding the sbp member or a polypeptide component thereof, by virtue of the sbp member or a polypeptide component thereof being expressed as a fusion with a capsid component of the rgdp. The displayed sbps may be selected by affinity with a complementary sbp member, and the DNA recovered from selected rgdps for expression of the selected sbp members. A phagemid may be used as an expression vector, with said capsid fusion helping to package the phagemid DNA.

5 Claims, 46 Drawing Sheets

U.S. PATENT DOCUMENTS

| | | | | |
|---|---|---|---|---|
| 5,837,242 | A | * | 11/1998 | Holliger et al. .......... 424/136.1 |
| 5,837,500 | A | | 11/1998 | Ladner et al. |
| 5,840,479 | A | | 11/1998 | Little et al. |
| 5,846,765 | A | | 12/1998 | Matthews et al. .......... 435/69.1 |
| 5,849,500 | A | | 12/1998 | Breitling et al. |
| 5,855,885 | A | | 1/1999 | Smith et al. |
| 5,858,657 | A | * | 1/1999 | Winter et al. ................... 435/6 |
| 5,871,907 | A | * | 2/1999 | Winter et al. ................... 435/6 |
| 5,885,793 | A | * | 3/1999 | Griffiths et al. ............ 435/69.1 |
| 5,935,823 | A | | 8/1999 | Fowlkes et al. |
| 5,948,635 | A | | 9/1999 | Kay et al. |
| 5,955,358 | A | | 9/1999 | Huse |
| 5,969,108 | A | * | 10/1999 | McCafferty et al. ....... 530/387.3 |
| 5,985,588 | A | | 11/1999 | Breitling et al. ............... 435/7.8 |
| 6,172,197 | B1 | | 1/2001 | McCafferty et al. ......... 530/387 |
| 6,225,447 | B1 | | 5/2001 | Winter et al. |
| 6,291,650 | B1 | | 9/2001 | Winter et al. |
| 6,331,415 | B1 | | 12/2001 | Cabilly et al. .............. 435/69.6 |
| 6,521,404 | B1 | * | 2/2003 | Griffiths et al. ................. 435/6 |
| 6,544,731 | B1 | * | 4/2003 | Griffiths et al. ................. 435/6 |
| 6,555,313 | B1 | * | 4/2003 | Griffiths et al. ................. 435/6 |
| 6,582,915 | B1 | * | 6/2003 | Griffiths et al. ................. 435/6 |
| 6,593,081 | B1 | * | 7/2003 | Griffiths et al. ................. 435/5 |
| 6,916,605 | B1 | * | 7/2005 | McCafferty et al. ............ 435/5 |
| 7,063,943 | B1 | * | 6/2006 | McCafferty et al. ............ 435/5 |
| 7,195,866 | B2 | | 3/2007 | Griffiths et al. |

FOREIGN PATENT DOCUMENTS

| | | |
|---|---|---|
| EP | 0 168 933 | 1/1986 |
| EP | 0324162 | 12/1988 |
| EP | 436597 B1 | 4/1997 |
| GB | 2137631 | 10/1984 |
| GB | B-0349578 B1 | 1/1990 |
| GB | A-0 368 684 | 5/1990 |
| GB | 9015198.6 | 7/1990 |
| GB | 9022845.3 | 10/1990 |
| GB | 9024503.6 | 11/1990 |
| GB | 91/25579.4 | 2/1991 |
| GB | 91/25582.8 | 2/1991 |
| GB | 9104744.9 | 3/1991 |
| GB | 9110549.4 | 5/1991 |
| WO | WO 83/02393 | 7/1983 |
| WO | WO 88/01649 | 3/1988 |
| WO | WO 88/06630 | 9/1988 |
| WO | WO 88/09344 | 12/1988 |
| WO | WO 90/02809 | 3/1990 |
| WO | WO 90/05144 | 5/1990 |
| WO | WO 90/14424 | 11/1990 |
| WO | WO 90/14430 | 11/1990 |
| WO | WO 90/14443 | 11/1990 |
| WO | WO 91/10737 | 7/1991 |
| WO | WO 91/17271 | 11/1991 |
| WO | WO 92-01047 | 1/1992 |
| WO | WO 92/06204 | 4/1992 |
| WO | WO 92/09690 | 6/1992 |
| WO | WO 92-18619 | 10/1992 |

OTHER PUBLICATIONS

Promega Technical Bulletin, printed Jan. 11, 2008, revised Dec. 2006, pGEM-3ZF(-) Vector, 9 pages.*

Stratagene Instruction Manual, printed Jan. 11, 2008, revised 2003, pBluescript II Phagemid Vectors, 37 pages.*

Clackson, T., et al., "Making Antibody Fragments Using Phage Display Libraries," MacMillan Journals Ltd., London, vol. 352, pp. 624-628 (Aug. 15, 1991).

Geysen, H.M., et al., "A Priori Delineation of a Peptide Which Mimics a Discontinuous Antigenic Determinant," Molecular Immunology, vol. 23, No. 7, pp. 709-715 (1986).

International Search Report dated Aug. 9, 2004 for European Patent Applc. No. 04005419.9.

Portolano, S., et al., "A Human Fab Fragment Specific For Thyroid Peroxidase Generated By Cloning Thryoid Lymphocyte-Derived Immunoglobulin Genes in a Bacteriophage Lambda Library" Biochemical and Biphysical Research Communications, vol. 179, No. 1, pp. 372-377 (Aug. 30, 1991).

U.S. Appl. No. 07/240,160, filed Mar. 22, 1990, Ladner application.

Amit, A.G. el al., "Three-Dimentional Structure of an Antigen-Antibody Complex at 2.8 Å Resolution," *Science*, 233:747-753 (Aug. 1986).

Armstrong, J. et al., "Domain Structure of Bacteriophage fd Adsorption Protein," *FEBS Lett.*, 135(1):167-172 (Nov. 1981).

Bass et al., "Hormone Phage: An Enrichment Method for Variant Proteins With Altered Binding Properties," *Proteins: Structure, Function and Genetics*. 8:309-314 (1990).

Berek, C. et al., "Molecular events during maturation of the immune response to oxazolone," *Nature*. 316:412-418 (Aug. 1985).

Better, M. et al., "*Escherichia coli* Secretion of an Active Chimeric Antibody Fragment." *Science*. 240:1041-1043 (May, 1988).

Bhat, T.N. et al., "Small rearrangements in structures of Fv and Fab fragments of antibody D1.3 on antigen binding," *Nature*, 347:483-485 (Oct. 1990).

Bird, R.E. et al., "Single chain antibody variable regions," *TIBTECH*, 9:132-137 (Apr. 1991).

Bird, R.E. et al., "Single-Chain Antigen-Binding Proteins," *Science*, 242:423-426 (Oct. 1988).

Boeke, J.D. et al., "Effects of Bacteriophage fl Gene III Protein on the Host Cell Membrane," *Mol. Gen. Genet.*, 186:185-192 (1982).

Boyle, W., "An Extension of the $^{51}$Cr-Release Assay for the Estimation of Mouse Cytotoxins," *Transplantation*. 6(6):761-764 (1968).

Brenna, O. et al, "Affinity-Chromatography Purification of Alkaline Phosphatase from Calf Intestine," *Biochem. J.*, 151:291-296 (1975).

Brownstone, A. et al.. "Biological Studies with an Iodine-Containing Synthetic Immunological Determinant 4-Hydroxy-3-iodo-5-nitrophenylacetic Acid (NIP) and Related Compounds." *Immunology*, 10:481-492 (1966).

Brownstone, A. et al., "Chemical and Serological Studies with an Iodine-Containing Synthetic Immunological Determinant 4-Hydroxy-3-iodo-5-nitrophenylacetic Acid (NIP) and Related Compounds," *Immunology*, 10:465-479 (1966).

Carter, P. et al., "Improved oligonucleotide site-directed mutagenesis using M13 vectors" *Nucl. Acids Res.*. 13(12):4431-4443 (1985).

Casali, P. et al., "Human Monoclonals from Antigen-Specific Selection of B Lymphocytes and Transformation by EBV," *Science*, 234:476-479 (Oct. 1986).

Chaidaroglou, A. et al., "Function of Arginine-166 in the Active Site of *Escherichia coli* Alakaline Phosphatase," *Biochemistry*, 27:8338-8343 (1988).

Chang, C. N. et al., "Nuceotide sequence of the alkaline phosphatase gene of *Escherichia coli*," *Gene*, 44: 121-125 (1986).

Chaudhary, V.K. etal., "A rapid method of cloning functional variable-region antibody genes in *Escherichia coli* as single-chain immunotoxins," *Proc. Natl. Acad. Sci.*, USA, 87:1066-1070 (Feb. 1990).

Chiang, Y.L. et al., "Direct cDNA Cloning of the Rearranged Immunoglobulin Variable Region," *BioTechniques*, 7(4):360-366 (1989).

Chothia, C. et al., "Canonical Structures for the Hypervariable Regions of Immunoglobulins," *J. Mol. Biol.*, 196:901-917 (1987).

Chuchana, P. etal., "Definition of the human immunoglobulin variable lambda (IGLV) gene subgroups," *Eur. J. Immunol.*, 20:1317-1325 (1990).

Clackson, T. et al., "'Sticky feet'-directed mutagenesis and its applciation to swapping antibody domains." *Nucl. Acids Res.*, 17(24):10163-10170 (1989).

De Bellis, D. et al., "Regulated expression of foreign genes fused to *lac*: control by glucose levels in growth medium," *Nucl. Acids Res.*, 18(5):1311 (1980).

Dower, W .J. et al., "High efficiency transformation of *E. coli* by high voltage electroporation," *Nucl. Acids Res.*, 16(13):6127-6145 (1988).

Eckert, K.A. et al., "High fidelity DNA synthesis by the *Thermus aquaticus* DNA polymerase," *Nucl. Acids Res.*, 18(13):3739-3744 (1990).

Eisen, H.N., "Detemination of Antibody Affinity For Haptens and Antigens by Means of Fluorescence Quenching," *Meth. Med. Res.*, 10:115-121 (1964).

Evan, G.I. et al., "Isolation of Monoclonal Antibodies Specific for Human c-*myc* ProtoOncogene Product," *Mol. Cell. Biol.*, 5(12):3610-3616 (Dec. 1985).

Galfrè, G. et al., "Preparation of Monoclonal Antibodies: Strategies and Procedures," *Methods Enzymology*, 73:3-46 (1981).

Gherardi, E. et al., "A single-step procedure for cloning and selection of antibody-secreting hybridomas," *J. Immunol. Methods*. 126:61-68 (1990).

Gorick, B.D. et al., "Three Epitpoes on the Human Rh Antigen D Recognized by $^{125}$I-Labelled Human Monoclonal IgG Antibodies," *Vox. Sang.*, 55:165-170 (1988).

Gottesman, M.E. et al., "Transcription Antitermination by Bacteriophage Lambda N Gene Product," *J. Mol. Biol.*, 140:57-75 (1980).

Grant, R.A. et al., "Structure of the Filamentous Bacteriophage fl," *J. Biol. Chem.*, 256(1):539-546 (Jan. 1981).

Griffiths, G.M. et al., "Somatic mutation and the maturation of immune reponse to 2-phenyl oxazolone," *Nature*, 312:271-275 (1984).

Gronwald, R.G.K. et al., "Cloning and expression of a cDNA coding for the human platelet-derived growth factor receptor: Evidence for more than one receptor class," *Proc. Natl. Acad. Sci.*, USA, 85:3435-3439 (May 1988).

Harper, M. et al., "Antigen Specificity and Cross-Reactivity of Monoclonal Anti-Lysozyme Antibodies," *Molec. Immunol.*, 24(2):97-108 (1987).

Horton, R.M. et al., "Engineering hybrid genes without the use of restriction enzymes: gene splicing by overlap extension," *Gene*, 77:61-68 (1989).

Hughes-Jones, N.C. et al., "Nucleotide sequences and three-dimensional modelling of the $V_H$ and $V_L$ domains of two human monoclonal antibodies specific for the D antigen of the human Rh-blood-group system," *Biochem. J.*, 268:135-140 (1990).

Hull, W. E. et al., "$^{31}$P Nuclear Magnetic Resonance Study of Alkaline Phosphatase: The Role of Inorganic Phosphate in Limiting the Enzyme Turnover Rate at Alkaline pH," *Biochemistry*, 15(7):1547-1561 (1976).

Huse et al., "Generation of a Large Combinatorial Library of the Immunoglobulin Repertoire in Phage Lambda," *Science*, 246:1275-1281 (1989).

Huston, J.S. et al.,"Protein engineering of antibody binding sites: Recovery of specific activity in an anti-digoxin single-chain Fv analogue produced in *Escherichia coli*," *Proc. Natl. Acad. Sci.*, USA. 85:5879-5883 (Aug. 1988).

Kabat et al., *Sequences of Proteins of Immunological Interest*, 5th ed. pp. 339, 362, 430, 451 and 1418 (1991).

Kang, A.S. et al., "Linkage of recognition and replication functions by assembling combinatorial antibody Fab libraries along phage surfaces," *Proc. Natl. Acad. Sci.*, USA. 88(10):4363-4366 (1991).

Köhler, G. et al., "Continuous cultures of fused cells secreting antibody of predefined specificity," *Nature*, 256:495-497 (Aug. 1975).

Kornberg, A., *DNA Replication*, W.H. Freem & Co., San Francisco, pp. 15, 20, 287, 385, 368-369, 383-385, 393, 461, 474, 478-496, 505-506 (1974).

Larrick, J.W. et al., "Rapid Cloning of Rearranged Immunoglobulin Genes from Human Hybridoma Cells Using Mixed Primers and the Polymerase Chain Reaction," *Biochem. Biophys. Res. Commun.*, 160(3):1250-1255 (May 1989).

Lesk, A. M. et al.,,"Elbow motion in the immunoglobulins involves a molecular ball-and-socket joint," *Nature*. 335:188-190 (Sep. 1988).

Mäkelä, O. et al., "Inheritance of Antibody Specificity V Anti-2-Phenyloxazolone in the Mouse," *J. Exp. Med.*, 148:1644-1660 (Dec. 1978).

Malamy, M.H. et al., "Purification and Crystallization of the Alkaline Phosphatase of *Escherichia coli*," *Biochemistry*, 3(12):1893-1897 (Dec. 1964).

McCafferty et al., "Phage Antibodies: Filamentous Phage Displaying Antibody Variable Domains." *Nature*, 348:552-554 (1990).

McCracken, S. et al., "Functional and Structural Properties of Immobilized Subunits of *Escherichia coli* Alkaline Phosphatase," *J. Biol. Chem.*, 255(6):2396-2404 (Mar. 1980).

Melamed, M.D. et al., "Requirements for the establishment of heterohybridomas secreting monoclonal human antibody to rhesus (D) blood group antigen," *J. Immunological Methods*, 104:245-251 (1987).

Milstein F.R.S., C., "The Croonian Lecture, 1989 Antibodies: a paradigm for the biology of molecular recognition," *Proceedings of the Royal Society of London*, 239(1294):1-16 (1990).

Munro, S. et al., "An Hsp70-like Protein in the ER: Identity with the 78 kd Glucose-Regulated Protein and Immunoglobulin Heavy Chain Binding Protein," *Cell*, 46:291-300 (Jul. 1986).

Nagai, K. et al., "Synthesis and Sequence-Specific Proteolysis of Hybrid Proteins Produced in *Escherichia coli*," *Methods Enzymology*, 153:461-481 (1987).

Neuberger, M.S. et al., "Recombinant antibodies possessing novel effector functions," *Nature*, 312:604-608 (1984).

Ohlson, S. et al., "Novel Approach to Affinity Chromatography Using "Weak" Monoclonal Antibodies," *Anal. Biochem.*, 169:204-208 (1988).

Orlandi, R. et al., "Cloning immunoglobulin variable domains for expression by the polymerase chain reaction," *Proc. Natl. Acad. Sci.*, USA. 86:3833-3837 (May 1989).

Parmley et al., "Antibody-selectable Filamentous fd Phage, Vectors: Affinity Purification of Target Genes," *Gene*, 73(2):305-318 (Dec. 1988).

Perelson, A.S., "Immune Network Theory," *Immunol. Reviews*, 110:5-36 (1989).

Pratt, D. et al., "Conditional Lethal Mutants of the Small Filamentous Coliphage M13 II. Two Genes for Coat Proteins," *Virology*, 39:42-53 (1969).

Riechmann, L. et al., "Reshaping human antibodies for therapy," *Nature*, 332:323-327 (Mar. 1988).

Rossomando, E.F. et al., "Studies on the Bacteriophage fl I. Alkali-induced Disassembly of the Phage into DNA and Protein," *J. Mol. Biol.*, 36:387-399 (1968).

Saiki, R.K. et al., "Primer-Directed Enzymatic Amplification of DNA with a Thermostable DNA Polymerase," *Science*, 239:487-491 (Jan. 1988).

Sambrook et al., Molecular Cloning: A Laboratory Manual, 4.13-4. 14, 4.17-4.19, 4.46 and A.12 (1989).

Sastry, L. et al., "Cloning of the immunological repertoire in *Escherichia coli* for generation of monoclonal catalytic antibodies: Construction of a heavy chain variable region-specific cDNA library," *Proc. Natl. Acad. Sci.*, USA. 86:5728-5732 (Aug. 1989).

Schaaper; R.M. et al., "*Escherichia coli* mutT Mutator Effect during in Vitro DNA Synthesis," *J. Biol. Chem.*, 262(34):16267-16270 (Dec. 1987).

Schapper, R.M., "Mechanisms of mutagenesis in the *Escherichia coli* mutator mutD5: Role of DNA mismatch repair," *Proc. Natl. Acad. Sci.*, USA. 85:8126-8130 (Nov. 1988).

Shimatake, H. et al. , "Purified λ regulatory protein cII positively activates promoters for lysogenic development," *Nature*, 292:128-132 (Jul. 1981).

Short et al., "Lambda ZAP: A Bacteriophage Lambda Expression Vector with in Vivo Excision Properties," *Nucleic Acids Research*, 16(15):7583-7600 (Aug. 1988).

Skerra, A. et al., "Assembly of a Functional Immunoglobulin $F_v$ Fragment in *Escherichia coil*," *Science*, 240:1038-1040 (May 1988).

Smith, G.P., "Filamentous Fusion Phage: Novel Expression Vectors that Display Cloned Antigens on the Virion Surface," *Science*, 228(4705):1315-1317 (Jun. 1985).

Smith, G.P., "Filamentous Phage Assembly: Morphogenetically Defective Mutants That Do Not Kill the Host," *Virology*, 167:156-165 (1988).

Stengele, I. et al., "Dissection of Functional Domains in Phage fd Adsorption Protein Discrimination between Attachment and Penetration Sites," *J. Mol. Biol.*, 212(1):143-149 (1990).

Strauch, K. L. et al., "An *Escherichia coli* mutation preventing degradation of abnormal periplasmic proteins," *Proc. Natl. Acad. Sci.*, USA, 85:1576-1580 (Mar. 1988).

Tsunetsugu-Yokota et al., "Expression of an Immunogenic Region of HIV by a Filamentous Bacteriophage Vector," *Gene*, 99(2):261-265 (Mar. 1991).

Van Wezenbeek, P. et al., "Nucleotide sequence of the filamentous bacteriophage M13 DNA genome: comparison with phage fd," *Gene*, 11:129-148 (1980).

Venkitaraman, A.R., "Use of modified T7 DNA polymerase (sequence version 2O™) for oligonucleotide site-directed mutagenesis," *Nucl. Acids Res.*, 17(8):3314 (Apr. 1989).

Vieira, J. et al., "Production of Single-Stranded Plasmid DNA," *Methods Enzymol.*, 153:3-11 (1987).

Von Boehmer, H. et al., "The Separation of Different Cell Classes from Lymphoid Organs. IX. A Simple and Rapid Method for Removal of Damaged Cells From Lymphoid Cell Suspensions," *J. Immunol. Methods*, 2:293-301 (1973).

Ward, E.S. et al., "Binding activities of a repertoire of single immunoglobulin variable domains secreted from *Escherichia coli*," *Nature*, 341:544-546 (Oct. 1989).

Webster, R.E. et al., "Morphogenesis of the Filamentous Single-stranded DNA Phages," In: *The Single Stranded DNA Phages*, Cold Spring Harbor Laboratory Press, pp. 557-569 (1978).

White, M. R. H. et al., "Imaging of Firefly Luciferase Expression in Single Mammalian Cells Using High Sensitivity Charge-Coupled Device Cameras," *Technique (PHILA)*, 2 (4) 194-201 (1990).

Williams, A.F. et al., "The Immunoglobulin Superfamily—Domains for Cell Surface Recognition$_{1,2}$," *Ann. Rev. Immunol.*, 6:381-405 (1988).

Winter et al., "Man-made Antibodies," *Nature*, 349(6307):293-299 (Jan. 1991).

Yanisch-Perron, C. et al., "Improved M13 phage cloning vectors and host strains: nucleotide sequences of the M13mp18 and pUC19 vectors," *Gene*, 33:103-119 (1985).

Geider, K., et al., "A plasmid cloning system utilizing replication and packaging functions of the filamentous bactiophage fd," Gene, 33 (1985) pp. 341-349.

Mead, D., et al., "Chimeric Single-Stranded DNA Phage-Plasmid Cloning Vectors," Biotechnology, vol. 10, (1988), pp. 85-102.

Williams, W. V. et al., "Development of biologically active peptides based on antibody structure," PNAS, 86 (1989), pp. 5537-5541.

Taub, (1989) A Monoclonal Antibody against the Platelet Fibrinogen Receptor Contains a Sequence that Mimics a Receptor Domain in Fibrinogen, JBC, 264(1):259-265.

Weir, R. C., et al., "The Antigen-binding Capacity of the Peptide Chains of Horse Antibodies," J. Biochem. 100: (1966) 69-72.

U.S. Appl. No. 08/484,893 Advisory Action dated Nov. 3, 1997.
U.S. Appl. No. 08/484,893 Final office action dated Mar. 28, 1997.
U.S. Appl. No. 08/484,893 Non-final office action dated Jul. 20, 1999.
U.S. Appl. No. 08/484,893 Non-Final office action dated Jun. 17, 1996.
U.S. Appl. No. 08/484,893 Non-final office action dated Jun. 9, 1998.
U.S. Appl. No. 08/484,893 Notice of Allowance dated Mar. 29, 2000.
U.S. Appl. No. 08/484,893 Restriction Requirement dated Dec. 7, 1998.
U.S. Appl. No. 09/196,522 Examiners Amendment dated Jan. 28, 2004.
U.S. Appl. No. 09/196,522 Restriction Requirement dated Nov. 27, 1999.
U.S. Appl. No. 09/196,522 Non-final office action dated Apr. 20, 2000.
U.S. Appl. No. 09/196,522 Non-final office action dated Jan. 3, 2001.
U.S. Appl. No. 09/196,522 Notice of Allowance dated May 3, 2004.
U.S. Appl. No. 09/196,586 Advisory Action dated Dec. 5, 2008.
U.S. Appl. No. 09/196,586 Advisory Action dated May 4, 2007.
U.S. Appl. No. 09/196,586 Final office action dated Sep. 22, 2006.
U.S. Appl. No. 09/196,586 Final office action dated Apr. 17, 2001.
U.S. Appl. No. 09/196,586 Final office action dated Dec. 22, 2004.
U.S. Appl. No. 09/196,586 Final office action dated Sep. 15, 2008.
U.S. Appl. No. 09/196,586 Non final office action dated Apr. 10, 2000.
U.S. Appl. No. 09/196,586 Non-final office action dated Apr. 4, 2002.
U.S. Appl. No.09/196,586 Non-final office action dated Dec. 28, 2005.
U.S. Appl. No. 09/196,586 Non-Final office action dated Jan. 9, 2008.
U.S. Appl. No. 09/196,586 Non-final office action dated May 19, 2004.
U.S. Appl. No. 09/196,586 Restriction Requirement dated Dec. 21, 1999.
U.S. Appl. No. 09/196,673 Advisory Action dated Nov. 6, 2002.
U.S. Appl. No. 09/196,673 Advisory Action dated Mar. 24, 2003.
U.S. Appl. No. 09/196,673 Final office action dated Dec. 22, 2004.
U.S. Appl. No. 09/196,673 Final office action dated May 14, 2002.
U.S. Appl. No. 09/196,673 Non-final office action dated Apr. 11, 2000.
U.S. Appl. No. 09/196,673 Non-final office action dated Jan. 18, 2001.
U.S. Appl. No. 09/196,673 Non-final office action dated Mar. 4, 2004.
U.S. Appl. No. 09/196,673 Notice of Allowance dated Nov. 3, 2005.
U.S. Appl. No. 09/196,673 Restriction Requirement dated Dec. 21, 1999.
U.S. Appl. No. 09/309,639 Non-final office action dated Jan. 3, 2001.
U.S. Appl. No. 09/309,639 Official communication dated Aug. 22, 2003.
U.S. Appl. No. 09/309,639 Restriction Requirement dated Sep. 1, 2000.
U.S. Appl. No. 09/416,902 Advisory Action dated Sep. 6, 2006.
U.S. Appl. No. 09/416,902 Final office action dated Mar. 10, 2006.
U.S. Appl. No. 09/416,902 Non-final office action dated Jul. 28, 2005.
U.S. Appl. No. 09/416,902 Non-final office action dated Aug. 16, 2007.
U.S. Appl. No. 09/416,902 Non-final office action dated Feb. 3, 2009.
U.S. Appl. No. 09/416,902 Non-final office action dated Sep. 19, 2008.
U.S. Appl. No. 09/416,902 Notice of Allowance dated Feb. 4, 2008.
U.S. Appl. No. 09/416,902 Restriction Requirement dated Sep. 18, 2000.
U.S. Appl. No. 09/417,478 Advisory Action dated Jan. 29, 2007.
U.S. Appl. No. 09/417,478 Final office action dated Apr. 1, 2009.
U.S. Appl. No. 09/417,478 Final office action dated Dec. 14, 2007.
U.S. Appl. No. 09/417,478 Final office action dated Jul. 5, 2006.
U.S. Appl. No. 09/417,478 Non-final office action dated Jan. 20, 2000.
U.S. Appl. No. 09/417,478 Non-final office action dated Jun. 12, 2008.
U.S. Appl. No. 09/417,478 Non-final office action dated May 17, 2007.
U.S. Appl. No. 09/417,478 Non-final office action dated Nov. 20, 2000.
U.S. Appl. No. 09/417,479 Non-final office action dated May 3, 2006.
U.S. Appl. No. 09/417,479 Restriction Requirement dated Jun. 26, 2000.
U.S. Appl. No. 09/706,507 Non-final office action dated May 5, 2006.
U.S. Appl. No. 09/706,507 Restriction Requirement dated May 21, 2001.
U.S. Appl. No. 09/726,219 Non-final office action dated Aug. 12, 2003.
U.S. Appl. No. 09/726,219 Notice of Allowance dated Feb. 25, 2004.
U.S. Appl. No. 09/726,219 Restriction Requirement dated Mar. 12, 2003.
U.S. Appl. No. 07/971,857 Advisory Action dated Aug. 15, 1996.
U.S. Appl. No. 07/971,857 Examiners Interview Summary Record dated Dec. 13, 1996.
U.S. Appl. No. 07/971,857 Examiners Interview summary Record dated Apr. 24, 1997.
U.S. Appl. No. 07/971,857 Final office action dated Apr. 23, 1996.
U.S. Appl. No. 07/971,857 Non-final office action dated Jun. 30, 1995.
U.S. Appl. No. 07/971,857 Notice of Allowance dated Jul. 23, 1997.
U.S. Appl. No. 07/971,857 Response to 312 Amendment dated Apr. 20, 1999.
U.S. Appl. No. 10/803,622 Examiners Interview Summary dated Mar. 20, 2008.
U.S. Appl. No. 10/803,622 Advisory Action dated Jul. 31, 2007.

U.S. Appl. No. 10/803,622 Final office action dated Apr. 10, 2007.
U.S. Appl. No. 10/803,622 Final office action dated Feb. 17, 2009.
U.S. Appl. No. 10/803,622 Non-final office action dated Jul. 3, 2008.
U.S. Appl. No. 10/803,622 Non-final office action dated Jul. 5, 2006.
U.S. Appl. No. 10/803,622 Non-final office action dated Oct. 2, 2007.
U.S. Appl. No. 10/803,622 Restriction Requirement dated Apr. 10, 2006.
U.S. Appl. No. 11/555,464 Non-final office action dated Mar. 5, 2009.
U.S. Appl. No. 11/555,519 Non-final office action dated Mar. 5, 2009.
Abbas, et al., "Cellular and Molecular Immunology," Saunders, Third Edition, p. 412 (1997).
Alberts, et al., "Molecular Biology of the Cell," Garland Publications, Third Edition, p. 96 (1994).
Avrameas and Ternynck, "Natural Antibodies," in Delves, P., and I. Roitt, The Encyclopedia of Immunology, Second Edition, Academic Press, pp. 1806-1809 (1998).
Barbas, et al., "Assembly of Combinatorial Antibody Libraries on Phage Surfaces: The Gene III Site," Proc. Natl. Acad. Sci. (USA), vol. 88, pp. 7978-7982 (1991).
Barbas, et al., "Combinatorial Immunoglobulin Libraries on the Surface of Phage (Phabs): Rapid Selection of Antigen Specific Fabs," Methods: Companion Methods Enzymol., vol. 2, pp. 119 (1991).
Beidler, et al., "Cloning and High Level Expression of a Chimeric Antibody with Specificity for Human Carcinoembryonic Antigen," J. Immunology, vol. 141, pp. 4053-4060 (1988).
Berborowicz and Jaroszewski, "Carcinoembryonic Antigen as an Autoantigen," Immunol. Ser., vol. 52, pp. 65-83 (1982).
Berzofsky, et al., "Antigen-Antibody Interactions and Monoclonal Antibodies," in Paul, W., Fundamental Immunology, Second Edition, Chapter 12, pp. 332 (see also, Fourth Edition, 1994 (1999) Chapter 4, p. 91).
Beste, G., et al., "Small Antibody-like Proteins with Prescribed Ligand Specificities Derived from the Lipocalin Fold," Sci. USA, vol. 96, No. 5, pp. 1898-19903, ISSN 0027-8424 (1999) Abstract.
Boerner, et al., "Production of Antigen-Specific Human Monoclonal Antibodies From in Vitro-Primed Human (Splenocytes)," J. Immunol. vol. 147, pp. 86-95 (1991).
Breitling, et al., "A Surface Expression Vector for Antibody Screening," Gene, vol. 104, pp. 147-153 (1991).
Buck, Cell Biology, vol. 3, pp. 179-188 (1992).
Burton, et al., "A Large Array of Human Monoclonal Antibodies to Type 1 Human Immunodeficiency Virus from Combinatorial Libraries of Asymptomatic Seropositive Individuals," Proc. Natl. Acad. Sci., vol. 88, pp. 10134-10137 (1991).
Casali and Notkins, "Probing the Human [B-cell] Repertoire with EBV: Polyreactive Antibodies and CD5+ B Lymphocytes," Ann. Rev. Immunol., vol. 7, pp. 513-535 (1989).
Chang, et al., "Expression of Antibody Fab Domains on Bacteriophage Surfaces: Potential Use of Antibody Selection," J. Immunol., vol. 1047, pp. 3610-3614 (1991).
de la Cruz, et al., "Immunogenicity and Epitope Mapping of Foreign Sequences via Genetically Engineered Filamentous Phage," J. Biol. Chem., vol. 263, No. 9, pp. 4318-4322 (1988).
Delves, P.J., "Autoimmunity," in Delves, P. and I. Roitt, The Encyclopedia of Immunology, Second Edition, Academic Press, p. 292 (1998).
Dighiero, et al., "Naturally Occurring Autoantibodies Against Nine Common Antigens in Human Sera," J. Immunol., vol. 218, No. 128, pp. 2788-2792 (1982).
Dildrop, R., "A New Classification of Mouse $V_H$ sequences," Immunol. Today, vol. 5, No. 4, pp. 85-85 (1984).
Fomsgaard, et al., "Auto-antibodies to Tumor Necrosis Factor in Healthy Humans and Patients with Inflammatory Diseases and Gram-Negative Bacterial Infections," Scand. J. Immunol., vol. 30, pp. 219-223 (1989).
Golub, E., "The Limits of Medicine: How Science Shapes our Hope for the Cure," Times Books/Random House, p. 117-120 (1994).
Golub, E., and Green, D., "Immunology: A Synthesis," Sinauer Associates, Second Edition, p. 531 (1991).

Goodnow, et al., "Altered Immunoglobulin Expression and Functional Silencing of Self-Reactive B Lymphocytes in Transgenic Mice," Nature, vol. 334, pp. 676-682 (1988).
Gram, et al., "In vitro Selection and Affinity Maturation of Antibodies from a Naïve Combinatorial Immunoglobulin Library," Proc. Natl. Acad. Sci USA, vol. 89, pp. 3576-3580 (1992).
Griffiths, et al., Human Anti-Self Antibodies with High Specificity from Phage Display Libraries, EMBO J., vol. 12, pp. 725-734 (1993).
Griffiths, et al., "Isolation of High Affinity Human Antibodies Directly from Large Synthetic Repertoires," EMBO J., vol. 13, pp. 3245-3260 (1994).
Guilbert, et al., "Naturally Occurring Antibodies Against Nine Common Antigens in Human Sera," J. Immunol., vol. 128, pp. 2779-2787 (1982).
Hartley, O., "The Use of Phage Display in the Study of Receptors and Their Ligands," J. Of Receptors and Signal Transduction, vol. 22, Nos. 1-4, pp. 373-393 (2002).
Hartman and Wright, "Identification of Autoantibodies Specific for the Neutrophil Adhesion Glycoproteins CD11b/CD18 in Patients with Autoimmune Disease (Neutroenia," Blood, vol. 78, pp. 1096-1104 (1991).
Hirohata, et al., "Frequency Analysis of Human Peripheral Blood B Cells Producing IGM-Rheumatoid Factor," J. Immunol., vol. 145, pp. 1681-1686 (1990).
Holness, et al., Journal of Cell Science, vol. 107, pp. 2065-2070 (1994).
Hoogenboom, et al., "Building Antibodies from their Genes," Rev. Fr. Transfus. Hemobiol., vol. 36, pp. 19-47 (1993).
Hoogenboom, et al., "Multi-Subunit Proteins on the Surface of Filamentous Phage: Methodologies for Displaying Antibody (Fab) Heavy and Light Chains," Nucl. Acids Res., vol. 19, pp. 4133-4137 (1991).
Huse, "Combinatorial Antibody Expression Libraries in Filamentous Phage," Chapter 5 of Antibody Engineer, Borrebaeck (ed.), W.H. Freemand and Co. N.Y. (1992).
Jacobsson, K., et al., "Shot-gun Phage Display Mapping of Two Streptococcal Cell-Surface Proteins," Microbial Research, vol. 152, No. 2, pp. 121-128, ISSN 0944-4013 (1997) Abstract.
Kabat, et al., "Sequences of Proteins of Immunological Interest," 4th ed., p. 181, (1987).
Kaushik, et al., "Comparative Analysis of Natural Antibody Specificities Among Hybridomas Originating from Spleen and Peritoneal Cavity of Adult NZB and BALB/c Mince," Scand. J. Immunol., vol. 27, pp. 461-471 (1988).
Klein and Horejsi, "Immunology" [Chapter 20, "immunological Tolerance"], Blackwell Scientific, Second Edition, p. 527 (1997).
Koga, et al., "Mouse-Human Chimeric Monoclonal Antibody to Carcinoembryonic Antigen (CEA): in Vitro and in Vivo Activities," Hybridoma, vol. 9, pp. 43-56 (1990).
Landsteiner, K., "The Specificity of the Immune Response," quoted in Golub, E., Immunology: A Synthesis, Sinauer Associates, p. 19-25 [1991 book] (1987).
Lehninger, et al., Principles of Biochemistry, 2nd ed., Title Page, copy right page and p. G-4 only (1993).
Lobel, L.I., et al., "Filamentous Phage Displaying the Extracellular Domain of the hLH/CG Receptor Bind hCG Specifically," Endocrinology, vol. 138, No. 3, pp. 1232-1239, ISSN: 0013-7227 (1997) Abstract.
Logtenberg, et al., "Analysis of the Human Tonsil B Cell Repertoire by Somatic Hybridization: Occurrence of Both "Monospecific" and "Multispecific" (auto) Antibody-Secreting Cells," Eur. J. Immunol., vol. 17, pp. 855-859 (1987).
Lydyard, et al., "The Antibody Repertoire of Early Human B Cells," Scand. J. Immunol., vol. 31, pp. 33-43 (1990).
Mamula, et al., "The Specificity of Human Anti-Cycochrome c Autoantibodies that Arise in Autoimmune Disease," J. Immunol., vol. 144, pp. 1835-1840 (1990).
Marks, et al., "Molecular Evolution of Proteins on Filamentous Phage," J. Biol. Chem., vol. 267, p. 16007-16010 (1992).
McCafferty, J., et al., "Phage-Enzymes: Expression and Affinity Chromatography of Functional Alkaline Phosphatase on the Surface of Bacteriophage," Protein Engineering, vol. 4, No. 8, pp. 955-961 (1991).

McHeyzer-Williams, et al., "Clonal Analysis of Autoantibody-Producing Cell Precursors in the Preimmune B Cell Repertoire," J. Immunol., vol. 141, pp. 4118-4123 (1988).

Mullinax, et al., "Identification of Human Antibody Fragment Clones Specific for Tetanus Toxoid in a Bacteriophage a Immunoexpression Library," Proc. Natl. Acad. Sci., USA, vol. 87, pp. 8095-8099 (1990).

Nemazee and Burk, "Clonal Deletion of B Lymphocytes in a Transgenic Mouse Beaming Anti-MHC Class I Antibody Genes," Nature, vol. 377, pp. 562-566 (1989).

Neumaier, et al., "Cloning of the Genes for T84.66, an Antibody that has a High Specificity and Affinity for Carcinoembryonic Antigen, and Expression of Chimeric Human/Mouse T84.66 Genes in Myeloma and Chinese Hamster Ovary Cells," Cancer Research, vol. 50, pp. 2128-2134 (1990).

Nossal, G.V.J., "Cellular Mechanisms of Immune[ologic] Tolerance," Ann. Rev. Immunol., vol. 1, pp. 33-62 (1983).

Nossal, G.V.J., "Molecular and Cellular Aspects of Immunologic Tolerance," Eur. J. Biochem., vol. 202, pp. 729-737 (1991).

Persson, et al., "Generation of Diverse High-Affinity Human Monoclonal Antibodies by Repertoire Cloning," Proc. Natl. Acad. Aci., vol. 88, pp. 2432-2436 (1991).

Roitt, et al., Immunology, Second Edition, 1989, Ivan Roitt, et al., Gower Publishing, New York, p. 51 (1989).

Ruf., et al., "Various Expressions of a Unique Anti-Human Thymoglobulin Antibody Repertoire in Normal State and Autoimmune Disease, " Blood, vol. 78, pp. 1096-1104 (1991).

Smith, et al., "Phage Display," Chem. Rev., vol. 97, pp. 391-410 (1997).

Svenson, et al., "IgG Autoantibodies Against Interleukin Iα in Sera of Normal Individuals," Scand. J. Immunol., vol. 29 pp. 489-492 (1989).

Tomlinson, et al., "The Repertoire of Human Germline Vh Segments Sequences Reveals about Fifty Groups of VH Segments with Different Hypervariable Loops," J. Mol. Biol., vol. 227, pp. 776-798 (1992).

Ura, et al., "Studies on Circulating Antibody Against Carcinoembryonic Antigen (CEA) and CEA-like Antigen in Cancer Patients," Cancer Letters, vol. 25, pp. 283- 295 (1985).

Waterhouse, et al., "Combinatorial Infection and in Vivo Recombination: A Strategy for Making Large Phage Antibody Repertoires," Nucl. Acids Res., vol. 21, pp. 2265-2266 (1993).

Weidanz, J.A., et al., "Display of Functional Alphabets Single-Chain T-Cell Receptor Molecules on the Surface of Bacteriophage," J. Immunol. Methods, vol. 221, (1-2), pp. 59-76, ISSN 0022-1759 (1998) Abstract.

Wilson and Stanfield, "Antibody-Antigen Interactions: New Structures and New Conformational Changes," Curr. Opin. Structural Biol., vol. 4, pp. 857-867 (1994).

Winter, et al., "Making Antibodies by Phage Display Technology," Annu. Rev. Immunol., vol. 12, pp. 433-455 (1994).

Promega Technical Bulletin, printed Jan. 11, 2008, revised Dec. 2006, pGEM-3ZF(+) Vector, 9 pages.

Promega Technical Bulletin, printed Jan. 11, 2008, revised Dec. 2006, pGEM-3ZF(-) Vector, 9 pages.

Stratagene Instruction Manual, printed Jan. 11, 2008, revised 2003, pBluescript II Phagemic Vectors, 37 pages.

First Amended Complaint, Filed Mar. 8, 2002 - *Morphosys AG v. Cambridge Antibody Technology Limited*, Case No. 1:00-CV-00146 (24 pages) (U.S. District Court, District of Columbia)(signed by John S. Skilton, Attorney for Plaintiff).

Cambridge Antibody Technology Limited's Answer to First Amended Complaint, Filed Mar. 22, 2002 - *Morphosys AG v. Cambridge Antibody Technology Limited*, Case No. 1:00-CV-00146 (30 pages) (U.S. District Court, District of Columbia)(signed by Brian H. Corcoran, Attorney for Defendant).

Il'ichev, A.A., etal., "M13 Filamentous Bacteriophage in Protein Engineering", Molekulyarnaya Biologiya, vol. 24, No. 2, pp. 530-535, (Mar.-Apr. 1990).

Iliychev, A.A., et al., "M13 Filamentous Bactiophage for Protein Engineering", Molekulyarnaya Biologiya, vol. 24, No. 2, pp. 530-535, (Mar.-Apr. 1990). (In Russian with Translated Abstract).

Deposition Transcript of David W. Clough, taken Apr. 19, 2002 (*Morphosys AG v. Cambridge Antibody Technology Limited*, U.S. District Court, Northern District of Illinois, Eastern Division).

*E.I. du Pont de Nemours v. Cetus Corp.*, 19 USPQ2d 1174, (DC N.Cal. 1990).

*OddzOn Products Inc. v. Just Toys Inc.*, 43 USPQ2d 1641(CAFC 1997).

Deposition Transcript of George P. Smith, Ph.D., taken May 14, 2002, *Morphosys AG v. Cambridge Antibody Technology Limited*, Case No. 1:00-CV-00146 (30 pages) (U.S. District Court, District of Columbia.).

Deposition Transcript of Dr. David Chiswell, taken Apr. 29, 2002; *Morphosys AG v. Cambridge Antibody Technology Limited*, Case No. 1:00-CV-00146 (30 pages) (U.S. District Court, District of Columbia.).

Deposition Transcript of Dr. Gregory Paul Winter, taken Apr. 30, 2002; *Morphosys AG v. Cambridge Antibody Technology Limited*, Case No. 1:00-CV-00146 (30 pages) (U.S. District Court, District of Columbia.).

Vol. I - Deposition Transcript of Sean Malcolm Walton, taken May 1, 2002, *Morphosys AG v. Cambridge Antibody Technology Limited*, Case No. 1:00-CV00146 (30 pages) (U.S. District Court, District of Columbia.).

Vol. ll - Deposition Transcript of Sean Malcolm Walton, taken May 2, 2002, *Morphosys AG v. Cambridge Antibody Technology Limited*, Case No. 1:00-CV-00146 (30 pages) (U.S. District Court, District of Columbia.).

Declaration of George P. Smith, Ph.D., Under 37 C.F.R. § 1.132, executed Jun. 30, 1995 (submitted during the prosecution of U.S. Appl. No. 08/322,352).

Declaration of Brian K. Kay, Ph.D., executed Jun. 28, 1998, (submitted during the prosecution of European Appln. No. 91913039.3).

Abstract of George P. Smith, Grant No. 1R01GM41478-01A1, Project Start Date: Jul. 1, 1989, Dept. of Health & Human Services. Smith Grant Application, entitled: "Filamentous Phage Physiology", dated Nov. 1, 1988.

*Northern Telecom Inc. v. Datapoint Corp.*, 15 USPQ 1321., (CAFC 1990). Letter of Dr. Smith Re: NIH grant proposals, Dated Jun. 27, 1997.

Letter of Dr. Smith Re: NIH grant proposals dated Jun. 27, 1997.

Barbas and Lerner "Combinatorial Immunoglobulin Libraries on the surface of phage (Phabs): rapid selection of anti-specific fabs." Methods: a companion to methods in Enzymology vol. 2 (2): 119-124 (1991).

Interlocutory Decision in Opposition Proceedings to the European Patent EP-B-0589877 dated Apr. 15, 2002 (reference No. SMW/CP9503921).

Notice of Appeal to the European Patent EP-B-0589877 from Dyax Corp., filed Jun. 17, 2002.

Communication from EPO on Notice of Appeal filed by Dyax, issued Oct. 21, 2002.

Notice of Appeal to the European Patent EP-B-0589877 from BioInvent Therapeutic AB, filed Jun. 14, 2002.

Appeal No. T0639/02-334 from BioInvent Therapeutic AB to the European Patent EP-B-0589877, filed Aug. 22, 2002.

Notice of Appeal to the European Patent EP-B-0589877 from MorphoSys AG filed Jun. 20 2002 and Grounds of the Appeal filed Aug. 22, 2002.

Notice of Appeal filed Jun. 24, 2002 and Grounds of Appeal filed Aug. 22, 2002 from Cambridge Antibody Technology Limited against the Decision of the Opposition Division.

Notice of Opposition to the European Patent EP-B-0589877 from BioInvent International AB, filed Oct. 24 2002.

Document D83 in Appeal No. T0639/02-334: Letter dated Aug. 26, 1999 from Cambridge Antibody Technology Ltd in opposition proceedings against EP 0 527 839.

Document D85 in Appeal No. T0639/02-334: Proprietor's letter of Nov. 12, 1997 and amended claims.

Document D87 in Appeal No. T0639/02-334: Proprietor's letter of Nov. 15, 2000.

Document D88 in Appeal No. T0639/02-334: Grounds of Appeal dated Aug. 22, 2002 from present opponent in opposition proceedings against EP 0589 877.

Document D90 in Appeal No. T0639/02-334: Marvin & Hohn (1969). Bacteriological Rev 33(2), 172-209.
Document D91 in Appeal No. T0639/02-334: Better et al. (1988). Science 240, 1041-1043.
Document D92 in Appeal No. T0639/02-334: Sambrook & Russell (2001). Molecular cloning: a laboratory manual 3rd Edition, Cold Spring Harbor Press; particular pp. 18.115 to 18.122 "Filamentous phage display".
Notice of Opposition to the European Patent EP-B-0589877 from Crucell Holland B.V, filed Oct. 30, 2002.
Document D13: Communication of the European Office of Jun. 28, 2001.
Document D17: Vieira and Messing (1987), Methods Enzymol. 153, 3-11.
Document D7: Pluckthun and Skerra, "Expression of functional antibody Fv and Fab fragments in *Escherichia coli*," Methods in Enzymology, vol. 178 (1989), pp. 497-515.
Document D8: Hoogenboom et al., "Multi-subunit proteins on the surface of filamentous phage: methodology for displaying antibody (Fab) heavy and light chains," Nucleic Acids Research, vol. 19, No. 15 (1991), pp. 4133-4137.
Notice of Opposition to the European Patent EP-B-0589877 from MorphoSys, filed Oct. 30 2002.
Opposition to European patent EP-B-0589877, cited opposition document D2: Nelson et al. "Filamentous phage DNA cloning vectors: a noninfective mutant with a nonpolar deletion in gene III", Virology 108: 338-350 (1981).
Opposition to European patent EP-B-0589877, cited opposition document D3: McCoy and Khorana "Introduction and characterization of amber mutations in the bacteriorhodopsin gene", J. Bio. Chem. 258: 8456-8461 (1983).
Opposition to European patent EP-B-0589877, cited opposition document D5: Bullock et al. "XL1-blue: a high efficiency plasmid transforming recA Escherichia coli strain with beta-galactosidase selection", Bio Techniques 5: 376-378 (1987).
Opposition to European patent EP-B-0589877, cited opposition document D6: Schnee et al. "Construction and expression of a recombinant antibody-targeted plasminogen activator", Proc. Natl. Acad. Sci. USA 84:6904-6908 (1987).
Opposition to European patent EP-B-0589877, cited opposition document D9: De La Cruz et al. "Immunogenicity and epitope mapping of foreign sequences via genetically engineered filamentous phage", J. Bio. Chem. 263: 4318-4322 (1988).
Opposition to European patent EP-B-0589877, cited opposition document D15: Parmley and Smith "Filamentous fusion phage cloning vectors for the study of epitopes and design of vaccines", Adv. Exp. Med. Biol. 251: 215-218 (1989).
Opposition to European patent EP-B-0589877, cited opposition document D18: Chaudhary et al. "A recombinant immunotoxin consisting of two antibody variable domains fused to Pseudomonas exotoxin", Nature 339: 394-397 (1989).
Opposition to European patent EP-B-0589877, cited opposition document D23: US 517 659 "Affymax priority document", entitled "Recombinant Library Screening Methods", priority document filed May 1, 1990 for EP-A-0 527 839 (Article 54(3) EPC).
Opposition to European patent EP-B-0589877, cited opposition document D26: Scott and Smith "Searching for peptide ligands with an epitope library", Science 249: 386-389 (1990).
Opposition to European patent EP-B-0589877, cited opposition document D27: Devlin et al. "Random peptide libraries: a source of specific protein binding molecules", Science 249: 404-405 (1990).
Opposition to European patent EP-B-0589877, cited opposition document D37: Markland et al. "Design, construction and function of a multicopy display vector using fusions to the major coat protein of bacteriophage M13", Gene 109: 13-19 (1991).
Opposition to European patent EP-B-0589877, cited opposition document D38: Roberts et al. "Directed evolution of a protein: selection of potent neutrophil elastase inhibitors displayed on M13 fusion phage", Proc. Natl. Acad. Sci. USA 89: 2429-2433 (1992).
Opposition to European patent EP-B-0589877, cited opposition document D39: Glockshuber et al. "The disulfide bonds in antibody variable domains: effects on stability, folding in vitro, and functional expression in Escherichia coli", Biochemistry 31: 1270-1279 (1992).

Opposition to European patent EP-B-0589877, cited opposition document D41: Kay et al. "Phage display of peptides and proteins", A laboratory Manual (1996) (Cover page and Foreword enclosed).
Opposition to European patent EP-B-0589877, cited opposition document D42: Proba et al. "A natural antibody missing a cysteine in VH: consequences for thermodynamic stability and folding", J. Mol. Biol. 265: 161-172 (1997).
Opposition to European patent EP-B-0589877, cited opposition document D43: Proba et al. "Antibody scFv fragments without disulfide bonds made by molecular evolution", J. Mol. Biol. 275: 245-253 (1998).
Opposition to European patent EP-B-0589877, cited opposition document D44: Letter of Nov. 18, 1992 to EPO from Kilburn Strode in prosecution of EP-B-0 349 578.
Opposition to European patent EP-B-0589877, cited opposition document D45: p. 3 of EPO letter of Oct. 19, 1993 addressed to Plougmann, Ole (c/o Plougmann Vingtoft A/S) in prosecution of EP-B-0 768 377.
Opposition to European patent EP-B-0589877, cited opposition document D46: Letter of Sep. 22, 1994 to EPO from Plougmann & Vingtoft in prosecution of EP-B-0 768 377.
Opposition to European patent EP-B-0589877, cited opposition document D47: Extract from OD Decision in opposition proceedings against EP-B-0 201 184, (1995).
Opposition to European patent EP-B-0589877, cited opposition document D48: Letter of Feb. 14, 1996 to EPO from Hepworth, Lawrence, Bryer & Bizley in prosecution of EP-A-0 527 839, 1996.
Opposition to European patent EP-B-0589877, cited opposition document D49: the Boards of Appeal of the European Patent Office decision of May 8, 1996, case No. T694/92 - 3.3.4.
Opposition to European patent EP-B-0589877, cited opposition document D50: Extract from opposition proceeding against EP-B-0 349 578 (1996).
Opposition to European patent EP-B-0589877, cited opposition document D51: Extract from OD Decision in proceedings against EP-B-0 349 578 (1998).
Opposition to European patent EP-B-0589877, cited opposition document D53: Declaration of professor sir Aaron Klug, Ph.D. with exhibits, (Jun. 23, 1998).
Opposition to European patent EP-B-0589877, late filed document D56: claim for infringement of Sep. 24, 1998, from Cambridge Antibody Technology Limited to EPO.
Opposition to European patent EP-B-0589877, late filed document D58: McConnell et al. "Constrained peptide libraries as a tool for finding mimotopes", Gene 151: 115-118 (1994).
Opposition to European patent EP-B-0589877, late filed document D59: two chapters of "Lambda II" (eds. Hendrix et al.) Cold Spring Harbour Laboratory, Cold Spring Harbour, New York, 1983: "A Beginner's Guide to Lambda Biology" (Arber) (pp. 381-395) and "Tail Assembly and Injection" (Katsura)(pp. 331-346).
Opposition to European patent EP-B-0589877, late filed document D60: Parmley & Smith "Filamentous fusion phage cloning vectors for the study of epitopes and design vaccines", Adv. Exp. Med. Biol. 251: 251-8 (1989). The document was not admitted to the proceedings.
Opposition to European patent EP-B-0589877, late filed document D63: Declaration of William D. Huse, MD, Ph.D. (Aug. 17, 1999). The document was not admitted to the proceedings.
Opposition to European patent EP-B-0589877, late filed document D66: Crissman & Smith, "Gene-III protein of filamentous phages: evidence for a carboxyl-terminal domain with a role in morphogenesis", Virology 132: 445-455 (1994).
Opposition to European patent EP-B-0589877, late filed document D67: Declaration of Dr. Viia Valge-Archer (May 3, 2000).
Opposition to European patent EP-B-0589877, late filed document D68: Declaration of Dr. Hiroshi Ueda (3 May 3, 2000).
Opposition to European patent EP-B-0589877, late filed document D69: First Declaration of Dr. Rachel B. Kent (4 Feb., 2000). The document was objected to by patentees.
Opposition to European patent EP-B-0589877, late filed document D71: letter of patentees filed at USPTO on Jul. 16, 1996. The document was objected to by patentees.

Opposition to European patent EP-B-0589877, late filed document D72: letter of patentees filed at USPTO on Mar. 6, 1997. The document was objected to by patentees.

Opposition to European patent EP-B-0589877, late filed document D75: Declaration of Prof. Andreas Pluckhun (May 3, 2000). The document was objected to by patentees.

Opposition to European patent EP-B-0589877, late filed document D77: Endemann and Model "Location of filamentous phage minor coat proteins in phage and in infected cells", J. Mol. Biol. 250: 496-506 (1995). The document was objected to by patentees.

Opposition to European patent EP-B-0589877, late filed document D80: Written Decision dated May 26, 2000 to revoke EP-B-0436597.

Opposition to European patent EP-B-0589877, late filed document D81: 2nd Declaration of Dr. Viia Valge-Archer (May 31, 2000).

Complaint filed Apr. 23, 1999.

First Amended Complaint filed May 6, 1999.

Defendant Cambridge Antibody Technology, Limited's Motion to Dismiss plaintiff MorPhosys Ag's Complaint filed Jun. 8, 1999.

Response of Plaintiff MorphoSys Ag to Cambridge Antibody Technology Ltd's First Set of Interrogatories and Request for Production of Documents and Things filed Oct. 18, 1999.

Response of Plaintiff-MorphoSys AG to Cambridge Antibody Technology Ltd.'s First Set of Interrogatories and Request for Production of Documents and Things filed Mar. 27, 2000.

Response of Plaintiff MorphoSys AG to Cambridge Antibody Technology Ltd.'s Second set of Interrogatories filed Jul. 3, 2000.

Response of MorphoSys AG to Cambridge Antibody Technology's Third Set of Interrogatories filed Aug. 14, 2000.

Declaration of Edward S. Golub, Ph.D. In Support of Morpho Sys Motion for Partial Summary Judgment of Noninfringement filed Sep. 1, 2000.

Expert Report of Edward S. Golub, Ph.D. dated Jun. 2000 (with Exhibit 1) E. S. Golub Curriculum Vitae-Exhibit 2 E.S. Golub Validity Report and Exhibit 3 Declaration of E.S. Golub regarding Immunological Concepts.

Reply of Edward S. Golub, Ph.D. to Rebuttal Expert Reports of Edward P. Cohen, M.D. and Ronald II, Jackson, Ph.D. dated Aug. 1, 2000.

Declaration of Carlos F. Barbas III, Ph.D. in Support of MorphoSys Motion for Partial Summary Judgment of Noninfringement filed Sep. 1, 2000.

* cited by examiner

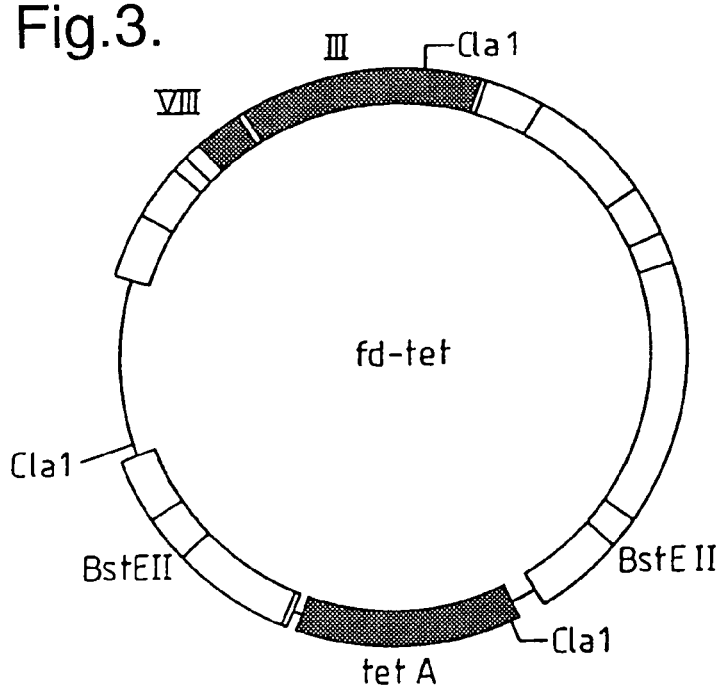
Fig.3.
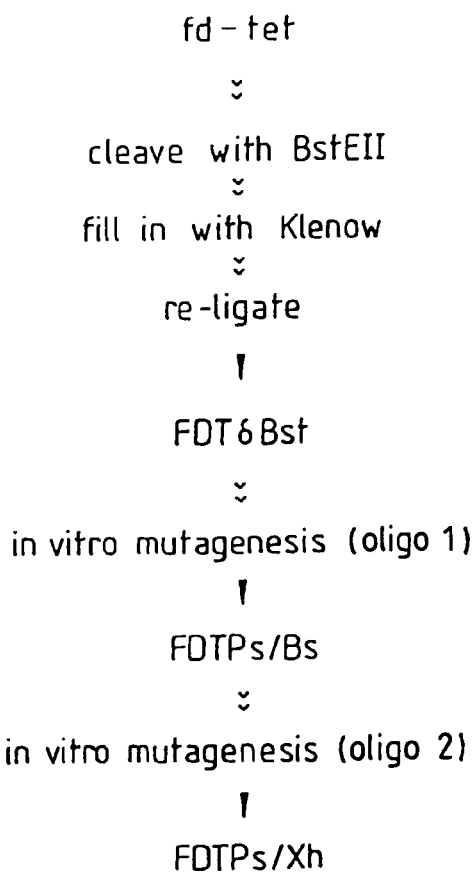

Fig. 4a

Oligo 1  (1653)
ACA ACT TTC AAC AGT TGA GGA GAC GGT GAC CGT AAG CTT CTG CAG TTG GAC CTG AGC  (SEQ ID NO. 177)
GGA GTG AGA ATA (1620)

Oligo 2  (1653)
ACA ACT TTC AAC AGT TTC CCG TTT GAT CTC GAG CTC CTG CAG TTG GAC CTG  (SEQ ID NO. 178)

Oligo 3  (1704)
GTC GTC TTT CCA GAC GTT AGT  (SEQ ID NO. 179)

Fig. 4b

```
                 GENE III
                 SIGNAL
              CLEAVAGE SITE
              (1624)                                                                                        (1650)
A  TCT CAC TCC GCT                                                                                                              GAA ACT GTT GAA AGT  (SEQ ID NO. 180)

Q   V   Q   L   Q (SEQ ID NO. 1)   V   T   V   S   S  (SEQ ID NO. 2)
B  TCT CAC TCC GCT CAG GTC CAA CTG CAG AAG CTT ACG GTC ACC GTC TCC TCA ACT GTT GAA AGT  (SEQ ID NO. 181)
                              PstI                                  BstEII

Q   V   Q   L   Q (SEQ ID NO. 1)  L   E   I   K   R  (SEQ ID NO. 3)
C  TCT CAC TCC GCT CAG GTC CAA CTG CAG GAG CTC GAG ATC AAA CGG     GAA ACT GTT GAA AGT  (SEQ ID NO. 182)
                              PstI                      XhoI
```

GENE III

Fig. 5a

```
                          rbs              M   K   Y   L   L   P   T   A   A
GCATGCAAATTCTATTTCAAGGAGACAGTCATAATGAAATACCTATTGCCTACGGCAGCC
         10        20        30        40        50        60
SphI
         PelB leader
  A   G   L   L   L   L   A   A   Q   P   A   M   A   Q   V   Q   L   Q   E   S
GCTGGATTGTTATTACTCGCTGCCCAACCAGCGATGGCCCAGGTGCAGCTGCAGGAGTCA
         70        80        90       100       110       120
                                                      PstI G   P   G   L   V   A   P   S   Q   S   L   S   I   T   C   T   V   S   G   F
GGACCTGGCCTGGTGGCGCCCTCACAGAGCCTGTCCATCACATGCACCGTCTCAGGGTTC
        130       140       150       160       170       180

S   L   T   G   Y   G   V   N   W   V   R   Q   P   P   G   K   G   L   E   W
TCATTAACCGGCTATGGTGTAAACTGGGTTCGCCAGCCTCCAGGAAAGGGTCTGGAGTGG
        190       200       210       220       230       240

VHD1.3
  L   G   M   I   W   G   D   G   N   T   D   Y   N   S   A   L   K   S   R   L
CTGGGAATGATTTGGGGTGATGGAAACACAGACTATAATTCAGCTCTCAAATCCAGACTG
        250       260       270       280       290       300

S   I   S   K   D   N   S   K   S   Q   V   F   L   K   M   N   S   L   H   T
AGCATCAGCAAGGACAACTCCAAGAGCCAAGTTTTCTTAAAAATGAACAGTCTGCACACT
        310       320       330       340       350       360

D   D   T   A   R   Y   Y   C   A   R   E   R   D   Y   R   L   D   Y   W   G
GATGACACAGCCAGGTACTACTGTGCCAGAGAGAGAGATTATAGGCTTGACTACTGGGGC
        370       380       390       400       410       420

Linker Peptide
  Q   G   T   T   V   T   V   S   S   G   G   G   G   S   G   G   G   G   S   G
CAAGGCACCACGGTCACCGTCTCCTCAggtggaggcggttcaggcggaggtggctctggc
        430       440       450       460       470       480
            BstEII G   G   G   S   D   I   E   L   T   Q   S   P   A   S   L   S   A   S   V   G
ggtggcggatcgGACATCGAGCTCACTCAGTCTCCAGCCTCCCTTTCTGCGTCTGTGGGA
        490       500       510       520       530       540
              SacI
```

Fig.5 b

```
          E   T   V   T   I   T   C   R   A   S   G   N   I   H   N   Y   L   A   W   Y
         GAAACTGTCACCATCACATGTCGAGCAAGTGGGAATATTCACAATTATTTAGCATGGTAT
              550         560         570         580         590         600

Q   Q   K   Q   G   K   S   P   Q   L   L   V   Y   Y   T   T   T   L   A   D
         CAGCAGAAACAGGGAAAATCTCCTCAGCTCCTGGTCTATTATACAACAACCTTAGCAGAT
              610         620         630         640         650         660

VKD1.3
          G   V   P   S   R   F   S   G   S   G   S   G   T   Q   Y   S   L   K   I   N
         GGTGTGCCATCAAGGTTCAGTGGCAGTGGATCAGGAACACAATATTCTCTCAAGATCAAC
              670         680         690         700         710         720

S   L   Q   P   E   D   F   G   S   Y   Y   C   Q   H   F   W   S   T   P   R
         AGCCTGCAACCTGAAGATTTTGGGAGTTATTACTGTCAACATTTTTGGAGTACTCCTCGG
              730         740         750         760         770         780

Myc Tag (TAG1)
          T   F   G   G   G   T   K   L   E   I   K   R   E   Q   K   L   I   S   E   E
         ACGTTCGGTGGAGGGACCAAGCTCGAGATCAAACGGGAACAAAAACTCATCTCAGAAGAG
              790         800         810         820         830         840
                                  XhoI

D   L   N   *   *          (SEQ ID NO. 183)
         GATCTGAATTAATAATGATCAAACGGTAATAAGGATCCAGCTCGAATTC   (SEQ ID NO. 184)
              850         860         870         880
                                                        EcoRI
```

Fig. 10a

```
                                        M  K  Y  L  L  P  T  A  A
GCATGCAAATTCTATTTCAAGGAGACAGTCATAATGAAATACCTATTGCCTACGGCAGCC
      10        20        30        40        50        60

A  G  L  L  L  L  A  A  Q  P  A  M  A  Q  V  Q  L  Q  E  S
GCTGGATTGTTATTACTCGCTGCCCAACCAGCGATGGCCCAGGTGCAGCTGCAGGAGTCA
      70        80        90       100       110       120

G  P  G  L  V  A  P  S  Q  S  L  S  I  T  C  T  V  S  G  F
GGACCTGGCCTGGTGGCGCCCTCACAGAGCCTGTCCATCACATGCACCGTCTCAGGGTTC
     130       140       150       160       170       180

S  L  T  G  Y  G  V  N  W  V  R  Q  P  P  G  K  G  L  E  W
TCATTAACCGGCTATGGTGTAAACTGGGTTCGCCAGCCTCCAGGAAAGGGTCTGGAGTGG
     190       200       210       220       230       240

L  G  M  I  W  G  D  G  N  T  D  Y  N  S  A  L  K  S  R  L
CTGGGAATGATTTGGGGTGATGGAAACACAGACTATAATTCAGCTCTCAAATCCAGACTG
     250       260       270       280       290       300

S  I  S  K  D  N  S  K  S  Q  V  F  L  K  M  N  S  L  H  T
AGCATCAGCAAGGACAACTCCAAGAGCCAAGTTTTCTTAAAAATGAACAGTCTGCACACT
     310       320       330       340       350       360

D  D  T  A  R  Y  Y  C  A  R  E  R  D  Y  R  L  D  Y  W  G
GATGACACAGCCAGGTACTACTGTGCCAGAGAGAGAGATTATAGGCTTGACTACTGGGGC
     370       380       390       400       410       420

Q  G  T  T  V  T  V  S  S  A  S  T  K  G  P  S  V  F  P  L
CAAGGCACCACGGTCACCGTCTCCTCAGCCTCCACCAAGGGCCCATCGGTCTTCCCCCTG
     430       440       450       460       470       480

A  P  S  S  K  S  T  S  G  G  T  A  A  L  G  C  L  V  K  D
GCACCCTCCTCCAAGAGCACCTCTGGGGGCACAGCGGCCCTGGGCTGCCTGGTCAAGGAC
     490       500       510       520       530       540
```

Fig.10b

```
          Y  F  P  E  P  V  T  V  S  W  N  S  G  A  L  T  S  G  V  H
       TACTTCCCCGAACCGGTGACGGTGTCGTGGAACTCAGGCGCCCTGACCAGCGGCGTGCAC
         550       560       570       580       590       600

T  F  P  A  V  L  Q  S  S  G  L  Y  S  L  S  S  V  V  T  V
       ACCTTCCCGGCTGTCCTACAGTCCTCAGGACTCTACTCCCTCAGCAGCGTGGTGACCGTG
         610       620       630       640       650       660

P  S  S  S  L  G  T  Q  T  Y  I  C  N  V  N  H  K  P  S  N
       CCCTCCAGCAGCTTGGGCACCCAGACCTACATCTGCAACGTGAATCACAAGCCCAGCAAC
         670       680       690       700       710       720

T  K  V  D  K  K  V  E  P  K  S  S  *  *     (SEQ ID NO. 187)
       ACCAAGGTCGACAAGAAAGTTGAGCCCAAATCTTCATAATAACCCGGGAGCTTGCATGCA
         730       740       750       760       770       780

M  K  Y  L  L  P  T  A  A  A  G  L
       AATTCTATTTCAAGGAGACAGTCATAATGAAATACCTATTGCCTACGGCAGCCGCTGGAT
         790       800       810       820       830       840

L  L  L  A  A  Q  P  A  M  A  D  I  E  L  T  Q  S  P  A  S
       TGTTATTACTCGCTGCCCAACCAGCGATGGCCGACATCGAGCTCACCCAGTCTCCAGCCT
         850       860       870       880       890       900

L  S  A  S  V  G  E  T  V  T  I  T  C  R  A  S  G  N  I  H
       CCCTTTCTGCGTCTGTGGGAGAAACTGTCACCATCACATGTCGAGCAAGTGGGAATATTC
         910       920       930       940       950       960

N  Y  L  A  W  Y  Q  Q  K  Q  G  K  S  P  Q  L  L  V  Y  Y
       ACAATTATTTAGCATGGTATCAGCAGAAACAGGGAAAATCTCCTCAGCTCCTGGTCTATT
         970       980       990       1000      1010      1020
```

Fig.10c

```
         T  T  T  L  A  D  G  V  P  S  R  F  S  G  S  G  S  G  T  Q
        ATACAACAACCTTAGCAGATGGTGTGCCATCAAGGTTCAGTGGCAGTGGATCAGGAACAC
          1030      1040      1050      1060      1070      1080

Y  S  L  K  I  N  S  L  Q  P  E  D  F  G  S  Y  Y  C  Q  H
        AATATTCTCTCAAGATCAACAGCCTGCAGCCTGAAGATTTTGGGAGTTATTACTGTCAAC
          1090      1100      1110      1120      1130      1140

F  W  S  T  P  R  T  F  G  G  G  T  K  L  E  I  K  R  T  V
        ATTTTTGGAGTACTCCTCGGACGTTCGGTGGAGGCACCAAGCTCGAGATCAAACGGACTG
          1150      1160      1170      1180      1190      1200

A  A  P  S  V  F  I  F  P  P  S  D  E  Q  L  K  S  G  T  A
        TGGCTGCACCATCTGTCTTCATCTTCCCGCCATCTGATGAGCAGTTGAAATCTGGAACTG
          1210      1220      1230      1240      1250      1260

S  V  V  C  L  L  N  N  F  Y  P  R  E  A  K  V  Q  W  K  V
        CCTCTGTTGTGTGCCTGCTGAATAACTTCTATCCCAGAGAGGCCAAAGTACAGTGGAAGG
          1270      1280      1290      1300      1310      1320

D  N  A  L  Q  S  G  N  S  Q  E  S  V  T  E  Q  D  S  K  D
        TGGATAACGCCCTCCAATCGGGTAACTCCCAGGAGAGTGTCACAGAGCAGGACAGCAAGG
          1330      1340      1350      1360      1370      1380

S  T  Y  S  L  S  S  T  L  T  L  S  K  A  D  Y  E  K  H  K
        ACAGCACCTACAGCCTCAGCAGCACCCTGACGCTGAGCAAAGCAGACTACGAGAAACACA
          1390      1400      1410      1420      1430      1440

V  Y  A  C  E  V  T  H  Q  G  L  S  S  P  V  T  K  S  F  N
        AAGTCTACGCCTGCGAAGTCACCCATCAGGGCCTGAGCTCGCCCGTCACAAAGAGCTTCA
          1450      1460      1470      1480      1490      1500

R  G  E  S  *  *                    (SEQ ID NO. 188)
        ACCGCGGAGAGTCATAGTAAGAATTC          (SEQ ID NO. 189)
          1510      1520
```

FabD1.3 in pUC19

Fig. 13.

```
  Q    V    Q    L    Q    E    S    G    G    G    L    V    Q    P    G    G
 CAG  GTG  CAG  CTG  CAG  GAG  TCA  GGA  GGA  GGC  TTG  GTA  CAG  CCT  GGG  GGT
                PstI
  S    L    R    L    S    C    A    T    S    G    F    T    F    S    N    Y
 TCT  CTG  AGA  CTC  TCC  TGT  GCA  ACT  TCT  GGG  TTC  ACC  TTC  AGT  AAT  TAC

Y    M    G    W    V    R    Q    P    P    G    K    A    L    E    W    L
 TAC  ATG  GGC  TGG  GTC  CGC  CAG  CCT  CCA  GGA  AAG  GCA  CTT  GAG  TGG  TTG

G    S    V    R    N    K    V    N    G    Y    T    T    E    Y    S    A
 GGT  TCT  GTT  AGA  AAC  AAA  GTT  AAT  GGT  TAC  ACA  ACA  GAG  TAC  AGT  GCA

S    V    K    G    R    F    T    I    S    R    D    N    F    Q    S    I
 TCT  GTG  AAG  GGG  CGG  TTC  ACC  ATC  TCC  AGA  GAT  AAT  TTC  CAA  AGC  ATC

L    Y    L    Q    I    N    T    L    R    T    E    D    S    A    T    Y
 CTC  TAT  CTT  CAA  ATA  AAC  ACC  CTG  AGA  ACT  GAG  GAC  AGT  GCC  ACT  TAT

Y    C    A    R    G    Y    D    Y    G    A    W    F    A    Y    W    G
 TAC  TGT  GCA  AGA  GGC  TAT  GAT  TAC  GGG  GCC  TGG  TTT  GCT  TAC  TGG  GGC

Q    G    T     L    V    T     v    s    s    g   g   g   g   s   g   g   g   g   s
 CAA  GGG  ACC   CTG  GTC  ACC   gtc  tcc  tca  ggtggaggcggttcaggcggaggtggctct
                 BstEII
  g   g   g   g   s   d    i    E    L    T    Q    T    P    L    S    L    P    V
 ggcggtggcggatcggac atc  GAG  CTC  ACC  CAA  ACT  CCA  CTC  TCC  CTG  CCT  GTC
                         SacI
  S    L    G    D    Q    A    S    I    S    C    R    S    S    Q    S    I
 AGT  CTT  GGA  GAT  CAA  GCC  TCC  ATC  TCT  TGC  AGA  TCT  AGT  CAG  AGC  ATT V    H    S    N    G    N    T    Y    L    E    W    Y    L    Q    K    P
 GTA  CAT  AGT  AAT  GGA  AAC  ACC  TAT  TTA  GAA  TGG  TAC  CTG  CAG  AAA  CCA
                                                            PstI
  G    Q    S    P    K    L    L    I    Y    K    V    S    N    R    F    S
 GGC  CAG  TCT  CCA  AAG  CTC  CTG  ATC  TAC  AAA  GTT  TCC  AAC  CGA  TTT  TCT G    V    P    D    R    F    S    G    S    G    S    G    T    D    F    T
 GGG  GTC  CCA  GAC  AGG  TTC  AGT  GGC  AGT  GGA  TCG  GGG  ACA  GAT  TTC  ACA L    K    I    S    R    V    E    A    E    D    L    G    V    Y    Y    C
 CTC  AAG  ATC  AGC  AGA  GTG  GAG  GCT  GAG  GAT  CTG  GGA  GTT  TAT  TAC  TGC F    Q    G    S    H    V    P    Y    T    F    G    G    G    T    K    L
 TTT  CAA  GGT  TCA  CAT  GTT  CCG  TAC  ACG  TTC  GGA  GGG  GGG  ACC  AAG  CTC E    I    K    R
 GAG  ATC  AAA  CGG    (SEQ ID NO. 190)
 XhoI                  (SEQ ID NO. 191)
```

5' END

```
                            R   T   P   E   M   P   V   L    (SEQ ID NO:192)
TCT CAC AGT GCA CAA ACT GTT GAA CGG ACA CCA GAA ATG CCT GTT CTG (SEQ ID NO:193)
        ApaL1
```

3' END

```
  K   A   A   L   G   L   K
                                                                  (SEQ ID NO:194)
AAA GCC GCT CTG GGG CTG AAA GCG GCC GCA GAA ACT GTT GAA AGT etc. (SEQ ID NO:195)
                             Not I
```

Fig. 17.
1) PRIMARY PCR
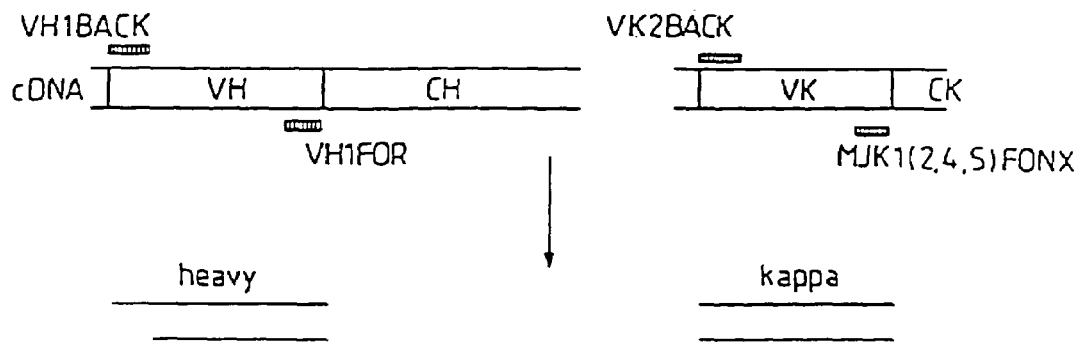
2) ASSEMBLY PCR
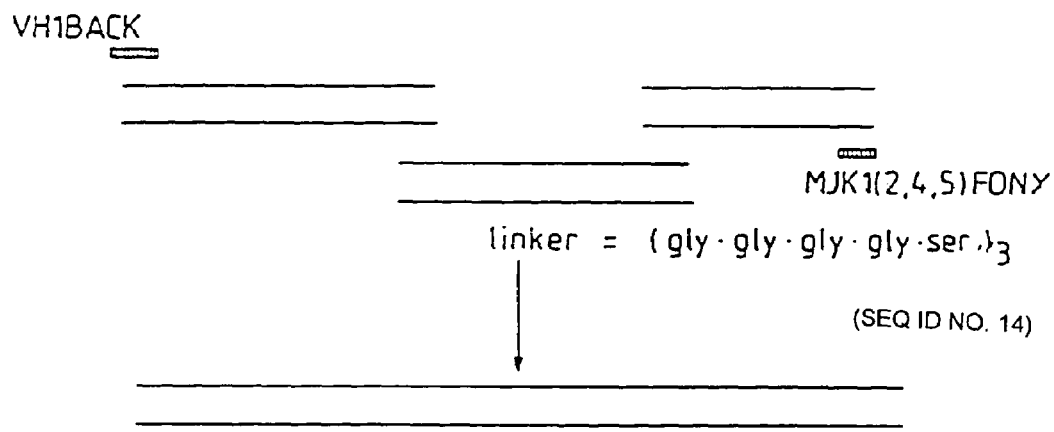
linker = (gly·gly·gly·gly·ser.)₃
(SEQ ID NO. 14)
3) ADDING RESTRICTION SITES
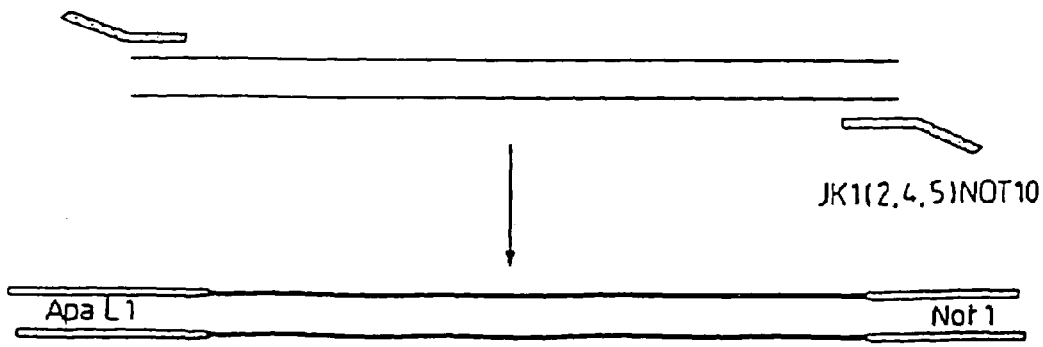

Fig. 24a

VH sequences from combinatorial library:

| | | CDR1 | | CDR2 | | CDR3 | | |
|---|---|---|---|---|---|---|---|---|
| A | QVQLQQSGAELARPGASVKMSCKASGYTFT | SYTMH | WVKQRPGQGLEWIG | YINPSCGYTNYNQKFKD | KATLTADKSSSTAYMQLSSLTSEDSAVYYCAR | RYGAY | WGQGTTVTVSS x4 | (SEQ ID NO. 214) |
| B | QVKLQQSGAELARPGASVKMSCKASGYTFT | RDMH | WLKQRPGQGLEWIG | YINPSTGYTETNQKFKD | KATLTADKSSSTAYHQLSSLTSEDSAVYYCAR | NYGLY | WGQGTTVTVSS x3 | (SEQ ID NO. 215) |
| C | QVKLQQSGPELVKPGASVKHSCKASGYTFT | STYDI | WVKQKPGQGLEWIG | YINPYNDGTKYNEKFKD | KATLTSDKSSSTAYMELSLTSEDSAVYYCAI | YRJFPY | WGQGTTVTVSS x3 | (SEQ ID NO. 216) |
| D | QVKLQQSGPELVKPGASVKISCKASGYSFT | GTFDI | WVKQSNGKSLEWIC | RINPYNODTFYNQKFKD | KATLTVDKRSSTAIDHELLSLTSEDSAVYYCVG | ITTRFAY | WGQGTTVTVSS x2 | (SEQ ID NO. 217) |
| E | QVQLQESGPQLVAPSQSLSITCTVBQF5LT | SYGVH | WVRQPPGKGLEWLG | VIWAGGSYNTYSALHS | RLSISKDNSKSQVFLKDISLQTDDTAHYYCAR | URGDY | WGQGTTVTVSS | (SEQ ID NO. 218) |
| F | QVKLQQSGPELAKPGASVKMSCKASGYTFT | STLHI | WVKQRPGQGLKWIG | YINPSTGYTEYNQKFKD | KNTLTADKGSSTAYHQLSSLTSEDSAVYYCAR | DYGTY | WGQGTTVTVSS | (SEQ ID NO. 219) |
| G | QVKLQQSGAELVRPGASVRLSCKASGYTFT | RTLHI | WVKQRPGQGLEWIG | YINPSTGYTEYNQKFKD | ENTLTADKSSITAYHQLSSLTSEDSAVYYCAR | DYGTY | WGQGTTVTVSS | (SEQ ID NO. 220) |
| H | QVQLQQSGPELMKPGASVKISCKASGYTSFG | RDTPI | WVKQBIICKBLEWIG | YIAPFNGGTTTYNQKFKD | KATLTVDRSSSTAYMQLSSLTSEDSAVYYCAT | DYGRD | WGQGTTVTVSS | (SEQ ID NO. 221) | from hierarchical library VH-rep x Vk-d:

| | | CDR1 | | CDR2 | | CDR3 | | |
|---|---|---|---|---|---|---|---|---|
| I | QVKLQQSGPELARPCVSVKMSCKASGYTFT | STAHI | WVKQSQSKSLEWIG | VIGTYNGHYNYNQKFKD | KATMYVDKSSSTATHELARLTEDSAIYYCAR | DTGDY | WGQGTTVTVSS | (SEQ ID NO. 222) |
| J | QVKLQQSGABLARPGASVKHSCKASGYTFT | RITDI | WVKQRPGQGLEMIG | YINPBGYTNYNYNQKFKD | KATLTADKSSSTAYHQLSSLLTSEDSAVYYCAR | DRGAY | WGQGTTVTVSE | (SEQ ID NO. 223) |
| K | QVKLQQSGAELARPGASVKHSCKASGYTFT | RDMHH | WVKQRPGQGLEMIG | YINPSTGYTETNQKFKD | KATLTADKBSSTAYMQLSSLTSEDSAVYYCAR | NYGLY | WGQGTTVTVSS x3 | (SEQ ID NO. 224) |
| L | QVQLQQSGLELAKPGASVKHSCKASGYTFT | NYLDI | WVKQRPGQGLEMIG | YIHPSTGYTETNQKFKD | KATLTADKSSSTAYMQLSSLTBEDSAVYYCAR | DYGTY | WGQGTTVTVSS x3 | (SEQ ID NO. 225) |
| M | QVKLQQSGAELARPGAELARPGASVKHSCKASGYTFT | NYMHI | WVKQRPGQGLEWIG | YINPSTOYTETNQKFKD | KATLTADKS6STAYMQLGSLYBDDSAVYYCAR | DYGYF | WGQGTTVTVSS | (SEQ ID NO. 226) |
| N | QVKLQQSGAELARPGASVKLBCKTEGYTFT | SYTRI | WVKQRPGQGLEWIG | YINPSGYTHYNQKFKD | KATLTADKS6STAYMQLGGLTSEDSAVYYCAR | DYGTY | WGQGTTVTVSS | (SEQ ID NO. 227) |
| O | QVKLQQSGAELARPGASVKHSCEASGYTFT | SHLHI | WVKQRPGQGLEMIG | YIHPRTGYTETNQKFKD | KATLTADKBSSTAYMQL6SLTSE6SAVYYCAR | DYGAT | WGQGTTVTVSE | (SEQ ID NO. 228) |
| P | QVKLQQSGAELAKPGASVTHSCKAAGYTFT | SYMRI | WVKQRPGQGLEWIG | YINPSTGYTETNQKFKD | KATFTADKSSSTAYMQL6SLTBEDSAVYYCAR | DYGTY | WGQGTTVTVSE | (SEQ ID NO. 229) |
| Q | QVKLQQSGAELARPGASVKHSCKATGYTFT | STLHI | WVKQRPGQGLEMIQ | YINPSTGYTEYNQKFKD | KNTLTADKJ9BSTAYHQLGGLTGEDSAVYYCAR | DYGTY | WGQGTTVTVSS | (SEQ ID NO. 230) |
| R | QVKLQQSGAELAKPGASVKHSCKASGYTFT | SYYDH | WVKQRPOQGLEWIG | YINPSBGYTHNYNNQKFKD | KATLTADKSSSFTAYMQLSSLTSEDSAVYYCAR | NIGII | WGQGTTVTVSS | (SEQ ID NO. 231) |
| S | QVQLQQSGAELAKPGAEVKHSCKAAGYTFT | TPLDI | WVKQRPGQGLEWIG | YINPSTGYTETNQKFKD | KNTLTADK9BSTAYMQLSELYGEDSAVYYCAR | DYGTY | WGQGTTVTVSS | (SEQ ID NO. 232) |
| T | QVKLQQSGAELAKPGAGVKHSCKASGYTFT | SYTHI | WVKQRPQQGLCWIG | YINPSBGYTNNNQKFKD | KATLTADKSGSTAYMQLS9LTSEDSAVYYCAR | DYGTY | WGQGTTVTVSS x2 | (SEQ ID NO. 233) |
| U | QVKLQQSGAELAKPGASVKHSCKASGYTFT | 6YTRI | WVKQRPGQGLEWIG | YIIUPTGYTETNQKFKD | KATLTADKGSSTAYMQLSGLTGEDSAVYYCAR | DYGTY | WGQGTTVTVSS x6 | (SEQ ID NO. 234) |
| V | QVKLQQSGAELAKPOASVKMSCKASGYTFT | RDMHI | WLKQRPGQGLEWIG | YINPSTGYTETNQKFKD | KATLTADKS9STATMQLSSLYBEDSAVYYCAR | NYGLY | WGQGTTVTVSS | (SEQ ID NO. 235) |

Fig.24b

Vκ sequences from combinatorial library:

| | | CDR1 | | CDR2 | | CDR3 | | | | |
|---|---|---|---|---|---|---|---|---|---|---|
| a | DIELTQSPSSLSASLGERVSLTC | RASQEISCYLS | WLQQKPDGSIKRLIY | AASTLES | GVPKDFSGSRSGSDYSLTISSLESEDFADYYC | LQYASYPT | FGAGTKLEIKRA | V | ακ-like | (SEQ ID NO. 236) |
| b | DIELTQSPAIHSAASPGEKVTMTC | RASSVGGSYLH | MYQQKSGASPKVMIY | BTSNLAS | GVPARFSGGGGTGYSLTISSVEAEDAATYYC | QQYSGYPLT | FGAGTKLEIKRA | IV | ακ-like | (SEQ ID NO. 237) |
| c | DIELTQSPTTHAASPGEKITITC | SASSSISSNYLH | MYQQKPGFSPKLLIY | RTSNLAG | GVPARFSGGGSGTSYSLTIGTHEAEDVATYYC | QQGSSIPLT | FGAGTKLEIKRA | IV | ακ-like | (SEQ ID NO. 238) |
| d | DIELTQSPTTHAASPGEKITITC | SASSSISNYLH | MFQQKPGFSPKLLIS | RTSNLAG | GVPARFSGGSGTSYSLTIGTHEAEDVATYYC | QQGSTIPFT | FGSGTKLEIKRA | IV | ακ-like | (SEQ ID NO. 239) |
| e | DIELTQSPAIMSAFPGEKVTMTC | SASSVNTDGI | MFQQKPCTSPKLMIY | STSNLAS | GVPTRFSGSGSGTSYSLTISRMEAEDAATYYC | QQRSSYPPT | FGSGTKLEIKRA | IV | ακ-like | (SEQ ID NO. 240) |
| f | DIELTQSPAIMSASPGEKVTMTC | SASSVSTRN | MYQQKSGTSPKRHIY | DTSKLAS | GVPARFSGSGSGTSYSLTISSHEAEDAATYYC | QQFSSNPLT | FGAGTKLEIKRA | VI | Vκoxι | (SEQ ID NO. 241) |
| g | DIELTQSPAIMSASPGEKVTMTC | SASSSINYDI | MYQQRPGASPKRNIY | DTSKLAS | GVPARFSGSGSGTSYSLTISSVTISSHEAEDAATYYC | IQRNSYPHT | FGGGTKLEIKRA | VI | ακ-like | (SEQ ID NO. 242) | from hierarchical library VH-B x Vκ-rep:

| | | CDR1 | | CDR2 | | CDR3 | | | | |
|---|---|---|---|---|---|---|---|---|---|---|
| h | DIELTQSPAIHSASPGEKVTITC | SASSVSTGI | MYQQKSGTSPKLMIY | DTSKLAS | GVPARFSGSGSGTSYSLTISSHEAEDAATYYC | QQHSSNPLT | FGAGTKLEIKRA x4 | IV/VI | Vκoxι | (SEQ ID NO. 243) |
| i | DIELTQSPAIMSASPGEKVTITC | SASSVSTIH | MFQQKPGTSPKLMIY | STSNLAS | GVPARFSGSGSGTSYSLTISSHEAEDAATYYC | QQYHSTPLT | FGAGTKLEIKRA | V | ακ-like? | (SEQ ID NO. 244) |
| j | DIELTQSPTTHAASPGEKITITC | SASSISSNTLH | MFQQKPGFSPKLLIY | RTSNLAS | GVPPRFSGSGSGTSYSLTISSVEAEDVATYYC | QQGSSIPLT | FGGGTKLEIKRA | V | ακ-like | (SEQ ID NO. 245) |
| k | DIELTQSPTTHAASPGEKITITC | SATSSISSNTLH | MFQQKPGFSPKLLIT | RTSNLAS | GVPPRFSGSGSGTSYSLTISSVEAEDVATYYC | QQGSSIPYT | FGAGTKLEIKRA | V | ακ-like | (SEQ ID NO. 246) |
| l | DIELTQSPAIHSASPGEKITITC | SASSISNYLH | MYQQKPGFSPKLLIY | RTSNLAS | GVPARFSGGGSGTSYSLTIGTNEAEDVATYYC | QQGSSIPYT | FGGGTKLEIKRA | V | ακ-like | (SEQ ID NO. 247) |
| m | DIELTQSPTTHAASPGEKVTITC | SASSISSNHLH | MFQQKPGFSPKLLIY | RTGNLAS | GVPARFSGSGSGTSYSLTIGTNEAEDVATYYC | QQGGIPYT | FGGGTKLEIKRA | V | ακ-like | (SEQ ID NO. 248) |
| n | DIELTQSPAIHAASPGEKITITC | SASSISNHLH | MYQQKPGFSPKLLIY | RTSNLAS | GVPARFSGSGSGTSYSLTICTMEAEDVATYYC | QQGSSIPFT | FGAGTKLEIKRA | V | ακ-like | (SEQ ID NO. 249) |
| o | DIELTQSPAIHSASPGEKITITC | SASSISNYLH | MYQQKPGFSPKLLIY | RTSNLAS | GVPARFSGSGSGTSYSLTIGTMEAEDVATYYC | QQGSBIPYT | FGGGTKLEIKRA x2 | V | ακ-like | (SEQ ID NO. 250) |
| p | DIELTQSPAIMSASPGEKVTMTC | SASSVSTRH | MYQQKSGTSPKRHIY | DTSKLAS | GVPARFSGSGSGTGYSLTISSHEAEDAATYYC | QQHSSNPLT | FGAGTKLEIKRA x2 | VI | Vκoxι | (SEQ ID NO. 251) |
| q | DIELTQSPAIMSASPGEKVTMTC | SASSVSTRH | MFQQKEGTSPKRHIT | DTGKLAS | GVPARFSGEGCGTSYGLTISSHEAEDAATYYC | QQWTSNPPT | FGGGTKLEIKRA | IV/VI | Vκoxι | (SEQ ID NO. 252) |
| r | DIELTQSPAIMSASPGEKVTMTC | SASSVRYVN | MFQQKSGTSPKRHIT | DTSKLAS | GVPARFSGSGSGTSYSLTISSHEAEDAATYYC | QQWSTNALT | FGAGTKLEIKRA | IV/VI | Vκoxι | (SEQ ID NO. 253) |
| s | DIELTQSPAIHSASPGEKVTMTC | SASSVSTMI | MYQQKEGASPKLMVT | STSNLAS | GVPARFSGSGCGTSYSLTIGVEAEDAATYYC | QQYSGYPLT | FGAGTKLEIKRA | IV/VI | ακ-like | (SEQ ID NO. 254) |
| t | DIELTQSPAIHSASPGEKVTMTC | RASSVTSBYLH | MYQQKSGASPKLMIT | STSNLAS | GVPARFSG8GSGTSYSLTISRMEAEDAATYYC | QQRSSYPLT | FGAGTKLEIKRA | IV/VI | ακ-like | (SEQ ID NO. 255) |
| u | DIELTQSPAIHSASPGEKVTMTC | RASSVSGSYLH | MYQQKSGASPKLMIT | STSNLAS | GVPARFSGGGSGTSYSLTISVEAEDAATYYC | QQISSYPLT | FGAGTKLEIKRA | IV/VI | ακ-like | (SEQ ID NO. 256) |
| v | DIELTQSPAIHBASPGEKVTMTC | RASSVSSSYLH | MYQQKGASPKLMIY | STBNLAS | GVPARFSGSGSGTSYSLTISVEAEDAATYYC | QQYGCYPLT | FGAGTKLEIKRA | IV/VI | ακ-like | (SEQ ID NO. 257) |
| w | DIELTQSPTTHAASPGEKITITC | SASSISSNYLH | MYQQKPGFSPKLLIY | RTSNLAS | GVPARFSGSGSGTSYSLTICTNEAEDVATYYC | QQGSSIPLT | FGAGTKLEIKRA x3 | IV/VI | ακ-like | (SEQ ID NO. 258) |

Fig.28.
Fab
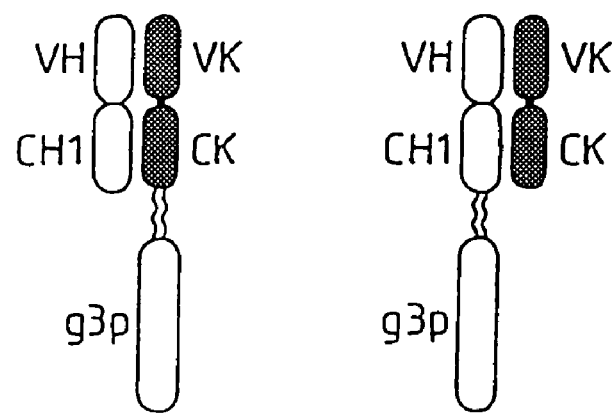
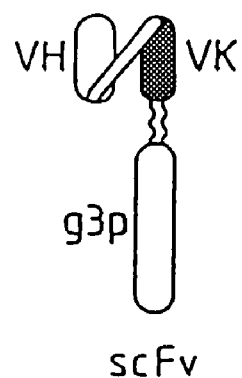
scFv

Fig. 44a

```
          10         20         30         40         50         60         70         80         90
TTCTATTCTCACAGTGCACAGGTCCAGCTGCAGCAGTCTGGGGCTGAGCTTGTGAAGCCTGGGGCTTCAGTGAAGCTGTCCTGCAAGCT
AAGATAAGAGTGTCACGTGTCCAGTGCCACGTCGACGGTCGACGTCTCAGACGTCGAACACTTCGAACAGTCACTTCGACAGGACGTTCCGA
PheTyrSerHisSerAlaGlnValGlnLeuGlnGlnSerGlyAlaGluLeuValLysProGlyAlaSerValLysLeuSerCysLysAla 100        110        120        130        140        150        160        170        180
TCTGGCTACACCTTCACCAGCTACTGGATGCACTGGGTGAAGCAGAGGCCTGAGTGGATTGGAAGGATTGATCCTAAT
AGACCGATGTGGAAGTGGTCGATGACCTACGTGACCCACTTCGTCTCCGGACTCGTCGACTTCGTCTCCGGACTCACCTACCTTCCTAACTAGGATTA
SerGlyTyrThrPheThrSerTyrTrpMetHisTrpValLysGlnArgProGluTrpIleGlyArgIleAspProAsn 190        200        210        220        230        240        250        260        270
AGTGGTGGTACTAAGTACACAATGAGAAGTTCAAGAGCAAGGCCACACTGACTGTAGACAAACCCTCCAGCACAGCCTACATGCAGCTCAGC
TCACCACCATGATTCATGTTACTCTTCAAGTTCTCGTTCCGGTGTGACTGACATCTGTTTGGGAGGTCGTCGGATGTACGTCGAGTCG
SerGlyThrLysTyrAsnGluLysPheLysSerLysAlaThrLeuThrValAspLysProSerSerThrAlaTyrMetGlnLeuSer 280        290        300        310        320        330        340        350        360
AGCCTGACATCTGAGGACTCTGCGGTCTATTATTGTGCAAGATACGACTACGGTAGTAGCTACTTTGACTACTGGGGCCAAGGACC
TCGGACTGTAGACTCCTGAGACGCCAGAGACGCCAGAATAACACTTCTATGCTGATGCCATCATCGATGATGAAACTGATGACCCCGGTTCCCTGG
SerLeuThrSerGluAspSerAlaValTyrTyrCysAlaArgTyrAspTyrGlySerSerTyrPheAspTyrTrpGlyGlnGlyThr 370        380        390        400        410        420        430        440        450
ACGGTCACCGTCTCCTCAGGTGGAGGCGGTTCAGGCGGAGGTGGCTCTGGCGGTGGCGGATCCGAGGTGTTGGACAACAGGAATCTGCA
TGCCAGTGGCAGAGGAGTCCACCTCCGCCAAGTCCGCCTCCACCGAGACCGCCACCGCCTAGGCTCCACAACCTGTTGTCCTTAGACGT
ThrValThrValSerSerGlyGlyGlyGlySerGlyGlyGlyGlySerGlyGlyGlyGlySerGlnAlaValGlyThrGlnGluSerAla 460        470        480        490        500        510        520        530        540
CTCACCACATCACCTGGTGAAACAGTCACACTTGTCGTCAGTGATGGGGCTCGTTCAACTAGTAACTATGCCAACTGGTCCAA
GAGTGGTGTAGTGGACCACTTTGTCAGTGTGAACAGCAGTCACTACCCCGAGCAAGTTGATCATTGATACGTTGACCAGGTT
LeuThrThrSerProGlyGluThrValThrLeuThrCysArgSerSerThrGlyAlaValThrThrSerAsnTyrAlaAsnTrpValGln 550        560        570        580        590        600        610        620        630
GAAAACCAGATCATTTATTCACTGGTCTAATAGGTGGTACCAACAACCGAGCTCCAGTTCCTGCCAGATTCTCAGGCTCCGGCTCCTGATT
CTTTTGGTCTAGTAATAAGTGACCAGATTATCCACCATGGTTGTTGGCTCGAGGTCAAGGACGGTCTAAGAGTCCGAGGACTAAGAGTCCGAGGACTAA
GluLysProAspHisLeuPheThrGlyLeuIleGlyGlyThrAsnAsnArgAlaProGlyValProAlaArgPheSerGlySerLeuIle
```

Fig. 44 b

```
          640         650         660         670         680         690         700    C    G  710         720
GGAGACAAGGCTGCCCTGCCCTCACCATCACAGGGGGCACAGAGACTGAGGATGAGGCAATATATTTCTGTGCTCTATGGTACAGCAACCATTGGGTG
CCTCTGTTCCGACGGAGTGGTAGTGTCCCCGGTGTCCTGACTGTCTCCTACTCCGTTATATAAAGACACGAGATACCATGTCGTTGGTAACCCAC
GlyAspLysAlaAlaLeuThrIleThrGlyAlaGlnThrGluAspGluAlaIleTyrPheCysAlaLeuTrpTyrSerAsnHisTrpVal
  730         740         750         760         770
TTCGTGGAGGAACAAACTGACTGTCCTCGAGATCAAACGGGCGGCCGC    (SEQ ID NO. 261)
AAGCCACCTCCTTGGTTTGACTGACAGGAGCTCTAGTTTGCCCGCCGGCG
PheGlyGlyThrLysLeuThrValLeuGluIleLysArgAlaAla       (SEQ ID NO. 262)
```

Fig. 48a

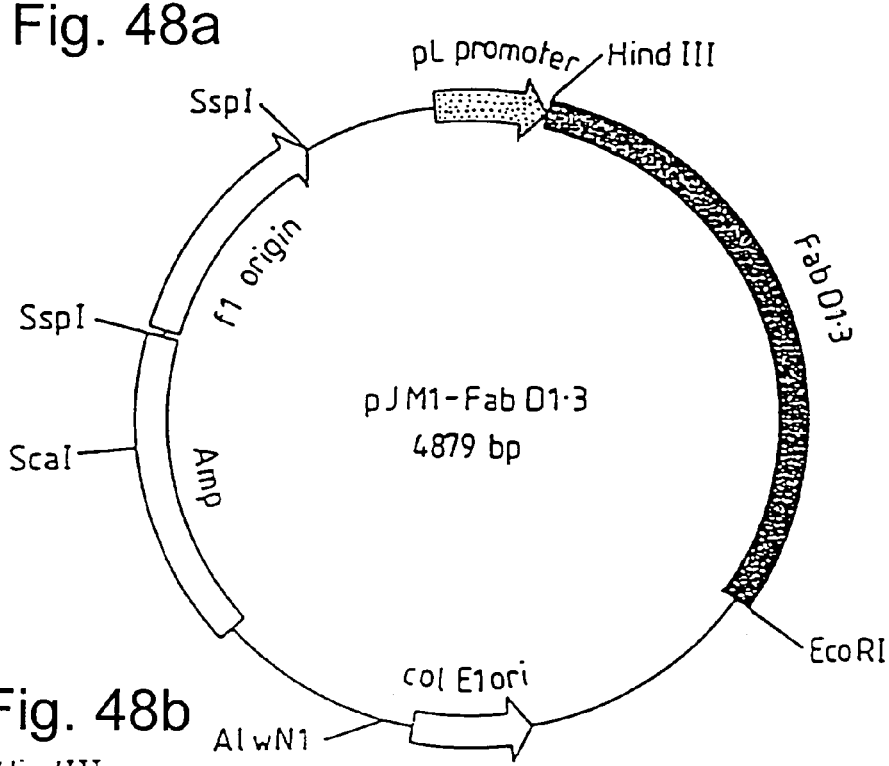

Fig. 48b

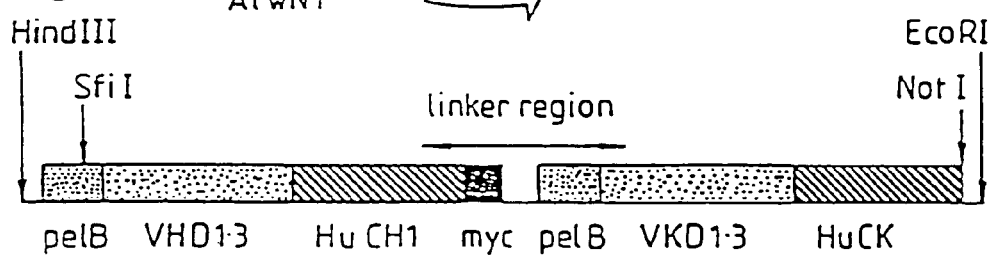

Fig. 48c

```
◄─────────── 3' Human CH1 and hinge ───────────
  K  P  S  N  T  K  V  D  K  K  V  E  P  K  S  S  T  K  T  H  T
AACCCCAGCAACACCAAGGTCGACAAGAAAGTTGAGCCCAAATCTTCAACTAAGACGCACACA ──►│ ◄── myc peptide tag ──►
  S  G  G  E  Q  K  L  I  S  E  E  D  L  N  *  *        (SEQ ID NO. 263)
TCAGGAGGTGAACAGAAGCTCATCTCAGAAGAGGATCTGAATTAATAAGGGAGCTTGCATGCA ◄────── pelB leader ──────
                   M  K  Y  L  L  P  T  A  A  A  G  L
AATTCTATTTCAAGGAGACAGTCATAATGAAATACCTATTGCCTACGGCAGCCGCTGGATTGT ──────────►│◄── 5' Vk ──►
  L  L  P  A  A  Q  P  A  M  A  D  I  E  L  T  Q  S  P     (SEQ ID NO. 264)
TATTACCTGCTGCCCAACCAGCCGATGGCCGACATCGAGTTCACCCAGTCTCC       (SEQ ID NO. 265)
```

Fig. 52.

|  | CDR 1 | CDR 2 |
|---|---|---|
| D1.3 | DIQMTQSPASLSASVGETVTITCRASGNIHNYLA | WYQQKQGKSPQLLVYYTTTLAD |
| M1F | DIELTQSPSSLSASLGERVSLTCRASQDIGSSLN | WLQQEPDGTIKRLIYATSSLDS |
| M21 | DIELTQSPALMAASPGEKVTITCSVSSSISSSNLH | WYQQKSETSPKPWIYGTSNLAS |

|  | CDR 3 |
|---|---|
| D1.3 | GVPSRFSGSGSGTQYSLKINSLQPEDFGSYYCQHFWSTPRTFGGGTKLEIKR |
| M1F | GVPKRFSGSRSGSDYSLTISSLESEDFVDYYCLQYASSPWTFGGGTKLELKR |
| M21 | GVPVRFSGSGSGTSYSLTISSMEAEDAATYYCQQWSSYPLTFGAGTKLEIKR |

METHODS FOR PRODUCING MEMBERS OF SPECIFIC BINDING PAIRS

This is a divisional of U.S. application Ser. No. 09/726,219 filed Nov. 28, 2000 now U.S. Pat. No. 6,806,079, which in turn is a continuation of U.S. application Ser. No. 08/484,893, filed Jun. 7, 1995 which issued as U.S. Pat. No. 6,172,197 on Jan. 9, 2001, which in turn is a continuation of U.S. application Ser. No. 07/971,857, which in turn is the U.S. national phase of PCT/GB91/01134, filed 10 Jul. 10 1991, which issued as U.S. Pat. No. 5,969,108 on Oct. 19, 1999.

The present invention relates to methods for producing members of specific binding pairs. The present invention also relates to the biological binding molecules produced by these methods.

Owing to their high specificity for a given antigen, the advent of monoclonal antibodies (Kohler, G. and Milstein C; 1975 Nature 256: 495) represented a significant technical break-through with important consequences both scientifically and commercially.

Monoclonal antibodies are traditionally made by establishing an immortal mammalian cell line which is derived from a single immunoglobulin producing cell secreting one form of a biologically functional antibody molecule with a particular specificity. Because the antibody-secreting mammalian cell line is immortal, the characteristics of the antibody are reproducible from batch to batch. The key properties of monoclonal antibodies are their specificity for a particular antigen and the reproducibility with which they can be manufactured.

Structurally, the simplest antibody (IgG) comprises four polypeptide chains, two heavy (H) chains and two light (L) chains inter-connected by disulphide bonds (see FIG. 1). The light chains exist in two distinct forms called kappa (K) and lambda (λ). Each chain has a constant region (C) and a variable region (V). Each chain is organized into a series of domains. The light chains have two domains, corresponding to the C region and the other to the V region. The heavy chains have four domains, one corresponding to the V region and three domains (1, 2 and 3) in the C region. The antibody has two arms (each arm being a Fab region), each of which has a VL and a VH region associated with each other. It is this pair of V regions (VL and VH) that differ from one antibody to another (owing to amino acid sequence variations), and which together are responsible for recognising the antigen and providing an antigen binding site (ABS). In even more detail, each V region is made up from three complementarity determining regions (CDR) separated by four framework regions (FR). The CDR's are the most variable part of the variable regions, and they perform the critical antigen binding function. The CDR regions are derived from many potential germ line sequences via a complex process involving recombination, mutation and selection.

It has been shown that the function of binding antigens can be performed by fragments of a whole antibody. Example binding fragments are (i) the Fab fragment consisting of the VL, VH, CL and CH1 domains; (ii) the Fd fragment consisting of the VH and CH1 domains; (iii) the Fv fragment consisting of the VL and VH domains of a single arm of an antibody, (iv) the dAb fragment (Ward, E. S. et al., Nature 341, 544-546 (1989) which consists of a VH domain; (v) isolated CDR regions; and (vi) F(ab')$_2$ fragments, a bivalent fragment comprising two Fab fragments linked by a disulphide bridge at the hinge region.

Although the two domains of the Fv fragment are coded for by separate genes, it has proved possible to make a synthetic linker that enables them to be made as a single protein chain (known as single chain Fv (scFv); Bird, R. E. et al., Science 242, 423-426 (1988) Huston, J. S. et al., Proc. Natl. Acad. Sci., USA 85, 5879-5883 (1988)) by recombinant methods. These scFv fragments were assembled from genes from monoclonals that had been previously isolated. In this application, the applicants describe a process to assemble scFv fragments from VH and VL domains that are not part of an antibody that has been previously isolated.

Whilst monoclonal antibodies, their fragments and derivatives have been enormously advantageous, there are nevertheless a number of limitations associated with them.

Firstly, the therapeutic applications of monoclonal antibodies produced by human immortal cell lines holds great promise for the treatment of a wide range of diseases (Clinical Applications of Monoclonal Antibodies. Edited by E. S. Lennox. British Medical Bulletin 1984. Publishers Churchill Livingstone). Unfortunately, immortal antibody-producing human cell lines are very difficult to establish and they give low yields of antibody (approximately 1 μg/ml). In contrast, equivalent rodent cell lines yield high amounts of antibody (approximately 100 μg/ml). However, the repeated administration of these foreign rodent proteins to humans can lead to harmful hypersensitivity reactions. In the main therefore, these rodent-derived monoclonal antibodies have limited therapeutic use.

Secondly, a key aspect in the isolation of monoclonal antibodies is how many different clones of antibody producing cells with different specificities, can be practically established and sampled compared to how many theoretically need to be sampled in order to isolate a cell producing antibody with the desired specificity characteristics (Milstein, C., Royal Soc. Croonian Lecture, Proc. R. Soc. London B. 239; 1-16, (1990)). For example, the number of different specificities expressed at any one time by lymphocytes of the murine immune system is thought to be approximately $10^7$ and this is only a small proportion of the potential repertoire of specificities. However, during the isolation of a typical antibody producing cell with a desired specificity, the investigator is only able to sample $10^3$ to $10^4$ individual specificities. The problem is worse in the human, where one has approximately $10^{12}$ lymphocyte specificities, with the limitation on sampling of $10^3$ or $10^4$ remaining.

This problem has been alleviated to some extent in laboratory animals by the use of immunisation regimes. Thus, where one wants to produce monoclonal antibodies having a specificity against a particular epitope, an animal is immunised with an immunogen expressing that epitope. The animal will then mount an immune response against the immunogen and there will be a proliferation of lymphocytes which have specificity against the epitope. Owing to this proliferation of lymphocytes with the desired specificity, it becomes easier to detect them in the sampling procedure. However, this approach is not successful in all cases, as a suitable immunogen may not be available. Furthermore, where one wants to produce human monoclonal antibodies (eg for therapeutic administration as previously discussed), such an approach is not practically, or ethically, feasible.

In the last few years, these problems have in part, been addressed by the application of recombinant DNA methods to the isolation and production of e.g. antibodies and fragments of antibodies with antigen binding ability, in bacteria such as *E. coli*.

This simple substitution of immortalised cells with bacterial cells as the 'factory', considerably simplifies procedures for preparing large amounts of binding molecules. Furthermore, a recombinant production system allows scope for producing tailor-made antibodies and fragments thereof. For example, it is possible to produce chimaeric molecules with new combinations of binding and effector functions, humanised antibodies (e.g. murine variable regions combined with human constant domains or murine-antibody CDRs grafted onto a human FR) and novel antigen-binding molecules. Furthermore, the use of polymerase chain reaction (PCR) amplification (Saiki, R. K., et al., Science 239, 487-491 (1988)) to isolate antibody producing sequences from cells (e.g. hybridomas and B cells) has great potential for speeding up the timescale under which specificities can be isolated. Amplified VH and VL genes are cloned directly into vectors for expression in bacteria or mammalian cells (Orlandi, R., et al., 1989, Proc. Natl. Acad. Sci., USA 86, 3833-3837; Ward, E. S., et al., 1989 supra; Larrick, J. W., et al., 1989, Biochem. Biophys. Res. Commun. 160, 1250-1255; Sastry, L. et al., 1989, Proc. Natl. Acad. Sci., USA., 86, 5728-5732). Soluble antibody fragments secreted from bacteria are then screened for binding activities.

However, like the production system based upon immortalised cells, the recombinant production system still suffers from the selection problems previously discussed and therefore relies on animal immunization to increase the proportion of cells with desired specificity. Furthermore, some of these techniques can exacerbate the screening problems. For example, large separate H and L chain libraries have been produced from immunized mice and combined together in a random combinatorial manner prior to screening (Huse, W. D. et al., 1989, Science 246, 1275-1281, WO90/14443; WO90/14424 and WO90/14430). Crucially however, the information held within each cell, namely the original pairing of one L chain with one H chain, is lost. This loses some, of the advantage gained by using immunization protocols in the animal. Currently, only libraries derived from single VH domains (dAbs; Ward, E. S., et al., 1989, supra.) do not suffer this drawback. However, because not all antibody VH domains are capable of binding antigen, more have to be screened. In addition, the problem of directly screening many different specificities in prokaryotes remains to be solved.

Thus, there is a need for a screening system which ameliorates or overcomes one or more of the above or other problems. The ideal system would allow the sampling of very large numbers of specificities (eg $10^6$ and higher), rapid sorting at each cloning round, and rapid transfer of the genetic material coding for the binding molecule from one stage of the production process, to the next stage.

The most attractive candidates for this type of screening, would be prokaryotic organisms (because they grow quickly, are relatively simple to manipulate and because large numbers of clones can be created) which express and display at their surface a functional binding domain eg. an antibody, receptor, enzyme etc. In the UK patent GB 2137631B methods for the co-expression in a single host cell of the variable H and L chain genes of immunoglobulins were disclosed. However, the protein was expressed intracellularly and was insoluble. Further, the protein required extensive processing to generate antibody fragments with binding activity and this generated material with only a fraction of the binding activity expected for antibody fragments at this concentration. It has already been shown that antibody fragments can be secreted through bacterial membranes with the appropriate signal peptide (Skerra, A. and Pluckthun, A. 1988 Science 240 1038-1040; Better, M et al 1988, Science 240 1041-1043) with a consequent increase in the binding activity of antibody fragments. These methods require screening of individual clones for binding activity in the same way as do mouse monoclonal antibodies.

It has not been shown however, how a functional binding domain eg an antibody, antibody fragment, receptor, enzyme etc can be held on the bacterial surface in a configuration which allows sampling of say its antigen binding properties and selection for clones with desirable properties. In large part, this is because the bacterial surface is a complex structure, and in the gram-negative organisms there is an outer wall which further complicates the position. Further, it has not been shown that eg an antibody domain will fold correctly when expressed as a fusion with a surface protein of bacteria or bacteriophage.

Bacteriophage are attractive prokaryote related organisms for this type of screening. In general, their surface is a relatively simple structure, they can be grown easily in large numbers, they are amenable to the practical handling involved in many potential mass screening programmes, and they carry genetic information for their own synthesis within a small, simple package. The difficulty has been to practically solve the problem of how to use bacteriophages in this manner. A Genex Corporation patent application number WO88/06630 has proposed that the bacteriophage lambda would be a suitable vehicle for the expression of antibody molecules, but they do not provide a teaching which enables the general idea to be carried out. For example WO88/06630 does not demonstrate that any sequences: (a) have been expressed as a fusion with gene V; (b) have been expressed on the surface of lambda; and (c) have been expressed so that the protein retains biological activity. Furthermore there is no teaching on how to screen for suitable fusions. Also, since the lambda virions are assembled within the cell, the fusion protein would be expressed intracellularly and would be predicted to be inactive. Bass et al., in December 1990 (after the earliest priority date for the present application) describe deleting part of gene III of the filamentous bacteriophage M13 and inserting the coding sequence for human growth hormone (hGH) into the N-terminal site of the gene. The growth hormone displayed by M13 was shown to be functional. (Bass, S., et al. Proteins, Structure, Function and Genetics (1990) 8: 309-314). A functional copy of gene III was always present in addition, when this fusion was expressed. A Protein Engineering Corporation patent application WO90/02809 proposes the insertion of the coding sequence for bovine pancreatic trypsin inhibitor (BPTI) into gene VIII of M13. However, the proposal was not shown to be operative. For example, there is no demonstration of the expression of BPTI sequences as fusions with protein VIII and display on the surface of M13. Furthermore this document teaches that when a fusion is made with gene III, it is necessary to use a second synthetic copy of gene III, so that some unaltered gene III protein will be present. The embodiments of the present application do not do this. In embodiments where phagemid is rescued with M13K07 gene III deletion phage, there is no unaltered gene III present.

WO90/02809 also teaches that phagemids that do not contain the full genome of M13 and require rescue by coinfection with helper phage are not suitable for these purposes because coinfection could lead to recombination.

In all embodiments where the present applicants have used phagemids, they have used a helper phage and the only sequences derived from filamentous bacteriophage in the phagemids are the origin of replication and gene III sequences.

WO90/02809 also teaches that their process needed information such as nucleotide sequence of the starting molecule and its three-dimensioned structure. The use of a pre-existing repertoire of binding molecules to select for a binding member, such as is disclosed herein, for example using an immunoglobulin gene repertoire of animals, was not disclosed. Further, they do not discuss favouring variegation of their binding molecules in natural blocks of variation such as CDRs of immunoglobulins, in order to favour generation of improved molecules and prevent unfavourable variations. WO90/02809 also specifically excluded the application of their process to the production of scFv molecules.

In each of the above discussed patents (WO88/06630 and WO90/02809), the protein proposed for display is a single polypeptide chain. There is no disclosure of a method for the display of a dimeric molecule by expression of one monomer as a fusion with a capsid protein and the other protein in a free form.

Another disclosure published in May 1991 (after the earliest priority date for the present application) describes the insertion into gene VIII of M13, the coding sequences for one of the two chains of the Fab portion of an antibody with co-expression of the other from a plasmid. The two chains were demonstrated as being expressed as a functional Fab fragment on the surface of the phage (Kang A. S. et al., (1991) Proc. Natl. Acad. Sci, USA, 88 p4363-4366). No disclosure was made of the site of insertion into gene VIII and the assay for pAb binding activity by ELISA used a reagent specific for antibody L chain rather than for phage. A further disclosure published in March 1991 (after the earliest priority date for the present application) describes the insertion of a fragment of the AIDS virus protein gag into the N-terminal portion of gene III of the bacteriophage fd. The expression of the gag protein fragment was detected by immunological methods, but it was not shown whether or not the protein was expressed in a functional form (Tsunetsugu-Yokota Y et al. (1991) Gene 99 p261-265).

The problem of how to use bacteriophages in this way is in fact a difficult one. The protein must be inserted into the phage in such a way that the integrity of the phage coat is not undermined, and the protein itself should be functional retaining its biological activity with respect to antigen binding. Thus, where the protein of choice is an antibody, it should fold efficiently and correctly and be presented for antigen binding. Solving the problem for antibody molecules and fragments would also provide a general method for any biomolecule which is a member of a specific binding pair e.g. receptor molecules and enzymes.

Surprisingly, the applicants have been able to construct a bacteriophage that expresses and displays at its surface a large biologically functional binding molecule (eg antibody fragments, and enzymes and receptors) and which remains intact and infectious. The applicants have called the structure which comprises a virus particle and a binding molecule displayed at the viral surface a 'package'. Where the binding molecule is an antibody, an antibody derivative or fragment, or a domain that is homologous to an immunoglobulin domain, the applicants call the package a 'phage antibody' (pAb). However, except where the context demands otherwise, where the term phage antibody is used generally, it should also be interpreted as referring to any package comprising a virus particle and a biologically functional binding molecule displayed at the viral surface.

pAbs have a range of applications in selecting antibody genes encoding antigen binding activities. For example, pAbs could be used for the cloning and rescue of hybridomas (Orlandi, R., et al (1989) PNAS 86 p3833-3837), and in the screening of large combinatorial libraries (such as found in Huse, W. D. et al., 1989, Science 246, 1275-1281). In particular, rounds of selection using pAbs may help in rescuing the higher affinity antibodies from the latter libraries. It may be preferable to screen small libraries derived from antigen-selected cells (Casali, P., et al., (1986) Science 234 p476-479) to rescue the original VH/VL pairs comprising the Fv region of an antibody. The use of pAbs may also allow the construction of entirely synthetic antibodies. Furthermore, antibodies may be made which have some synthetic sequences e.g. CDRs, and some naturally derived sequences. For example, V-gene repertoires could be made in vitro by combining unrearranged V genes, with D and J segments. Libraries of pAbs could then be selected by binding to antigen, hypermutated in vitro in the antigen-binding loops or V domain framework regions, and subjected to further rounds of selection and mutagenesis.

As previously discussed, separate H and L chain libraries lose the original pairing between the chains. It is difficult to make and screen a large enough library for a particularly advantageous combination of H and L chains.

For example, in a mouse there are approximately $10^7$ possible H chains and $10^7$ possible L chains. Therefore, there are $10^{14}$ possible combinations of H and L chains, and to test for anything like this number of combinations one would have to create and screen a library of about $10^{14}$ clones. This has not previously been a practical possibility.

The present invention provides a number of approaches which ameliorate this problem.

In a first approach, (a random combinatorial approach, see examples 20 and 21) as large a library as is practically possible is created which expresses as many of the $10^{14}$ potential combinations as possible. However, by virtue of the expression of the H and L chains on the surface of the phage, it is reasonably practicable to select the desired combination, from all the generated combinations by affinity techniques (see later for description of selection formats).

In a second approach (called a dual combinatorial approach by the present applicants, see example 26), a large library is created from two smaller libraries for selection of the desired combination. This ameliorates the problems still further. The approach involves the creation of: (i) a first library of say $10^7$ e.g. H chains which are displayed on a bacteriophage (as a fusion with the protein encoded by gene III) which is resistant to e.g. tetracycline; and (ii) a second library of say $10^7$ e.g. L chains in which the coding sequences for these light chains are within a plasmid vector containing an origin of replication for a bacteriophage (a phagemid) which is resistant to e.g. ampicillin (i.e. a different antibiotic) and are expressed in the periplasmic space of a host bacterium. The first library is then used to infect the bacteria containing the second library to provide $10^{14}$ combinations of H and L chains on the surface of the resulting phage in the bacterial supernatant.

The advantage of this approach is that two separate libraries of eg $10^7$ are created in order to produce $10^{14}$ combinations. Creating a $10^7$ library is a practical possibility.

The $10^{14}$ combinations are then subjected to selection (see later for description of selection formats) as disclosed by the present application. This selection will then produce a population of phages displaying a particular combination of H and L chains having the desired specificity. The phages selected however, will only contain DNA encoding one partner of the paired H and L chains (deriving from either the phage or phagemid). The sample eluate containing the population is then divided into two portions. A first portion is grown on e.g. tetracycline plates to select those bacteriophage containing DNA encoding H chains which are involved in the desired antigen binding. A second portion is grown on e.g. ampicillin plates to select those bacteriophage containing phagemid DNA encoding L chains which are involved in the desired antigen binding. A set of colonies from individually isolated clones e.g. from the tetracycline plates are then used to infect specific colonies e.g. from the ampicillin plates. This results in bacteriophage expressing specific combinations of H and L chains which can then be assayed for antigen binding.

In a third approach (called a hierarchical dual combinational approach by the present applicants), an individual colony from either the H or L chain clone selected by growth on the antibiotic plates, is used to infect a complete library of clones encoding the other chain (H or L). Selection is as described above. This favours isolation of the most favourable combination.

In a fourth approach (called a hierarchical approach by the present applicants, see examples 22 and 46) both chains are cloned into the same vector. However, one of the chains which is already known to have desirable properties is kept fixed. A library of the complementary chain is inserted into the same vector. Suitable partners for the fixed chain are selected following display on the surface of bacteriophage.

In a fifth approach (see example 48), to improve the chances of recovering original pairs, the complexity of the combinatorial libraries can be reduced by using small B populations of B-lymphocytes selected for binding to a desired antigen. The cells provide e.g. mRNA or DNA, for preparing libraries of antibody genes for display on phage. This technique can be used in combination with the above mentioned four approaches for selection of antibody specificities.

Phagemids have been mentioned above. The applicants have realised and demonstrated that in many cases phagemids will be preferred to phage for cloning antibodies because it is easier to use them to generate more comprehensive libraries of the immune repertoire. This is because the phagemid DNA is approximately 100 times more efficient than bacteriophage DNA in transforming bacteria (see example 19). Also, the use of phagemids gives the ability to vary the number of gene III binding molecule fusion proteins displayed on the surface of the bacteriophage (see example 17). For example, in a system comprising a bacterial cell containing a phagemid encoding a gene III fusion protein and infected with a helper phage, induction of expression of the gene III fusion protein to different extents, will determine the number of gene III fusion proteins present in the space defined between the inner and outer bacterial membranes following superinfection. This will determine the ratio of gene III fusion protein to native gene III protein displayed by the assembled phage.

Expressing a single fusion protein per virion may aid selection of antibody specificities on the basis of affinity by avoiding the 'avidity' effect where a phage expressing two copies of a low affinity antibody would have the same apparent affinity as a phage expressing one copy of a higher affinity antibody. In some cases however, it will be important to display all the gene III molecules derived by superinfection of cells containing phagemids to have fusions (e.g. for selecting low affinity binding molecules or improving sensitivity on ELISA). One way to do this is to superinfect with a bacteriophage which contains a defective gene III. The applicants have therefore developed and used a phage which is deleted in gene III. This is completely novel.

The demonstration that a functional antigen-binding domain can be displayed on the surface of phage, has implications beyond the construction of novel antibodies. For example, if other protein domains can be displayed at the surface of a phage, phage vectors could be used to clone and select genes by the binding properties of the displayed protein. Furthermore, variants of proteins, including epitope libraries built into the surface of the protein, could be made and readily selected for binding activities. In effect, other protein architectures might serve as "nouvelle" antibodies.

The technique provides the possibility of building antibodies from first principles, taking advantage of the structural framework on which the antigen binding loops fold. In general, these loops have a limited number of conformations which generate a variety of binding sites by alternative loop combinations and by diverse side chains. Recent successes in modelling antigen binding sites augurs well for de novo design. In any case, a high resolution structure of the antigen is needed. However, the approach is attractive for making e.g. catalytic antibodies, particularly for small substrates. Here side chains or binding sites for prosthetic groups might be introduced, not only to bind selectively to the transition state of the substrate, but also to participate directly in bond making and breaking. The only question is whether the antibody architecture, specialised for binding, is the best starting point for building catalysts. Genuine enzyme architectures, such as the triose phosphate isomerase (TIM) barrel, might be more suitable. Like antibodies, TIM enzymes also have a framework structure (a barrel of β-strands and α-helices) and loops to bind substrate. Many enzymes with a diversity of catalytic properties are based on this architecture and the loops might be manipulated independently on the frameworks for design of new catalytic and binding properties. The phage selection system as provided by the present disclosure can be used to select for antigen binding activities and the CDR loops thus selected, used on either an antibody framework or a TIM barrel framework. Loops placed on a e.g. a TIM barrel framework could be further modified by mutagenesis and subjected to further selection. Thus, there is no need to select for high affinity binding activities in a single step. The strategy of the immune system, in which low affinity evolves to high affinity seems more realistic and can be mimicked using this invention.

One class of molecules that could be useful in this type of application are receptors. For example, a specific receptor could be displayed on the surface of the phage such that it would bind its ligand. The receptor could then be modified by, for example, in vitro mutagenesis and variants having higher binding affinity for the ligand selected. The selection may be carried out according to one or more of the formats described below with reference to FIG. 2 (which refers particularly to pAbs) in which the pAb antibody is replaced with a phage receptor and the antigen with a ligand 1.

Alternatively, the phage-receptor could be used as the basis of a rapid screening system for the binding of ligands, altered ligands, or potential drug candidates. The advantages of this system namely of simple cloning, convenient expression, standard reagents and easy handling makes the drug screening application particularly attractive. In the context of this discussion, receptor means a molecule that binds a specific, or group of specific, ligand(s). The natural receptor could be expressed on the surface of a population of cells, or it could be the extracellular domain of such a molecule (whether such a form exists naturally or not), or a soluble molecule performing a natural binding function in the plasma, or within a cell or organ.

Another possibility, is the display of an enzyme molecule or active site of an enzyme molecule on the surface of a phage (see examples 11, 12, 30, 31, 32 and 36). Once the phage enzyme is expressed, it can be selected by affinity chromatography, for instance on columns derivatized with transition state analogues. If an enzyme with a different or modified specificity is desired, it may be possible to mutate an enzyme displayed as a fusion on bacteriophage and then select on a column derivatised with an analogue selected to have a higher affinity for an enzyme with the desired modified specificity.

Although throughout this application, the applicants discuss the possibility of screening for higher affinity variants of pAbs, they recognise that in some applications, for example low affinity chromatography (Ohlson, S. et al Anal. Biochem. 169, p204-208 (1988)), it may be desirable to isolate lower affinity variants.

Examples 21 and 23 show that the present invention provides a way of producing antibodies with low affinities (as seen in the primary immune response or in unimmunised animals). This is made possible by displaying multiple copies of the antibody on the phage surface in association with gene III protein. Thus, pAbs allow genes for these antibodies to be isolated and if necessary, mutated to provide improved antibodies.

pAbs also allow the selection of antibodies for improved stability. It has been noted for many antibodies, that yield and stability are improved when the antibodies are expressed at 30☐ C. rather than 37☐ C. If pAbs are displayed at 37☐ C., only those which are stable will be available for affinity selection. When antibodies are to be used in vivo for therapeutic or diagnostic purposes, increased stability would extend the half-life of antibodies in circulation.

Although stability is important for all antibodies and antibody domains selected using phage, it is particularly important for the selection of Fv fragments which are formed by the non-covalent association of VH and VL fragments. Fv fragments have a tendency to dissociate and have a much reduced half-life in circulation compared to whole antibodies. Fv fragments are displayed on the surface of phage, by the association of one chain expressed as a gene III protein fusion with the complementary chain expressed as a soluble fragment. If pairs of chains have a high tendency to dissociate, they will be much less likely to be selected as pAbs. Therefore, the population will be enriched for pairs which do associate stably. Although dissociation is less of a problem with Fab fragments, selection would also occur for Fab fragments which associate stably. pAbs allow selection for stability to protease attack, only those pAbs that are not cleaved by proteases will be capable of binding their ligand and therefore populations of phage will be enriched for those displaying stable antibody domains.

The technique of displaying binding molecules on the phage surface can also be used as a primary cloning system. For example, a cDNA library can be constructed and inserted into the bacteriophage and this phage library screened for the ability to bind a ligand. The ligand/binding molecule combination could include any pair of molecules with an ability to specifically bind to one another e.g. receptor/ligand, enzyme/substrate (or analogue), nucleic acid binding protein/nucleic acid etc. If one member of the complementary pair is available, this may be a preferred way of isolating a clone for the other member of the pair.

It will often be necessary to increase the diversity of a population of genes cloned for the display of their proteins on phage or to mutate an individual nucleotide sequence. Although in vitro or in vivo mutagenesis techniques could be used for either purpose, a particularly suitable method would be to use mutator strains. A mutator strain is a strain which contains a genetic defect which causes DNA replicated within it to be mutated with respect to its parent DNA. Hence if a population of genes as gene III fusions is introduced into these strains it will be further diversified and can then be transferred to a non-mutator strain, if desired, for display and selection. Example 38 covers the use of mutator strains with phage antibodies (an example of in vitro mutagenesis and selection of phage antibodies is given in example 45).

Targeted Gene Transfer

A useful and novel set of applications makes use of the binding protein on the phage to target the phage genome to a particular cell or group of cells. For example, a pAb specific for a cell surface molecule could be used to bind to the target cell via the surface molecule. The phage could then be internalised, either through the action of the receptor itself or as the result of another event (e.g. an electrical discharge such as in the technique of electroporation). The phage genome would then be expressed if the relevant control signals (for transcription and translation and possibly replication) were present. This would be particularly useful if the phage genome contained a sequence whose expression was desired in the target cell (along with the appropriate expression control sequences). A useful sequence might confer antibiotic resistance to the recipient cell or label the cell by the expression of its product (e.g. if the sequence expressed a detectable gene product such as a luciferase, see White, M, et al, Techniques 2(4), p194-201 (1990)), or confer a particular property on the target cell (e.g. if the target cell was a tumour cell and the new sequence directed the expression of a tumour suppressing gene), or express an antisense construct designed to turn off a gene or set of genes in the target cell, or a gene or gene product designed to be toxic to the target cell.

Alternatively, the sequence whose expression is desired in the target cell can be encoded on a phagemid. The phagemid DNA may then be incorporated into a phage displaying an antibody specific for a cell surface receptor. For example, incorporation may be by superinfection of bacteria containing the phagemid, with a helper phage whose genome encodes the antibody fragment specific for the target cell. The package is then used to direct the phagemid to the target cell.

This technique of "targeted gene transfer" has a number of uses in research and also in therapy and diagnostics. For example, gene therapy often aims to target the replacement gene to a specific cell type that is deficient in its activity. Targetting pAbs provide a means of achieving this.

In diagnostics, phage specific for particular bacteria or groups of bacteria have been used to target marker genes, e.g. luciferase, to the bacterial host (sec, for example, Ulitzer, S., and Kuhn, J., EPA 85303913.9). If the host range of the phage is appropriate, only those bacteria that are being tested for, will be infected by the phage, express the luciferase gene and be detected by the light they emit. This system has been used to detect the presence of Salmonella. One major problem with this approach is the initial isolation of a bacteriophage with the correct host range and then the cloning of a luciferase gene cassette into that phage, such that it is functional. The pAb system allows the luciferase cassette to be cloned into a well characterised system (filamentous phage) and allows simple selection of an appropriate host range, by modifying the antibody (or other binding molecule) specificity that the pAb encodes.

The present applicants have also been able to develop novel selection systems and assay formats which depend on the unique properties of these replicable genetic display packages e.g. pAbs.

Terminology

Much of the terminology discussed in this section has been mentioned in the text where appropriate.

Specific Binding Pair

This describes a pair of molecules (each being a member of a specific binding pair) which are naturally derived or synthetically produced. One of the pair of molecules, has an area on its surface, or a cavity which specifically binds to, and is therefore defined as complementary with a particular spatial and polar organisation of the other molecule, so that the pair have the property of binding specifically to each other. Examples of types of specific binding pairs are antigen-antibody, biotin-avidin, hormone-hormone receptor, receptor-ligand, enzyme-substrate, IgG-protein A.

Multimeric Member

This describes a first polypeptide which will associate with at least a second polypeptide, when the polypeptides are expressed in free form and/or on the surface of a substrate. The substrate may be provided by a bacteriophage. Where there are two associated polypeptides, the associated polypeptide complex is a dimer, where there are three, a trimer etc. The dimer, trimer, multimer etc or the multimeric member may comprise a member of a specific binding pair.

Example multimeric members are heavy domains based on an immunoglobulin molecule, light domains based on an immunoglobulin molecule, T-cell receptor subunits.

Replicable Genetic Display Package (Rgdp)

This describes a biological particle which has genetic information providing the particle with the ability to replicate. The particle can display on its surface at least part of a polypeptide. The polypeptide can be encoded by genetic information native to the particle and/or artificially placed into the particle or an ancestor of it. The displayed peptide may be any member of a specific binding pair eg. heavy or light chain domains based on an immunoglobulin molecule, an enzyme or a receptor etc.

The particle may be a virus eg. a bacteriophage such as fd or M13.

Package

This describes a replicable genetic display package in which the particle is displaying a member of a specific binding pair at its surface. The package may be a bacteriophage which displays an antigen binding domain at its surface. This type of package has been called a phage antibody (pAb).

Antibody

This describes an immunoglobulin whether natural or partly or wholly synthetically produced. The term also covers any protein having a binding domain which is homologous to an immunoglobulin binding domain. These proteins can be derived from natural sources, or partly or wholly synthetically produced.

Example antibodies are the immunoglobulin isotypes and the Fab, F(ab$^1$)$_2$, scFv, Fv, dAb, Fd fragments.

Immunoglobulin Superfamily

This describes a family of polypeptides, the members of which have at least one domain with a structure related to that of the variable or constant domain of immunoglobulin molecules. The domain contains two β-sheets and usually a conserved disulphide bond (see A. F. Williams and A. N. Barclay 1988 Ann. Rev Immunol. 6 381-405).

Example members of an immunoglobulin superfamily are CD4, platelet derived growth factor receptor (PDGFR), intercellular adhesion molecule. (ICAM). Except where the context otherwise dictates, reference to immunoglobulins and immunoglobulin homologs in this application includes members of the immunoglobulin superfamily and homologs thereof.

Homologs

This term indicates polypeptides having the same or conserved residues at a corresponding position in their primary, secondary or tertiary structure. The term also extends to two or more nucleotide sequences encoding the homologous polypeptides.

Example homologous peptides are the immunoglobulin isotypes.

Functional

In relation to a sbp member displayed on the surface of a rgdp, means that the sbp member is presented in a folded form in which its specific binding domain for its complementary sbp member is the same or closely analogous to its native configuration, whereby it exhibits similar specificity with respect to the complementary sbp member. In this respect, it differs from the peptides of Smith et al, supra, which do not have a definite folded configuration and can assume a variety of configurations determined by the complementary members with which they may be contacted.

Genetically Diverse Population

In connection with sbp members or polypeptide components thereof, this is referring not only to diversity that can exist in the natural population of cells or organisms, but also diversity that can be created by artificial mutation in vitro or in vivo.

Mutation in vitro may for example, involve random mutagenesis using oligonucleotides having random mutations of the sequence desired to be varied. In vivo mutagenesis may for example, use mutator strains of host microorganisms to harbour the DNA (see Example 38 below).

Domain

A domain is a part of a protein that is folded within itself and independently of other parts of the same protein and independently of a complementary binding member.

Folded Unit

This is a specific combination of an α-helix and/or β-strand and/or β-turn structure. Domains and folded units contain structures that bring together amino acids that are not adjacent in the primary structure.

Free Form

This describes the state of a polypeptide which is not displayed by a replicable genetic display package.

Conditionally Defective

This describes a gene which does not express a particular polypeptide under one set of conditions, but expresses it under another set of conditions. An example, is a gene containing an amber mutation expressed in non-suppressing or suppressing hosts respectively.

Alternatively, a gene may express a protein which is defective under one set of conditions, but not under another set. An example is a gene with a temperature sensitive mutation.

Suppressible Translational Stop Codon

This describes a codon which allows the translation of nucleotide sequences downstream of the codon under one set of conditions, but under another set of conditions translation ends at the codon. Example of suppressible translational stop codons are the amber, ochre and opal codons.

Mutator Strain

This is a host cell which has a genetic defect which causes DNA replicated within it to be mutated with respect to its parent DNA. Example mutator strains are NR9046mutD5 and NR9046 mut T1 (see Example 38).

Helper Phage

This is a phage which is used to infect cells containing a defective phage genome and which functions to complement the defect. The defective phage genome can be a phagemid or a phage with some function encoding gene sequences removed. Examples of helper phages are M13KO7, M13K07 gene III no. 3; and phage displaying or encoding a binding molecule fused to a capsid protein.

Vector

This is a DNA molecule, capable of replication in a host organism, into which a gene is inserted to construct a recombinant DNA molecule.

Phage Vector

This is a vector derived by modification of a phage genome, containing an origin of replication for a bacteriophage, but not one for a plasmid.

Phagemid Vector

This is a vector derived by modification of a plasmid genome, containing an origin of replication for a bacteriophage as well as the plasmid origin of replication.

Secreted

This describes a rgdp or molecule that associates with the member of a sbp displayed on the rgdp, in which the sbp member and/or the molecule, have been folded and the package assembled externally to the cellular cytosol.

Repertoire of Rearranged Immunoglobulin Genes

A collection of naturally occurring nucleotides eg DNA sequences which encoded expressed immunoglobulin genes in an animal. The sequences are generated by the in vivo rearrangement of eg V, D and J segments for H chains and eg the V and J segments for L chains. Alternatively the sequences may be generated from a cell line immunised in vitro and in which the rearrangement in response to immunisation occurs intracellularly.

Library

A collection of nucleotide eg DNA, sequences within clones.

Repertoire of Artificially Rearranged Immunoglobulin Genes

A collection of nucleotide eg DNA, sequences derived wholly or partly from a source other than the rearranged immunoglobulin sequences from an animal. This may include for example, DNA sequences encoding VH domains by combining unrearranged V segments with D and J segments and DNA sequences encoding VL domains by combining V and J segments.

Part or all of the DNA sequences may be derived by oligonucleotide synthesis.

Secretory Leader Peptide

This is a sequence of amino acids joined to the N-terminal end of a polypeptide and which directs movement of the polypeptide out of the cytosol.

Eluant

This is a solution used to breakdown the linkage between two molecules. The linkage can be a non-covalent or covalent bond(s). The two molecules can be members of a sbp.

Derivative

This is a substance which derived from a polypeptide which is encoded by the DNA within a selected rgdp. The derivative polypeptide may differ from the encoded polypeptide by the addition, deletion, substitution or insertion of amino acids, or by the linkage of other molecules to the encoded polypeptide. These changes may be made at the nucleotide or protein level. For example the encoded polypeptide may be a Fab fragment which is then linked to an Fc tail from another source. Alternatively markers such as enzymes, flouresceins etc may be linked to eg Fab, scFv fragments.

SUMMARY OF THE INVENTION

The present invention provides a method for producing a replicable genetic display package or population such rgdps of which method comprises the steps of:
a) inserting a nucleotide sequence encoding a member of a specific binding pair eg. a binding molecule within a viral genome;
b) culturing the virus containing said nucleotide sequence, so that said binding molecule is expressed and displayed by the virus at its surface.

The present invention also provides a method for selecting a rgdp specific for a particular epitope which comprises producing a population of such rgdps as described above and the additional step of selecting for said binding molecule by contacting the population with said epitope so that individual rgdps with the desired specificity may bind to said epitope. The method may comprise one or more of the additional steps of: (i) separating any bound rgdps from the epitope; (ii) recovering any separated rgdps and (iii) using the inserted nucleotide sequences from any separated rgdps in a recombinant system to produce the binding molecule separate from virus. The selection step may isolate the nucleotide sequence encoding the binding molecule of desired specificity, by virtue of said binding molecule being expressed in association with the surface of the virus in which said encoding nucleic acid is contained.

The present invention also provides a method of producing a multimeric member of a specific binding pair (sbp), which method comprises: expressing in a recombinant host organism a first polypeptide chain of said sbp member or a genetically diverse population of said sbp member fused to a component of a secreted replicable genetic display package (rgdp) which thereby displays said polypeptide at the surface of the package, and expressing in a recombinant host organism a second polypeptide chain of said multimer and causing or allowing the polypeptide chains come together to form said multimer as part of said rgdp at least one of said polypeptide chains being expressed from nucleic acid that is capable of being packaged using said component therefor, whereby the genetic material of each said rgdp encodes a said polypeptide chain. Both said chains may be expressed in the same host organism.

The first and second chains of said multimer may be expressed as separate chains from a single vector containing their respective nucleic acid.

At least one of said polypeptide chains may be expressed from a phage vector.

At least one of said polypeptide chains may be expressed from a phagemid vector, the method including using a helper phage, or a plasmid expressing complementing phage genes, to help package said phagemid genome, and said component of the rgdp is a capsid protein therefor. The capsid protein may be absent, defective or conditionally defective in the helper phage.

The method may comprise introducing a vector capable of expressing said first polypeptide chain, into a host organism which expresses said second polypeptide chain in free form, or introducing a vector capable of expressing said second polypeptide in free form into a host organism which expresses said first polypeptide chain.

Each of the polypeptide chain may be expressed from nucleic acid which is capable of being packaged as a rgdp using said component fusion product, whereby encoding nucleic acid for both said polypeptide chains are packaged in respective rgdps.

The nucleic acid encoding at least one of said first and second polypeptide chains may be obtained from a library of nucleic acid including nucleic acid encoding said chain or a population of variants of said chain. Both the first and second polypeptide chains may be obtained from respective said libraries of nucleic acid.

The present invention also provides a method of producing a member of a specific binding pair (sbp), from a nucleic acid library including nucleic acid encoding said sbp member or a genetically diverse population of said type of sbp members, which method comprises:

expressing in recombinant host cells polypeptides encoded by said library nucleic acid fused to a component of a secreted replicable genetic display package (rgdp) or in free form for association with a polypeptide component of said sbp member which is expressed as a fusion to said rgdp component so that the rgdp displays said sbp member in functional form at the surface of the package, said library nucleic acid being contained within the host cells in a form that is capable of being packaged using said rgdp component, whereby the genetic material of an rgdp displaying an sbp member contains nucleic acid encoding said sbp member or a polypeptide component thereof.

The nucleotide sequences for the libraries may be derived from eg animal spleen cells or peripheral blood lymphocytes. Alternatively the nucleotide sequence may be derived by the in vitro mutagenesis of an existing antibody coding sequence.

The present invention also provides a method of producing a member of a specific binding pair (sbp), which method comprises:

expressing in recombinant host cells nucleic acid encoding said sbp member or a genetically diverse population of said type of sbp member wherein the or each said sbp member or a polypeptide component thereof is expressed as a fusion with a component of a secreted replicable genetic display package (rgdp) which displays said sbp member at the surface of the package, nucleic acid encoding said sbp member or a polypeptide component thereof being contained within the host cell in a form that is capable of being packaged using said rgdp component whereby the genetic material of the rgdp displaying said sbp member encodes said sbp member or a polypeptide component thereof, said host organism being a mutator strain which introduces genetic diversity into the sbp member to produce said mixed population.

The present invention also provides a method of producing a member of a specific binding pair (sbp), which method comprises:

expressing in recombinant host cells nucleic acid encoding said sbp member or a genetically diverse population of said type of sbp member wherein the or each said sbp member or a polypeptide component thereof is expressed as a fusion with a component of a secreted replicable genetic display package (rgdp) which displays said sbp member in functional form at the surface of the package, nucleic acid encoding said sbp member or a polypeptide component thereof being contained within the host cell in a form that is capable of being packaged using said rgdp component whereby the genetic material of the rgdp displaying an sbp member encodes said sbp member or a polypeptide component thereof, said fusions being with bacteriophage capsid protein and the rgdps being formed with said fusions in the absence of said capsid expressed in wild-type form.

The present invention also provides a method of producing a member of a specific binding pair (sbp) which method comprises:

expressing in recombinant host cells nucleic acid encoding said sbp member or a genetically diverse population of said type of sbp member or a polypeptide component thereof fused to a component of a secreted replicable genetic display package (rgdp) which displays said sbp member in functional form at the surface of the package, nucleic acid encoding said sbp member or a polypeptide component thereof being contained within the host cell in a form that is capable of being packaged using said rgdp component whereby the genetic material of the rgdp displaying an sbp member or a polypeptide component thereof encodes said sbp member or a polypeptide component thereof, said sbp member or polypeptide component thereof being expressed from a phagemid as a capsid fusion, and a helper phage, or a plasmid expressing complementing phage genes, is used along with said capsid fusions to package the phagemid nucleic acid.

The library or genetically diverse population may be obtained from:

(i) the repertoire of rearranged immunoglobulin genes of an animal immunised with complementary sbp member, (ii) the repertoire of rearranged immunoglobulin genes of an animal not immunised with complementary sbp member, (iii) a repertoire of artificially rearranged immunoglobulin gene or genes (iv) a repertoire of immunoglobulin homolog gene or genes; or (v) a mixture of any of (i), (ii), (iii) and (iv).

The capsid protein may be absent, defective or conditionally defective in the helper phage.

The host cell may be a mutator strain which introduces genetic diversity into the sbp member nucleic acid.

The sbp member may comprise a domain which is, or is homologous to, an immunoglobulin domain.

The rgdp may be a bacteriophage, the host a bacterium, and said component of the rgdp a capsid protein for the bacteriophage. The phage may be a filamentous phage. The phage may be selected from the class I phages fd, M13, f1, If1, Ike, ZJ/Z, Ff and the class II phages Xf, Pf1 and Pf3. The phage may be fd or a derivative of fd. The derivative may be tetracycline resistant. The said sbp member or polypeptide chain thereof may be expressed as a fusion with the gene III capsid protein of phage fd or its counterpart in another filamentous phage. The sbp member or polypeptide chain thereof may be inserted in the N-terminal region of the mature capsid protein downstream of a secretory leader peptide. The sequence may be inserted after amino acid +1 of the mature protein. The site for insertion may be flanked by short sequences corresponding to sequences which occur at each end of the nucleic acid to be inserted. For example where 4 the protein domain is an immunoglobulin domain, the insertion site in the phage may be flanked by nucleotide sequences which code for the first five amino acids and the last five amino acids of the Ig domain. Such flanking nucleotide sequences are shown in FIG. 4(b) B and C, wherein the site-flanking nucleotide sequences encode amino acid sequences QVQLQ (SEQ ID NO:1) and VTVSS (SEQ ID NO:2) which occur at either end of the VH domain, or QVQLQ (SEQ ID NO:1) and LEIKR (SEQ ID NO:3) which occur at either end of the Fv (combined VH+VL) domain. Each of these sequences flanking the insertion site may include a suitable cleavage site, as shown in FIG. 4a and FIG. 4b.

Alternatively, the flanking nucleotide sequences shown in FIG. 4(b) B and C as described above, may be used to flank the insertion site for any nucleic acid to be inserted, whether or not that nucleic acid codes an immunoglobulin.

The host may be E. coli.

Nucleic acid encoding an sbp member polypeptide may be linked downstream to a viral capsid protein through a suppressible translational stop codon.

As previously mentioned, the present invention also provides novel selection systems and assay formats. In these systems and formats, the gene sequence encoding the binding molecule (eg. the antibody) of desired specificity is separated from a general population of rgdps having a range of specifies, by the fact of its binding to a specific target (eg the antigen or epitope). Thus the rgdps formed by said expression may be selected or screened to provide an individual sbp member or a selected mixed population of said sbp members associated in their respective rgdps with nucleic acid encoding said sbp member or a polypeptide chain thereof. The rgdps may be selected by affinity with a member complementary to said sbp member.

Any rgdps bound to said second member may be recovered by washing with an eluant. The washing conditions may be varied in order to obtain rgdps with different binding affinities for said epitope. Alternatively, to obtain eg high affinity rgdps, the complementary member (eg an epitope) may be presented to the population of rgdps (eg pAbs) already bound to a binding member in which case pAbs with a higher affinity for the epitope will displace the already bound binding member. Thus the eluant may contain a molecule which competes with said rgdp for binding to the complementary sbp member. The rgdp may be applied to said complementary sbp member in the presence of a molecule which competes with said package for binding to said complementary sbp member. Nucleic acid derived from a selected or screened rgdp may be used to express said sbp member or a fragment or derivative thereof in a recombinant host organism. Nucleic acid from one or more rgdps may be taken and used to provide encoding nucleic acid in a further said method to obtain an individual sbp member or a mixed population of sbp members, or encoding nucleic acid therefor. The expression end product may be modified to produce a derivative thereof.

The expression end product or derivative thereof may be used to prepare a therapeutic or prophylactic medicament or a diagnostic product.

The present invention also provides recombinant host cells harbouring a library of nucleic acid fragments comprising fragments encoding a genetically diverse population of a type of member of a specific binding pair (sbp), each sbp member or a polypeptide component thereof being expressed as a fusion with a component of a secretable replicable genetic display package (rgdp), so that said sbp members are displayed on the surface of the rgdps in functional form and the genetic material of the rgdps encode the associated sbp member or a polypeptide component thereof. The type of sbp members may be immunoglobulins or immunoglobulin homologs, a first polypeptide chain of which is expressed as a said fusion with a component of the rgdp and a second polypeptide chain of which is expressed in free form and associates with the fused first polypeptide chain in the rgdp.

The present invention also provides a helper phage whose genome lacks nucleic acid encoding one of its capsid proteins, or whose encoding nucleic acid therefor is conditionally defective, or which encodes said capsid protein in defective or conditionally defective form.

The present invention also provides a bacterial host cell containing a filamentous phage genome defective for a capsid protein thereof and wherein the host cell is capable of expressing capsid protein complementing said defect such that infectious phage particles can be obtained therefrom. The complementing capsid protein may be expressed in said host from another vector contained therein. The defective capsid protein may be gene III of phage fd or its counterpart in another filamentous phage.

The present invention also provides recombinant E. coli TG1 M13KO7 gIII No. 3 (NCTC 12478).

The present invention also provides a phage antibody having the form of a replicable genetic display package displaying on its surface in functional form a member of a specific binding pair or a specific binding domain thereof.

In the above methods, the binding molecule may be an antibody, or a domain that is homologous to an immunoglobulin. The antibody and/or domain may be either naturally derived or synthetic or a combination of both. The domain may be a Fab, scFv, Fv dAb or Fd molecule. Alternatively, the binding molecule may be an enzyme or receptor or fragment, derivative or analogue of any such enzyme or receptor. Alternatively, the binding molecule may be a member of an immunoglobulin superfamily and which has a structural form based on an immunoglobulin molecule.

The present invention also provides rgdps as defined above and members of specific binding pairs eg. binding molecules such as antibodies, enzymes, receptors, fragments and derivatives thereof, obtainable by use of any of the above defined methods. The derivatives may comprise members of the specific binding pairs fused to another molecule such as an enzyme or a Fc tail.

The invention also includes kits for carrying out the methods hereof. The kits will include the necessary vectors. One such vector will typically have an origin of replication for single stranded bacteriophage and either contain the sbp member nucleic acid or have a restriction site for its insertion in the 5' end region of the mature coding sequence of a phage capsid protein, and with a secretory leader coding sequence upstream of said site which directs a fusion of the capsid protein exogenous polypeptide to the periplasmic space.

The restriction sites in the vectors are preferably those of enzymes which cut only rarely in protein coding sequences.

The kit preferably includes a phagemid vector which may have the above characteristics, or may contain, or have a site for insertion, of sbp member nucleic acid for expression of the encoded polypeptide in free form.

The kits will also contain ancillary components required for carrying out the method, the nature of such components depending of course on the particular method employed.

Useful ancillary components may comprise helper phage, PCR primers, and buffers and enzymes of various kinds.

PCR primers and associated reagents for use where the sbp members are antibodies may have the following characteristics:

(i) primers having homology to the 5' end of the sense or anti-sense strand of sequences encoding domains of antibodies; and (ii) primers including tag sequences 5' to these homologous sequences which incorporate restriction sites to allow insertion into vectors; together with sequences to allow assembly of amplified VH and VL regions to enable expression as Fv, scFv or Fab fragments.

Buffers and enzymes are typically used to enable preparation of nucleotide sequences encoding Fv, scFv or Fab fragments derived from rearranged or unrearranged immunoglobulin genes according to the strategies described herein.

The applicants have chosen the filamentous F-specific bacteriophages as an example of the type of phage which could provide a vehicle for the display of binding molecules e.g. antibodies and antibody fragments and derivatives thereof, on their surface and facilitate subsequent selection and manipulation.

The F-specific phages (e.g. fl, fd and M13) have evolved a method of propagation which does not kill the host cell and they are used commonly as vehicles for recombinant DNA (Kornberg, A., DNA Replication, W. H. Freeman and Co., San Francisco, 1980). The single stranded DNA genome (approximately 6.4 Kb) of fd is extruded through the bacterial membrane where it sequesters capsid sub-units, to produce mature virions. These virions are 6 nm in diameter, 1 µm in length and each contain approximately 2,800 molecules of the major coat protein encoded by viral gene VIII and four molecules of the adsorption molecule gene III protein (g3p) the latter is located at one end of the virion. The structure has been reviewed by Webster et al., 1978 in The Single Stranded DNA Phages, 557-569, Cold Spring Harbor Laboratory Press. The gene III product is involved in the binding of the phage to the bacterial F-pilus.

Although these phages do not kill their host during normal replication, disruption of some of their genes can lead to cell death (Kornberg, A., 1980 supra.) This places some restraint on their use. The applicants have recognized that gene III of phage fd is an attractive possibility for the insertion of biologically active foreign sequences. There are however, other candidate sites including for example gene VIII and gene VI.

The protein itself is only a minor component of the phage coat and disruption of the gene does not lead to cell death (Smith, G. 1988, Virology 167: 156-165). Furthermore, it is possible to insert some foreign sequences (with no biological function) into various positions within this gene (Smith, G. 1985 Science 228: 1315-1317., Parmley, S. F. and Smith, G. P. Gene: 73 (1988) p. 305-318., and de la Cruz, V. F., et al., 1988, J. Biol. Chem., 263: 4318-4322). Smith et al described the display of peptides on the outer surface of phage but they did not describe the display of protein domains. Peptides can adopt a range of structures which can be different when in free solution, than when bound to, for example, an antibody, or when forming part of a protein (Stanfield, R. I. et al., (1990) Science 248, p712-719). Proteins in general have a well defined tertiary structure and perform their biological function only when adopting this structure. For example, the structure of the antibody D1.3 has been solved in the free form and when bound to antigen (Bhat, T. N. et al., (1990) Nature 347, p483-485). The gross structure of the protein is identical in each instance with only minor variations around the binding site for the antigen. Other proteins have more substantial conformation changes on binding of ligand, for instance the enzymes hexokinase and pyruvate dehydrogenase during their catalytic cycle, but they still retain their overall pattern of folding. This structural integrity is not confined to whole proteins, but is exhibited by protein domains. This leads to the concept of a folded unit which is part of a protein, often a domain, which has a well defined primary, secondary and tertiary structure and which retains the same overall folding pattern whether binding to a binding partner or not. The only gene sequence that Smith et al., described that was of sufficient size to encode a domain (a minimum of perhaps 50 amino acids) was a 335 bp fragment of a β-galactosidase corresponding to nucleotides 861-1195 in the β-galactosidase gene sequence (Parmley, S.+Smith, G. P. 1988 supra. This would encode 112 amino acids of a much larger 380 amino acid domain. Therefore, prior to the present application, no substantially complete domain or folded unit had been displayed on phage. In these cases, although the infectivity of the virion was disrupted, the inserted sequences could be detected on the phage surface by use of e.g. antibodies.

The protein encoded by gene III has several domains (Pratt, D., et al., 1969 Virology 39:42-53., Grant, R. A., et al., 1981, J. Biol. Chem. 256: 539-546 and Armstrong, J., et al., FEBS Lett. 135: 167-172 1981.) including: (i) a signal sequence that directs the protein to the cell membrane and which is then cleaved off; (ii) a domain that anchors the mature protein into the bacterial cell membrane (and also the phage coat); and (iii) a domain that specifically binds to the phage receptor, the F-pilus of the host bacterium. Short sequences derived from protein molecules have been inserted into two places within the mature molecule (Smith, G., 1985 supra., and Parmley, S. F. and Smith G. P., 1988 supra.). Namely, into an inter-domain region and also between amino acids 2 and 3 at the N-terminus. The insertion sites at the N-terminus were more successful in maintaining the structural integrity of the gene III protein and displaying the peptides on the surface of the phage. By use of antisera specific for the peptides, the peptides inserted into this position were shown to be on the surface of the phage. These authors were also able to purify the phage, using this property. However, the peptides expressed by the phage, did not possess measurable biological functions of their own.

Retaining the biological function of a molecule when it is expressed in a radically different context to its natural state is difficult. The demands on the structure of the molecule are heavy. In contrast, retaining the ability to be bound by specific antisera is a passive process which imposes far less rigorous demands on the structure of the molecule. For example, it is the rule rather than the exception that polyclonal antisera will recognise totally denatured, and biologically inactive, proteins on Western blots (see for example, Harlow, E. and Lane, D., Antibodies, a Laboratory Manual, Cold Spring Harbor Laboratory Press 1988). Therefore, the insertion of peptides into a region that allows their structure to be probed with antisera teaches only that the region allows the inserted sequences to be exposed and does not teach that the region is suitable for the insertion of large sequences with demanding structural constraints for the display of a molecule with a biological or binding function. In particular, it does not teach that domains or folded units of proteins can be displayed from sequences inserted in this region.

This experience with Western blots is a graphic practical demonstration which shows that retaining the ability to be bound by specific antisera imposes far less rigorous demands on the structure of a polypeptide, than does folding for the retention of a biological function.

Studies have been carried out, in which *E. coli* have been manipulated to express the protein β-adrenergic receptor as a fusion with the outer membrane protein lamB. The β-adrenergic receptor was expressed in a functional form as determined by the presence of binding activity. However, when an equivalent antibody fusion was made with lamB, the antibody fusion was toxic to the host cell.

The applicants have investigated the possibility of inserting the gene coding sequence for biologically active antibody fragments into the gene III region of fd to express a large fusion protein. As is apparent from the previous discussion, this approach makes onerous demands on the functionality of the fusion protein. The insertion is large, encoding antibody fragments of at least 100-200 amino acids; the antibody derived domain must fold efficiently and correctly to display antigen-binding; and most of the functions of gene III must be retained. The applicants approach to the construction of the fusion molecule was designed to minimise the risk of disrupting these functions. In an embodiment of the invention, the initial vector used was fd-tet (Zacher, A. N., et al., 1980, Gene 9, 127-140) a tetracycline resistant version of fd bacteriophage that can be propagated as a plasmid that confers tetracycline resistance to the infected E. coli host. The applicants chose to insert after the signal sequence of the fd gene III protein for several reasons. In particular, the applicants chose to insert after amino acid 1 of the mature protein to retain the context for the signal peptidase cleavage. To retain the structure and function of gene III itself, the majority of the original amino acids are synthesized after the inserted immunoglobulin sequences. The inserted immunoglobulin sequences were designed to include residues from the switch region that links VH-VL to CH1-CL (Lesk, A., and Chothia, C., Nature 335, 188-190, 1988).

Surprisingly, by manipulating gene III of bacteriophage fd, the present applicants have been able to construct a bacteriophage that displays on its surface large biologically functional antibody, enzyme, and receptor molecules whilst remaining intact and infective. Furthermore, the phages bearing antibodies of desired specificity, can be selected from a background of phages not showing this specificity.

The sequences coding for a population of antibody molecules and for insertion into the vector to give expression of antibody binding functions on the phage surface can be derived from a variety of sources. For example, immunised or non-immunised rodents or humans, and from organs such as spleen and peripheral blood lymphocytes. The coding sequences are derived from these sources by techniques familiar to those skilled in the art (Orlandi, R., et al., 1989 supra; Larrick, J. W., et al., 1989 supra; Chiang, Y. L., et al., 1989 Bio Techniques 7, p. 360-366; Ward, E. S, et al., 1989 supra; Sastry, L., et al., 1989 supra.) or by novel linkage strategies described in examples 14, 33, 40 and 42. Novel strategies are described in examples 7, 25, 33, 39 and 40 for displaying dimeric molecules eg Fab and Fv fragments on the surface of a phage. Each individual pAb in the resulting library of pAbs will express antibodies or antibody derived fragments that are monoclonal with respect to their antigen-binding characteristics.

The disclosure made by the present applicants is important and provides a significant breakthrough in the technology relating to the production of biological binding molecules, their fragments and derivatives by the use of recombinant methods.

In standard recombinant techniques for the production of antibodies, an expression vector containing sequences coding for the antibody polypeptide chains is used to transform e.g. E. coli. The antibody polypeptides are expressed and detected by use of standard screening systems. When the screen detects an antibody polypeptide of the desired specificity, one has to return to the particular transformed E. coli expressing the desired antibody polypeptide. Furthermore, the vector containing the coding sequence for the desired antibody polypeptide then has to be isolated for use from E. coli in further processing steps.

In the present invention however, the desired antibody polypeptide when expressed, is already packaged with its gene coding sequence. This means that when the an antibody polypeptide of desired specificity is selected, there is no need to return to the original culture for isolation of that sequence. Furthermore, in previous methods in standard recombinant techniques, each clone expressing antibody needs to be screened individually. The present application provides for the selection of clones expressing antibodies with desired properties and thus only requires screening of clones from an enriched pool.

Because a rgdp (eg a pAb) is a novel structure that displays a member of a specific binding pair (eg. an antibody of monoclonal antigen-binding specificity) at the surface of a relatively simple replicable structure also containing the genetic information encoding the member, rgdps eg pAbs, that bind to the complementary member of the specific binding pair (eg antigen) can be recovered very efficiently by either eluting off the complementary member using for example diethylamine, high salt etc and infecting suitable bacteria, or by denaturing the structure, and specifically amplifying the sequences encoding the member using PCR. That is, there is no necessity to refer back to the original bacterial clone that gave rise to the pAb.

For some purposes, for example immunoprecipitation and some diagnostic tests, it is advantageous to use polyclonal antibodies or antibody fragments. The present invention allows this to be achieved by either selection of an enriched pool of pAbs with desired properties or by mixing individually isolated clones with desired properties. The antibodies or antibody fragments may then be expressed in soluble form if desired. Such a selected polyclonal pAb population can be grown from stocks of phage, bacteria containing phagemids or bacteria expressing soluble fragments derived from the selected polyclonal population. Thus a reagent equivalent to a polyclonal antiserum is created which can be replicated and routinely manufactured in culture without use of animals.

Selection Formats and Affinity Maturation

Individual rgdps eg pAbs expressing the desired specificity eg for an antigen, can be isolated from the complex library using the conventional screening techniques (e.g. as described in Harlow, E., and Lane, D., 1988, supra Gherardi, E et al. 1990. J. Immunol. meth. 126 p61-68).

The applicants have also devised a series of novel selection techniques that are practicable only because of the unique properties of rgdps. The general outline of some screening procedures is illustrated in FIG. 2a and FIG. 2b using pAbs as an example type of rgdp. The population/library of pAbs to be screened could be generated from immunised or other animals; or be created in vitro by mutagenising pre-existing phage antibodies (using techniques well-known in the art such as oligonucleotide directed mutagenesis (Sambrook, J., et al., 1989 Molecular Cloning a Laboratory Manual, Cold Spring Harbor Laboratory Press). This population can be screened in one or more of the formats described below with reference to FIG. 2a and FIG. 2b, to derive those individual pAbs whose antigen binding properties are different from sample C.

Binding Elution

FIG. 2(a) shows antigen (ag) bound to a solid surface (s) the solid surface (s) may be provided by a petri dish, chromatography beads, magnetic beads and the like. The population/library of pAbs is then passed over the ag, and those individuals p that bind are retained after washing, and optionally detected with detection system d. A detection system based upon anti-fd antisera is illustrated in more detail below in example 4. If samples of bound population p are removed under increasingly stringent conditions, the binding affinity represented in each sample will increase. Conditions of increased stringency can be obtained, for example, by increasing the time of soaking or changing the pH of the soak solution, etc.

Competition

Referring to FIG. 2(b) antigen ag can be bound to a solid support s and bound to saturation by the original binding molecule c. If a population of mutant pAb (or a set of unrelated pAbs) is offered to the complex, only those that have higher affinity for antigen ag than c will bind. In most examples, only a minority of population c will be displaced by individuals from population p. If c is a traditional antibody molecule, all bound material can be recovered and bound p recovered by infecting suitable bacteria and/or by use of standard techniques such as PCR.

An advantageous application is where ag is used as a receptor and c the corresponding ligand. The recovered bound population p is then related structurally to the receptor binding site/and or ligand. This type of specificity is known to be very useful in the pharmaceutical industry.

Another advantageous application is where ag is an antibody and c its antigen. The recovered bound population p is then an anti-idiotype antibody which have numerous uses in research and the diagnostic and pharmaceutical industries.

At present it is difficult to select directly for anti-idiotype antibodies. pAbs would give the ability to do this directly by binding pAb libraries (eg a naive library) to B cells (which express antibodies on their surface) and isolating those phage that bound well.

In some instances it may prove advantageous to pre-select population p. For example, in the anti-idiotype example above, p can be absorbed against a related antibody that does not bind the antigen.

However, if c is a pAb, then either or both c and p can advantageously be marked in some way to both distinguish and select for bound p over bound c. This marking can be physical, for example, by pre-labelling p with biotin; or more advantageously, genetic. For example, c can be marked with an EcoB restriction site, whilst p can be marked with an EcoK restriction site (see Carter, P. et al., 1985, Nucl. Acids Res. 13, 4431-4443). When bound p+c are eluted from the antigen and used to infect suitable bacteria, there is restriction (and thus no growth) of population c (i.e. EcoB restricting bacteria in this example). Any phage that grew, would be greatly enriched for those individuals from p with higher binding affinities. Alternatively, the genetic marking can be achieved by marking p with new sequences, which can be used to specifically amplify p from the mixture using PCR.

Since the bound pAbs can be amplified using for example PCR or bacterial infection, it is also possible to rescue the desired specificity even when insufficient individuals are bound to allow detection via conventional techniques.

The preferred method for selection of a phage displaying a protein molecule with a desired specificity or affinity will often be elution from an affinity matrix with a ligand (eg example 21). Elution with increasing concentrations of ligand should elute phage displaying binding molecules of increasing affinity. However, when eg a pAb binds to its antigen with high affinity or avidity (or another protein to its binding partner) it may not be possible to elute the pAb from an affinity matrix with molecule related to the antigen. Alternatively, there may be no suitable specific eluting molecule that can be prepared in sufficiently high concentration. In these cases it is necessary to use an elution method which is not specific to eg the antigen-antibody complex. Some of the non-specific elution methods generally used reduce phage viability for instance, phage viability is reduced with time at pH12 (Rossomando, E. F. and Zinder N. D. J. Mol. Biol. 36 387-399 1968). There may be interactions between eg antibodies and affinity matrices which cannot be disrupted without completely removing phage infectivity. In these cases a method is required to elute phage which does not rely on disruption of eg the antibody—antigen interaction. A method was therefore devised which allows elution of bound pAbs under mild conditions (reduction of a dithiol group with dithiothreitol) which do not disrupt phage structure (example 47).

This elution procedure is just one example of an elution procedure under mild conditions. A particularly advantageous method would be to introduce a nucleotide sequence encoding amino acids constituting a recognition site for cleavage by a highly specific protease between the foreign gene inserted, in this instance a gene for an antibody fragment, and the sequence of the remainder of gene III. Examples of such highly specific proteases are Factor X and thrombin. After binding of the phage to an affinity matrix and elution to remove non-specific binding phage and weak binding phage, the strongly bound phage would be removed by washing the column with protease under conditions suitable for digestion at the cleavage site. This would cleave the antibody fragment from the phage particle eluting the phage. These phage would be expected to be infective, since the only protease site should be the one specifically introduced. Strongly binding phage could then be recovered by infecting eg. *E. coli* TG1 cells.

An alternative procedure to the above is to take the affinity matrix which has retained the strongly bound pAb and extract the DNA, for example by boiling in SDS solution. Extracted DNA can then be used to directly transform *E. coli* host cells or alternatively the antibody encoding sequences can be amplified, for example using PCR with suitable primers such as those disclosed herein, and then inserted into a vector for expression as a soluble antibody for further study or a pAb for further rounds of selection.

Another preferred method for selection according to affinity would be by binding to an affinity matrix containing low amounts of ligand.

If one wishes to select from a population of phages displaying a protein molecule with a high affinity for its ligand, a preferred strategy is to bind a population of phage to an affinity matrix which contains a low amount of ligand. There is competition between phage, displaying high affinity and low affinity proteins, for binding to the ligand on the matrix. Phage displaying high affinity protein is preferentially bound and low affinity protein is washed away. The high affinity protein is then recovered by elution with the ligand or by other procedures which elute the phage from the affinity matrix (example 35 demonstrates this procedure).

In summary then, for recovery of the packaged DNA from the affinity step, the package can be simply eluted, it can be eluted in the presence of a homologous sbp member which competes with said package for binding to a complementary sbp member; it could be removed by boiling, it could be removed by proteolytic cleavage of the protein; and other methods will be apparent to those skilled in the art eg. destroying the link between the substrate and complementary sbp member to release said packaged DNA and sbp member. At any rate, the objective is to obtain the DNA from the package so that it can be used directly or indirectly, to express the sbp member encoded thereby.

The efficiency of this selection procedure for pAbs and the ability to create very large libraries means that the immunisation techniques developed to increase the proportion of screened cells producing antibodies of interest will not be an absolute requirement. The technique allows the rapid isolation of binding specificities eg antigen-binding specificities, including those that would be difficult or even unobtainable by conventional techniques, for example, catalytic or antiidiotypic antibodies. Removal of the animal altogether is now possible, once a complete library of the immune repertoire has been constructed. The novel structure of the pAb molecule can be used in a number of other applications, some examples of which are:

Signal Amplification

Acting as a novel molecular entity in itself, rgdps eg pAbs combine the ability to bind a specific molecule eg antigen with amplification, if the major coat protein is used to attach another moiety. This moiety can be attached via immunological, chemical, or any other means and can be used, for example, to label the complex with detection reagents or cytotoxic molecules for use in vivo or in vitro.

Physical Detection

The size of the rgdps eg pAbs can be used as a marker particularly with respect to physical methods of detection such as electron microscopy and/or some biosensors, e.g. surface plasmon resonance.

Diagnostic Assays

The rgdps eg pAbs also have advantageous uses in diagnostic assays, particularly where separation can be effected using their physical properties for example centrifugation, filtration etc.

In order that the invention is more fully understood, embodiments will now be described in more detail by way of example only and not by way of limitation with reference to the figures described below.

BRIEF DESCRIPTION OF THE DRAWINGS

FIG. 3 shows the vector fd-tet and a scheme for the construction of vectors, fdTPs/Bs (for insertion of VH coding sequences) and fdTPs/Xh for the insertion of scFv coding sequences.

FIGS. 4a-4b show the nucleotide sequences for the oligonucleotides and vectors. All sequences are drawn 5' to 3' and are numbered according to Beck et al., 1978, Nucl. Acid Res., 5: 4495-4503. 4a shows the sequences of the oligonucleotides used for mutagenesis (oligo's 1 and 2) or sequencing (oligo 3). The sequences shown were synthesized on an Applied Biosystems, oligonucleotide synthesizer and are complementary to the single stranded form of fd-tet (they are in the anti-sense form with respect to gene III). 4b shows the sequences of the various constructs around the gene III insertion site. These sequences are drawn in the sense orientation with respect to gene III; (A) fd-tet (and fdTδBst) (B) fdTPs/Bs and (C) fdTPs/Xh. The key restriction enzyme sites are shown along with the immunoglobulin amino acids contributed by the vectors, (amino acid single letter code is used, see Harlow, E., and Lane, D., 1988 supra.).

FIG. 5a-5b shows the nucleotide and amino acid sequences for scFv in the vector scFvD1.3 myc. This gives the sequence of the anti-lysozyme single chain Fv and surrounding sequences in scFvD1.3 myc, showing the N-terminal pel B signal peptide sequence and the C-terminal myc tag sequence (Ward, E. S., et al., 1989, supra.). Also shown is the peptide sequence linking the VH and VL regions. The amino acid sequence is represented above the nucleotide sequence by the single letter code, see Harlow, E., and Lane D., 1988 supra.

FIG. 13 shows the sequence of the anti-oxazolone antibody fragment NQ11 scFv. The sequence contributed by the linker is shown in the lower case. The sequence for VH is before the linker sequence and the sequence for VL is after the linker.

FIG. 17 shows schematically the protocol for PCR assembly of mouse VH and VLK repertoires for phage display described in example 14.

FIGS. 24a-24b shows VH and VK gene sequences derived from the combinatorial library in example 21 and the hierarchical library in example 22.

FIGS. 25a-26b shows a matrix of ELISA signals for clones derived from random combinatorial library. Designation of the clones is as in FIG. 24. The number of clones found with each combination is shown by the numerals.

FIG. 28. Three ways of displaying antibody fragments on the surface of phage by fusion to gene III protein.

a) fd-phoAla166 grown in TG1 cells
b) fd-phoAla166 grown in KS272 cells
c) fdCCAT2 grown in TG1 cells
d) fdCAT2 grown in TG1 cells, mixed with 13 ng of purified alkaline phosphatase
e) fd-phoAla166 grown in TG1 cells
f) fdCAT2 grown in TG1 cells.

Figure 35A:
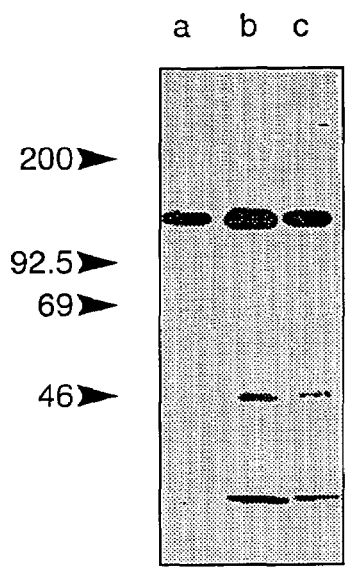
Figure 35B:
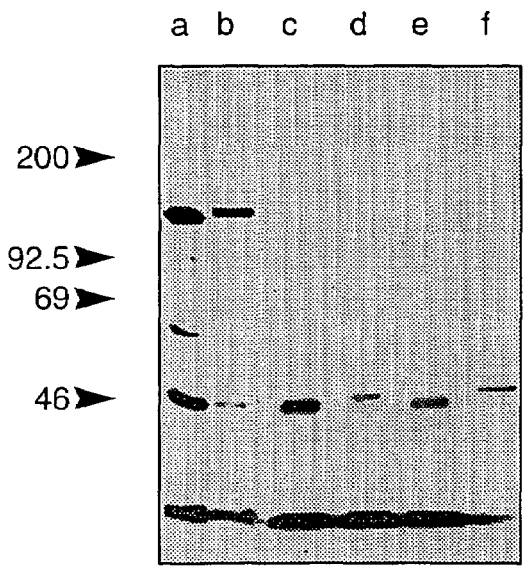

FIGS. 35A-35B are Western Blots showing ultrafiltration of phage-enzyme 100 µl of 50 fold concentrate of phage (representing 5 mls of culture supernatant) was centrifuged through ultrafiltration membranes with nominal molecular weight retention of 300,000 daltons. Western blots of flow through and retentate fractions were detected with anti-alkaline phosphatase antiserum. The equivalent of 800 µl of original culture supernatant was run on the gel.

FIG. 35A. Phage were grown in TG1 cells. a) fd-phoAla166 before ultrafiltration (short exposure). b) fd-phoAla166 before ultrafiltration. c) fd-phoAla166 material retained on ultrafiltration membrane.A FIG. 35B. Phage were grown in KS272 cells. a) fd-phoAla166 before ultrafiltration. b) fd-phoAla166 material retained on ultrafiltration membrane. c) fdCAT2. d) fdCAT2 mixed with purified alkaline phosphatase before ultrafiltration. e) Retentate from sample d. f) Flow through from sample d.

Figure 36:
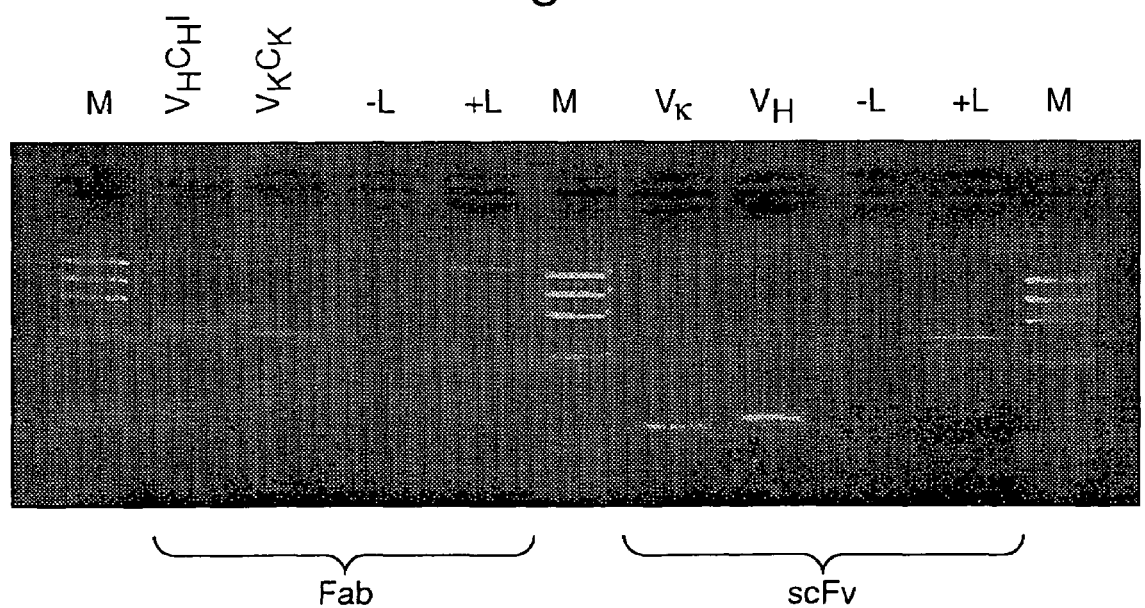

FIG. 36 Electrophoresis of samples from stages of a Fab assembly. Samples from different stages in the PCR Fab assembly process described in example 33 were subjected to electrophoresis on a 1% TAE-agarose gel. Samples from a comparable scFv assembly process (as in example 14) are shown for comparison. Samples left to right are:

| | |
|---|---|
| M = | Markers |
| VHCH1 = | sequences encoding VHCH1 domains amplified by PCR |
| VKCK = | sequences encoding VKCK domains amplified by PCR |
| −L = | Fab assembly reaction performed in absence of linker |
| +L = | Fab PCR assembly reaction product VHCH1 plus VKCK plus linker |
| M = | Markers |
| VK = | sequences encoding VK domain amplified by PCR |
| VL = | sequences encoding VH domains amplified by PCR |
| −L = | scFv assembly reaction in absence of linker |
| +L = | scFv assembly reaction in presence of linker |
| M = | Markers |

Figure 37:
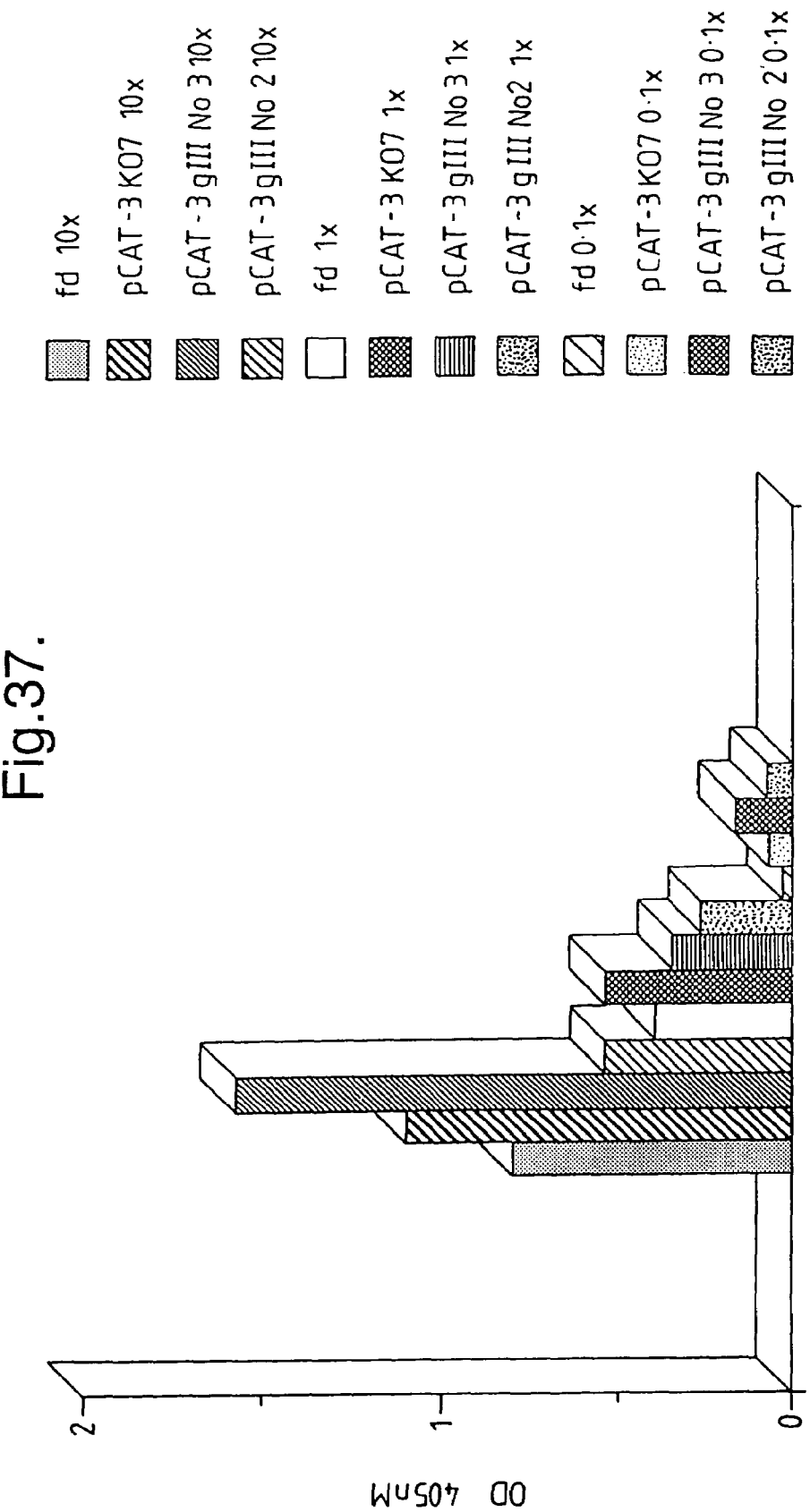

FIG. 37. Comparison of ELISA signals with scFv D1.3 cloned in fd-CAT2 (fd) or pCAT-3. pCAT-3 scFv1.3 has been rescued with M13K07 (KO7). M13KO7ΔgIII No 3 (gIII No 3) or M13KO7 gIIIΔNo 2 (g111No2). Phage antibodies are compared at 10 times (10×) 1 times (1×) or 0.1 times (0.1×) concentrations relative to concentration in the supernatant after overnight growth. The fdCAT2 and pCAT-3 non-recombinant vector signals were <0.01 at 10× concentration. M13KO7 gIIIΔNo 1 did not rescue at all, as judged by no signal above background in this ELISA.

Figure 38A:
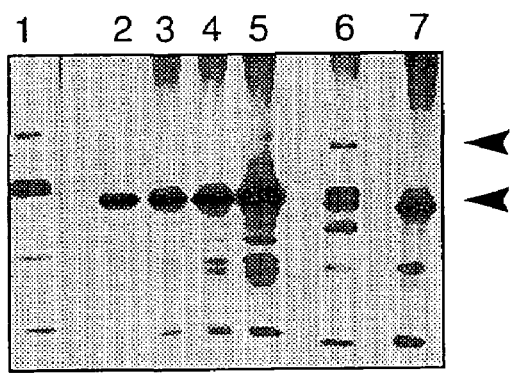
Figure 38B:
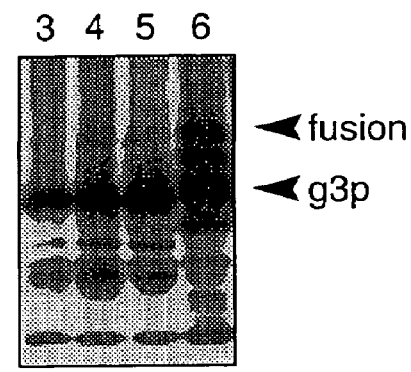

FIGS. 38A-38B. Western blot of PEG precipitated phage used in ELISA probed with anti-g3p. Free g3p and the g3p-scFvD1.3 fusion bands are arrowed.

| | |
|---|---|
| Sample 2 | pCAT3 vector |
| Sample 3 | pCAT3 scFvD1.3 rescued with M131KO7, no IPTG |
| Sample 4 | pCAT3 scFvD1.3 rescued with M13KO7, 50 µM IPTG |
| Sample 5 | pCAT3 scFvD1.3 rescued with M13KO7, 100 µM IPTG |
| Sample 6 | pCAT3 scFvD1.3 rescued with M13KO7 gIIIΔ No 3 (no IPTG) |
| Sample 7 | pCAT3 scFvD1.3 rescued with M13KO7 gIIIΔ No 2 (no IPTG) |

FIG. 38A samples contain the equivalent of 8 µl of phagemid culture supernatant per track, and 80 µl of the fd supernatant (10-fold lower phage yield than the phagemid). FIG. 38B phagemid samples are those used in FIG. 38A at a five-fold higher sample loading (equivalent to 40 µl of culture supernatant per track) to enable visualisation of the fusion band in samples rescued with parental M13K07.

Figure 39:
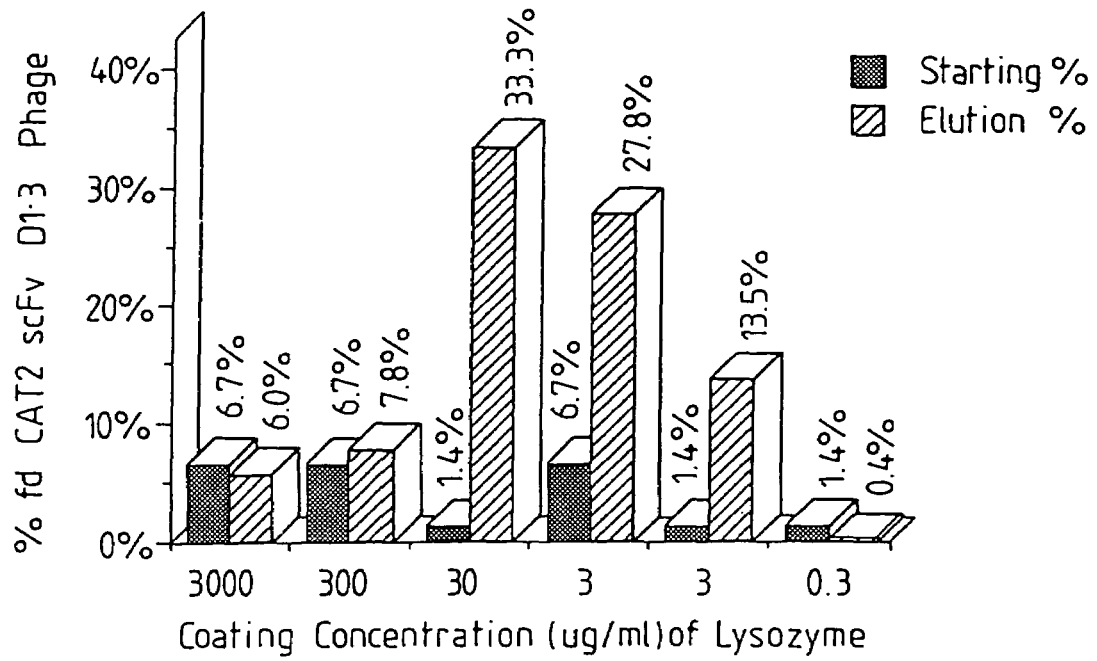

FIG. 39 is a graph showing fdCAT2scFvD1.3 enrichment produced from a mixture of fdCAT2scFvD1.3 and fdCAT2TPB4 by one round of panning.

Figure 40:
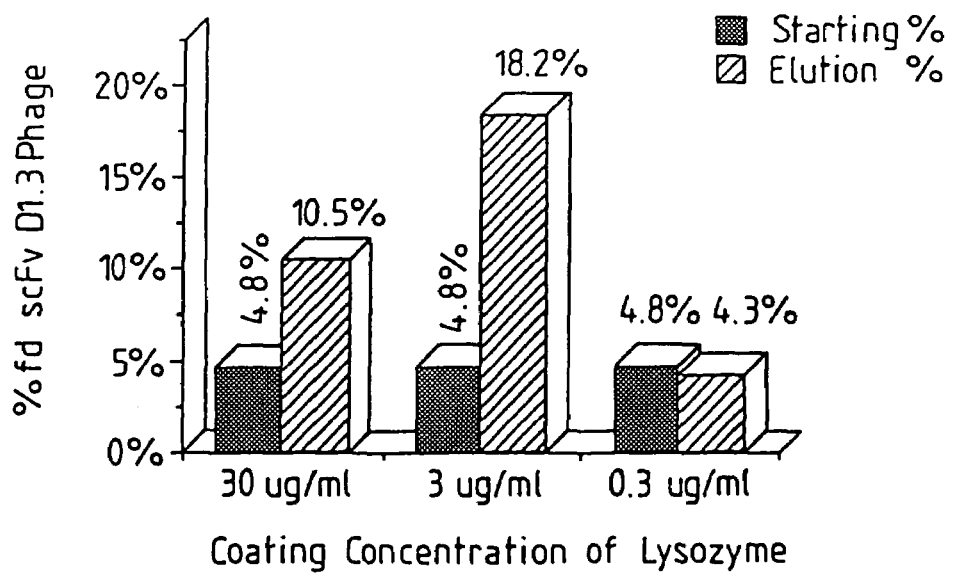

FIG. 40 is a graph showing fdCAT2scFvD1.3 enrichment produced from a mixture of fdCAT2scFvD1.3 and fdCAT2TPB1 by one round of panning.

Figure 41:
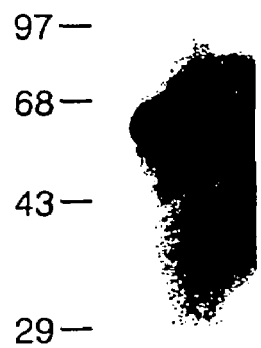

FIG. 41. Western blot of phage proteins of fdCAT2(1) and fd-tet-SNase(2) with anti-g3p antiserum. Marker molecular weights bands are indicated (kD).

Figure 42:

FIG. 42. Nuclease assay of soluble SNase (3 ng) (A-1), fd-tet-SNase ($4 \times 10^9$TU, (B-1), fd-CAT2 ($2 \times 10^{10}$TU) (C-1) and of a PEG-precipitated fdCAT2 and SNase mixture ($2 \times 10^{10}$TU and 0.7 ug) (D-1) in a 10-fold dilution series (1 to 3 or 4). Marker (M) is a HindIII digest of λ-DNA (New England Biolabs).

Figure 43:
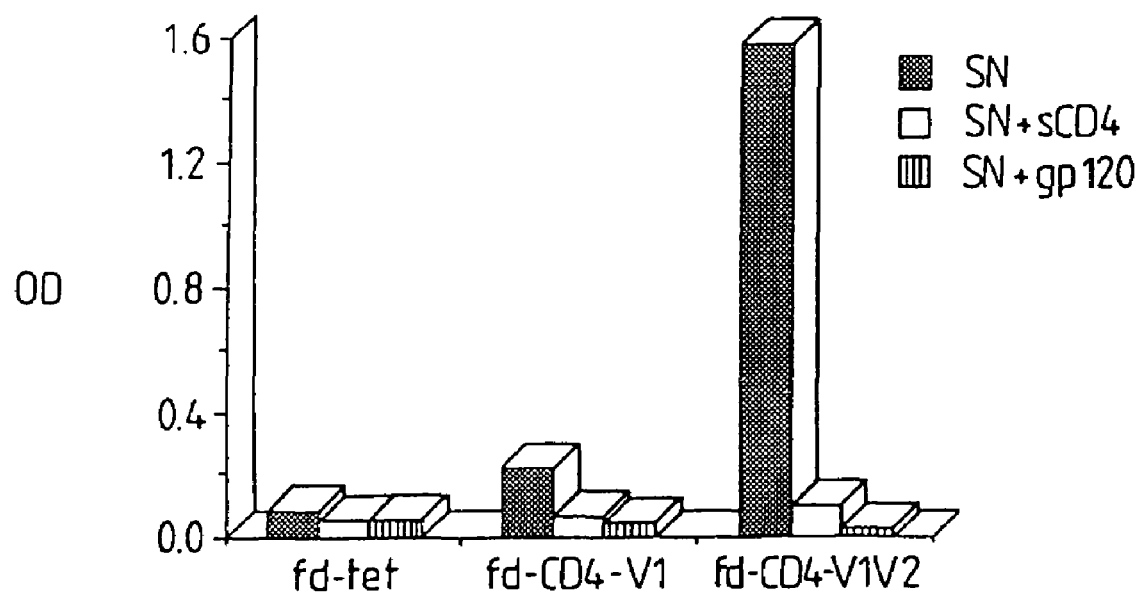

FIG. 43. ELISA signals obtained with fd-tet, fd-CD4-V1 and fd-CD4-V1V2. In each group of three, the samples are left to right phage concentrate (SN); phage concentrate plus soluble CD4(SN+sCD4); phage concentrate plus gp 120 (SN+gp 120).

FIGS. 44a-44b show the DNA sequence of scFv B18 (anti-NP).

Figure 45:
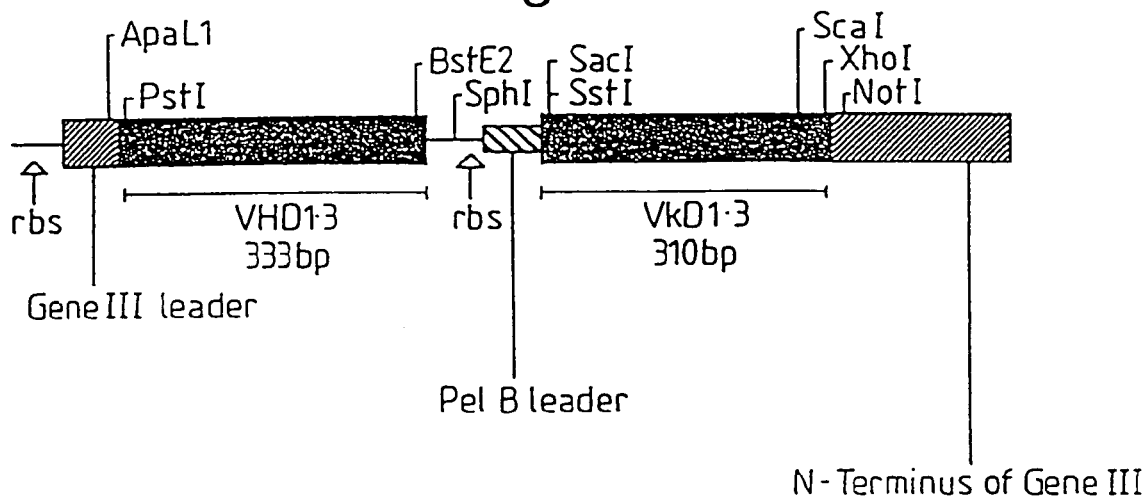

FIG. 45 shows a map of the insert of sequences encoding FvD1.3 present in fd-tet FvD1.3 (example 39). rbs designates the ribosome binding site. Gene III is now shown in its full length.

Figure 46:
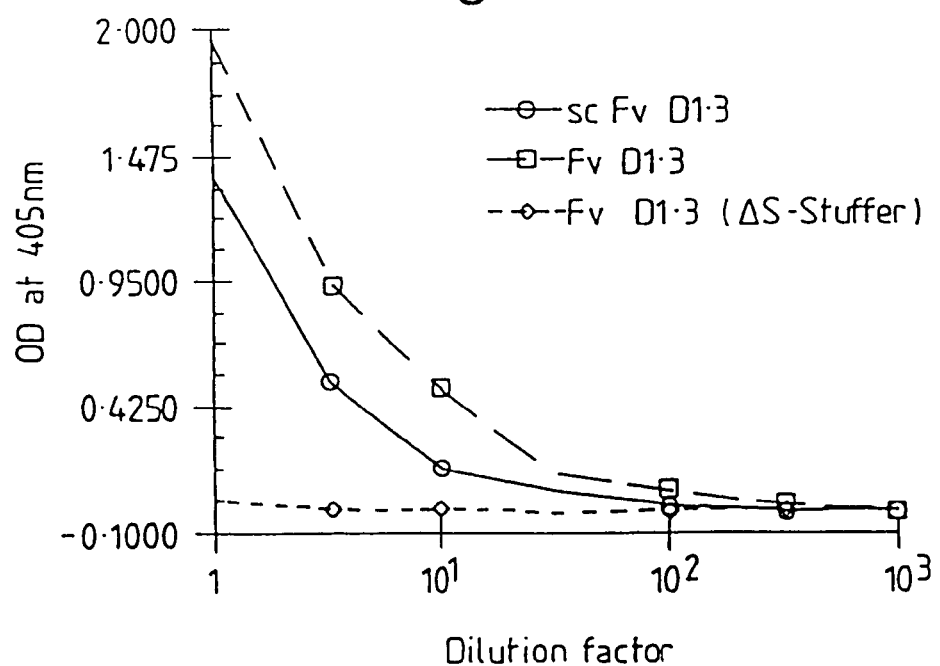

FIG. 46. shows an ELISA assay of phages displaying FvD1.3 or scFvD1.3 by binding to plates coated with lysogyme. Signals obtained at various dilution factors are shown. FvD1.3 (ΔS-Stuffer) which does not express Fv was used as a control.

Figure 47:
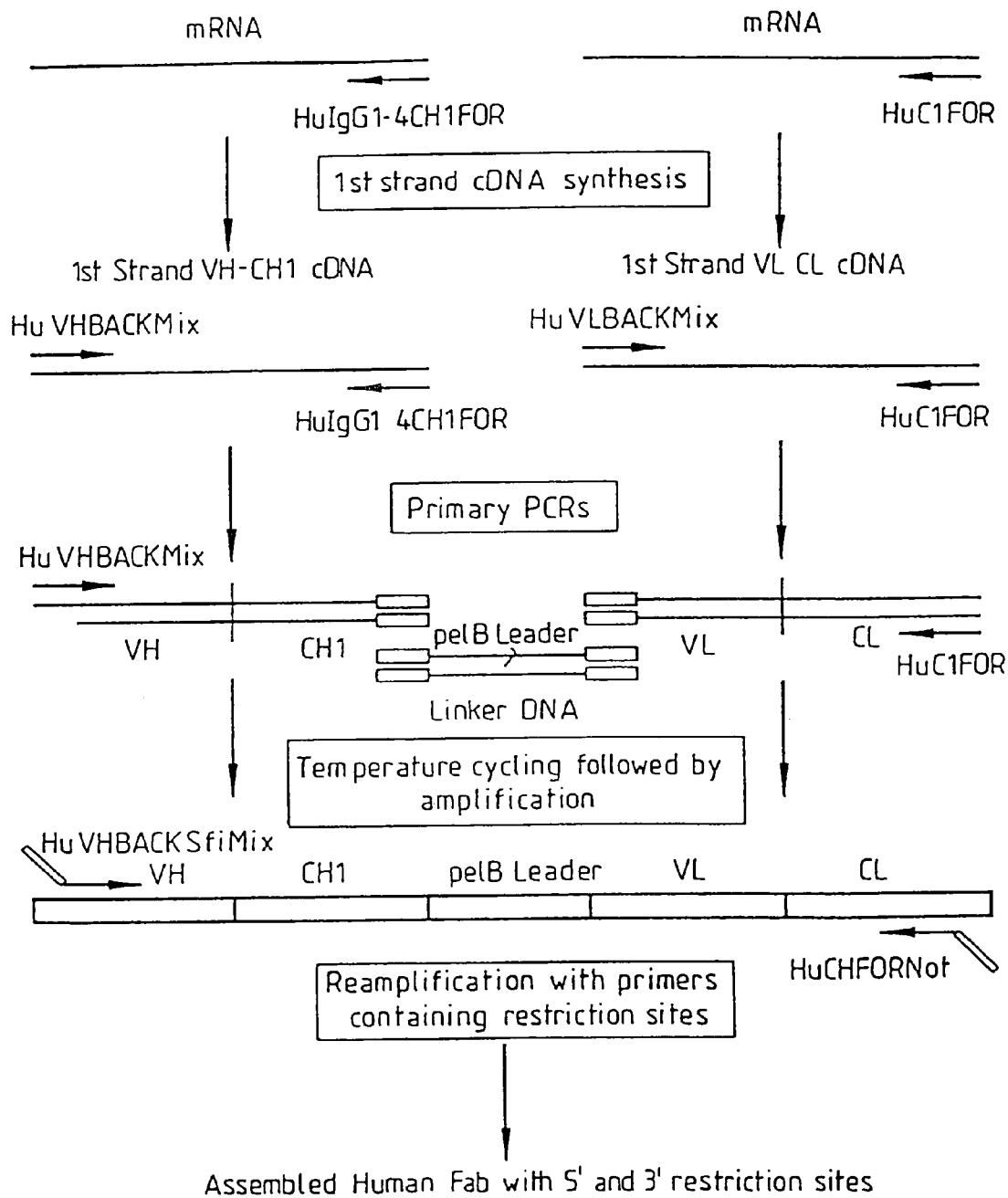

FIG. 47. shows a schematic representation of steps involved in the PCR assembly of nucleotide sequences encoding human Fab fragments. Details are in example 40.

FIG. 48a shows a map of plasmid pJM1-FabD1.3 which is used for the expression of soluble human Fab fragments and as a template for the synthesis of linker DNA for Fab assembly. FIG. 48b is a schematic representation of sequences encoding a Fab construct. FIG. 48(c) shows the sequence of DNA template for the synthesis of linker DNA for Fab assembly.

Figure 49:
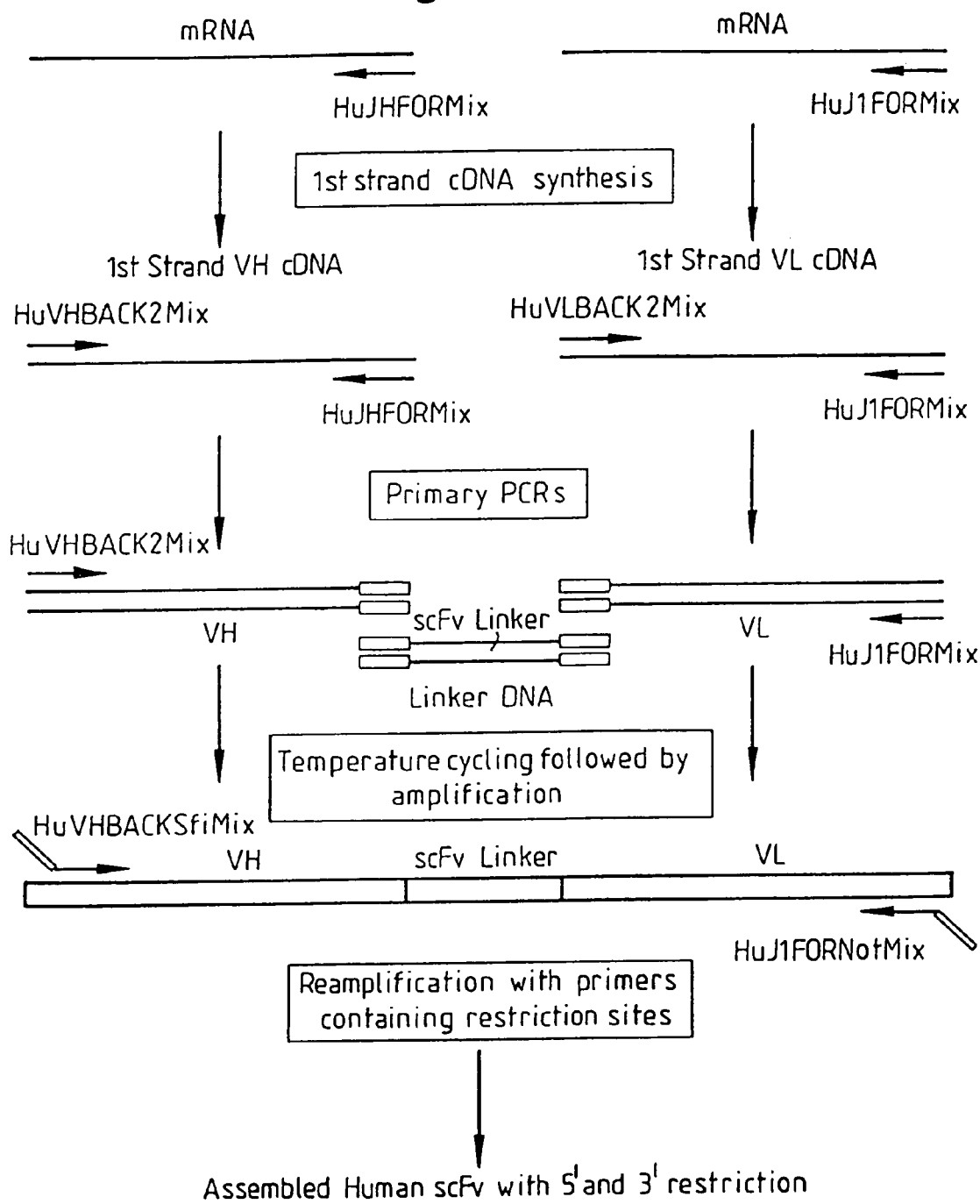

FIG. 49. shows a schematic representation of steps involved in the PCR assembly of nucleotide sequences encoding human scFv fragments. Details are in example 42.

Figure 50A:
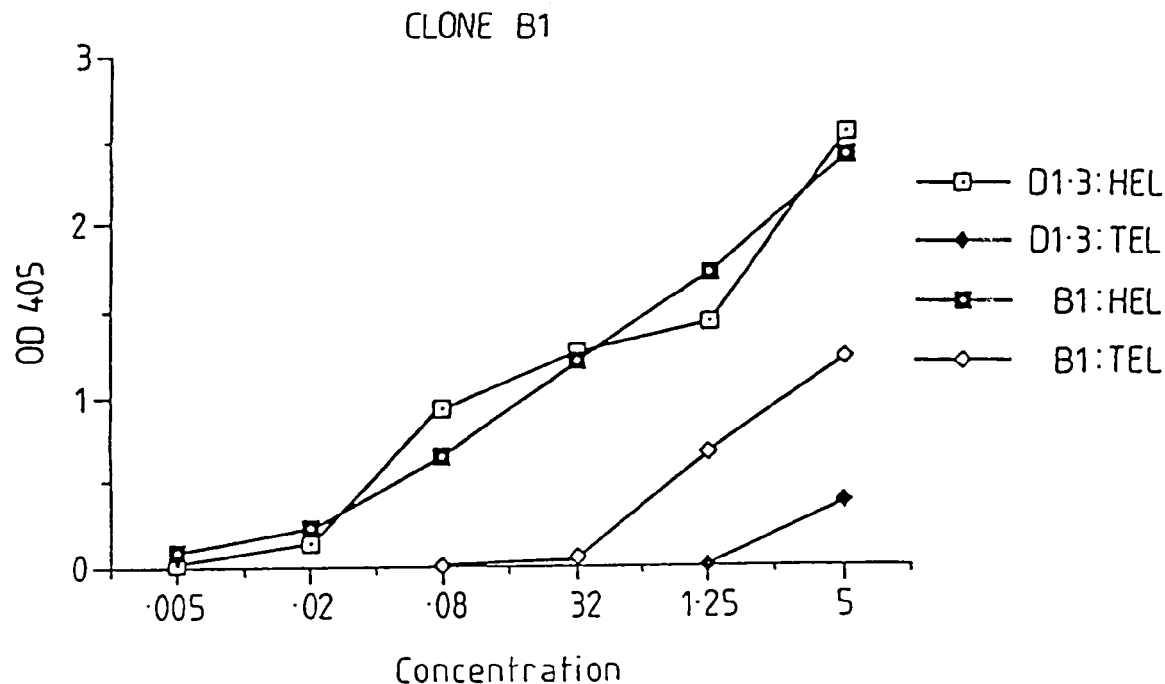
Figure 50B:
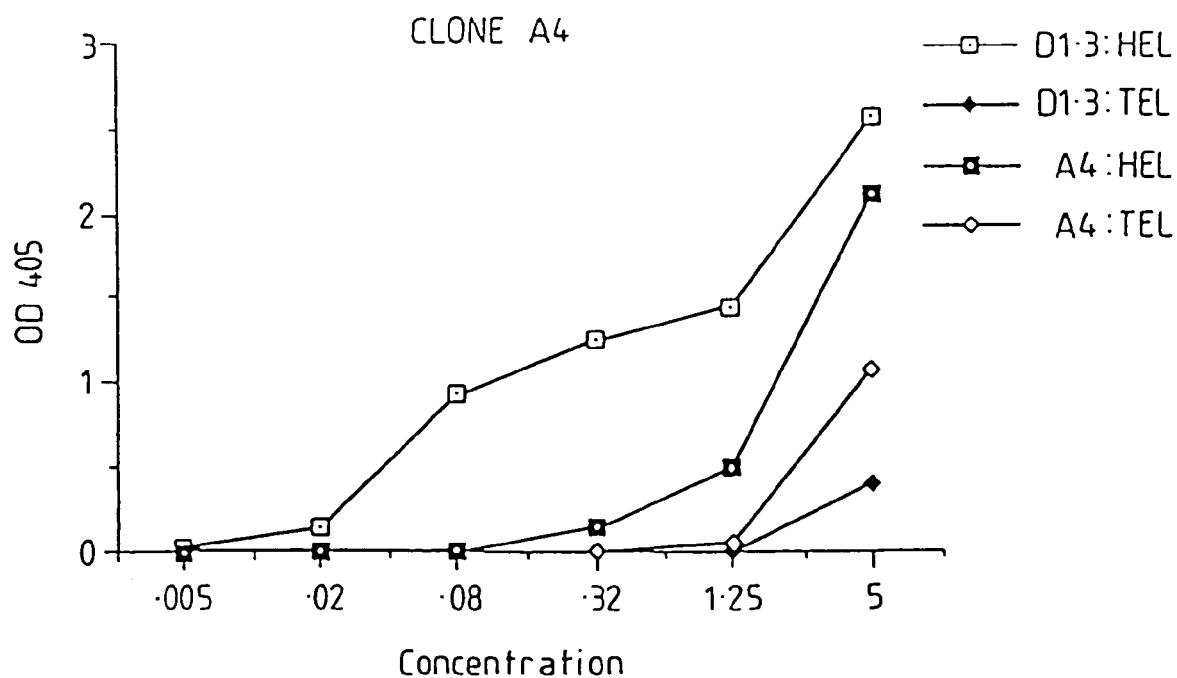

FIGS. 50a-50b. ELISA assay of phage antibodies using plates coated with turkey egg lysozyme. Two clones B1 and A4 are shown derived by mutagenesis and selection from pAbD1.3 (example 45). Concentration (x axis) refers to the concentration of phage for each sample relative to the concentration in culture supernatant. B1 has raised binding to turkey egg lysogyme compared to D1.3. A4 has reduced binding to hen egg lysogyme compared to D1.3.

Figure 51:
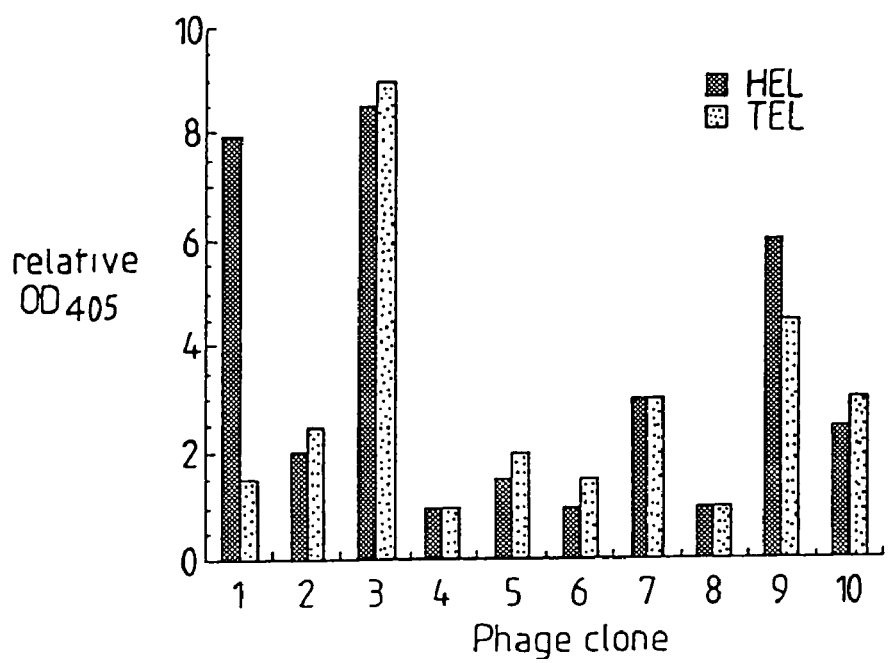

FIG. 51. ELISA of phage antibodies binding to HEL and TEL. Clone 1 is fdCAT2scFvD1.3. Clones 2 to 10 were obtained from the library (example 46) after selection. The background values as defined by binding of these clones to BSA were subtracted.

FIG. 52. shows the DNA sequence of the light chains D1.3 M1F and M21 derived by selection from a hierarchical library in example 46.

Figure 53:
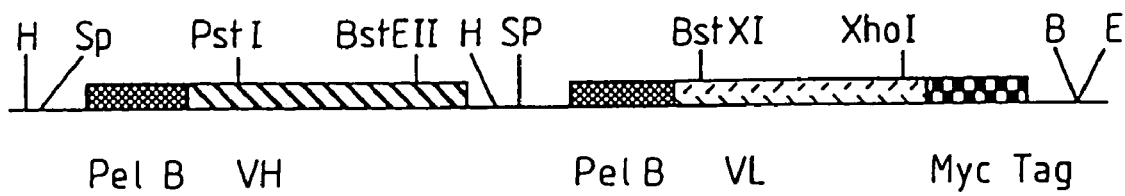

FIG. 53 shows a Fv lambda expression vector (example 48) derived from pUC119. It contains the rearranged lambda1 germ line gene. The heavy and light chain cassettes each contain a ribosome binding site upstream of the pel B leader (Restriction sites shown as: H=Hind III; Sp=SphI; B=BamHI, E=EcoRI.

MATERIALS AND METHODS

The following procedures used by the present applicants are described in Sambrook, J. et al., 1989 supra.: restriction digestion, ligation, preparation of competent cells (Hanahan method), transformation, analysis of restriction enzyme digestion products on agarose gels, purification of DNA using phenol/chloroform, 5'-end labelling of oligonucleotides, filter screening of bacterial colonies, preparation of 2×TY medium and plates, preparation of tetracycline stock solutions, PAGE of proteins, preparation of phosphate buffered saline.

All enzymes were supplied by New England Biolabs (CP Laboratories, PO Box 22, Bishop's Stortford, Herts., England) and were used according to manufacturer's instructions unless otherwise stated.

The vector fd-tet (Zacher, A. N. et al., 1980, supra) was obtained from the American Type Culture Collection (ATCC No. 37000) and transformed into competent TG1 cells (genotype: K12δ (lac-pro), sup E, thi, hsdD5/F traD36, pro A+B+, Lac $1^q$, lac δM15).

Viral particles were prepared by growing TG1 cells containing the desired construct in 10 to 100 mls 2×TY medium with 15 µg/ml tetracycline for 16-24 hours. The culture supernatant was collected by centrifugation for 10 mins at 10,000 rpm in an 8×50 ml rotor, Sorval RC-5B centrifuge. Phage particles were precipitated by adding ⅕th volume 20% polyethylene glycol (PEG)/2.5M NaCl and leaving at 4□ C. for 1 hour. These were spun for 15 minutes as described above and the pellets resuspended in 10 mM Tris/HCl pH 8, 1 mM EDTA to ¹⁄₁₀₀th of the original volume. Residual bacteria and undissolved material were removed by spinning for 2 minutes in a microcentrifuge. Single stranded DNA for mutagenesis or sequencing was prepared from concentrated phage according to Sambrook, J., et al., 1989, supra.

INDEX OF EXAMPLES

Example 1

Design of Insertion Point Linkers and Construction of Vectors

This example covers the construction of two derivatives of the phage vector fd-tet: a) fdTPs/Bs for the insertion of VH coding sequences; and b) fdTPs/Xh for the insertion of scFv coding sequences. The derivative vectors have a new BstEII site for insertion of sequences.

Example 2

Insertion of Immunoglobulin Fv Domain into Phage

This example covers the insertion of scFv coding sequences derived from an anti-lysozyme antibody D1.3 into fdTPs/Xh to give the construct fdTscFvD1.3.

Example 3

Insertion of Immunoglobulin VH Domain into Phage

This example covers the insertion of VH coding sequences derived from an anti-lysozyme antibody D1.3 into fdTPs/Bs to give the construct fdTVHD1.3.

Example 4

Analysis of Binding Specificity of Phage Antibodies

This example investigates the binding specificities of the constructs fdTscFvD1.3 and fdTVHD1.3.

Example 5

Construction of fdCAT2

This example covers the construction of the derivative fdCAT2 of the phage vector fdTPs/Xh. The derivative has restriction sites for enzymes that cut DNA infrequently.

Example 6

Specific Binding of Phage Antibody (pAb) to Antigen

This example shows the binding of pAb fdTscFvD1.3 to lysozyme by ELISA.

Example 7

Expression of FabD1.3

This example concerns the display of an antibody Fab fragment at the phage surface. The VH-CH1 chain is expressed by fdCAT2. The VL-CL chain is expressed by pUC19 in a bacterial host cell also infected with fdCAT2.

Example 8

Isolation of Specific, Desired Phage from a Mixture of Vector Phage

This example shows how a phage (e.g. fdTscFvD1.3) displaying a binding molecule can be isolated from vector phage by affinity techniques.

Example 9

Construction of pAb Expressing Anti-Hapten Activity

This example concerns the insertion of scFv coding sequences derived from the anti-oxazolone antibody NQ11 into fdTPs/Xh to generate the construct pAbNQ11. The example shows the binding of pAbNQ11 to oxazalone by ELISA.

Example 10

Enrichment of pAbD1.3 from Mixtures of other pAbs by Affinity Purification

This example shows how a phage (eg. pAbD1.3) displaying one sort of binding molecule can be isolated from phage (e.g. pAbNQ11) displaying another sort of binding molecule by affinity techniques.

Example 11

Insertion of a Gene Encoding an Enzyme (Alkaline Phosphate) into fdCAT2

This example concerns the invention of coding sequences for an enzyme into the vector fdCAT2 to give the phage enzyme, fdphoAla116.

Example 12

Measuring Enzyme Activity Phage—Enzyme

This example shows the functionality of an enzyme (alkaline phosphatase) when displayed at the phage surface (fdphoAla166).

Example 13

Insertion of Binding Molecules into Alternative Sites in the Phage

This example covers the insertion of scFv coding sequences derived from a) the anti-lysozyme antibody D1.3; and b) the anti-oxazalone antibody NQ11 into a BamH1 site of fdTPs/Xh to give the constructs fdTBam1 having an NQ11 insert.

Example 14

PCR Assembly of Mouse VH and VLK Repertoires for Phage Display

This example concerns a system for the display on phage of all VH and VLK repertoires encoded by a mouse. The system involves the following steps. 1) Preparation of RNA from spleen. 2) Preparation of cDNA from the RNA 3) Use of primers specific for antibody sequences to PCR amplify all VH and VLK cDNA coding sequences 4) Use of PCR to create a linker molecule from linking pairs of VH and VLK sequences 5) Use of PCR to assemble continuous DNA molecules each comprising a VH sequence, a linker and a VLK sequence. The specific VH/VLK combination is randomly derived 6) Use of PCR to introduce restriction sites.

Example 15

Insertion of the Extracellular Domain of a Human Receptor for Platelet Derived Growth Factor (PDGF) Isoform BB into fdCAT2

This example concerns the insertion of coding sequences for the extracellular domain of the human receptor for PDGF into the vector fdCAT2 to give the construct fdhPDGFBR.

Example 16

Binding of 125 I-PDGF-BB to the Extracellular Domain of the Human Receptor for PDGF Isoform BB Displayed on the Surface of fd Phage. Measured using an Immunoprecipitation Assay This example shows that the human receptor PDGF Isoform BB is displayed on the surface of the phage in a form which has the ability to bind its ligand.

Example 17

Construction of Phagemid Containing Gene III Fused with the Coding Sequence for a Binding Molecule This example concerns the construction of two phagemids based on pUC119 which separately contain gene III from fdCAT2 and the gene III scFv fusion fdCAT2seFvDI.3 to generate pCAT2 and pCAT3 scFvDI.3 respectively.

Example 18

Rescue of Anti-Lysozyme Antibody Specificity from pCAT3scFvD1.3 by M13KO7

This example describes the rescue of the coding sequence for the gene IIIscFv fusion from pCAT3scFvD1.3 by M13MO7 helper phage growth, phage were shown to be displaying scFv anti-lypozyme activity by ELISA.

Example 19

Transformation Efficiency of PCAT-3 and pCAT-3 scFvD1.3 Phagemids

This example compared the efficiency of the phagemids pVC119, pCAT-3 and pCAT3scFvD1.3 and the phage fdCAT2 to transform *E. coli*.

Example 20

PCR Assembly of a Single Chain Fv Library from an Immunised Mouse

This example concerns a system for the display on phage of scFv (comprising VH and VL) from an immunised mouse using the basic technique outlined in example 14 (cDNA preparation and PCR assembly of the mouse VH and VLK repertoires) and ligating the PCR assembled sequences into fdCAT2 to create a phage library of $10^5$ clones. Testing of 500 clones showed that none showed specificity against phox.

Example 21

Selection of Antibodies Specific for 2-phenyl-5-oxazolone from a Repertoire from an Immunised Mouse This example shows that phage grown from the library established in example 20 can be subjected to affinity selection using phOX to select those phage displaying scFv with the desired specificity.

Example 22

Generation of Further Antibody Specificities by the Assembly of Hierarchical Libraries This example concerns the construction of hierarchical libraries in which a given VH sequence is combined with the complete VLK repertoire and a given VLK sequence is combined with the complete VH repertoire and selection from these libraries of novel VH and VL pairings.

Example 23

Selection of Antibodies Displayed on Bacteriophage with Different Affinities for 2-phenyl-5

This example concerns the separation by affinity techniques of phages displaying scFv fragments with differing binding affinities for a given antigen.

Example 24

Figure 26A:
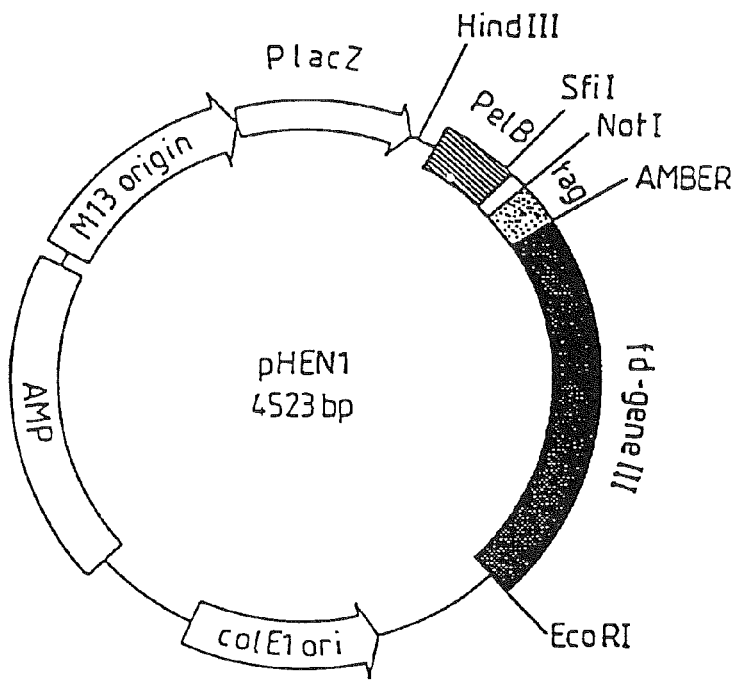
FIG. 26A shows the phagemid pHEN1 a derivative of pUC119 described in example 24; and the cloning sites in the phagemid pHEN.
Figure 26B:
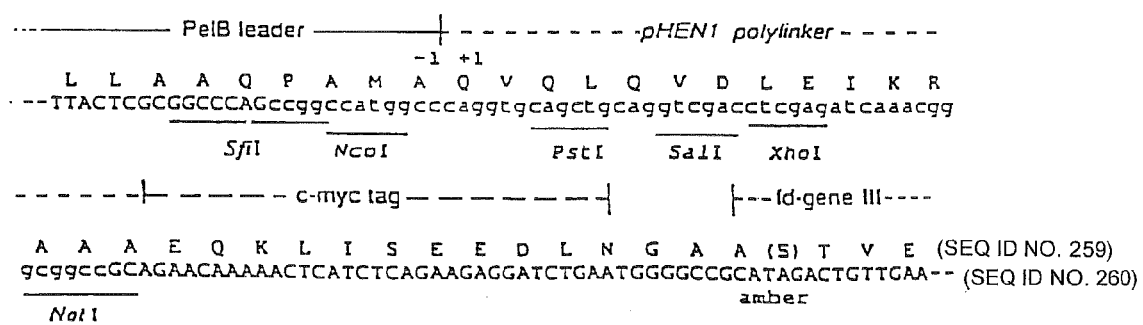

Construction of Phagemid pHEN1 for the Expression of Antibody Fragments Expressed on the Surface of Bacteriophage Following Superinfection This example concerns the construction of the phagemid pHEN1 derived from pUC119. pHEN1 has the features shown in FIG. 26

Example 25

Display of Single Chain Fv and Fab Fragments Derived from the Anti-Oxazolone Antibody NQ 10.12.5 on Bacteriophage fd using pHEN1 and fdCAT2

This example describes the display of scFv and Fab fragment with a specificity against phOx on the surface of a bacteriophage. For display of scFv the phagemid pHEN1 comprises the sequences encoding scFv (VH and VL) for rescue by either the phages VSM13 or fdCAT2. For display of Fab the phage fdCAT2 comprises the sequence for either the H or L chain as a fusion with g3p and the phagemid pHEN1 comprises the sequence for the appropriate H or L chain partner.

Example 26

Rescue of Phagemid Encoding a Gene III Protein Fusion with Antibody Heavy or Light Chains by Phage Encoding the Complementary Antibody Displayed on Phage and the Use of this Technique to Make Dual Combinatorial Libraries This example covers the use of phage antibodies encoding the antibody heavy or light chain to rescue a phagemid encoding a gene 3 protein fusion with the complementary chain and the assay of Fab fragments displayed on phage in ELISA. The use of this technique in the preparation of a dual combinatorial library is discussed.

Example 27

Induction of Soluble scFv and Fab Fragments Using Phagemid pHEN1

This example covers the generation of soluble scFv and Fab fragments from gene III fusions with sequences encoding these fragments by expression of clones in pHEN1 in an *E. coli* strain which does not suppress amber mutations.

Example 28

Increased Sensitivity in ELISA of Lysozyme Using fdTscFvD1.3 as Primary Antibody Compared to Soluble scFvD1.3

This example covers the use of fdTscFvD1.3 in ELISA showing that lower amounts of lysozyme can be detected with phage antibody fdTscFvD1.3 than with soluble scFvD1.3.

Example 29

Direct Rescue and Expression of Mouse Monoclonal Antibodies as Single Chain Fv Fragments on the Surface of Bacteriophage fd This example covers the display on phage as functional scFv fragments of two clones directly derived from cells expressing monoclonal antibodies directed against oestriol. Both clones were established to be functional using ELISA.

Example 30

Kinetic Properties of Alkaline Phosphatase Displayed on the Surface of Bacteriophage fd This example concerns the demonstration that the kinetic properties of an enzyme, alkaline phosphatase, displayed on phage are qualitatively similar to those of the same enzyme when in solution.

Example 31

Demonstration Using Ultrafiltration that Cloned Alkaline Phosphatase Behaves as Part of the Virus Particle This example concerns the construction of the phage enzyme fdphoArg166 and the demonstration that both the fusion protein made and the catalytic activity observed derive from the phage particle.

Example 32

Affinity Chromatography of Phage Alkaline Phosphatase

This example concerns the binding of alkaline phosphatase displayed on phage to an arsenate-Sepharose affinity column and specific elution of these phage using the reaction product, phosphate.

Example 33

PCR Assembly of DNA Encoding the Fab Fragment of an Antibody Directed Against Oxazolone This example covers the construction of a DNA insert encoding a Fab fragment by separate amplification of heavy and light chain DNA sequences followed by assembly. The construct was then inserted into the phage vector fdCAT2 and the phagemid vector pHEN1 and the Fab fragment displayed on the surface was shown to be functional.

Example 34

Construction of a Gene III Deficient Helper Phage

This example describes the construction of a helper phage derived from M13KO7 by deleting sequences in gene III. Rescue of pCAT3-scFvD1.3 is described. The scFvD1.3 is expressed at a high level as a fusion using the deletion phage, equivalent to expression using fdCAT2-scFvD1.3.

Example 35

Selection of Bacteriophage Expressing scFv Fragments Directed Against Lysozyme from Mixtures According to Affinity Using a Panning Procedure This example concerns the selection of bacteriophage according to the affinity of the scFv fragment directed against lysozyme which is expressed on their surface. The phage of different affinities were bound to Petri dishes coated with lysozyme and, following washing, bound phage eluted using triethylamine. Conditions were found where substantial enrichment could be obtained for a phage with a 5-fold higher affinity than the phage with which it was mixed.

Example 36

Expression of Catalytically Active Staphylococcal Nuclease on the Surface of Bacteriophage fd This example concerns the construction of a phage enzyme which expresses Staphylococcal nuclease and the demonstration that the phage enzyme retains nuclease activity.

Example 37

Display of the Two Aminoterminal Domains of Human CD4 on the Surface of fd Phage This example covers the cloning of genes for domains of CD4, a cell surface receptor and member of the immunoglobulin superfamily, into bacteriophage fd. The receptor is shown to be functional on the surface of phage by binding to the HIV protein gp120.

Example 38

Generation and Selection of Mutants of an Anti-4-hydroxy-3-nitrophenylacetic acid (NP) Antibody Expressed on Phage Using Mutator Strains This example covers the introduction of mutations into a gene for an antibody cloned in phage by growth of the phage in strains which randomly mutate DNA due to defects in DNA replication. Several mutations are introduced into phage which can then be selected from parent phage.

Example 39

Expression of a Fv Fragment on the Surface of Bacteriophage by Non-Covalent Association of VH and VL Domains This example shows that functional Fv fragments can be expressed on the surface of bacteriophage by non-covalent association of VH and VL domains. The VH domain is expressed as a gene III fusion and the VL domain as a soluble polypeptide. Sequences allowing expression of these domains from the anti-lysozyme antibody D1.3 in this form were introduced into phage and the resulting displayed Fv fragment shown to be functional by ELISA.

Example 40

A PCR Based Technique for One Step Cloning of Human V-Genes as Fab Constructs This example gives methods for the assembly of Fab fragments from genes for antibodies. Examples are given for genes for antibodies directed against Rhesus-D in a human hybridoma and a polyclonal lymphoblastic cell line.

Example 41

Selection of Phage Displaying a Human Fab Fragment Directed Against the Rhesus-D Antigen by Binding to Cells Displaying the Rhesus D Antigen on their Surface This example concerns the construction of, and display of phage antibodies from, a phagemid encoding a human Fab fragment directed against the Rhesus D antigen. Phage displaying this antigen were then affinity selected from a background of phage displaying scFvD1.3 anti-lysozyme on the basis of binding to Rhesus-D positive red blood cells.

Example 42

A PCR Based Technique for One Step Cloning of Human scFv Constructs

This example describes the generation of libraries of scFv fragments derived from an unimmunized human. Examples are given of the preparation for phage display of libraries in phagemids of scFv fragments derived from IgG and IgM sequences.

Example 43

Isolation of Binding Activities from a Library of scFvs from an Unimmunized Human This example describes the isolation, from the library of scFv fragments derived from IgM genes of an unimmunized human, of clones for phage antibodies directed against BSA, lysozyme and oxazolone. Selection was by panning or affinity chromatography and analysis of binding specificity by ELISA. Sequencing of the clones showed them to be of human origin.

Example 44

Rescue of Human IgM Library Using Helper Phage Lacking Gene 3 (g3)

This example covers the isolation, from the library of scFv fragments of unimmunized human IgM genes, of clones of phage antibodies of clones for phage antibodies specific for thyroglobulin and oxazolone. In this example rescue was with M13K07gIII No3 (NCTC12478), a helper phage defective in gene III. Fewer rounds of selection appeared necessary for a phagemid library rescued with this phage compared to one rescued with M13K07.

Example 45

Alteration of Fine Specificity of scFvD1.3 Displayed on Phage by Mutagenesis and Selection on Immobilized Turkey Lysozyme This example covers the in vitro mutagenesis of pCATscFvD1.3 by replacement, with random amino acids, of residues known to be of importance in the preferential recognition of hen egg lysozyme over turkey egg lysozyme by scFvD1.3. Following selection for phage antibodies recognising turkey egg lysozyme by affinity chromatography, clones were analysed for specificity by ELISA. Two groups of clones were found with more equal recognition of hen and turkey lysozymes, one with increased ELISA signal with the turkey enzyme and one with reduced signal for the hen enzyme.

Example 46

Modification of the Specificity of an Antibody by Replacement of the VLK Domain by a VLK Library Derived from an Unimmunised Mouse This example shows that replacement of the VL domain of scFvD1.3 specific for hen eggwhite lysozyme (HEL) with a library of VL domains allows selection of scFv fragments which bind also to turkey eggwhite lysozyme (TEL). The scFv fragments were displayed on phage and selection by panning on tubes coated with TEL. Analysis by ELISA showed clones with enhanced binding to TEL compared to HEL. Those with highest binding to TEL were sequenced.

Example 47

Selection of a Phage Antibody Specificity by Binding to an Antigen Attached to Magnetic Beads. Use of a Cleavable Reagent to Allow Elution of Bound Phage Under Mild Conditions This examples covers the use of a cleavable bond in the affinity selection method to a low release of bound phage under mild conditions. pAbNQ11 was enriched approximately 600 fold from a mixture with pAbD1.3 by selection using biotinylated Ox-BSA bound to magnetic beads. The cleavage of a bond between BSA and the biotin allows elution of the phage.

Example 48

Use of Cell Selection to Provide an Enriched Pool of Antigen Specific Antibody Genes, Application to Reducing the Complexity of Repertoires of Antibody Fragments Displayed on the Surface of Bacteriophage This example covers the use of cell selection to produce an enriched pool of genes encoding antibodies directed against 4-hydroxy-3-nitrophenylacetic acid and describes how this technique could be used to reduce the complexity of antibody repertoires displayed on the surface of bacteriophage.

Example 1

Design of Insertion Point Linkers and Construction of Vectors

The vector fd-tet has two BstEII restriction sites flanking the tetracycline resistance gene (FIG. 3). Since the strategy for inserting the VH fragments was to ligate them into a newly inserted BstEII site within gene III, it was advantageous to delete the original BstEII sites from fd-tet. This was achieved by digesting fd-tet with the restriction enzyme BstEII, filling-in the 5' overhangs and re-ligating to generate the vector fdTδBst. Digestion of fd-tet with BstEII (0.5 units/µl) was carried out in 1×KGB buffer (100 mM potassium glutamate, 23 mM Tris-acetate (pH 7.5), 10 mM magnesium acetate, 50 µg/ml bovine serum albumin, 0.5 mM dithiothreitol (Sambrook, J., et al., 1989, supra.) with DNA at a concentration of 25 ng/µl. The 5' overhang was filled in, using 2×KGB buffer, 250 µM each dNTP's (Pharmacia Ltd., Pharmacia House, Midsummer Boulevard, Milton Keynes, Bucks., UK.) and Klenow Fragment (Amersham International, Lincoln Place, Green End, Aylesbury, Bucks., UK) at 0.04 units/µl. After incubating for 1 hour at room temperature, DNA was extracted with phenol/chloroform and precipitated with ethanol.

Ligations were carried out at a DNA concentration of 50 ng/µl). Ligations were transformed into competent TG1 cells and plated onto TY plates supplemented with 15 µg/ml tetracycline. This selects for vectors where the gene for tetracycline resistance protein has reinserted into the vector during the ligation step. Colonies were picked into 25 mls of 2×TY medium supplemented with 15 µg/ml tetracycline and grown overnight at 37□ C.

Double stranded DNA was purified form the resulting clones using the gene-clean II kit (Bio101 Inc., PO Box 2284, La Jolla, Calif., 92038-2284, USA.) and according to the small scale rapid plasmid DNA isolation procedure described therein. The orientation of 5 of the resulting clones was checked using the restriction enzyme ClaI. A clone was chosen which gave the same pattern of restriction by ClaI as fd-tet, but which had no BstE II sites.

In vitro mutagenesis of fdTδBst was used to generate vectors having appropriate restriction sites that facilitate cloning of antibody fragments downstream of the gene III signal peptide and in frame with the gene III coding sequence. The oligonucleotide directed mutagenesis system version 2 (Amersham International) was used with oligo 1 (FIG. 4a) to create fdTPs/Bs (to facilitate cloning of VH fragments). The sequence offdTPs/Bs (FIG. 4a) was confirmed using the SEQUENASE version 2.0 kit (USB Corp., PO Box 22400, Cleveland, Ohio, 44122, UsA.) with oligo 3 (FIG. 4) as a primer.

A second vector fdTPs/Xh (to facilitate cloning of single chain Fv fragments) was generated by mutagenising fdTPs/Bs with oligo 2 according to the method of Venkitaraman, A. R., Nucl. Acid Res. 17, p 3314. The sequence of fdTPs/Xh (FIG. 4) was confirmed using the sequenase version 2.0 kit (USB Corp.) with oligo 3 as a primer.

Clearly, alternative constructions will be apparent to those skilled in the art. For example, M13 and/or its host bacteria could be modified such that its gene III could be disrupted without the onset of excessive cell death; the modified fd gene III, or other modified protein, could be incorporated into a plasmid containing a single stranded phage replication origin, such as pUC119, superinfection with modified phage such as KO7 would then result in the encapsulation of the phage antibody genome in a coat partially derived from the helper phage and partly from the phage antibody gene III construct.

The detailed construction of a vector such as fdTPs/Bs is only one way of achieving the end of a phage antibody. For example, techniques such as sticky feet cloning/mutagenesis (Clackson, T. and Winter, G. 1989 Nucl. Acids. Res., 17, p 10163-10170) could be used to avoid use of restriction enzyme digests and/or ligation steps.

Example 2

Insertion of Immunoglobulin Fv Domain into Phage

The plasmid scFv D1.3 myc (gift from g. Winter and A. Griffiths) contains VH and VL sequences from the antibody D1.3 fused via a peptide linker sequence to form a single chain Fv version of antibody D1.3. The sequence of the scFv and surrounding sequences in scFvD1.3 myc is shown in FIG. 5.

The D1.3 antibody is directed against hen egg lysozyme (Harper, M. et al., 1987, Molec. Immunol. 24, 97-108) and the scFv form expressed in E. coli has the same specificity (A. Griffiths and G. Winter personal Communication).

Digestion of scFv D1.3 myc with PstI and XhoI (these restriction sites are shown on FIG. 5), excises a fragment of 693 bp which encodes the bulk of the scFv. Ligation of this fragment into fdTPs/Xh cleaved with Pst1 and Xhol gave rise to the construct fdTscFvD1.3 encoding the gene III signal peptide and first amino acid fused to the complete D1.3 scFv, followed by the mature gene III protein from amino acid 2.

The vector fdTPs/Xh was prepared for ligation by digesting with the Pst1 and Xhol for 2 hours followed by digestion with calf intestinal alkaline phosphatase (Boehringer Mannheim UK Ltd., Bell Lane, Lewes, East Sussex, BN7 1LG) at one unit/ul for 30 minutes at 37□C. Fresh calf intestinal alkaline phosphatase was added to a final total concentration of 2 units/ul and incubated for a further 30 minutes at 37□C. The reaction was extracted three times with phenol/chloroform, precipitated with ethanol and dissolved in water. The insert from scFvD1.3 myc was excised with the appropriate restriction enzymes (PstI and XhoI) extracted twice with phenol/chloroform, precipitated with ethanol and dissolved in water. Ligations were carried out as described in example 1, except both vector and insert samples were at a final concentration of 5 ng/ul each. The formation of the correct construct was confirmed by sequencing as described in example 1.

To demonstrate that proteins of the expected size were produced, virions were concentrated by PEG precipitation as described above. The samples were prepared for electrophoresis as described in Sambrook J. et al 1989 supra. The equivalent of 2 mls of supernatant was loaded onto an 18% SDS polyacrylamide gel. After electrophoresis, the gel was soaked in gel running buffer (50 mM tris, 380 mM Glycine, 0.1% SDS) with 20% methanol for 15 minutes. Transfer to nitrocellulose filter was executed in fresh 1× running buffer/ 20% methanol using TE70 Semi Phor a semi-dry blotting apparatus (Hoeffer, 654 Minnesota Street, Box 77387, San Francisco, Calif. 94107, USA.).

After transfer, the filter was blocked by incubation for 1 hour in a 2% solution of milk powder (Marvel) in phosphate buffered saline (PBS). Detection of scFv and VH protein sequences in the phage antibody fusion proteins was effected by soaking the filter for 1 hour with a 1/1000 dilution (in 2% milk powder) of a rabbit polyclonal antiserum raised against affinity purified, bacterially expressed scFv fragment (gift from G. Winter). After washing with PBS (3×5 minute washes), bound primary antibody was detected using an anti-rabbit antibody conjugated to horseradish peroxidase (Sigma, Fancy Road, Poole, Dorset, BH17 7NH, UK.) for 1 hour. The filter was washed in PBS/0.1% triton X-100 and developed with 0.5 mg/ml 3,3'-diaminobenzidine tetrahydrochloride (DAB), 0.02% cobalt chloride, 0.03% hydrogen peroxide in PBS.

The results showed that with clones fdTVHD1.3 (from example 3 incorporating sequences coding for VH) and fdTscFvD1.3 (incorporating sequences coding for scFv) a protein of between 69,000 and 92,500 daltons is detected by the anti-Fv serum. This is the expected size for the fusion proteins constructed. This product is not observed in supernatants derived from fd-tet, fdTδBst or fdTPs/Xh.

Example 3

Insertion of Immunoglobulin VH Domain into Phage Antibody

The VH fragment from D1.3 was generated from the plasmid pSW1-VHD1.3-TAG1 (Ward, E. S. et al., 1989 supra.). Digestion of this plasmid with Pst1 and BstEII generates the fragment shown between positions 113 and 432 in FIG. 5. Cloning of this fragment into the Pst1 and BstEII sites of fdTPs/Bs gave rise to the construct fdTVHD1.3 which encodes a fusion protein with a complete VH domain inserted between the first and third amino acids of the mature gene III protein (amino acid two has been deleted).

The methods used were exactly as in example 2 except that the vector used was fdTPs/Bs digested with Pst1 and BstEII.

Example 4

Analysis of Binding Specificity of Phage Antibodies

The binding of the various phage antibodies to the specific antigen, lysozyme, was analysed using ELISA techniques. Phage antibodies (e.g. fdTVHD1.3 and fdTsc/FvD1.3) were grown in *E. coli* and Phage antibody particles were precipitated with PEG as described in the materials and methods. Bound phage antibody particles were detected using polyclonal sheep serum raised against the closely related phage M13.

ELISA plates were prepared by coating 96 well plates (Falcon Microtest III flexible plate. Falcon: Becton Dickinson Labware, 1950 Williams Drive, Oxnard, Calif., 93030, USA.) with 200 ul of a solution of lysozyme (1 mg/ml unless otherwise stated) in 50 mm NaHCO3 for 16-24 hours. Before use, this solution was removed, the plate rinsed several times in PBS and incubated with 200 ul of 2% milk powder/PBS for 1 hour. AFter rinsing several times with PBS, 100 ul of the test samples were added and incubated for 1 hour. Plates were washed (3 rinses in 0.05% Tween 20/PBS followed by 3 rinses in PBS alone). Bound phage antibodies were detected by adding 200 ul/well of a 1/1000 dilution of sheep anti-M13 polyclonal antiserum (gift from G. Winter, although an equivalent antibody can be readily made by one skilled in the art using standard methodologies) in 2% milk powder/PBS and incubating for 1 hour. After washing as above, plates were incubated with biotinylated anti-sheep antibody (Amersham International) for 30 minutes. Plates were washed as above, and incubated with streptavidin-horseradish peroxidase complex (Amersham International). After a final wash as above, 0.5 mg/ml ABTS substrate in citrate buffer was added (ABTS=2'2'-azinobis (3-ethylbenzthiazoline sulphonic acid); citrate buffer=50 mM citric acid, 50 mM tri-sodium citrate at a ratio of 54:46. Hydrogen peroxide was added to a final concentration of 0.003% and the plates incubated for 1 hour. The optical density at 405 nm was read in a Titertek multiskan plate reader.

Figure 6:
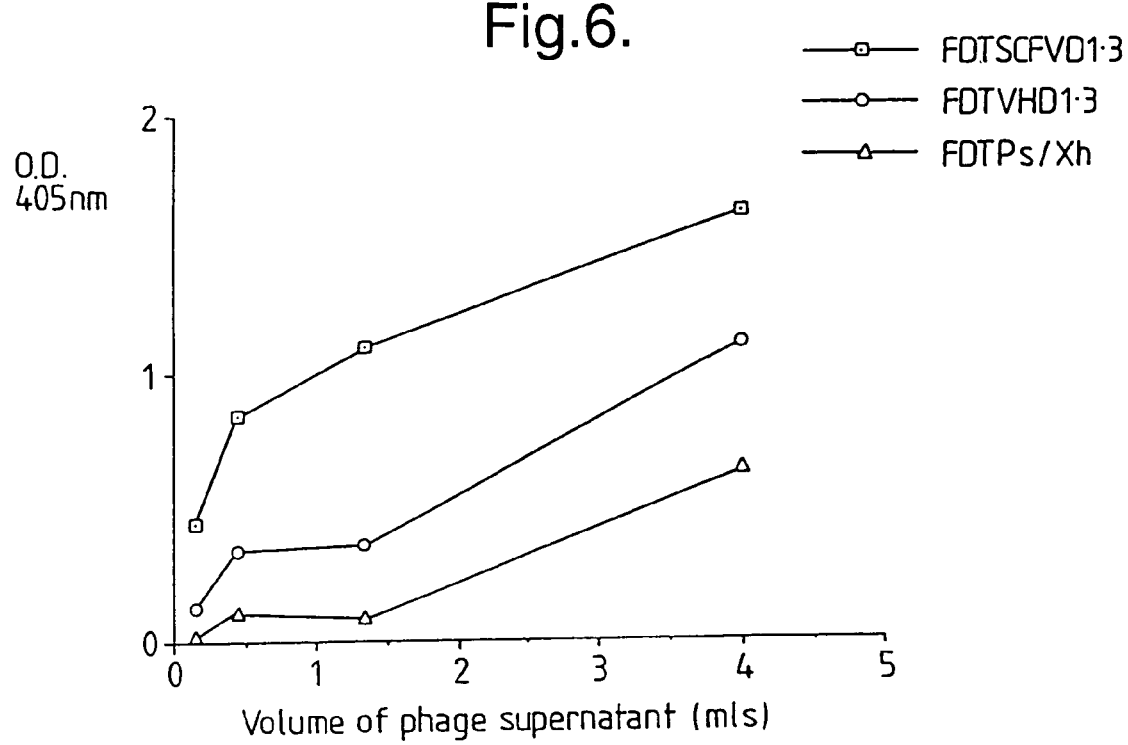
FIG. 6 shows the binding of pAbs to lysozyme and the effect of varying the amount of supernatant. Each point is the average of duplicate samples. Lysozyme was coated at 1 mg/ml in 50 mM $NaHCO_3$.

FIG. 6 shows the effect of varying the amount of phage antibody. 100 ul of various dilutions of PEG precipitated phage were applied and the amount expressed in terms of the original culture volume from which it was derived. Signals derived from both the scFv containing phage antibody (fdTscFvD1.3) and the VH containing phage antibody (fdTVHD1.3) and the VH containing phage antibody were higher than that derived from the phage antibody vector (fdTPs/Xh). The highest signal to noise ratio occurs using the equivalent of 1.3 mls of culture.

Figure 7:
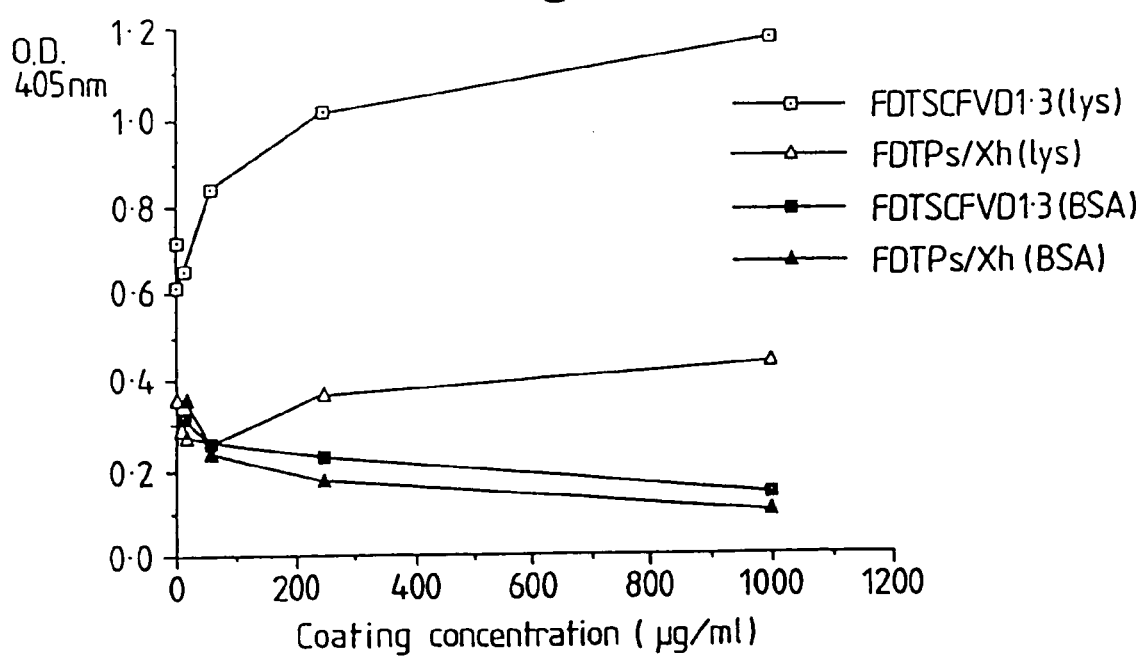
FIG. 7 shows the effect of varying the coating concentration of lysozyme or bovine serum albumin on the binding of pAbs to lysozyme in graphical form. Each point is the average of duplicate samples.

FIG. 7 shows the results of coating the plates with varying concentrations of lysozyme or bovine serum albumin (BSA). The equivalent of 1 ml of the original phage antibody culture supernatant was used.

The signals from supernatants derived from fdTscFvD1.3 were again higher than those derived from fdTPs/Xh when lysozyme coated wells were used. There was no significant difference between these two types of supernatant when the plates were coated with BSA.

Broadly speaking the level of signal on the plates is proportional to the amount of lysozyme coated. These results demonstrate that the binding detected is specific for lysozyme as the antigen.

Example 5

Construction of fd CAT 2

It would be useful to design vectors that enable the use of restriction enzymes that cut DNA infrequently, thus avoiding unwanted digestion of the antibody gene inserts within their coding sequence. Enzymes with an eight base recognition sequence are particularly useful in this respect, for example Not1 and Sfi1. Chaudhary et al (PNAS 87 p1066-1070, 1990) have identified a number of restriction sites which occur rarely in antibody variable genes. The applicant has designed and constructed a vector that utilises two of these sites, as an example of how this type of enzyme can be used. Essentially sites for the enzymes ApaL1 and Not1 were engineered into fdTPs/Xh to create fdCAT2.

Figure 8:
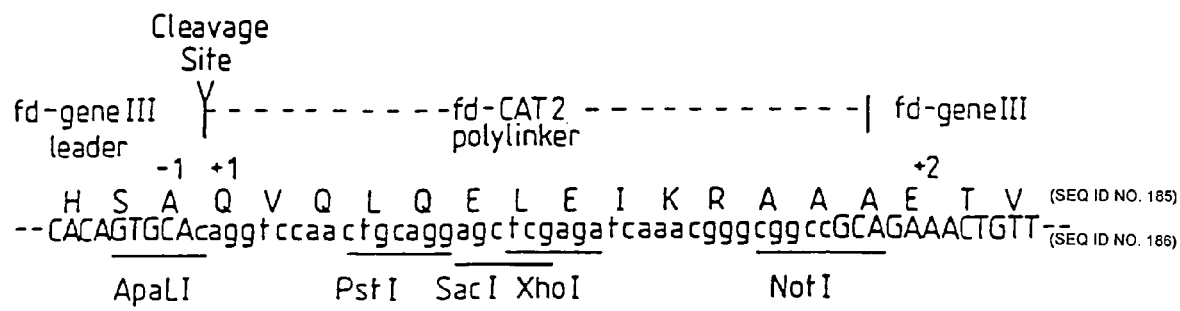
FIG. 8 shows the sequence around the cloning site in gene III of fd-CAT2. Restriction enzyme sites are shown as well as the amino acids encoded by antibody derived sequences. These are flanked at the 5' end by the gene III signal peptide and at the 3' end by 3 alanine residues (encoded by the Not 1 restriction site) and the remainder of the mature gene III protein. The arrow shows the cleavage site for cutting of the signal peptide.

The oligonucleotide:
5'ACT TTC AAC AGT TTC TGC GGC CGC CCG TTT GAT CTC GAG CTC CTG CAG TTG GAC CTG TGC ACT GTG AGA ATA GAA 3' (SEQ ID NO:4) was synthesised (supra FIG. 4 legend) and used to mutagenise fdTPs/Xh using an in vitro mutagenesis kit from Amersham International as described in example 1, to create fd-CAT2. The sequence of fd-CAT2 was checked around the site of manipulation by DNA sequencing. The final sequence around the insertion point within gene III is shown in FIG. 8. N.B. fdCAT2 is also referred to herein by the alternative terminologies fd-tet-DOG1 and fdDOG1.

Example 6

Specific Binding of Phage-Antibody (pAb) to Antigen

The binding of pAb D1.3 (fdTscFvD1.3 of example 2) to lysozyme was further analysed by ELISA.

Methods.

1. Phage Growth.

Cultures of phage transduced bacteria were prepared in 10-100 mls 2×TY medium with 15 µg/ml tetracycline and grown with shaking at 37° C. for 16-24 hrs. Phage supernatant was prepared by centrifugation of the culture (10 min at 10,000 rpm, 8×50 ml rotor, Sorval RC-5B centrifuge). At this stage, the phage titre was $1-5 \times 10^{10}$/ml transducing units. The phage were precipitated by adding ⅕ volume 20% PEG 2.5 M NaCl, leaving for 1 hr at 4° C., and centrifuging (supra). The phage pellets were resuspended in 10 mM Tris-HCl, 1 mM EDTA pH 8.0 to 1/100th of the original volume, and residual bacteria and aggregated phage removed by centrifugation for 2 min in a bench microcentrifuge.

ELISA

Figure 9:
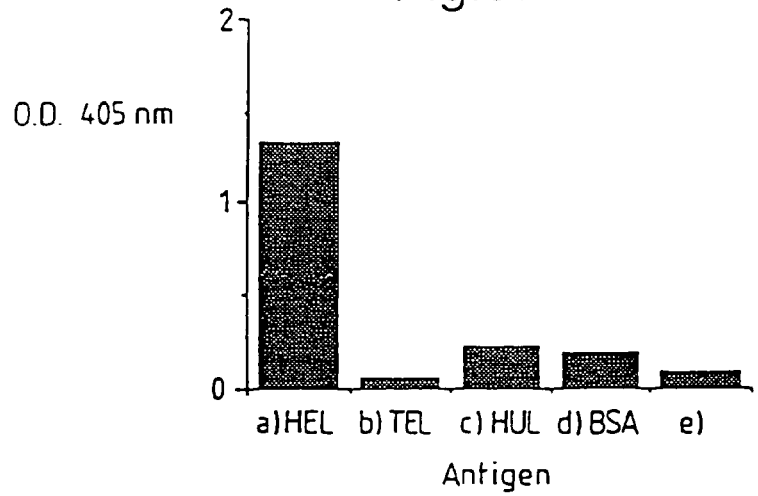
FIG. 9 shows the binding of pAb (1.3) to lysozymes. Binding of phage as detected by ELISA to (a) hen egg-white lysozyme (HEL) (b) turkey egg-white lysozyme (TEL), (c) human lysozyme (HUL), (d) bovine serum albumin (BSA). A further control of (e) fdTPs/Bs to HEL.

Plates were coated with antigen (1 mg/ml antigen) and blocked as described in example 4. $2 \times 10_{10}$ phage transducing units were added to the antigen coated plates in phosphate buffered saline (PBS) containing 2% skimmed milk powder (MPBS). Plates were washed between each step with three rinses of 0.5% Tween-20 in PBS followed by three rinses of PBS. Bound phage was developed by incubating with sheep anti-M13 antisera and detected with horseradish peroxidase (HRP) conjugated anti-goat serum (Sigma, Poole, Dorset, UK) which also detects sheep immunoglobulins and ABTS (2'2'-azinobis (3-ethylbenzthiazoline sulphonic acid). Readings were taken at 405 nm after a suitable period. The results (FIG. 9) show that the antibody bearing-phage had the same pattern of reactivity as the original D1.3 antibody (Harper, M., Lema, F., Boulot, G., and Poljak, F. J. (1987) Molec. Immunol. 24, 97-108), and bound to hen egg-white lysozyme, but not to turkey egg-white lysozyme, human lysozyme or bovine serum albumin. The specificity of the phage is particularly illustrated by the lack of binding to the turkey egg-white lysozyme that differs from hen egg-white lysozyme by only 7 amino acids.

Example 7

Expression of Fab D1.3

Figure 1:
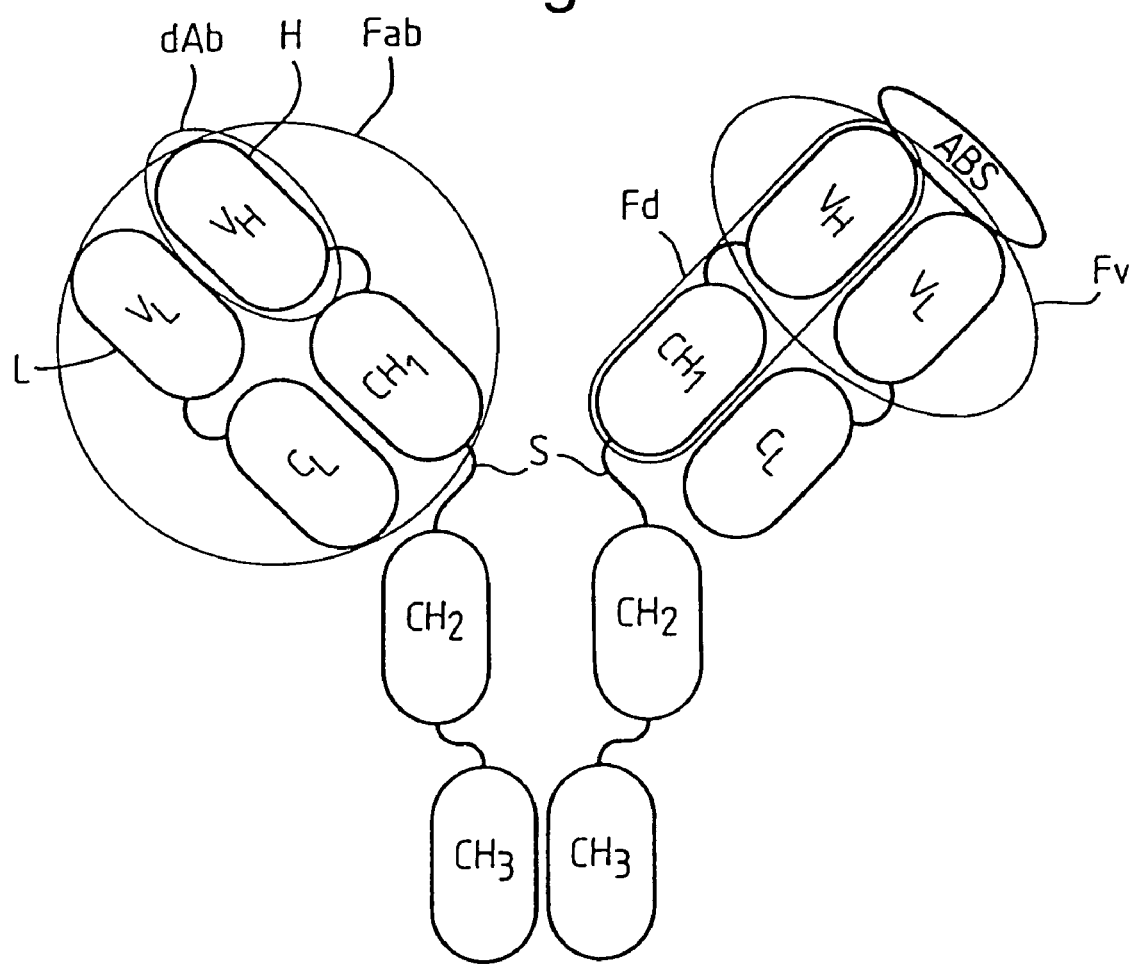
FIG. 1 shows the basic structure of the simplest antibody molecule IgG.
Figure 2A:
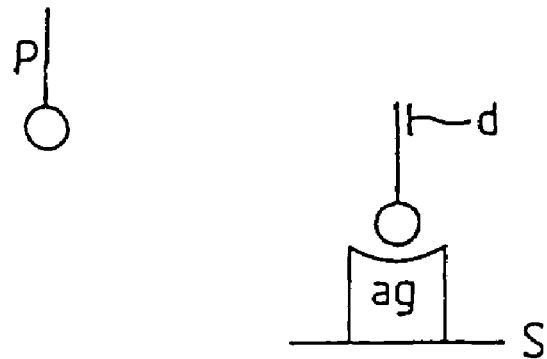
FIGS. 2a and 2b show schematically selection techniques which utilise the unique properties of pAbs; 2a shows a binding/elution system; and (2b) shows a competition system (p=pAb; ag=antigen to which binding by pAb is required; c=competitor population e.g. antibody, pAb, ligand; s=substrate (e.g. plastic beads etc); d=detection system.
Figure 2B:
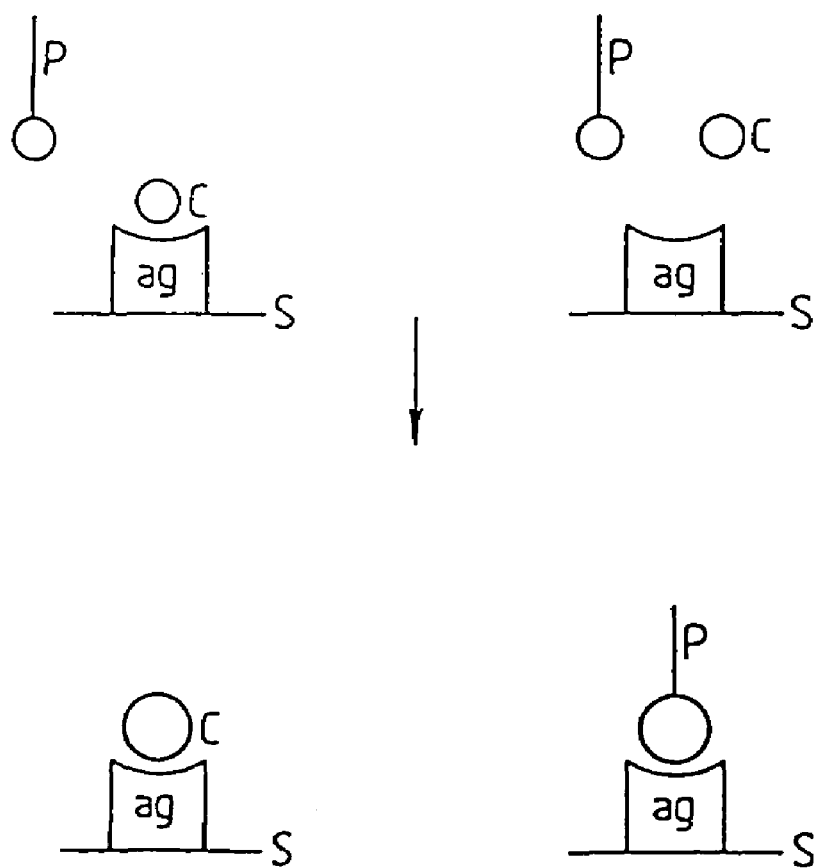

The aim of this example was to demonstrate that the scFv format used in example 2 was only one way of displaying antibody fragments in the pAb system. A more commonly used antibody fragment is the Fab fragment (FIG. 1) and this example describes the construction of a pAb that expresses a Fab-like fragment on its surface and shows that it binds specifically to its antigen. The applicant chose to express the heavy chain of the antibody fragment consisting of the VH and CH1 domains from coding sequences within the pAb itself and to co-express the light chain in the bacterial host cell infected with the pAb. The VH and CH1 regions of anti-lysozyme antibody D1.3 were cloned in fd CAT2, and the corresponding light chain cloned in plasmid pUC19. The work of Skerra and Pluckthun (Science 240, p1038-1040 (1988)) and Better et al 1988 supra; demonstrated that multimeric antigen binding fragments of the antibody molecule could be secreted into the periplasm of the bacterial cell in a functional form using suitable signal sequences. However, in these publications, special measures were described as being needed to recover the binding protein from the cell, for example Skerra and Pluckham needed to recover the Fv fragment from the periplasm by affinity chromatography. The present applicants have shown that it is possible to direct the binding molecule to the outside of the cell on a phage particle, a process that requires several events to occur: correct secretion and folding of the binding molecule; association of the chains of the binding molecule; correct assembly of the phage particle; and export of the intact phage particle from the cell.

Alternatively, it is possible however, to express the light chain from within the pAb genome by, for example, cloning an expression cassette into a suitable place in the phage genome. Such a suitable place would be the intergenic region which houses the multicloning sites engineered into derivative of the related phage M13 (see, for example, Yanisch-Perron, C. et al., Gene 33, p103-119, (1985)).

Figure 10:
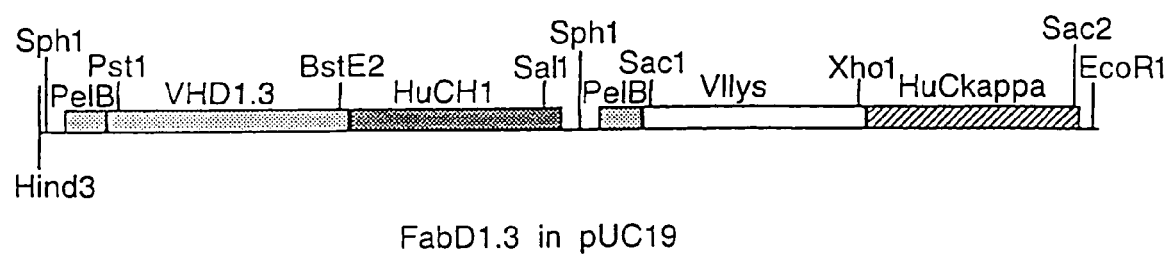
FIG. 10a-10d shows a map of FabD1.3 in pUC19.

The starting point for this example was the clone Fab D1.3 in pUC19, a map of which is shown in FIG. 10. The regions hybridising with the oligonucleotides KSJ6 and 7 below are shown underlined in FIG. 10. The sequence encoding the VH-CH1 region (defined at the 5' and 3' edges by the oligonucleotides KSJ6 and 7 below) was PCR amplified from Fab D1.3 in pUC19 using oligonucleotides KSJ 6 and 7, which retain the Pst I site at the 5' end and introduce a Xho I site at the 3' end, to facilitate cloning into fd CAT2. The sequences for the oligonucleotides KSJ6 and 7 are shown below. The underlined region of KSJ7 shows the portion hybridising with the sequence for D1.3.

KSJ6:                                    (SEQ ID NO:5)
5' AGG TGC AGC TGC AGG AGT CAG G 3'

KSJ7:                                    (SEQ ID NO:6)
5' GGT GAC CTC GAG <u>TGA AGA TTT GGG CTC AAC TTT C</u> 3'

PCR conditions were as described in example II, except that thirty cycles of PCR amplification were performed with denaturation at 92° C. for 45 seconds, annealing at 55° C. for 1 minute and extension at 72° C. for 1 minute. The template used was DNA from TG1 cells containing Fab D1.3 in pUC19 resuspended in water and boiled. The template DNA was prepared from the colonies by picking some colony material into 100 µl of distilled $H_2O$ and boiling for 10 mins. 1 µl of this mixture was used in a 20 µl PCR. This regime resulted in amplification of the expected fragment of approximately 600 bp. This fragment was cut with Pst I and Xho I, purified from an agarose gel and ligated into Pst 1/Xho 1-cut fdCAT2. The PCR mixture was extracted with phenol/chloroform and ethanol precipitated (Sambrook et al. supra.) before digestion with Pst1 and Xho1 (New England Biolabs according to manufacturers recommendations. The fragment was resolved on 1% Tris-Acetate EDTA agarose gel (Sambrook et al. supra) and purified using Geneclean (BIO 101, Geneclean, La Jolla, San Diego, Calif., USA) according to manufacturers recommendations.

fd-CAT2 vector DNA was digested with Pst 1 and Xho 1 (New England BioLabs) according to manufacturers recommendations, extracted with phenol/chloroform and ethanol precipitated (Sambrook et al. supra.).

75 ng of Pst 1/Xho 1-digested vector DNA was ligated to 40 ng of PCR-amplified Pst1/Xho I-digested hEGF-R fragment in 12 µl of ligation buffer (66 mM TrisHCl (pH7.6), 5 mM MgCl$_2$, 5 mM dithiothreitol, (100 µg/ml bovine serum albumin, 0.5 mM ATP, 0.5 mM Spermidine) and 400 units T4 DNA ligase (New England BioLabs) for 16 hours at 16° C.

Two µl of the ligation mixture was transformed into 200 µl of competent *E. coli* MC1061 cells, plated on 2TY agar containing 15 µg/ml tetracycline and incubated at 30° C. for 20 hours. A portion of the ligation reaction mixture was transformed into *E. coli* MC 1061 (Available from, for example Clontech Laboratories Inc, Palo Alto, Calif.) and colonies identified by hybridisation with the oligonucleotide D1.3CDR3A as described in example 10. The presence of the VHCH1 gene fragment was likewise confirmed by PCR, using oligonucleotides KSJ6 and 7. A representative clone was called fd CAT2VHCH1 D1.3. The heavy chain was deleted from Fab D1.3 in pUC19 by Sph I cleavage of Fab D1.3 plasmid DNA. The pUC 19 2.7 Kb fragment containing the light chain gene was purified from a TAB agarose gel, and 10 ng of this DNA self-ligated and transformed into competent *E. coli* TG1. Cells were plated on 2TY agar containing ampicillin (100 µg/ml) and incubated at 30° C. overnight. The resulting colonies were used to make miniprep DNA (Sambrook et al. supra), and the absence of the heavy chain gene confirmed by digestion with Sph I and Hind III. A representative clone was called LCD1.3 DHC.

An overnight culture of fd CAT2VHCH1 D1.3 cells was microcentrifuged at 13,000 Xg for 10 minutes and 50 µl of the supernatant containing phage particles added to 50 µl of an overnight culture of LCD1.3 DHC cells. The cells were incubated at 37° C. for 10 minutes and plated on 2TY agar containing ampicillin (100 µg/ml) and 15 µg/ml tetracycline. Phage were prepared from some of the resulting colonies and assayed for their ability to bind lysozyme as described in example 6.

Figure 11:
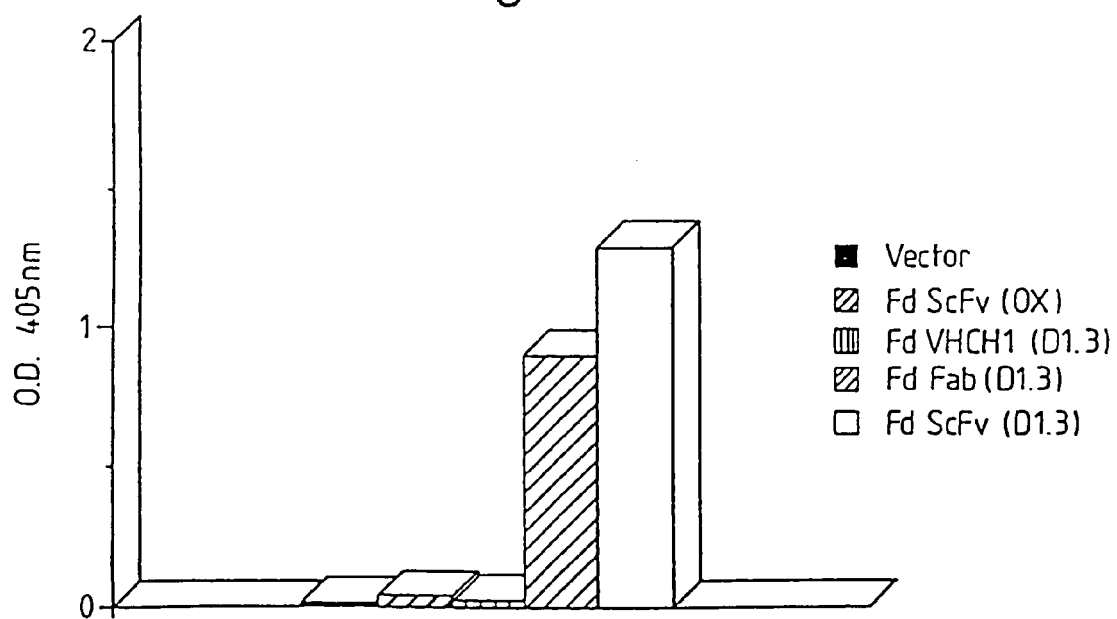
FIG. 11 shows the ELISA results providing a comparison of lysozyme-binding by phage-Fab and phage-scFv. Vector=fdCAT2 (example 5); fdscFv(OX)=pAbNQ11 (Example 9); fdVHCH1 (D1.3)=grown in normal cells (i.e. no L chain, see example 7); fdFab(D1.3) i.e. fdVHCH1 (D1.3) grown in cells containing D1.3 L chain; fdscFv (D1.3)= pAbD1.3.

The results (FIG. 11) showed that when the heavy and light chain Fab derivatives from the original antibody D1.3 were present, the pAb bound to lysozyme. pAb expressing the fd VHCH1 fragment did not bind to lysozyme unless grown in cells also expressing the light chain. This shows that a functional Fab fragment was produced by an association of the free light chain with VHCH1 fragment fused to gene III and expressed on the surface of the pAb.

Example 8

Isolation of Specific, Desired Phage from a Mixture of Vector Phage

Figure 12A:
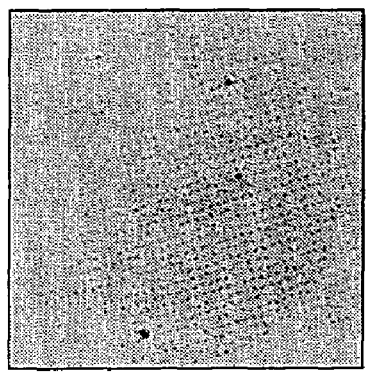
FIGS. 12a-12b show oligonucleotide probing of affinity purified phage. $10^{12}$ phage in the ratio of 1 pAb (D1.3) in $4 \times 10^4$ fdTPS/Bs phages were affinity purified and probed with an oligonucleotide specific for pAb (D1.3) A is a filter after one round of affinity purification (900 colonies total) and B is a filter after two rounds (372 colonies total).
Figure 12B:
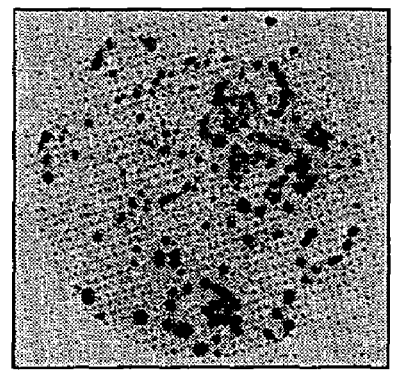

The applicant purified pAb (D1.3) (originally called fdTscFvD1.3 in example 2) from mixtures using antigen affinity columns. pAb (D1.3) was mixed with vector fd phage (see table 1) and approximately $10^{12}$ phage passed over a column of lysozyme-Sepharose (prepared from cyanogen bromide activated sepharose 4B (Pharmacia, Milton Keynes, Bucks, UK.) according to the manufacturers instructions. TG1 cells were infected with appropriate dilutions of the elutes and the colonies derived, were analysed by probing with an oligonucleotide that detects only the pAb (D1.3) see Table 1 and FIGS. 12A and 12B. A thousand fold enrichment of pAb(D1.3) was seen with a single column pass. By growing the enriched phage and passing it down the column again, enrichments of up to a million fold were seen.

Enrichment was also demonstrated using purely immunological criteria. For example, $10^{12}$ phage (at a ratio of 1 pAb (D1.3) to $4 \times 10^6$ fdTPs/Bs) was subjected to two rounds of affinity selection, and then 26 colonies picked and grown overnight. The phage was then assayed for lysozyme binding by ELISA (as example 6). Five colonies yielded phage with lysozyme binding activities, see table 1, and these were shown to encode the scFv (D1.3) by PCR screening (example 13, using 30 cycles of 1 minute at 92□C, 1 minute at 60□C, 1 minute at 72□C using CDR3PCR1 and oligo 3 (FIG. 4a) as primers).

Thus very rare pAbs can be fished out of large populations, by using antigen to select and then screen the phage.

In this example, affinity chromatography of pAbs and oligonucleotide probing were carried out as described below.

Approximately $10^{12}$ phage particles in 1 ml MPBS were loaded onto a 1 ml lysozyme-Sepharose affinity column which had been prewashed in MPBS. The column was washed in turn with 10 ml PBS; then 10 ml 50 mM Tris-HCl, 500 mM NaCl pH 7.5; then 10 ml 50 mM Tris-HCl 500 mM NaCl pH 8.5; then 5 mls 50 mM Tris-HCl, 500 mM NaCl pH 9.5 (adjusted with triethylamine) and then eluted with 5 ml 100 mM triethylamine. The eluate was neutralised with 0.5 M sodium phosphate buffer pH 6.8 and the phage plated for analysis. For a second round of affinity chromatography, the first column eluate was plated to about 30,000 colonies per petri dish. After overnight growth, colonies were then scraped into 5 ml 2×TY medium, and a 20 µl aliquot diluted into 10 ml fresh medium and grown overnight. The phage was PEG precipitated as described above, resuspended in 1 ml MPBS and loaded onto the column, washed and eluted as above. Oligonucleotides sythesised:

```
CDR3PCR1                              (SEQ ID NO:7)
5' TGA GGA C(A or T) C(A or T) GC CGT CTA CTA CTG
TGC 3'.
```

40 pmole of oligonucleotide VH1FOR (Ward, E. S., et al (1989) Nature 341, 544-546), specific to pAb (D1.3) was phosphorylated with 100 µCi α-32P ATP, hybridised (1 pmole/ml) to nitrocellulose filters at 67° C. in 6× saline sodium citrate (SSC) Sambrook et al., supra. buffer for 30 minutes and allowed to cool to room temperature for 30 mins, washed 3×1 min at 60° C. in 0.1×SSC.

Example 9

Construction of pAb Expressing Anti-Hapten Activity

Oxazolone is a hapten that is commonly used for studying the details of the immune response. The anti-oxazalone antibody, NQ11 has been described previously (E. Gherardi, R. Pannell, C. Milstein, J. Immunol. Method 126 61-68). A plasmid containing the VH and VL gene of NQ11 was converted to a scFv form by inserting the BstEII/SacI fragment of scFvD1.3 myc (nucleotides 432-499 of FIG. 5) between the VH and VL genes to generate pscFvNQ11, the sequence of which is shown in FIG. 13. This scFv was cloned into the Pst1/XhoI site of FdTPs/Xh (as described earlier) to generate pAb NQ11 has an internal Pst1 site and so it was necessary to do a complete digest of pscFvNQ11 with XhoI followed by a partial digest with Pst1).

The specific binding of pAb NQ11 was confirmed using ELISA. ELISA plates were coated at 37° C. in 50 mM NaHCO3 at a protein concentration of 200 µg/ml. Plates were coated with either hen egg lysozyme (HEL), bovine serum albumin (BSA), or BSA conjugated to oxazolone (OX-BSA) (method of conjugation in Makela O., Kartinen M., Pelkonen J. L. T., Karjalainen K. (1978) J. Exp. Med. 148 1644). Preparation of phage, binding to ELISA plates, washing and detection was as described in example 6. Samples were assayed in duplicate and the average absorbance after 10 minutes presented in FIG. 14.

Figures 14, 15:
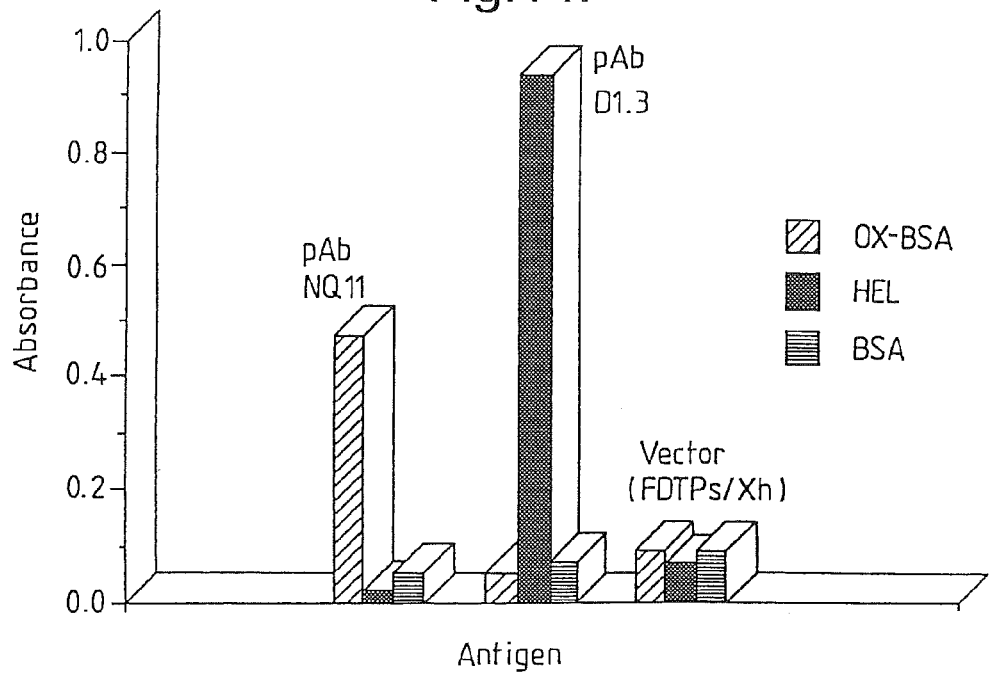
FIG. 14 shows the ELISA results for binding pAb NQ11 and pAb D1.3 and vector fdTPs/xh to specified antigens.
FIG. 15 shows the sequence surrounding the phoA insertion in fd-phoAla166. The restriction sites used for cloning are shown, as well as the amino acids encoded by phoA around the insertion site. The first five amino acids of the mature fusion come from gene III.

This result demonstrates that the pAb NQ11 binds the correct antigen. FIG. 14 also shows that pAb D1.3 and pAb NQ11 bind only to the antigen against which the original antibodies were raised.

Example 10

Enrichment of pAb D1.3 from Mixtures of Other pAb by Affinity Purification $3 \times 10^{10}$ phage in 10 mls of PBSM at the ratios of pAb D1.3 to pAb NQ11 shown in table 2 were passed over a 1 ml lysozyme Sepharose column. Washing, elution and other methods were as described in example 8 unless otherwise stated. Eluates from the columns were used to infect TG1 cells which were then plated out. Colonies were probed with a probe which distinguishes pAb D1.3 from pAb NQ11. The sequence of this oligonucleotide (D1.3CDR3A) is: -5'GTA GTC AAG CCT ATA ATC TCT CTC 3' (SEQ ID NO:8). Table 2 presents the data from this experiment. An enrichment of almost 1000 fold was achieved in one round and an enrichment of over a million fold in two rounds of purification. This parallels the result described in example 8.

Example 11

Insertion of a Gene Encoding an Enzyme (Alkaline Phosphatase) into fd-CAT2

As an example of the expression of a functional enzyme on the bacteriophage surface, the applicants have chosen bacterial alkaline phosphatase, an enzyme that normally functions as a dimer (McCracken, S. and Meighen, E., J. Biol. Chem. 255, p2396-2404, (1980)). The oligonucleotides were designed to generate a PCR product with an Apa L1 site at the 5' end of phoA gene and a Not 1 site at its 3' end, thus facilitating cloning into fd-CAT 2 to create a gene III fusion protein. The oligonucleotides synthesised were: phoA1:5' TAT TCT CAC AGT GCA CAA ACT GTT GAA CGG ACA CCA GAA ATG CCT GTT CTG 3' (SEQ ID NO:9) and, phoA2:5' ACA TGT ACA TGC GGC CGC TTT CAG CCC CAG AGC GGC TTT C 3' (SEQ ID NO:10). The sequence of the phoA gene is presented in Chang C. N. et al., Gene 44, p121-125 (1986). The plasmid amplified (pEK86) contains an alkaline phosphate gene which differs from the sequence of Chang et al, by a mutation which converts arginine to alamine at position 166.

The PCR reaction was carried out in 100 µl of 10 mM Tris/HCl pH 8.3, containing 50 mM KCl, 5 mMdNTP 2.5 mM MgCl2, 0.01% gelatin, 0.25 units/µl of Taq polymerase (Cetus/Perkin Elmer) and 0.5 µg/ml template. The template was the pEK86 plasmid (described by Chaidaroglou et al., Biochemistry 27 p8338-8343, 1988). The PCR was carried out in a Techne (Techne, Duxford, Cambridge, UK) PHC-2 dri-block using thirty cycles of 1 min at 92° C., 2 min at 50° C., 3 min at 72° C.

The resultant product was extracted with phenol:chloroform, precipitated with ethanol, and the pellet dissolved in 35 µl water. Digestion with 0.3 units/µl of Apa L1 as carried out in 150 µl volume according to manufacturers instructions for two hours at 37° C. After heat inactivation of the enzyme at 65° C., NaCl was added to a final concentration of 150 mM and 0.4 units/µl Not1 enzyme added. After incubation for 2 hours at 37° C., the digest was extracted with phenol:chloroform and precipitated as above, before being dissolved in 30 µl of water. The vector fd-CAT2 was sequentially digested with Apa L1 and Not1 according to the manufacturers instructions and treated with calf intestinal alkaline phosphatase as described in example 2. The sample was extracted three times with phenol:chloroform, precipitated with ethanol and dissolved in water. The ligations were performed with a final DNA concentration of 1-2 ng/µl of both the cut fd-CAT2 and the digested PCR product. The ligations were transformed into competent TG1 cells and plated on 2×TY tet plates. Identification of clones containing the desired insert was by analytical PCR performed using the conditions and primers above, on boiled samples of the resulting colonies. The correct clone containing the phoA gene fused in frame to gene III was called fd-phoAla166. The sequence at the junction of the cloning region is given in FIG. 15.

Example 12

Measuring Enzyme Activity of Phage-Enzyme

Overnight cultures of TG1 or KS272 (E. coli cells lacking phoA. Strauch K. L., and Beckwith J. PNAS 85 1576-1580, 1988) cells containing either fd-phoA1a 166 or fd-CAT2 were grown at 37° C. in 2×TY with 15 µg/ml tetracycline. Concentrated, PEG precipitated phages were prepared as described earlier. Enzyme assays (Malamy, M. H. and Horecker B. L., Biochemistry 3, p1893-1897, (1964)) were carried out at 24° C. in a final concentration of 1M Tris/HCl pH 8.0, 1 mM 4-nitrophenyl phosphate (Sigma), 1 mM MgCl2. 100 µl of a two times concentrate of this reaction mixture was mixed with 100 µl of the test sample in a 96 well plate. Absorbance readings were taken every minute for 30 minutes at a wavelength of 405 nm in a Titretek Mk 2 plate reader. Initial reaction rates were calculated from the rate of change of absorbance using a molar absorbance of 17000 l/mol/cm.

Standard curves (amount of enzyme vs. rate of change of absorbance) were prepared using dilutions of purified bacterial alkaline phosphatase (Sigma type III) in 10 mM Tris/HCl pH 8.0, 1 mM EDTA. The number of enzyme molecules in the phage samples were estimated from the actual rates of change of absorbance of the phage samples and comparison to this standard curve.

The results in Table 3 show that alkaline phosphatase activity was detected in PEG precipitated material in the sample containing fd-phoAla166 but not fd-CAT2. Furthermore, the level of activity was consistent with the expected number of 1-2 dimer molecules of enzyme per phage. The level of enzyme activity detected was not dependent on the host used for growth. In particular, fd-phoAla166 grown on phoA minus hosts showed alkaline phosphatase activity.

Therefore, the phage expressed active alkaline phosphatase enzyme, from the phoA-gene III fusion, on the phage surface.

Example 13

Insertion of Binding Molecules into Alternative Sites in the Phage

The availability of an alternative site in the phage for the insertion of binding molecules would open up the possibility of more easily expressing more than one binding molecule e.g. an antibody fragment in a single pAb. This may be used to generate single or multiple binding specificities. The presence of two distinct binding activities on a single molecule will greatly increase the utility and specificity of this molecule. It may be useful in the binding of viruses with a high mutational rate such as human immunodeficiency virus. In addition, it may be used to bring antigens into close proximity (e.g. drug targetting or cell fusion) or it may act as a "molecular clamp" in chemical, immunological or enzymatic processes.

The vector fd-tet and the derivatives described here, have a single BamH1 site in gene 3. This has previously been used for the expression of peptide fragments on the surface of filamentous bacteriophage (Smith G P. (1985) Science 228 p1315-1317 and de la Cruz et al. (1988) J. Biol. Chem. 263 p4318-4322). This provides a potential alternative site for the insertion of antibody fragments.

DNA fragments encoding scFv's from D1.3 or NQ11 were generated by PCR using the primers shown below. These primers were designed to generate a fragment with BamH1 sites near both the terminii, to enable cloning into the BamH1 site of gene3 (see FIG. 16a). The oligonucleotides used, also ensure that the resulting PCR product lacks Pst1 and XhoI restriction sites normally used for manipulating the scFv's (see FIG. 16a). This will facilitate subsequent manipulation of a second antibody fragment in the usual way at the N terminus of gene 3. The oligonucleotides used were:

```
G3Bam1                                    (SEQ ID NO:11)
5' TTT AAT GAG GAT CCA CAG GTG CAG CTG CAA GAG 3'

G3Bam2                                    (SEQ ID NO:12)
5' AAC GAA TGG ATC CCG TTT GAT CTC AAG CTT 3'.
```

Preparation of Vector and PCR Insert

The PCR reaction was carried out in an 80 µl reaction as described in example 11 using 1 ng/µl of template and 0.25 U/µl of Taq polymerase and a cycle regime of 94° C. for 1 minute, 60° C. for 1 minute and 70° C. for 2 minutes over 30 cycles. The template was either pscFvNQ11 (example 9) or scFvD1.3 myc (example 2). Reaction products were extracted with phenol:chloroform, precipitated, dissolved in water and digested with BamH1 according to manufacturers instructions. The digest was re-extracted with phenol:chloroform, precipitated and dissolved in water.

The vector fdTPs/Xh was cleaved with BamH1 and treated with calf intestinal phosphatase and purified as described in example 2. Ligations were set up at a vector concentration of approximately 6 ng/µl and a PCR insert concentration of approximately 3 ng/µl. These were ligated for 2.5 hours at room temperature before transforming into competent TG1 cells and plating on TY tet plates. The resultant colonies were probed as described in example 8. DNA was prepared from a number of colonies and the correct orientation and insert size confirmed by restriction digestion with Hind III in isolation or in combination with BamH1. (One Hind III site is contributed by one of the primers and the other by the vector).

Figure 16:
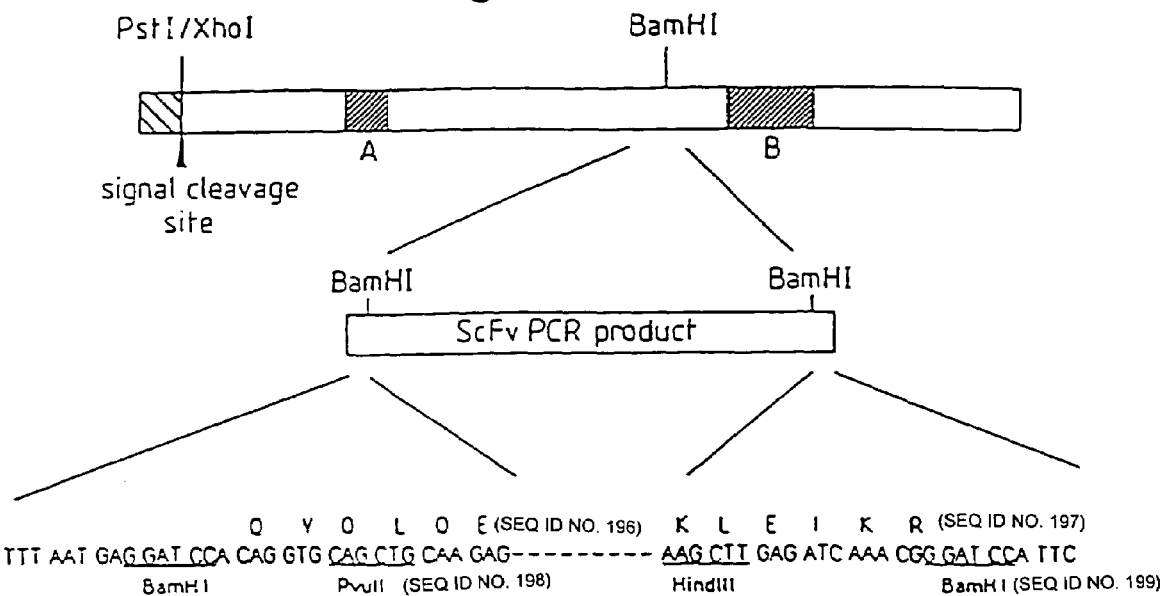
FIG. 16a shows the structure of gene III and the native BamHI site into which a scFv coding sequence was inserted in example 13 and FIG. 16b shows the natural peptide linker sites A and B for possible insertion of scFv coding sequences.
Figure 18:
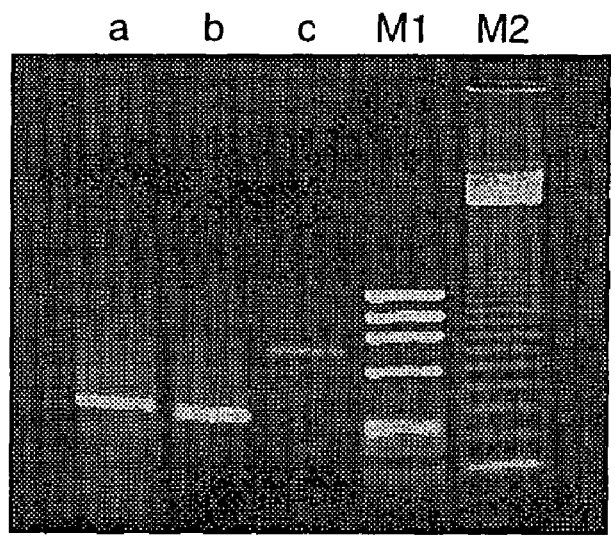
FIG. 18 shows examples of the final products obtained with the procedure of example 14. Lanes a and b show the products of the initial PCR using heavy and light chain primers respectively; lane c shows the complete assembled 700 bp product before final digestion with Not1 and ApaL1; M1, M2 markers Φ174 Hae III digest and 123 base pair ladder (BRL Limited, P.O. Box 35, Washington Road, Paisley, Scotland) respectively.

Two clones containing a D1.3 insert (fdTBam1) and fdT-Bam2) and one containing an NQ11 insert (NQ11Bam1) were grown up and phage prepared as described earlier. ELISAs were carried out as described in example 6. No specific signal was found for any of these clones suggesting that the natural BamH1 site is not a suitable site for insertion of a functional antibody (results not shown). It may be possible to clone into alternative sites to retain binding activity. The peptide repeats present in gene III may provide such a site (FIG. 16 blocks A and B). This can be done by inserting a BamH1 site and using the PCR product described above. To facilitate this, the natural BamH1 site was removed by mutagenesis with the oligonucleotide G3mutδBam shown below (using an in vitro mutagenesis kit (Amersham International)): -G3mutδBam 5' CA AAC GAA TGG <u>G</u>TC CTC CTC ATT A 3' (SEQ ID NO:13). The underlined residue replaces an A residue, thereby removing the BamH1 site. DNA was prepared from a number of clones and several mutants lacking BamH1 sites identified by restriction digestion.

The oligonucleotide G3 Bamlink was designed to introduce a BamH1 site at a number of possible sites within the peptide linker sites A and B, see FIG. 16b. The sequence of the linker is: Bamlink 5'CC (G or A) CC ACC CTC <u>GGA TCC</u> (G or A) CC ACC CTC 3' (SEQ ID NO:14). Its relationship to the peptide repeats in gene III is shown in FIG. 16

Example 14

PCR Assembly of Mouse VH and VL Kappa (VLK) Repertoires for Phage Display

The principle is illustrated in FIG. 17. Details are provided in sections A to F below but the broad outline is first discussed.

1. cDNA is prepared from spleen RNA from an appropriate mouse and the VH and VLK repertoires individually amplified. Separately, primers reverse and complementary to VH1FOR-2 (domain 1) and VLK2BACK (domain 2) are used to amplify an existing scFv-containing DNA by PCR. (The term FOR refers to e.g. a primer for amplification of sequences on the sense strand resulting in antisense coding sequences. The term BACK refers to e.g. a primer for amplification of sequences on the antisense strand resulting in sense coding sequences). This generates a 'linker' molecule encoding the linker with the amino acid sequence (1 letter code) (GGGGS)$_3$ (SEQ ID NO:15) which overlaps the two primary (VH and VLK) PCR products.

2. The separate amplified VH, VLK and linker sequences now have to be assembled into a continuous DNA molecule by use of an 'assembly' PCR. In the secondary 'assembly' PCR, the VH, VLK and linker bands are combined and assembled by virtue of the above referred to overlaps. This generates an assembled DNA fragment that will direct the expression of VH and one VLK domain. The specific VH/VLK combination is derived randomly from the separate VH and VLK repertoires referred to above. The assembly PCR is carried out in two stages. Firstly, 7 rounds of cycling with just the three bands present in the PCR, followed by a further 20 rounds in the presence of the flanking primers VH1BACK (referring to domain 1 of VH) and VLKFOR. The nucleotide sequences for these oligonucleotide primers are provided under the section entitled 'Primer Sequences' below. This two stage process, avoids the potential problem of preferential amplification of the first combinations to be assembled.

For cloning into the phage system, the assembled repertoires must be 'tagged' with the appropriate restriction sites. In the example provided below this is illustrated by providing an ApaL1 restriction site at the VH end of the continuous DNA molecule and a Not 1 site at the VLK end of the molecule. This is carried out by a third stage PCR using tagged primers. The nucleotide sequences for these oligonucleotide primers are also provided under the section entitled 'Primer Sequences' below. There are however, 4 possible kappa light chain sequences (whereas a single consensus heavy chain sequence can be used). Therefore 4 oligonucleotide primer sequences are provided for VLK.

For this third stage PCR, sets of primers which create the new restriction site and have a further 10 nucleotides on the 5' side of the restriction site have been used. However, long tags may give better cutting, in which case 15-20 nucleotide overhangs could be used.

Scrupulously clean procedures must be used at all times to avoid contamination during PCR. Negative controls containing no DNA must always be included to monitor for contamination. Gel boxes must be depurinated. A dedicated Geneclean kit (B10 101, Geneclean, La Jolla, San Diego, Calif., USA) can be used according to manufacturers instructions to extract DNA from an agarose gel. The beads, NaI and the NEW wash should be aliquoted.

All enzymes were obtained from CP Laboratories, P.O. Box 22, Bishop's Stortford, Herts CM20 3DH and the manufacturers recommended and supplied buffers were used unless otherwise stated.

A. RNA Preparation

RNA can be prepared using may procedures well known to those skilled in the art. As an example, the following protocol (Triton X-100 lysis, phenol/SDS RNase inactivation) gives excellent results with spleen and hybridoma cells (the addition of VRC (veronal ribosyl complex) as an RNase inhibitor is necessary for spleen cells). Guanidinium isothiocyanate/CsC1 procedures (yielding total cellular RNA) also give good results but are more time-consuming.

1. Harvest 1 to $5 \times 10^7$ cells by centrifugation in a bench tope centrifuge at 800 xg for 10 minutes at 4° C. Resuspend gently in 50 ml of cold PBS buffer. Centrifuge the cells again at 800 xg for 10 minutes at 4° C., and discard supernatant.
2. On ice, add 1 ml ice-cold lysis buffer to the pellet and resuspend it with a 1 ml Gilson pepette by gently pepetting up and down. Leave on ice for 5 minutes.
3. After lysis, remove cell debris by centrifuging at 1300 rpm for 5 minutes in a microfuge at 4° C., in precooled tubes.
4. Transfer 0.5 ml of the supernatant to each of two eppendorfs containing 60 µl 10% (w/v) SDS and 250 µl phenol (previously equilibrated with 100 mM Tris-HCl pH 8.0). Vortex hard for 2 minutes, then microfuge (13000 rpm) for five minutes at room temperature. Transfer the upper, aqueous, phase to a fresh tube.
5. Re-extract the aqueous upper phase five times with 0.5 ml of phenol.
6. Precipitate with 1/10 volume 3M sodium acetate and 2.5 volumes ethanol at 20° C. overnight or dry ice-isopropanol for 30 minutes.
7. Wash the RNA pellet and resuspended in 50 µl to check concentration by OD260 and check 2 µg on a 1% agarose gel. 4 µg of RNA was obtained from spleen cells derived from mice.

Lysis buffer is [10 mM Tris-HCl pH 7.4, 1 mM MgCl2, 150 mM NaCl, 10 mM VRC (New England Biolabs), 0.5% (w/v) Triton X-100], prepared fresh.

Lysis buffer is [10 mM Tris-HCl pH 7.4, 1 mM $MgCl_2$, 150 mM NaCl, 10 mM VRC (New England Biolabs), 0.5% (w/v) Triton X-100], prepared fresh.

B. cDNA Preparation cDNA can be prepared using many procedures well known to those skilled in the art. As an example, the following protocol can be used:

1. Set up the following reverse transcription mix:

|  | µl |
| --- | --- |
| H₂O (DEPC-treated) | 20 |
| 5 mM dNTP | 10 |
| 10× first strand buffer | 10 |
| 0.1M DTT | 10 |
| FOR primer(s) (10 pmol/µl) | 2 (each) (see below) |
| RNasin (Promega; 40 U/µl) | 4 |

NB
i) DEPC is diethylpyrocarbonate, the function of which is to inactivate any enzymes that could degrade DNA or RNA
ii) dNTP is deoxynucleotide triphosphate
iii) DTT is dithiothreitol the function of which is as an antioxidant to create the reducing environment necessary for enzyme function.
iv) RNasin is a ribonuclease inhibitor obtained from Promega Corporation, 2800 Woods Hollow Road, Madison, Wis., USA.

2. Dilute 10 µg RNA to 40 µl final volume with DEPC-treated water. Heat at 65° C. for 3 minutes and hold on ice for one minute (to remove secondary structure).
3. Add to the RNA the reverse transcription mix (58 µl) and 4 µl of the cloned reverse transcriptase 'Super RT' (Anglian Biotech Ltd., Whitehall House, Whitehall Road, Colchester, Essex) and incubate at 42° C. for one hour.
4. Boil the reaction mix for three minutes, cool on ice for one minute and then spin in a microfuge to pellet debris. Transfer the supernatant to a new tube. 10× first strand buffer is [1.4M KCl, 0.5M Tris-HCl pH 8.1 at 42° C. 80 mM $MgCl_2$].

The primers anneal to the 3' end. Examples of kappa light chain primers are MJK1FONX, MJK2FONX, MJK4FONX and MJK5FONX (provided under 'Primer Sequences' below) and examples of heavy chain primers are MIGG1, 2 (CTG GAC AGG GAT CCA GAG TTC CA) (SEQ ID NO:16) and MIGG3 (CTG GAC AGG GCT CCA TAG TTC CA) (SEQ ID NO:17) which anneal to CH1.

Alternatively, any primer that binds to the 3' end of the variable regions VH, VLK, VL, or to the constant regions CH1, CK or CL can be used.

C. Primary PCRs

For each PCR and negative control, the following reactions are set up (e.g. one reaction for each of the four VLKs and four VH PCRs). In the following, the Vent DNA polymerase sold by (C.P. Laboratories Ltd (New England Biolabs) address given above) was used. The buffers are as provided by C.P. Laboratories.

|  | µl |
| --- | --- |
| H₂O | 32.5 |
| 10× Vent buffer | 5 |
| 20× Vent BSA | 2.5 |
| 5 mM dNTPs | 1.5 |
| FOR primer 10 pmol/µl | 2.5 |
| BACK primer 10 pmol/µl | 2.5 |

The FOR and BACK primers are given in the section below entitled 'Primer Sequences'. For VH, the FOR primer is VH1FOR-2 and the BACK primer is VH1BACK. For VLK the FOR primers are MJK1FONX, MJK2FONX, MJK4FONX and MJK5FONX (for the four respective kappa light chains) and the BACK primer is VK2BACK. Only one kappa light chain BACK primer is necessary, because binding is to a nucleotide sequence common to the four kappa light chains.

UV this mix 5 minutes. Add 2.5 μl cDNA preparation (from B above), 2 drops paraffin oil (Sigma Chemicals, Poole, Dorset, UK). Place on a cycling heating block, e.g. PHC-2 manufactured by Techne Ltd. Duxford UK, pre-set at 94° C. Add 1 μl Vent DNA polymerase under the paraffin. Amplify using 25 cycles of 94° C. 1 min, 72° C. 2 min. Post-treat at 60° C. for 5 min.

Purify on a 2% lmp (low melting point agarose/TAE (tris-acetate EDTA) gel and extract the DNA to 20 μl H₂O per original PCR using a GENECLEAN kit (see earlier; Bio101, La Jolla Calif., USA) in accordance with the manufacturers instructions.

D. Preparation of Linker

Set up in bulk (e.g. 10 times)

|  | μl |
|---|---|
| H₂O | 34.3 |
| 10× Vent buffer | 5 |
| 20× Vent BSA | 2.5 |
| 5 mM dNTPs | 2 |
| LINKFOR primer 10 pmol/μl) | 2.5 |
| LINKBACK primer 10 pmol/μl | 2.5 |
| DNA from fcFv D1.3 (example 2) | 1 |
| Vent enzyme | 0.2 |

The FOR and BACK primers are given in the section below entitled 'Primer Sequences'. The FOR primer is LINKFOR and the BACK primer is LINKBACK. Cover with paraffin and place on the cycling heating block (see above) at 94° C. Amplify using 25 cycles of 94° C. 1 min 65° C. 1 min, 72° C. 2 min. Post-treat at 60° C. for 5 min.

Purify on 2% lmp/TAE gel (using a loading dye without bromophenol blue as a 93 bp fragment is desired) and elute with SPIN-X column (Costar Limited, 205 Broadway, Cambridge, Mass. USA.,) and precipitation. Take up in 5 μl H₂O per PCR reaction.

E. Assembly PCRs

A quarter of each PCR reaction product (5 μl) is used for each assembly. The total volume is 25 μl.

For each of the four VLK primers, the following are set up:

|  | |
|---|---|
| H₂O | 4.95 |
| 10× Vent buffer | 2.5 |
| 20× Vent BSA | 1.25 |
| 5 mM dNTPs | 0.8 |

UV irradiate this mix for 5 min. Add 5 μl each of Vh and VK band from the primary PCRs and 1.5 μl of linker as isolated from the preparative gels and extracted using the Geneclean kit as described in C and D above. Cover with paraffin. Place on the cycling heating block preset at 94° C. Add 1 μl Vent under the paraffin. Amplify using 7 cycles of 94° C. 2 min 72° C. 4 min. Then return the temperature to 94° C.

Add 1.5 μl each of VH1BACK and the appropriate VKFOR primers MJK1FONX, MJK2FONX, MJK4FONX or MJK5FONX (10 pmol/μl) at 94° C. The primers should have been UV-treated as above. Amplify using 20 cycles of 94° C. 1.5 min 72° C. 2.5 min. Post-treat at 60° C. for 5 min. Purify on 2% lmp/TAE gel and extract the DNA to 20 μl H₂O per assembly PCR using a Geneclean kit (see earlier) in accordance with the manufacturers instructions.

F. Adding Restriction Sites

For each assembly and control set up:

|  | μl |
|---|---|
| H₂O | 36.5 |
| 10× Taq buffer | 5 |
| 5 mM dNTPs | 2 |
| FOR primer (10 pmol/μl) | 2.5 |
| BACK primer (10 pmol/μl) | 2.5 |
| Assembly product | 1 |

The FOR and BACK primers are given in the section below entitled 'Primer Sequences'. The FOR primer is any of JK1NOT10, JK2NOT10, JK4NOT10 or JK5NOT10 (for the four respective kappa light chains) for putting a Not1 restriction site at the VLK end. The BACK primer is HBKAPA10 for putting an ApaL1 restriction site at the VH end.

Cover with paraffin and place on the cycling heating block preset at 94° C. Add 0.5 μl Cetus Taq DNA polymerase (Cetus/perkin-Elmer, Beaconsfield, Bucks, UK) under the paraffin. Amplification is carried out using 11 to 15 rounds of cycling (depends on efficiency) at 94° C. 1 min, 55° C. 1 min, 72° C. 2 min. Post-treat at 60° C. for 5 min.

10×Taq buffer is [0.1M Tris-HCl pH 8.3 at 25° C., 0.5M KCl, 15 mM MgCl₂, 1 mg/ml gelatin].

G. Work-up

Purify once with CHCl₃/IAA (isoamylalcohol), once with phenol, once with CHCl₃/IAA and back-extract everything to ensure minimal losses. Precipitate and wash twice in 70% EtOH. Dissolve in 70 μl H₂O.

| Digest overnight at 37° C. with NotI: | μl |
|---|---|
| DNA (joined seq) | 70 |
| NEB NotI buffer × 10 | 10 |
| NEB BSA × 10 | 10 |
| NotI (10 U/μl) | 10 |

The DNA (joined sequence) above refers to the assembled DNA sequence comprising in the 5' to 3' direction ApaL1 restriction site VH sequence Linker sequence VLK sequence Not 1 restriction site.

The VLK sequence may be any one of four possible kappa chain sequences.

The enzymes Not 1 above, ApaL1 below and the buffers NEB Not 1, NEB BSA above and the NEB buffer 4 (below) are obtainable from CP Laboratories, New England Biolabs mentioned above.

Re-precipitate, take up in 80 μl H₂O. Add to this 10 μl NEB buffer 4 and 10 μl Apal 1.

Add the enzyme ApaL1 in aliquots throughout the day, as it has a short half-life at 37° C.

Purify on 2% lmp/TAE gel and extract the DNA using a Geneclean kit, in accordance with the manufacturers instructions. Redigest if desired.

H. Final DNA product

The final DNA product is an approximate 700 bp fragment with Apa L1 and Not1 compatible ends consisting of randomly associated heavy and light chain sequences linked by a linker. A typical molecule of this type is the scFvD1.3 molecule incorporated into fdscFvD1.3 described in example 3. These molecules can then be ligated into suitable fd derived vectors, e.g. fdCAT2 (example 5), using standard techniques.

Primer Sequences

Primary PCR oligos (restrictions sites underlined):

```
VH1FOR-2   TGA GGA GAC GGT GAC CGT GGT CCC      (SEQ ID NO:18)
           TTG GCC CC

VH1BACK    AGG TSM ARC TGC AGS AGT CWG G        (SEQ ID NO:19)

MJK1FONX   CCG TTT GAT TTC CAG CTT GGT GCC      (SEQ ID NO:20)

MJK2FONX   CCG TTT TAT TTC CAG CTT GGT CCC      (SEQ ID NO:21)

MJK4FONX   CCG TTT TAT TTC CAA CTT TGT CCC      (SEQ ID NO:22)

MJK5FONX   CCG TTT CAG CTC CAG CTT GGT CCC      (SEQ ID NO:23)

VK2BACK    GAC ATT GAG CTC ACC CAG TCT CCA      (SEQ ID NO:24)
```

Ambiguity codes M=A or C, R=A or G, S=G or C, W=A or T

PCR oligos to make linker:

```
LINKFOR    TGG AGA CTC GGT GAG CTC AAT GTC      (SEQ ID NO:25)

LINKBACK   GGG ACC ACG GTC ACC GTC TCC TCA      (SEQ ID NO:26)
```

For adding restriction sites:

```
HBKAPA10   CAT GAC CAC AGT GCA CAG GTS MAR CTG CAG SAG TCW GG      (SEQ ID NO:27)

JKINOT10   GAG TCA TTC TGC GGC CGC CCG TTT GAT TTC CAG CTT GGT GCC (SEQ ID NO:28)

JK2NOT10   GAG TCA TTC TGC GGC CGC CCG TTT TAT TTC CAG CTT GGT CCC (SEQ ID NO:29)

JK4NOT10   GAG TCA TTC TGC GGC CGC CCG TTT TAT TTC CAA CTT TGT CCC (SEQ ID NO:30)

JK5NOT10   GAG TCA TTC TGC GGC CGC CCG TTT CAG CTC CAG CTT GGT CCC.(SEQ ID NO:31)
```

Example 15

Insertion of the Extracellular Domain of a Human Receptor for Platelet Derived Growth Factor (PDGF) Isoform BB into fd CAT2

A gene fragment encoding the extracellular domain of the human receptor for platelet derived growth factor isoform BB (h-PDGFB-R) was isolated by amplification, using the polymerase chain reaction, of plasmid RP41, (from the American Type Culture collection, Cat. No. 50735), a cDNA clone encoding amino-acids 43 to 925 of the PDGF-B receptor (Gronwald, R. G. K. et al PNAS 85 p3435-3439 (1988)). Amino acids 1 to 32 of h-PDGFB-R constitute the signal peptide. The oligonucleotide primers were designed to amplify the region of the h-PDGFB-R gene corresponding to amino acids 43 to 531 of the encoded protein. The primer RPDGF3 for the N-terminal region also included bases encoding amino acids 33 to 42 of the h-PDGFB-R protein (corresponding to the first ten amino acids from the N-terminus of the mature protein) to enable expression of the complete extracellular domain. The primers also incorporate a unique ApaL1 site at the N-terminal end of the fragment and a unique Xho1 site at the C terminal end to facilitate cloning into the vector fdCAT2. The sequence of the primers is:

```
RPDGF3                                          (SEQ ID NO:32)
5' CAC AGT GCA CTG GTC GTC ACA CCC CCG GGG CCA
GAG CTT GTC CTC AAT GTC TCC AGC ACC TTC GTT
CTG 3'

RPDGF2                                          (SEQ ID NO:33)
5' GAT CTC GAG CTT AAA GGG CAA GGA GTG TGG CAC 3'
```

PCR amplification was performed using high fidelity conditions (Eckert, K. A. and Kunkel, T. A. 1990 Nucl Acids Research 18 3739-3744). The PCR mixture contained: 20 mM TrisHCl (pH7.3 at 70° C., 50 mM KCl, 4 mM magnesium chloride, 0.01% gelatin, 1 mM each of dATP, dCTP, dGTP and dTTP, 500 ng/ml RP41 DNA, 1 µM each primer and 50 units/ml Taq polymerase (Cetus/Perkin Elmer, Beaconsfield, Bucks, U.K.). Thirty cycles of PCR were performed with denaturation at 92° C. for 1 min, annealing at 60° C. for 1 min and extension at 72° C. for 1.5 min. This reaction resulted in amplification of a fragment of ca. 1500 bp as expected.

fdCAT2 vector DNA (see example 5) was digested with ApaL1 and XhoI (New England Biolabs) according to manufacturers recommendations, extracted with phenol/chloroform and ethanol precipitated (Sambrook et al, supra). Cloning of amplified RP41 DNA into this vector and identification of the desired clones was performed essentially as in example 7 except that digestion of the PCR product was with ApaL1 and Xho 1. Colonies containing h-PDGFB-R DNA were identified by probing with 32p labelled RPDGF2 and the presence of an insert in hybridising colonies was confirmed by analytical PCR using RPDGF3 and RPDGF2 using the conditions described in example 7.

Example 16

Binding of 125I-PDGF-BB to the Extracellular Domain of the Human Receptor for Platelet Derived Growth Factor Isoform BB Displayed on the Surface of fd Phage. Measured Using an Immunoprecipitation Assay.

Phage particles, expressing the extracellular domain of the human platelet derived growth factor isoform BB receptor (fd h-PDGFB-R), were prepared by growing E. coli MC1061 cells transformed with fd h-PDGFB-R in 50 ml of 2×TY medium with 15 ug/ml tetracycline for 16 to 20 hours. Phage particles were concentrated using polyethylene glycol as described in example 6 and resuspended in PDGF binding buffer (25 mM HEPES, pH7.4, 0.15 mM NaCl, 1 mM magnesium chloride, 0.25% BSA) to ⅓rd of the original volume. Residual bacteria and undissolved material were removed by spinning for 2 min in a microcentrifuge. Immunoblots using an antiserum raised against gene III protein (Prof. I. Rashed, Konstanz, Germany) show the presence in such phage preparations of a geneIII-h-PDGFB-R protein of molecular mass 125000 corresponding to a fusion between h-PDGFB-R external domain (55000 daltons) and geneIII (apparent molecular mass 70000 on SDS-polyacrylamide gel).

Duplicate samples of 35 μl concentrated phage were incubated with $^{125}$I-PDGF-BB (78.7 fmol, 70 nCi, 882 Ci/mmol; Amersham International plc, Amersham, Bucks) for 1 hour at 37° C. Controls were included in which fdTPs/Bs vector phage (FIG. 4) or no phage replaced fd h-BDGFB-R phage. After this incubation, 10 μl of sheep anti-M 13 polyclonal antiserum (a gift from M. Hobart) was added and incubation continued for 30 min at 20° C. To each sample, 40 μl (20 μl packed volume) of protein G Sepharose Fast Flow (Pharmacia, Milton Keynes) equilibrated in PDGF binding buffer was added. Incubation was continued for 30 min at 20° C. with mixing by end over end inversion on a rotating mixer. The affinity matrix was spun down in a microcentrifuge for 2 min and the supernatant removed by aspiration. Non-specifically bound $^{125}$I-PDGF-BB was removed by resuspension of the pellet in 0.5 ml PDGF binding buffer, mixing by rotation for 5 min, centrifugation and aspiration of the supernatant, followed by two further washes with 0.5 ml 0.1% BSA, 0.2% Triton-X-100. The pellet finally obtained was resuspended in 100 μl PDGF binding buffer and counted in a Packard gamma counter. For displacement studies, unlabelled PDGF-BB (Amersham International) was added to the stated concentration for the incubation of $^{125}$I-PDGF-BB with phage.

Figure 19:
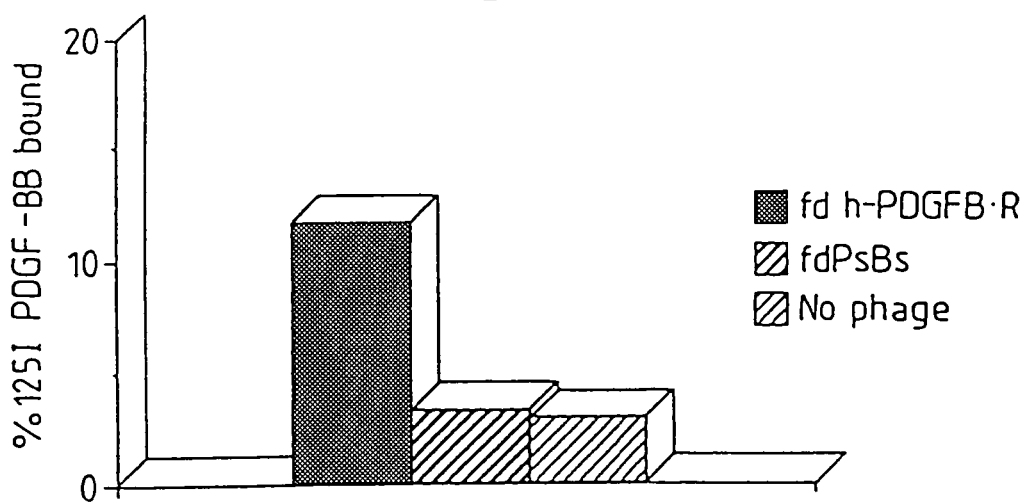
FIG. 19 shows the binding of $^{125}$I-PDGF-BB to fd h-PDGFB-R phage in immunoprecipitation assay and comparison to fdTPs/Bs and no phage controls; binding is expressed as a percentage of the total $^{125}$I-PDGF-BB added to the incubation.
Figure 20:
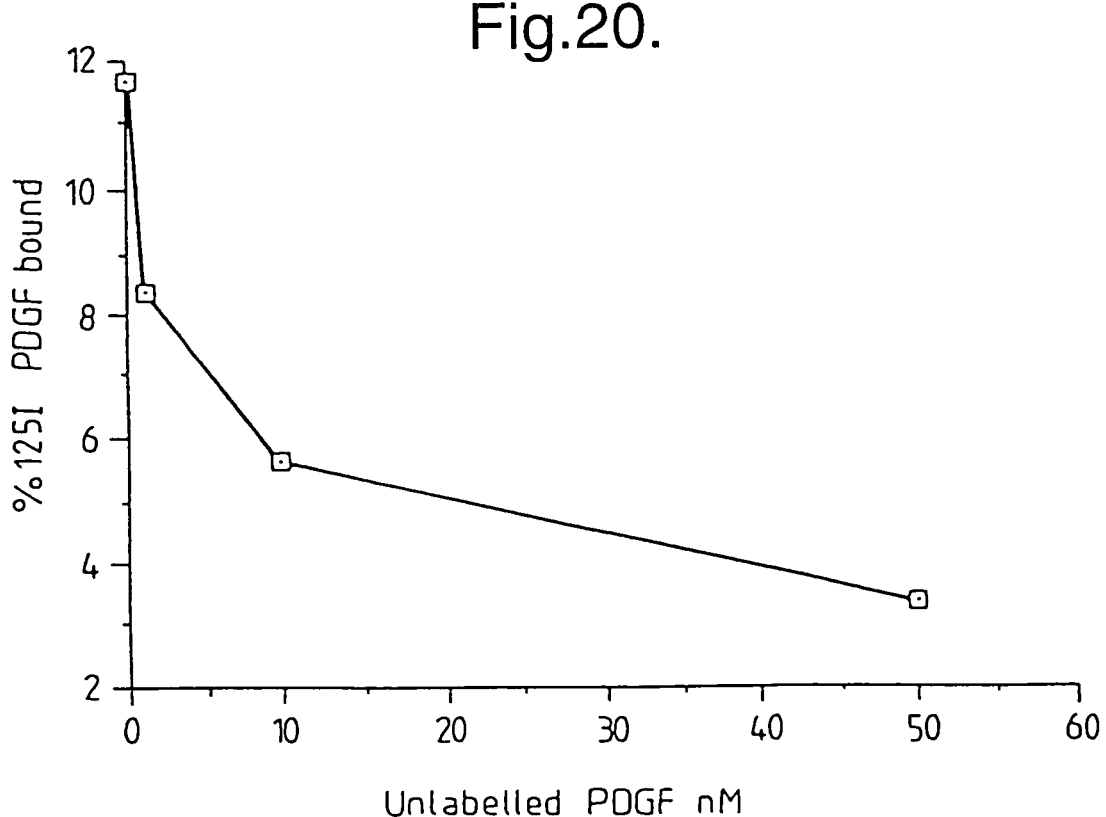
FIG. 20 shows the displacement of $^{125}$I-PDGF-BB bound to fd-h-PDGFB-R phage using unlabelled PDGF-BB measured using an immunoprecipitation assay. Binding is expressed as a percentage of the total $^{125}$I-PDGF-BB added to the incubation.
Figure 21:
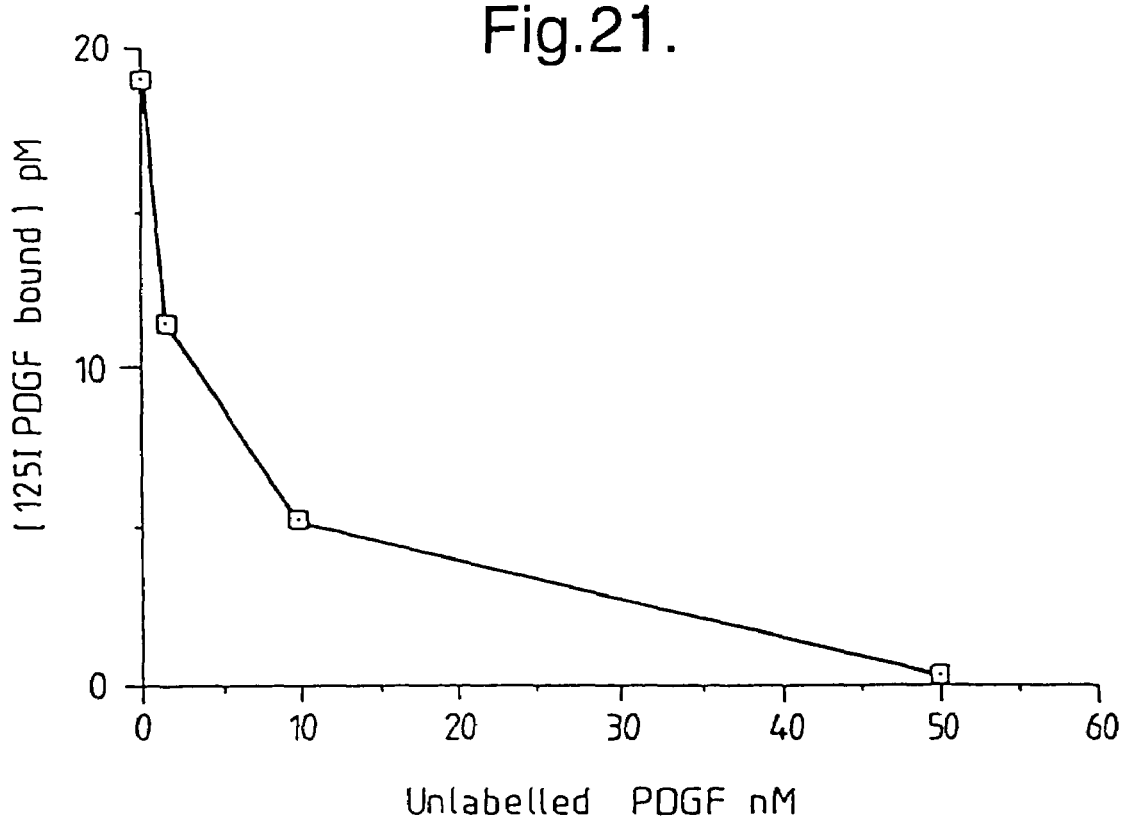
FIG. 21 shows the displacement of $^{125}$I-PDGF-BB bound to fd-h-PDGFB-R phage using unlabelled PDGF-BB measured using an immunoprecipitation assay. Non-specific binding of $^{125}$I-PDGF-BB to vector phage fdTPs/Bs in the absence of added unlabelled PDGF was deducted from each point.

$1_{25}$I-PDGF-BB bound to the fd h-PDGFB-R phage and was immunoprecipitated in this assay. Specific binding to receptor phage was 3.5 to 4 times higher than the non-specific binding with vector phage fdTPs/Bs or no phage (FIG. 19). This binding of $^{125}$I-PDGF-BB could be displaced by the inclusion of unlabelled PDGF-BB in the incubation with phage at 37□C (FIG. 20). At 50 nM, unlabelled PDGF-BB the binding of $^{125}$I-PDGF-BB was reduced to the same level as the fdTPs/Bs and no phage control. FIG. 21 shows the same data, but with the non-specific binding to vector deducted.

These results indicate that a specific saturable site for $^{125}$I-PDGF-BB is expressed on fd phage containing cloned h-PDGFB-R DNA. Thus, the phage can display the functional extracellular domain of a cell surface receptor.

Example 17

Construction of Phagemid Containing GeneIII Fused with the Coding Sequence for a Binding Molecule It would be useful to improve the transfection efficiency of the phage-binding molecule system and also to have the possibility of displaying different numbers and specificities of binding molecules on the surface of the same bacteriophage. The applicants have devised a method that achieves both aims.

The approach is derived from the phagemid system based on pUC119 [Vieira, J and Messing, J. (1987) Methods Enzymol. 153:3]. In brief, gene III from fd-CAT2 (example 5) and gene III scFv fusion from fd-CAT2 scFv D1.3 (example 2) were cloned downstream of the lac promoter in separate samples of pUC119, in order that the inserted gene III and gene III fusion could be 'rescued' by M13M07 helper phage [Vieira, J and Messing, J. et supra.] prepared according to Sambrootz et al. 1989 supra. The majority of rescued phage would be expected to contain a genome derived from the pUC119 plasmid that contains the binding molecule-gene III fusion and should express varying numbers of the binding molecule on the surface up to the normal maximum of 3-5 molecules of gene III of the surface of wild type phage. The system has been exemplified below using an antibody as the binding molecule.

An fdCAT2 containing the single chain Fv form of the D1.3 antilysozyme antibody was formed by digesting fdTscFvD1.3 (example 2) with PstI and XhoI, purifying the fragment containing the scFv fragment and ligating this into PstI and XhoI digested fdCAT2. The appropriate clone, called fdCAT2 scFvD1.3 was selected after plating onto 2×TY tetracycline (15 μg/ml) and confirmed by restriction enzyme and sequence analysis.

Gene III from fd-CAT2 (example 5) and the gene III scFv fusion from fd-CAT2 scFvD1.3 was PCR-amplified using the primers A and B shown below:

```
Primer A:                           (SEQ ID NO:34)
TGC GAA GCT TTG GAG CCT TTT TTT TTG GAG ATT
TTC AAC G.

Primer B:                           (SEQ ID NO:35)
CAG TGA ATT CCT ATT AAG ACT CCT TAT TAC GCA
GTA TGT TAG C.
```

Primer A anneals to the 5' end of gene III including the ribosome binding site is located and incorporates a Hind III site. Primer B anneals to the 3' end of gene III at the C-terminus and incorporates two UAA stop codons and an EcoR1 site. 100 ng of fd-CAT2 and fd-CAT2 scFv D1.3 DNA was used as templates for PCR-amplification in a total reaction volume of 50 μl as described in example 7, except that 20 cycles of amplification were performed: 94° C. 1 minute, 50° C. 1 minute, 72° C. 3 minutes. This resulted in amplification of the expected 1.2 Kb fragment from fd-CAT2 and a 1.8 Kb fragment from fd-CAT2 scFv D1.3.

The PCR fragments were digested with EcoR1 and Hind III, gel-purified and ligated into Eco-R1- and Hind III-cut and dephosphorylated pUC119 DNA and transformed into *E. coli* TG1 using standard techniques (Sambrook et al., et supra). Transformed cells were plated on SOB agar (Sambrook et al. 1989 supra) containing 100 μg/ml ampicillin and 2% glucose. The resulting clones were called pCAT-3 (derived from fd-CAT2) and pCAT-3 scFv D1.3 (derived from fd-CAT2 scFv D1.3).

Example 18

Rescue of Anti-Lysozyme Antibody Specificity from pCAT-3 scFv D1.3 by M13KO7

Single pCAT-3 and pCAT-3 scFv D1.3 colonies were picked into 1.5 ml 2TY containing 100 μg/ml ampicillin and 2% glucose, and grown 6 hrs at 30° C. 30 μl of these stationary cells were added to 6 mls 2YT containing 100 μg/ml ampicillin and 2% glucose in 50 ml polypropylene tubes (Falcon, Becton Dickinson Labware, 1950 Williams Drive, Oxnard, Calif. USA) and grown for 1.5 hrs at 30° C. at 380 rpm in a New Brunswick Orbital Shaker (New Brunswick Scientific Ltd., Edison House 163 Dixons Hill road, North Mimms, Hatfield, UK). Cells were pelleted by centrifugation at 5,000 g for 25 minutes and the tubes drained on tissue paper. The cell pellets were then suspended in 6 mls 2TY containing $1.25 \times 10^9$ p.f.u. ml$^{-1}$ M13KO7 bacteriophage added. The mixture was left on ice for 5 minutes followed by growth at 35° C. for 45 minutes at 450 rpm. A cocktail was then added containing 4 µl 100 µg/ml ampicillin, 0.5 µl 0.1M IPTG and 50 µl 10 mg/ml kanamycin, and the cultures grown overnight at 35° C., 450 rpm.

The following day the cultures were centrifuged and phage particles PEG precipitated as described in example 6. Phage pellets were resuspended in 100 µl TE (tris-EDTA see example 6) and phage titred on *E. coli* TG1. Aliquots of infected cells were plated on 2TY containing either 100 µg/ml ampicillin to select for pUC119 phage particles, or 50 µg/ml kanamycin to select for the M13 KO7 helper phage. Plates were incubated overnight at 37° C. and antibiotic-resistant colonies counted:

| DNA | amp$^R$ | kan$^R$ |
|---|---|---|
| pCAT-3 colonies | $1.8 \times 10^{11}$ colonies | $1.2 \times 10^9$ |
| pCAT-3scFv D1.3 colonies | $2.4 \times 10^{11}$ colonies | $2.0 \times 10^9$ |

This shows that the amp$^R$ phagemid particles are infective and present in the rescued phage population at a 100-fold excess over kan$^R$ M13KO7 helper phage.

Figure 22:
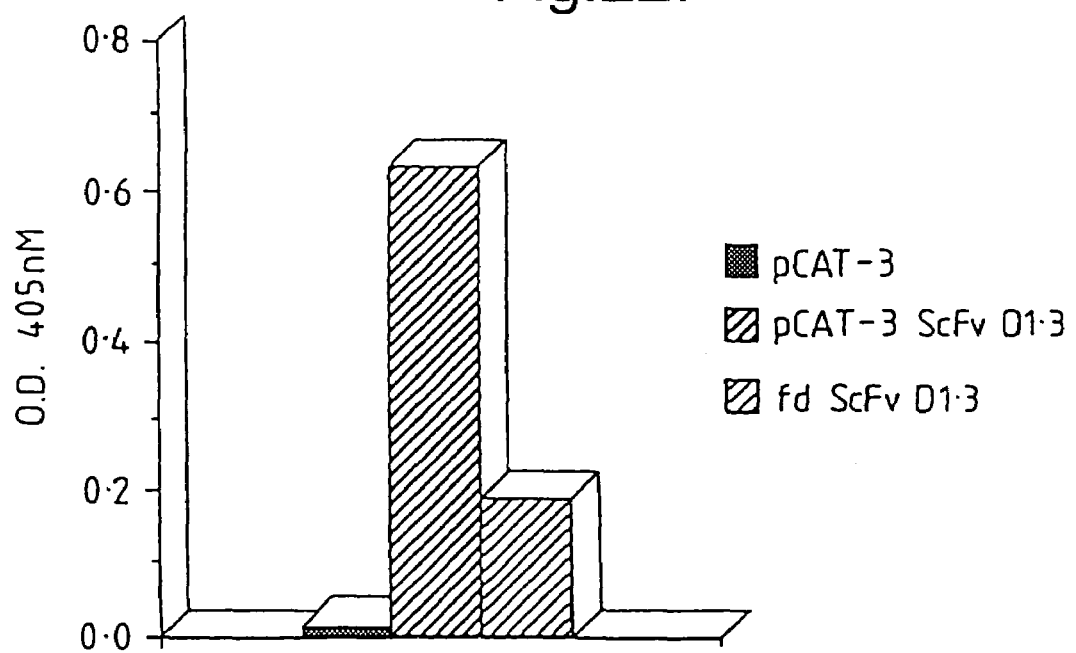
FIG. 22 shows the results of an ELISA of lysozyme binding by pCAT-3 scFv D1.3 phagemid in comparison with pCAT-3 vector (both rescued by M13K07) and fdCAT2 scFv D1.3 as described in example 17. The ELISA was performed as described in example 6 with modifications detailed in example 18.

Phage were assayed for anti-lysozyme activity by ELISA as described in example 6, with the following modifications:
1) ELISA plates were blocked for 3 hrs with 2% Marvel/PBS.
2) 50 µl phage, 400 µl 1×PBS and 50 µl 20% Marvel were mixed end over end for 20 minutes at room temperature before adding 150 µl per well.
3) Phage were left to bind for 2 hours at room temperature.
4) All washes post phage binding were:
   2 quick rinses PBS/0.5% Tween 20
   3×2 minute washes PBS/0.5% Tween 20
   2 quick rinses PBS no detergent
   3×2 minute washes PBS no detergent The result of this ELISA is shown in FIG. 22, which shows that the antibody specificity can indeed be rescued efficiently.

It is considered a truism of bacterial genetics that when mutant and wild-type proteins are co-expressed in the same cell, the wild-type proteins are co-expressed in same cell, the wild-type protein is used preferentially. This is analogous to the above situation wherein mutant (i.e. antibody fusion) and wild-type gene III proteins (from M13K07) are competing for assembly as part of the pUC119 phagemid particle. It is therefore envisaged that the majority of the resulting pUC119 phage particles will have fewer gene III-antibody fusion molecules on their surface than is the case for purely phage system described for instance in example 2. Such phagemid antibodies are therefore likely to bind antigen with a lower avidity than fd phage antibodies with three or more copies of the antibody fusion on their surfaces (there is no wild-type gene III, in the system described, for instance, in example 2), and provide a route to production of phage particles with different numbers of the same binding molecule (and hence different acidities for the ligand/antigen) or multiple different binding specificities on their surface, by using helper phage such as M13K07 to rescue cells expressing two or more gene III-antibody fusions.

It is also possible to derive helper phage that do not encode a functional gene III in their genomes (by for example deleting the gene III sequence or a portion of it or by incorporating an amber mutation within the gene). These defective phages will only grow on appropriate cells (for example that provide functional gene III in trans, or contain an amber supressor gene), but when used to rescue phage antibodies, will only incorporate the gene III antibody fusion encoded by the phagemid into the released phage particle.

Example 19

Transformation Efficiency of pCAT-3 and pCAT-3 scFv D1.3 Phagemids pUC 19, pCAT-3 and pCAT-3 scFv D1.3 plasmid DNAs, and fdCAT-2 phage DNA was prepared, and used to transform *E. coli* TG1, pCAT-3 and pCAT-3 scFv D1.3 transformations were plated on SOB agar containing 100 µg/ml ampicillin and 2% glucose, and incubated overnight at 3° C. fdCAT-2 transformations were plated on TY agar containing 15 µg/ml tetracycline and incubated overnight at 37° C. Transformation efficiencies are expressed as colonies per µg of input DNA.

| DNA | Transformation efficiency |
|---|---|
| pUC 19 | $1.10^9$ |
| pCAT-3 | $1.10^8$ |
| pCAT-3scFv D1.3 | $1.10^8$ |
| fd CAT-2 | $8.10^5$ |

As expected, transformation of the phagemid vector is approximately 100-fold more efficient that the parental fdCAT-2 vector. Furthermore, the presence of a scFv antibody fragment does not compromise efficiency. This improvement in transformation efficiency is practically useful in the generation of phage antibodies libraries that have large repertoires of different binding specificities.

Example 20

PCR Assembly of a Single Chain Fv Library from an Immunised Mouse

To demonstrate the utility of phage for the selection of antibodies from repertoires, the first requirement is to be able to prepare a diverse, representative library of the antibody repertoire of an animal and display this repertoire on the surface of bacteriophage fd.

Cytoplasmic RNA was isolated according to example 14 from the pooled spleens of five male Balb/c mice boosted 8 weeks after primary immunisation with 2-phenyl-5-oxazolone (ph OX) coupled to chicken serum albumin. cDNA preparation and PCR assembly of the mouse VH and VL kappa repertoires for phage display was as described in example 14. The molecules thus obtained were ligated into fdCAT2.

Figure 23A:
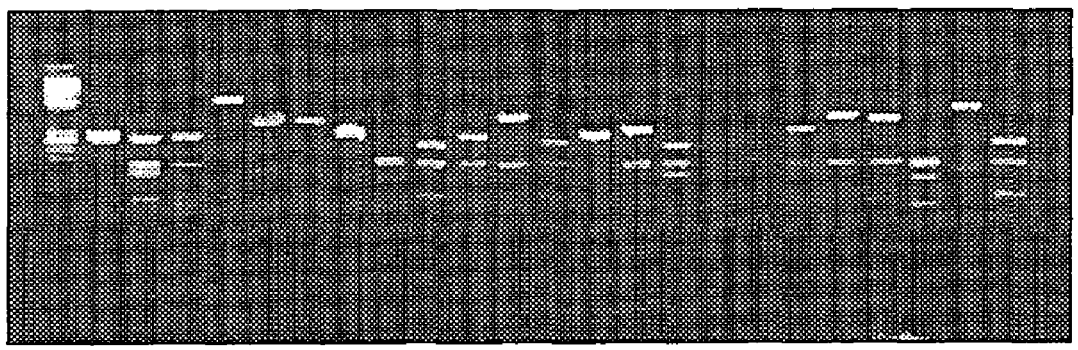
FIGS. 23a-23b show the digestion pattern seen when individual clones, selected at random from a library of single chain Fv antibody genes derived from an immunised mouse; are digested with BstN1
Figure 23B:
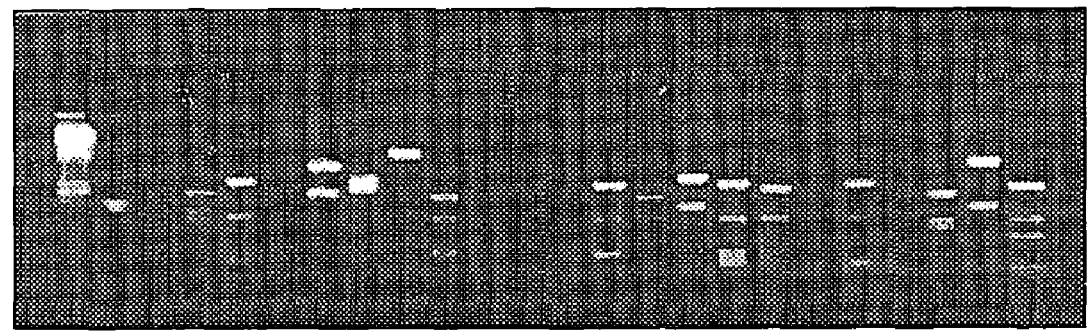

Vector fdCAT2 was extensively digested with Not1 and ApaL1., purified by electroelution (Sambrook et al. 1989 supra) and 1 µg ligated to 0.5 µg (5 µg for the hierarchical libraries: see example 22) of the assembled scFv genes in 1 ml with 8000 units T4 DNA ligase (New England Biolabs). The ligation was carried out overnight at 16□C. Purified ligation mix was electroporated in six aliquots into MC1061 cells (W. J. Dower, J. F. Miller & C. W. Ragsdale Nucleic Acids Res. 16 6127-6145 1988) and plated on NZY medium (Sambrook et al. 1989 supra) with 15 µg/ml tetracycline, in 243×243 mm dishes (Nunc): 90-95% of clones contained scFv genes by PCR screening. Recombinant colonies were screened by PCR (conditions as in example 7 using primers VH1BACK and MJK1FONX, MJK2FONX, MJK4FONX and MJK5FONX (see example 14) followed by digestion with the frequent cutting enzyme BstN1 (New England Biolabs, used according to the manufacturers instructions). The library of $2\times10^5$ clones appeared diverse as judged by the variety of digestion patterns seen in FIG. 23a and FIG. 23b, and sequencing revealed the presence of most VH groups (R. Dildrop, Immunol. Today 5 85-86. 1984) and VK subgroups (Kabat. E. A. et al. 1987 supra) (data not shown). None of the 568 clones tested bound to phOx as detected by ELISA as in example 9.

Thus the ability to select antibody provided by the use of phage antibodies (as in example 21) is essential to readily isolate antibodies with antigen binding activity from randomly combined VH and VL domains. Very extensive screening would be required to isolate antigen-binding fragments if the random combinatorial approach of Huse et al. 1989 (supra) were used.

Example 21

Selection of Antibodies Specific for 2-phenyl-5-oxazolone from a Repertoire Derived from an Immunised Mouse The library prepared in example 20 was used to demonstrate that ability of the phage system to select antibodies on the basis of their antibody specificity.

None of the 568 clones tested from the unselected library bound to phOx as detected by ELISA.

Screening for binding of the phage to hapten was carried out by ELISA: 96-well plates were coated with 10 µg/ml phOx-BSA or 10 µg/ml BSA in phosphate-buffered saline (PBS) overnight at room temperature. Colonies of phage-transduced bacteria were inoculated into 200 µl 2×TY with 12.5 µg/ml tetracycline in 96-well plates ('cell wells', Nuclon) and grown with shaking (300 rpm) for 24 hours at 37° C. At this stage cultures were saturated and phage titres were reproducible ($10^{10}$ TU/ml). 50 µl phage supernatant, mixed with 50 µl PBS containing 4% skimmed milk powder, was then added to the coated plates. Further details as in example 9.

The library of phages was passed down a phOx affinity column (Table 4A), and eluted with hapten. Colonies from the library prepared in example 22 were scraped into 50 ml 2×TY medium[37] and shaken at 37° C. for 30 min. Liberated phage were precipitated twice with polyethylene glycol and resuspended to $10^{12}$ TU (transducing units)/ml in water (titred as in example 8). For affinity selection, a 1 ml column of phOx-BSA-Sepharose (O. Makela, M. Kaartinen, J. L. T. Pelonen and K. Karjalainen J. Exp. Med. 148 1644-1660, 1978) was washed with 300 ml phosphate-buffered saline (PBS), and 20 ml PBS containing 2% skimmed milk powder (MPBS). $10^{12}$ TU phage were loaded in 10 ml MPBS, washed with 10 ml MPBS and finally 200 ml PBS. The bound phage were eluted with 5 ml 1 mM 4-ε-amino-caproic acid methylene 2-phenyl-oxazol-5-one (phOx-CAP; O. Makela et al. 1978, supra). About $10^6$ TU eluted phage were amplified by infecting 1 ml log phase *E. coli* TG1 and plating as above. For a further round of selection, colonies were scraped into 10 ml 2×TY medium and then processed as above. Of the eluted clones, 13% were found to bind to phOx after the first round selection, and ranged from poor to strong binding in ELISA.

To sequence clones, template DNA was prepared from the supernatants of 10 ml cultures grown for 24 hours, and sequenced using the dideoxy method and a Sequenase kit (USB), with primer LINKFOR (see example 14) for the VH genes and primer fdSEQ1 (5'-GAA TTT TCT GTA TGA GG-3') (SEQ ID NO:36) for the Vk genes. Twenty-three of these hapten-binding clones were sequenced and eight different VH genes (A to H) were found in a variety of pairings with seven different Vk genes (a to g) (FIG. 24). Most of the domains, such as VH-B and Vk-d were 'promiscuous', able to bind hapten with any of several partners.

The sequences of the V-genes were related to those seen in the secondary response to phOx, but with differences (FIG. 24). Thus phOx hybridomas from the secondary response employ somatically mutated derivatives of three types of Vk genes—Vkoxl. 'Vkox-like' and Vk45.1 genes (C. Berek, G. M. Griffiths & C. Milstein Nature 316 412-418 (1985). These can pair with VH genes from several groups, from Vkoxl more commonly pairs with the VHox1 gene (VH group 2. R. Dildrop uupra). Vkoxl genes are always, and Vkox-like genes often, found in association with heavy chains (including VHox1) and contain a short five residue CDR3, with the sequence motif Asp-X-Gly-X-X (SEQ ID NO:37) in which the central glycine is needed to create a cavity for phOx. In the random combinatorial library however, nearly all of the VH genes belonged to group 1, and most of the Vk genes were ox-like and associated with VH domains with a five residue CDR3, motif Asp/Asn-X-Gly-X-X (SEQ ID NO:38) (FIG. 24). Vkoxl and VHox1 were found only once (Vk-f and VH-E), and not in combination with each other. Indeed Vk-f lacks the Trp91 involved in phOx binding and was paired with a VH (VH-C) with a six residue CDR3.

Figure 25:
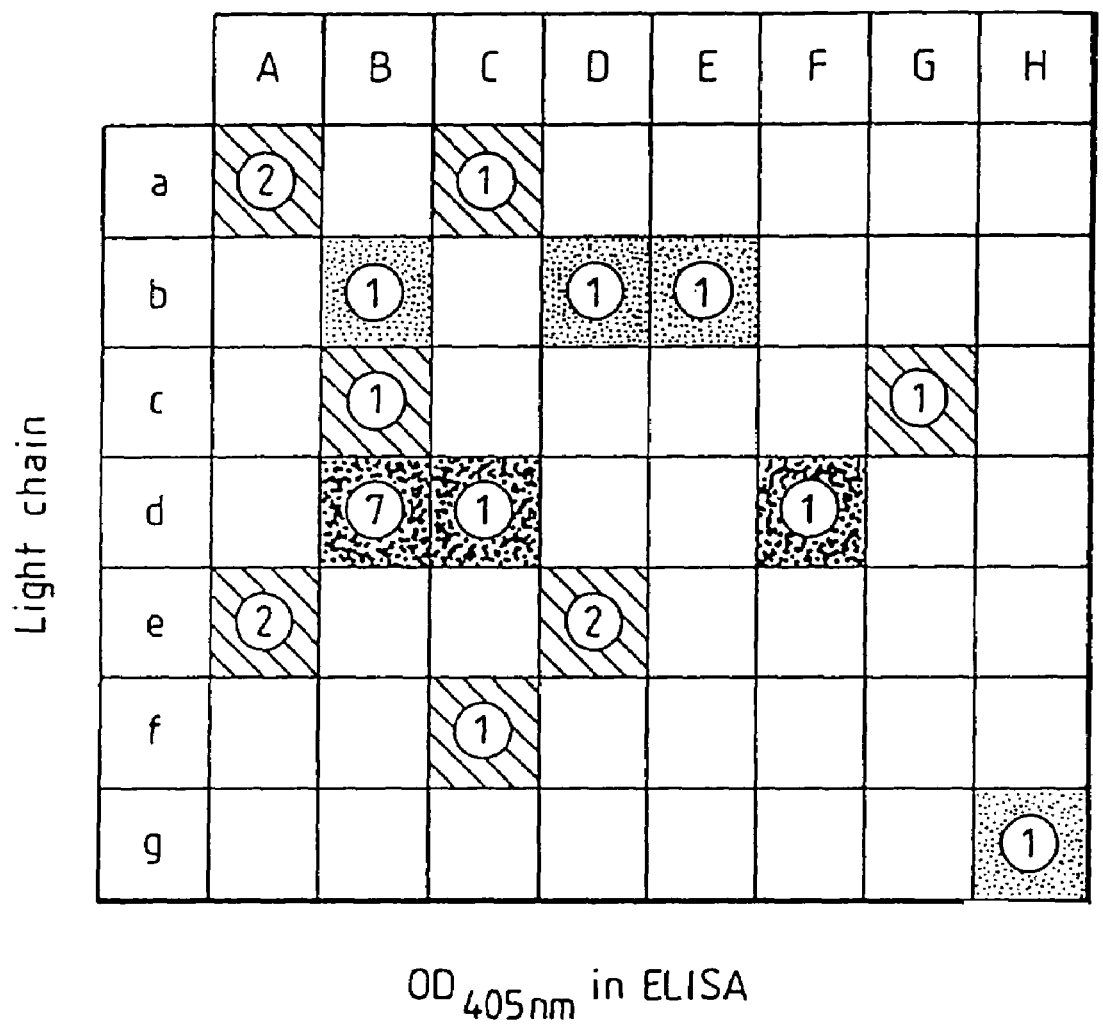

A matrix combination of VH and VK genes was identified in phOx-binding clones selected from this random combinational library. The number of clones found with each combination are shown in FIG. 25. The binding to phOx-BSA, as judged by the ELISA signal, appeared to vary (marked by shading in FIG. 25). No binding was seen to BSA alone.

A second round of selection of the original, random combinational library from immune mice resulted in 93% of eluted clones binding phOx (Table 4). Most of these clones were Vk-d combinations, and bound strongly to phOx in ELISA (data not shown). Few weak binders were seen. This suggested that affinity chromatography had not only enriched for binders, but also for the best.

Florescence quench titrations determined the Kd of VH-B/Vk-d for phOx-GABA as $10^{-8}$ M (example 23), indicating that antibodies with affinities representative of the secondary response can be selected from secondary response, only two (out of eleven characterised) secrete antibodies of a higher affinity than VH-B/Vk-d (C. Berek et al. 1985 supra). The Kd of VH-B/Vk-b for phOx-GABA was determined as $10^{-5}$ M (example 23). Thus phage bearing scFv fragments with weak affinities can be selected with antigen, probably due to the avidity of the multiple antibody heads on the phage.

This example shows that antigen specificities can be isolated from libraries derived from immunised mice. It will often be desired to express these antibodies in a soluble form for further study and for use in therapeutic and diagnostic applications. Example 23 demonstrates determination of the affinity of soluble scFv fragments selected using phage antibodies. Example 27 demonstrates that soluble fragments have similar properties to those displayed on phage. For many purposes it will be desired to construct and express an antibody molecule which contains the Fc portions of the heavy chain, and perhaps vary the immunoglobulin isotype. To accomplish this, it is necessary to subclone the antigen binding sites identified using the phage selection system into a vector for expression in mammalian cells, using methodology similar to that described by Orlandi, R. et al. (1989, supra). For instance, the VH and VL genes could be amplified separately by PCR with primers containing appropriate restriction sites and inserted into vectors such as pSV-gpt HuIgG1 (L. Riechmann et al Nature 332 323-327), 1988) which allows expression of the VH domain as part of a heavy chain IgG1 isotype and pSV-hyg HuCK which allows expression of the VL domain attached to the K light chain constant region. Furthermore, fusions of VH and VL domains can be made with genes encoding non-immunoglobulin proteins, for example, enzymes.

Example 22

Generation of Further Antibody Specificities by the Assembly of Hierarchical Libraries Further antibody specificities were derived from the library prepared and screened in examples 20 and 21 using a hierarchical approach.

The promiscuity of the VH-B and Vk-d domains prompted the applicants to force further pairings, by assembling these genes with the entire repertoires if either Vk or VH genes from the same immunised mice. The resulting 'hierarchical' libraries, (VH-B×Vk-rep and VH-rep×Vk-d), each with $4 \times 10^7$ members, were subjected to a round of selection and hapten-binding clones isolated (Table 4). As shown by ELISA, most were strong binders. By sequencing twenty-four clones from each library, the applicants identified fourteen new partners for VH-B and thirteen for Vk-d (FIG. 24). Apart from VH-B and Vk-c, none of the previous partners (or indeed other clones) from the random combinatorial library was isolated again. Again the Vk genes were mainly ox-like and the VH genes mainly group 1 (as defined in Dildrop, R. 1984 supra), but the only examples of Vkoxl (Vk-h, -p, -q and -r) have Trp91, and the VH-CDR3 motif Asp-X-Gly-X-X (SEQ ID NO:37) now predominates. Thus some features of the phOx hybridomas seemed to emerge more strongly in the hierarchical library. The new partners differed from each other mainly by small alterations in the CDRs, indicating that much of the subtle diversity had remained untapped by the random combinatorial approach. More generally it has been shown that a spectrum of related antibodies can be made by keeping one of the partners fixed and varying the other, and this could prove invaluable for fine tuning of antibody affinity and specificity.

Therefore, again, phage antibodies allow a greater range of antibody molecules to be analysed for desired properties.

This example, and example 21, demonstrate the isolation of individual antibody specificities through display on the surface of phage. However, for some purposes it may be more desirable to have a mixture of antibodies, equivalent to a polyclonal antiserum (for instance, for immunoprecipitation). To prepare a mixture of antibodies, one could mix clones and express soluble antibodies or antibody fragments or alternatively select clones from a library to give a highly enriched pool of genes encoding antibodies or antibody fragments directed against a ligand of interest and express antibodies from these clones.

Example 23

Selection of Antibodies Displayed on Bacteriophage with Different Affinities for 2-phenyl-5-oxazolone Using Affinity Chromatography The ELISA data shown in example 21 suggested that affinity chromatography had not only enriched for binders, but also for the best. To confirm this, the binding affinities of a strong binding and a weak binding phage were determined and then demonstrated that they could be separated from each other using affinity chromatography.

Clones VH-B/Vk-b and VH-B/Vk-d were reamplified with MJK1FONX, MJK2FONX, MJK4FONX and MJK5FONX (see example 14) and VH1BACK-SfiI (5'-TCG C GG CCC AGC CGG CCA TGG CC(G/C) AGG T(C/G)(A/C) A(A/G)C TGC AG(C/G) AGT C(A/T)G G-3') (SEQ ID NO:39), a primer that introduces an SfiI site (underlined) at the 5' end of the VH gene. VH-B/Vk-d was cloned into a phagemid e.g. pJM1 (a gift from A. Griffiths and J. Marks) as an SfiI-NotI cassette, downstream of the pelB leader for periplasmic secretion (M. Better at al. supra), with a C-terminal peptide tag for detection (see example 24 and figure), and under th control of a PL promoter (H. Shimatake & M. Rosenberg Nature 292 128-132 1981). The phagemid should have the following features: a) unique SfiI and Not1 restriction sites downstream of a pelB leader; b) a sequence encoding a C-terminal peptide tag for detection; and c) a $\lambda$ $P_L$ promoter controlling expression. 10 litre cultures of *E. coli* N4830-1 (M. E. Gottesman, S. Adhya & A. Das J. Mol. Biol 140 57-75 1980) harbouring each phagemid were induced as in K. Nagai & H. C. Thogerson (Methods Enzymol 153 461-481 1987) and supernatants precipitated with 50% ammonium sulphate. The resuspended precipitate was dialysed into PBS+0.2 mM EDTA (PBSE), loaded onto a 1.5 ml column of phOx: Sepharose and the column washed sequentially with 100 ml PBS: 100 ml 0.1 M Tris-HCl, 0.5 M NaCl, pH 8.0: 10 ml 50 mM citrate, pH 5.0: 10 ml 50 mM citrate, pH4.0, and 20 ml 50 mM glycine, pH 3.0. scFv fragments were eluted with 50 mM glycine, pH 2.0, neutralised with Tris base and dialysed against PBSE. VH-B/Vk-b was cloned into a phagemid vector based on pUC119 encoding identical signal and tag sequences to pJM1, and expression induced at 30° C. in a 10 litre culture of *E. coli* TG1 harbouring the phagemid as in D. de Bellis & I. Schwartz (1980 Nucleic Acids Res 18 1311). The low affinity of clone VH-B/Vk-b made its purification on phOx-Sepharose impossible. Therefore after concentration by ultrafiltration (Filtron, Flowgen), the supernatant (100 ml of 600 ml) was loaded onto a 1 ml column of protein A-Sepharose coupled (E. Harlow & D. Lane 1988 supra) to the monoclonal antibody 9E10 (Evan, G. I. et al. Mol. Cell Biol. 5 3610-3616 1985) that recognises the peptide tag. The column was washed with 200 ml PBS and 50 ml PBS made 0.5 M in NaCl. scFv fragments were eluted with 100 ml 0.2M glycine, pH 3.0, with neutralisation and dialysis as before.

The Kd ($1.0 \pm 0.2 \times 10^{-8}$ M) for clone VH-B/Vk-d was determined by fluorescence quench titration with 4-E-amino-butyric acid methylene 2-phenyl-oxazol-5-one (phOx-GABA Co. Makela et al, 1978 supra). Excitation was at 280 nm, emission was monitored at 340 nm and the $K_d$ calculated. The $K_d$ of the low affinity clone VH-B/Vk-b was determined as $1.8 \pm 0.3 \times 10^{-5}$ M (not shown). To minimise light adsorption by the higher concentrations of phOx-GABA required, excitation was at 260 nm and emission was monitored at 304 nm. In addition the fluorescence values were divided by those from a parallel titration of the lysozyme binding Fv fragment D1.3. The value was calculated as in H. N. Eisen Meth. Med. Res. 10 115-121 1964. A mixture of clones VH-B/Vk-b and VH-B/Vk-d, $7 \times 10^{10}$ TU phage in the ratio 20 VH-B/Vk-b:1 VH-B/Vk-d were loaded onto a phOx-BSA-Sepharose column in 10 ml MPBS and eluted as above. Eluted phage were used to reinfect *E. coli* TG1, and phage produced and harvested as before. Approximately $10^{11}$ TU phage were loaded onto a second affinity column and the process repeated to give a total of three column passes. Dilutions of eluted phage at each stage were plated in duplicate and probed separately with oligonucleotides specific for Vk-b (5'-GAG CGG GTA ACC ACT GTA CT-3')(SEQ ID NO:40) or Vk-d (5'-GAA TGG TAT AGT ACT ACC CT-3')(SEQ ID NO:41). After these two rounds, essentially all the eluted phage were VH-B/Vk-d (table 4). Therefore phage antibodies can be selected on the basis of the antigen affinity of the antibody displayed.

Example 24

Construction of Phagemid pHEN1 for the Expression of Antibody Fragments Expressed on the Surface of Bacteriophage Following Superinfection The phagemid pHEN1 (FIG. 26(*a*)) is a derivative of pUC119 (Vieira, J. & Messing, J. Methods Enzymol 153 pp 3-11, 1987). The coding region of g3p from fdCAT2, including signal peptide and cloning sites, was amplified by PCR, using primers G3FUFO and G3FUBA (given below) (which contain EcoRI and HindIII sites respectively), and cloned as a HindIII-EcoRI fragment into pUC119. The HindIII-NotI fragment encoding the g3p signal sequence was the replaced by a pelB signal peptide (Better, M. et al. Science 240 1041-1043, 1988) with an internal SfiI site, allowing antibody genes to be cloned as fiI-NotI fragments. A peptide tag, c-myc, (Munro, S. & Pelham, H. Cell 46 291-300, 1986) was introduced directly after the NotI site by cloning an oligonucleotide cassette, and followed by an amber codon introduced by site-directed mutagenesis using an in vitro mutagenesis kit (Amersham International) (FIG. 26(*b*)).

```
G3FUFO,                                            (SEQ ID NO:42)
5'-CAG TGA ATT CTT ATT AAG ACT CCT TAT TAC GCA
GTA TGT TAG C-3';

G3FUBA,                                            (SEQ ID NO:43)
5'-TGC GAA GCT TTG GAG CCT TTT TTT TTG GAG ATT
TTC AAC G-3';
```

Example 25

Display of Single Chain Fv and Fab Fragments Derived from the Anti-Oxazolone Antibody NQ10.12.5 on Bacteriophage fd Using pHEN1 and fdCAT2

Figure 27:
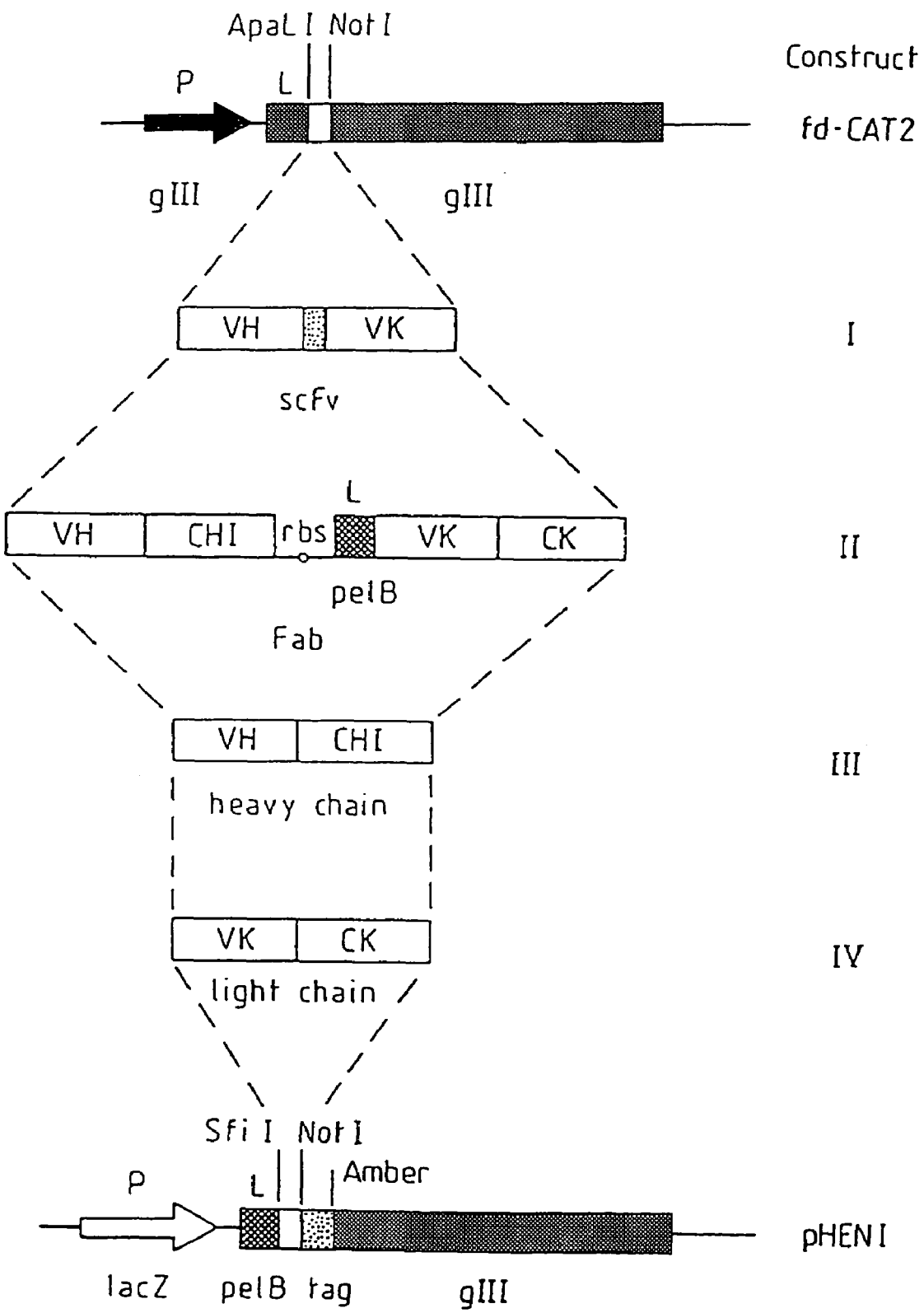
FIG. 27. The antibody constructs cloned into fd-CAT2 and pHEN1 for display on the surface of phage. Constructs I, II, III and IV were cloned into both fd-CAT2 (as ApaLI-NotI fragments) and pHEN1 (as SfiI-NotI fragments) and pHEN1 (as SfiI-NotI fragments). All the constructs contained the heavy chain (VH) and light chain (VK) variable regions of the mouse anti-phOx antibody NQ10.12.5. The constant domains were human CK and CH1 (γ1 isotype).

A range of constructs (see FIG. 27) were made from a clone (essentially construct II in pUC19) designed for expression in bacteria of a soluble Fab fragment (Better et al. 1988 see above) from the mouse anti-phOx (2-phenyl-5-oxazolone) antibody NQ10.12.5 (Griffiths, G. M. et al. Nature 312, 271-275, 1984). In construct II, the V-regions are derived from NQ10.12.5 and attached to human Ck and CH1 (γ1 isotype) constant domains. The C-terminal cysteine residues, which normally form a covalent link between light and heavy antibody chains, have been deleted from both the constant domains. To clone heavy and light chain genes together as Fab fragments (construct II) or as separate chains (constructs III and IV) for phage display, DNA was amplified from construct II by PCR to introduce a NotI restriction site at the 3' end, and at the 5' end either an ApaLI site (for cloning into fd-CAT2) or SfiI sie (for cloning into pHEN1). The primers FABNOTFOK with VH1BACKAPA (or VH1BACKSFI15) were used for PCR amplification of genes encoding Fab fragments (construct II), the primers FABNOTFOH with VH1BACKAPA (or VH1BACKSFI15) for heavy chains (construct III), and the primers FABNOTFOK and MVKBAAPA (or MVKBASFI) for light chains (construct IV).

The single-chain Fv version of NQ10.12.5 (construct I) has the heavy (VH) and light chain (Vk) variable domains joined by a flexible linker (Gly$_4$Ser)$_3$ (Huston, J. S. et al. Proc. Natl. Acad. Sci. USA 85 5879-5883, 1988) and was constructed from construct II by 'splicing by overlap extension' as in example 14. The assembled genes were reamplified with primers VK3F2NOT and VH1BACKAPA (or VH1BACKSFI15) to append restriction sites for cloning into fd-CAT2 (ApaLI-NotI) or pHEN1 (SfiI-NotI).

```
VH1BACKAPA,    5'-CAT GAC CAC AGT GCA CAG GT(C/G)        (SEQ ID NO:44)
               (A/C)A(A/G) CTG CAG (C/G)AG TC(A/T) GG-3';

VH1BACKSFI15,  5'-CAT GCC ATG ACT CGC GGC CCA GCC GGC     (SEQ ID NO:45)
               CAT GGC C(C/G)A GGT (C/G) (A/C)A (A/G)CT
               GCA G(C/G)A GTC (A/T)GG-3';

FABNOTFOH,     5'-CCA CGA TTC TGC GGC CGC TGA AGA TTT GGG  (SEQ ID NO:46)
               CTC AAC TTT CTT GTC GAC-3';

FABNOTFOK,     5'-CCA CGA TTC TGC GGC CGC TGA CTC TCC GCG  (SEQ ID NO:47)
               GTT GAA GCT CTT TGT GAC-3';

MVKBAAPA,      5'-CAC AGT GCA CTC GAC ATT GAG CTC ACC CAG   (SEQ ID NO:48)
               TCT CCA-3';

MVKBASFI,      5'-CAT GAC CAC GCG GCC CAG CCG GCC ATG GCC   (SEQ ID NO:49)
               GAC ATT GAG CTC ACC CAG TCT CCA-3';

VK3F2NOT,      5'-TTC TGC GGC CGC CCG TTT CAG CTC GAG CTT   (SEQ ID NO:50)
               GGT CCC-3'.
```

Restriction sites are underlined.

Rescue of Phage and Phagemid Particles

Constructs I-IV (FIG. 27) were introduced into both fd-CAT2 and pHEN1. Phage fd-CAT2 (and fd-CAT2-I, II, III or IV) was taken from the supernatant of infected E. coli TG1 after shaking at 37° C. overnight in 2×TY medium with 12.5 µg/ml tetracycline, and used directly in ELISA. Phagemid pHEN1 (and pHEN1-I and II) in E. coli TG1 (supE) were grown overnight in 2 ml 2×TY medium, 100 µg/ml ampicillin, and 1% glucose (without glucose, expression of g3p prevents later superinfection by helper phage). 10 µl of the overnight culture was used to innoculate 2 ml of 2×TY medium, 100 µg/ml ampicillin, 1% glucose, and shaken at 37° C. for 1 hour. The cells were washed and resuspended in 2×TY, 100 µg/ml ampicillin, and a phagemid particles rescued by adding 2 µl ($10^8$pfu) VCSM13 helper phage (Stratagene). After growth for one hour, 4 µl kanamycin (25 mg/ml) was added, and the culture grown overnight. The phagemid particles were concentrated 10-fold for ELISA by precipitation with polyethylene glycol.

ELISA

Detection of phage binding to 2-phenyl-5-oxazolone (phOx) was performed as in example 9. 96-well plates were coated with 10 µg/ml phOx-BSA or 10 µg/ml BSA in PBS overnight at room temperature, and blocked with PBSS containing 2% skimmed milk powder. Phage (mid) supernatant (50 µl) mixed with 50 µl PBS containing 4% skimmed milk powder was added to the wells and assayed. To detect binding of soluble scFv or Fab fragments secreted from pHEN1, the c-myc peptide tag described by Munro and Pelham 1986 supra, was detected using the anti-myc monoclonal 9E10 (Evan, G. I. et al. Mol Cell Biol 5 3610-3616, 1985) followed by detection with peroxidase-conjugated goat anti-mouse immunoglobulin. Other details are as in example 9.

The constructs in fdCAT2 and pHEN1 display antibody fragments of the surface of filamentous phage. The phage vector, fd-CAT2 (FIG. 8) is based on the vector fd-tet (Zacher, A. N. et al. Gene 9 127-140, 1980) and has restriction sites (ApaLI and NotI) for cloning antibody genes (or other protein) genes for expression as fusions to the N-terminus of the phage coat protein g3p. Transcription of the antibody-g3p fusions in fd-CAT2 is driven from the gene III promoter and the fusion protein targetted to the periplasm by means of the g3p leader. Fab abd scFv fragments of NQ10.12.5 cloned into fd-CAT2 for display were shown to bind to phOx-BSA (but not BSA) by ELISA (table 5). Phage were considered to be binding if $A_{405}$ of the sample was at least 10-fold greater that the background in ELISA.

The phagemid vector, pHEN1 (FIG. 26(a)), is based upon pUC119 and contains restriction sites (SfiI and NotI) for cloning the fusion proteins. Here the transcription of antibody-g3p fusions is driven from the inducible lacZ promoter and the fusion protein targetted to the periplasm by means of the pelB leader. Phagemid was rescued with VCSM13 helper phage in 2×TY medium containing no glucose or IPTG: under these conditions there is sufficient expression of antibody-g3p. Fab and scFv fragments of NQ10.12.5 cloned into pHEN1 for display were shown to bind to phOx-BSA (but not BSA) by ELISA (Table 5) using the same criterion as above.

An alternative methodology for preparing libraries of Fab fragments expressed on the surface of phage would be to:

1. Prepare a library of phage expressing heavy chain (VHCH) genes from inserts in the phage genome.
2. Prepare a library of light chain genes in a plasmid expression vector in E. coli, preferably a phagemid, and isolate the soluble protein light chins expressed from this library.
3. Bind the soluble protein light chains from the library to the heavy chain library displayed on phage.
4. Select phage with the desired properties of affinity and specificity. These will encode the heavy chain (VHCH) genes.
5. Isolate the light chain genes encoding light chains which form suitable antigen binding sites in combination with the selected heavy chains, preferably by using superinfectin of bacteria, containing phagemid expressing the light chain, with phage expressing the selected heavy chain (as described in example 20) and then assaying for antigen binding.

Example 26

Rescue of Phagemid Encoding a Gene III Protein Fusion with Antibody Heavy or Light Chains by Phage Encoding the Complementary Antibody Chain Displayed on Phage and the Use of this Technique to Make Dual Combinatorial Libraries With random combinatorial libraries there is a limitation on the potential diversity of displayed Fab fragments due to the transformation efficiency of bacterial cells. Described here is a strategy (dual combinatorial libraries) to overcome this problem, potentially increasing the number of phage surveyed by a factor of $10^7$.

For assembly of heavy and light chains expresses from different vectors, phagemid (pHEN1-III or IV) was grown in E. coli HB2151 (a non-supressor strain) to allow production of soluble chains, and rescued as above (example 27) except that helper phage were used expressing partner chains as fusions to g3p ($10^9$ TU fd-CAT2-IV or III respectively) and 2 µl tetracycline (12.5 mg/ml) in place of kanamycin.

Separate Vectors to Encode Fab Heavy and Light Chains

The heavy and light chains of Fab fragments can be encoded together in the same vector (example 25) or in different vectors. To demonstrate this the heavy chain (construct III) was cloned into pHEN1 (to provide soluble fragments) and the light chain (construct IV) into fd-CAT2 (to make the fusion with g3p). The phagemid pHEN1-III, grown in E. coli HB2151 (non-supressor) was rescued with fd-CAT2-IV phage, and phage(mid) shown to bind to phOx:BSA, but not to BSA (Table 5). This demonstrates that soluble light chain is correctly associating with the heavy chain anchored to the g3p, since neither heavy chain nor light chain alone bind antigen (Table 5).

Similar results were obtained in the reverse experiment (with phagemid pHEN-1-IV and fd-CAT2-III phage) in which the heavy chain was produced as a soluble molecule and the light chain anchored to g3p (Table 5). Hence a Fab fragment is assembled on the surface of phage by fusion of either heavy or light chain to g3p, provided the other chain is secreted using the same or another vector (FIG. 28).

The resulting phage population is a mixture of phage abd rescued phagemid. The ratio of the two types of particle was assessed by infecting log phase E. coli TG1 and plating on TYE plates with either 15 µg/ml tetracycline (to select for fd-CAT2) or 100 µg/ml ampicillin (to select for pHEN1). The titre of fd-CAT2 phage was $5\times10^{11}$ TU/ml and the titre of pHEN1 $2\times10^{10}$ TU/ml, indicating a packaging ratio of 25 phage per phagemid.

Demonstrated here is an alternative strategy involving display of the heterodimeric antibody Fab fragments on the surface of phage. One of the chains is fused to g3p and the other is secreted in soluble form into the periplasmic space of the *E. coli* where it associates non-covalently with the g3p fusion, and binds specifically to antigen. Either the light or heavy chain can be fused to the g3p: they are displayed on the phage as Fab fragments and bind antigen (FIG. 28). Described are both phage and phagemid vectors for surface display. Phagemids are probably superior to phage vectors for creation of large phage display libraries. Particularly in view of their higher transfection efficiencies (Two to three orders of magnitude higher), allowing larger libraries to be constructed. The phagemid vector, pHEN1 also allows the expression of soluble Fab fragments in non-suppressor *E. coli*.

Also demonstrated here is that heavy and light chains encoded on the same vector (construct II), or on different vectors (constructs III and IV) can be displayed as Fab fragments. This offers two distinct ways of making random combinatorial libraries for display. Libraries of heavy and light chain genes, amplified by PCR, could be randomly linked by a 'PCR assembly' process (example 14) based on 'splicing by overlap extension', cloned into phage(mid) display vectors and expressed from the same promoter as part of the same transcript (construct II) as above, or indeed from different promoters as separate transcripts. Here the phage(mid) vector encodes and displays both chains. For a combinatorial library of $10^7$ heavy chains and $10^7$ light chains, the potential diversity of displayed Fab fragments ($10^{14}$) is limited by the transfection efficiency of bacterial cells by the vector (about $10^9$ clones per μg cut and ligated plasmid at best) (W. J. Dower et al Nucl. Acids. Res. 16 6127-6145, 1988). Libraries thus prepared are analogous to the random combinatorial library method described by Huse, W. D. et al Science 246 1275-1281 (1989), but have the important additional feature that display on the surface of phage gives a powerful method of selecting antibody specificities from the large number of clones generated.

Alternatively, libraries of heavy and light chains could be cloned into different vectors for expression in the same cell, with a phage vector encoding the g3p fusion and a phagemid encoding the soluble chain. The phage acts as a helper, and the infected bacteria produced both packaged phage and phagemid. Each phage or phagemid displays both chains but encodes only one chain and thus only the genetic information for half of the antigen-binding site. However, the genes for both antibody chains can be recovered separately by plating on the selective medium, suggesting a means by which mutually complementary pairs of antigen binding heavy and light chain combinations could be selected from random combinatorial libraries. For example, a light chain repertoire on fd phage could be used to infect cells harbouring a library of soluble heavy chains on the phagemid. The affinity purified phagemid library could then be used to infect *E. coli*, rescued with the affinity purified phage library, and the new combinatorial library subjected to a further round of selection. Thus, antibody heavy and light chain genes are reshuffled after each round of purification. Finally, after several rounds, infected bacteria could be plated and screened individually for antigen-binding phage. Such 'dual' combinatorial libraries are potentially more diverse than those encoded on a single vector. By combining separate libraries of $10^7$ light chain phage (mid)s, the diversity of displayed Fab fragments (potentially $10^{14}$) is limited only by the number of bacteria ($10^{12}$ per litre). More simply, the use of two vectors should also facilitate the construction of 'hierarchical' libraries, in which a fixed heavy or light chain is paired with a library or partners (example 22), offering a means of 'fine-tuning' antibody affinity and specificity.

Example 27

Induction of Soluble scFv and Fab Fragments using Phagemid pHEN1

Further study of antibodies which have been expressed on the surface of phage would be greatly facilitated if it is simple to switch to expression in solution.

*E. coli* HB2151 was infected with pHEN phagemid (pHEN1-I or II), and plated on YTE, 100 μg/ml ampicillin plates. Colonies were shaken at 37° C. in 2×TY medium, 100 μg/ml ampicillin, 1% glucose to $OD_{550}$=0.5 to 1.0. Cells were pelleted, washed once in 2×TY medium, resuspended in medium with 100 μg/ml ampicillin, 1 mM isopropyl β-D-thiogalactoside (IPTG), and grown for a further 16 hours. Cells were pelleted and the supernatant, containing the secreted chains, used directly in ELISA.

Figure 29:
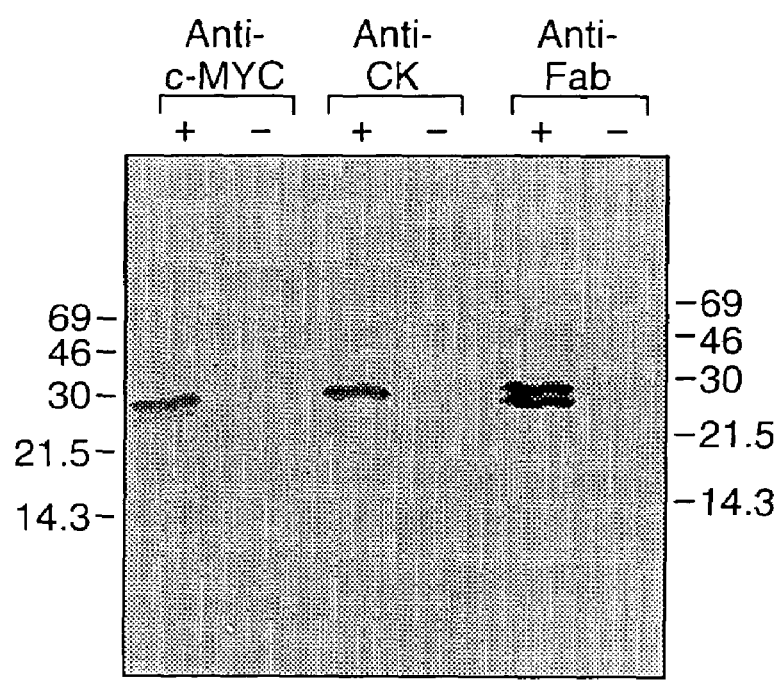
FIG. 29. Western blot of supernatant taken from pHEN1-II(+) or pHEN1(-) cultures in *E. coli* HB2151, showing secretion of Fab fragment from pHEN1-II only. The anti-human Fab detects both H and L chain. Due to the attached c-myc tag, the L chain, highlighted by both anti-c-myc tag and anti-human CK antisera, is slightly larger (calculated Mr 24625) than the H chain (calculated Mr23145).

The phagemid pHEN1 has the advantage over phage fd-CAT2, in that antibody can be produced either for phage display (by growth in supE strains of *E. coli*) or as a tagged soluble fragment (by growth in non-suppressor strains), as a peptide tag (example 24) and amber codon were introduced between the antibody and g3p. Secretion of soluble Fab fragments from pHEN1-II or scFv fragments from pHEN1-I was demonstrated after growth in *E. coli* HB2151 and induction with IPTG using Western blots (FIG. 29). For detection of secreted proteins, 10 μl supernatant of induced cultures were subjected to SDS-PAGE and proteins transferred by electroblotting to Immobilon-P (Millipore). Soluble heavy and light chain were detected with goat polyclonal anti-human Fab antiserum (Sigma) and peroxidase conjugated rabbit anti-goat immunoglobulin (Sigma), each at a dilution of 1:1000. The tagged VK domain was detected with 9E10 antibody (1:1000) and peroxidase conjugated goat anti-mouse immunoglobulin (Fc specific) (1:1000) (Sigma) or with a peroxidase labelled anti-human CK antiserum (Dako). 3,3'-diaminobenzidine (DAB; Sigma) was used as peroxidase substrate (Harlow E., et al. 1988 Supr). With the scFv, the fragments were detected using the 9E10 anti-myc tag antibody (data not shown). With the Fab, only the light chain was detected by 9E10 (or anti-human CK) antibody, as expected, while the anti-human Fab antiserum detected both heavy and light chains. Binding of the soluble scFv and Fab fragments to phOx-BSA (but not to BSA) was also demonstrated by ELISA (Table 5B). Thus scFv and Fab fragments can be displayed on phage or secreted as soluble fragments from the same phagemid vector.

Example 28

Increased Sensitivity in ELISA assay of Lysozyme Using FDTscFvD1.3 as Primary Antibody Compared to Soluble scFvD1.3

In principle the use of phage antibodies should allow more sensitive immunoassays to be performed than with soluble antibodies. Phage antibodies combine the ability to bind a specific antigen with the potential for amplification through the presence of multiple (ca. 2800) copies of the major coat protein (g8p) on each virion. This would allow the attachment of several antibody molecules directed against M13 to each virion followed by the attachment of several molecules of peroxidase-conjugated anti-species antibody (anti-sheep)

IgG in the case below). Thus for every phage antibody bound to antigen there is the potential for attaching several peroxidase molecules whereas when a soluble antibody is used as the primary antibody this amplification will not occur.

Figure 30:
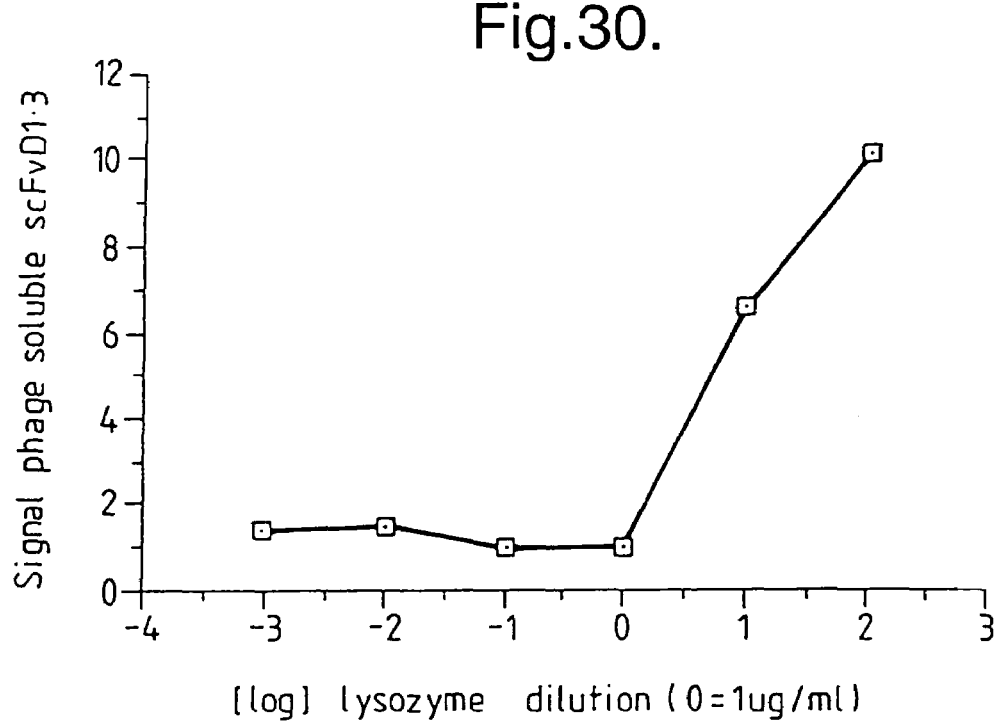
FIG. 30 is a plot showing the effect of lysozyme dilution on ratio of ELISA signals obtained using pAbD1.3 or soluble scFv D1.3.
Figure 31:
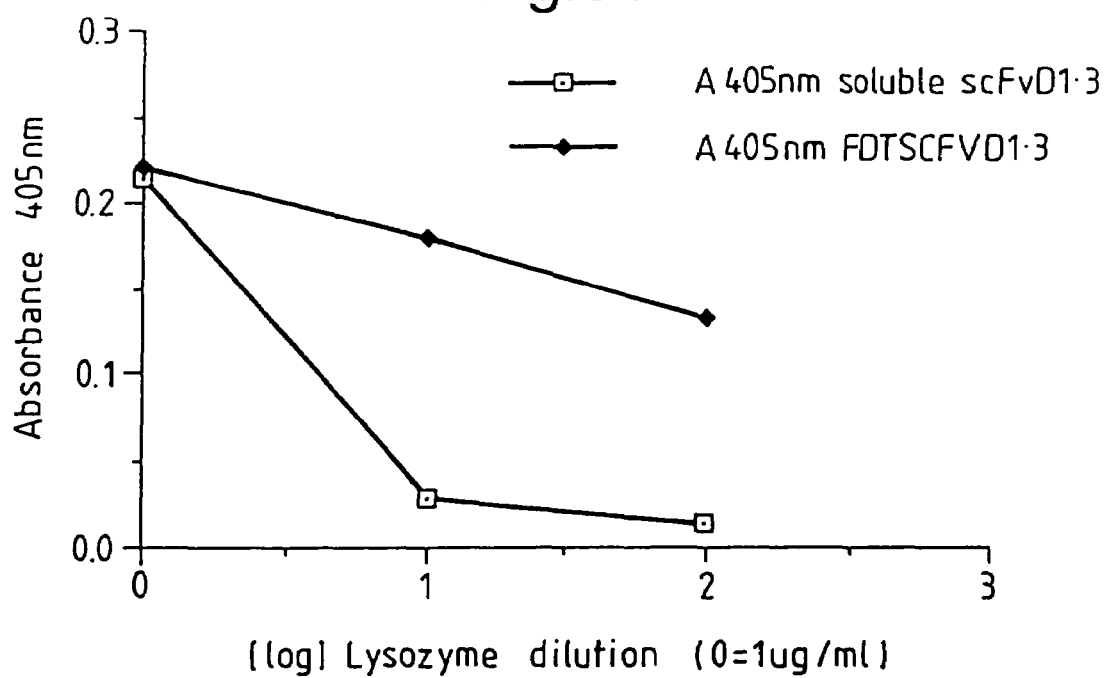
FIG. 31 is a plot showing the effect of lysozyme dilution on ELISA signals obtained using fdTscFvD1.3 and soluble scFvD1.3.

ELISA plates were coated overnight at room temperature using 200 μl of 10 fold dilutions of hen egg lysozyme (1000, 100, 10, 1, 0.1 and 0.01 μg/ml) in 50 mM NaHCO$_3$, pH9.6. ELISA was performed as described in example 4 except that (i) incubation with anti-lysozyme antibody was with either FDTscFvD1.3 (pAb; $10^{11}$ phage per well; 1.6 mol) or soluble affinity purified scFvD1.3 (18 μg per well; 0.7 nmol) (ii) incubation with second antibody was with 1/100 dilution of sheep anti-M13 serum for FDTscFvD1.3 samples or with or 1/100 dilution of rabbit anti-scFvD1.3 serum (from S. Ward) for soluble scFvD1.3 samples (iii) peroxidase-conjugated rabbit anti-goat immunoglobulin (Sigma; 1/5000) was used for FDTscFvD1.3 samples and peroxidase-conjugated goat anti-rabbit immunoglobulin (Sigma; 1/5000) was used for soluble scFvD1.3 samples. Absorbance at 405 nm was measured after 15 h. The results are shown in FIGS. 30 and 31. In these figures lysozyme concentrations for coating are shown on a log scale of dilutions relative to 1 μg/ml. (i.e. log=−3=1 mg/ml; log=2=0.01 μg/ml)

Higher signals were obtained with FDTscFvD1.3 at all concentrations of lysozyme (FIG. 31) but the difference was very marked at the greatest dilutions, where antigen quantities are most limiting (FIGS. 30 and 31). This suggests that phage antibodies may be particularly valuable for sandwich type assays where the capture of small amounts of antigen by the primary antibody will generate an amplified signal when phage antibodies directed against a different epitope are used as the second antigen binding antibody.

Example 29

Direct Rescue and Expression of Mouse Monoclonal Antibodies as Single Chain Fv Fragments on the Surface of Bacteriophage fd The principle is very similar to that described in example 14. It consists of the PCR assembly of single chain antibodies from cDNA prepared from mouse monoclonals. As an example, the rescue and expression of two such antibodies from monoclonals expressing antibodies against the steroid hormone oestriol is described.

A. RNA Preparation

RNA can be prepared using many procedures well known to those skilled in the art. In this example, the use of Triton X-100 lysis, phenol/SDS RNase inactivation gave excellent results.

1. The mouse monoclonal cells that were used here had been harvested by centrifugation and resuspended in serum free medium. They were then centrifuged and resuspended in saline and after a final centrifugation step, resuspended in sterile water at 1×10$^7$ cells per ml. (Normally cells would be washed in PBS buffer and finally resuspended in PBS buffer, but these particular cells were supplied to us as described frozen in water.).
2. To 750 μl of cells was added 250 ul of ice cold 4× lysis buffer (40 mM Tris HCl pH 7.4/4 mM MgCl$_2$/600 mM NaCl/40 mM VRC (Veronyl ribosyl complex)/2% Triton X-100). The suspension was mixed well and left on ice for 5 minutes.
3. Centrifugation was carried out at 4° C. in a microfuge at 13000 rpm for 5 min. The supernatant is then phenol extracted three times, phenol chloroform extracted three times and finally, ethanol precipitated as described in the materials and methods. The precipitate was resuspended in 50 ul water.
4. The optical density of the RNA at 260 nm with a 2.5 ul sample in 1 ml water was measured. The RNA was checked by electrophoresis of a 2 ug sample on a 1% agarose gel. RNA in the range of 32 ug to 42 ug was obtained by this method.

B. cDNA Preparation

The method used is the same as that described in example 14. Two cDNA preparations were made. These were from RNA extracted from the monoclonals known as cell lines 013 and 014 which both express antibodies against eh steroid hormone, oestriol.

C. Primary PCRs

The method used is essentially the same as that described in example 14. The VH region was amplified with the primers VH1BACK and VH1FOR-2. For the Vkappa region, four separate reactions were carried out using the primer VK2BACK and wither MJK1FONX, MJK2FONX, MJK4FONX or MJK5FONX. Samples (5 ul) were checked on a 1.5% agarose gel. From this it was observed that for cDNA prepared from the two oestriol monoclonals the primers VK2BACK and MJK1FONX gave the best amplification of the Vkappa region. The VH bands and the Vkappa bands amplified with VK2BACK/MJK1FONX were purified on 2% low melting point agarose gels for each monoclonals. The DNA bands were excised from the gel and purified using a dedicated Geneclean kit as described in example 14.

D. Preparation of Linker

The method used is essentially the same as that described in example 14. In this case, the amplified linker DNA was purified on a 2% agarose gel and recovered from the gel with a dedicated "Mermaid" kit (BIO 101, Geneclean, La Jolla, San Diego, Calif., USA) using the manufacturers instructions.

E. Assembly PCRs

The method used is essentially the same as that described in example 14. In this case, the assembled PCR product was purified on a 2% agarose gel and recovered from the gel with a dedicated "Mermaid" kit.

F. Adding Restriction Sites and Work-Up

The assembled product was "tagged" with Apa LI and Not I restriction sites. The DNA was then digested with Apa LI and Not I to give the appropriate sticky ends for cloning and then purified on a 2% low melting point agarose gel and extracted using a Geneclean kit. The method used is the same as that described in example 14.

G. Cloning into Vector fd-CAT2

A total of 15 ug of CsC1 purified fd-CAT2 DNA was digested with 100 units of the restriction enzyme Not I (New England Biolabs) in a total volume of 200 ul 1×NEB Not I buffer with 1×NEB acetylated BSA for a total of 3 hours at 37° C. The vector DNA was the treated twice with 15 ul Strataclean (a commercially available resin for the removal of protein), following the manufacturers instructions (Stratagene, 11099 North Torrey Pines Road, La Jolla, Calif., USA). The DNA was then ethanol precipitated and redissolved in TE buffer (Sambrook et al., 1989 supra). The DNA was then digested with 100 units of the restriction enzyme Apa LI (New England Biolabs) in a total volume of 200 ul 1×NEB Buffer 4 overnight at 37° C. The vector was then purified with a Chroma Spin 1000 column following the manufacturers instructions (Clontech Laboratories mc, 4030

Fabian way, Palo Alto, Calif., USA). This step removes the Apa LI/Not I fragment to give cut vector DNA for maximum ligation efficiency.

Ligation reactions were carried out with 2.5-10 ng of the DNA insert and long of vector in a total volume of 10 ul of 1×NEB ligase buffer with 1 ul of NEB ligase (New England Biolabs) at 16□C overnight (approx 16 hours).

H. Transformation and Growth

E. coli strain TG1 was made competent and transformed with the fdCAT2 recombinant DNA as described by Sambrook et al, 1989 Supra. The cells were plated out on LBtet plates (10 g tryptone, 5 g yeast extract, 10 g NaCl, 15 g bacto-agar per litre with 15 ug/ul of tetracycline added just before pouring the plates) and grown overnight.

Single well isolated colonies were then inoculated into 10 ml of LBtet broth (LB medium with 15 ug/ul of tetracycline) in 50 ml tubes. After overnight growth at 35□C/350 rpm in a bench top centrifuge. The supernatants were transferred to 15 ml centrifuge tubes and 2 ml 20% PEG 8000/2.5M NaCl added to each. After incubating at room temperature for 20-30 minutes, the recombinant phage was pelleted by centrifugation at 9000 rpm in a Sorval SM24 rotor for 30 minutes. The PEG supernatant was discarded. Any remaining PEG was removed with a pasteur pepette after a brief (2 minutes) centrifugation step. This last step was repeated to make sure that no PEG remained. The phage pellet was then resuspended in 500 ul PBS buffer. This was transferred to a microcentrifuge tube and spun at 13000 rpm to remove any remaining cells. The phage supernatant was transferred to a fresh tube.

I. Assay for Antibody Expression

Bacteriophage fd recombinants were screened for the expression of antibody against oestriol by ELISA. This method is described in example 6. In this case the following alterations are relevant.

1. Microtitre plates were coated overnight with 40 ug/ml oestriol-6 carboxymethyloxime-BSA (Steraloids, 31 Radcliffe Road, Croydon, CRO 5QJ, England).
2. 1st antibody was the putative phage anti oestriol antibody. 50 ul of phage in a final volume of 200 ul of sterile PBS combining 0.25% gelatin was added to each well.
3. 2nd antibody was sheep anti M13 at 1:1000 dilution.
4. 3rd antibody was peroxidase conjugated rabbit anti goat immunoglobulin.

Figure 32:
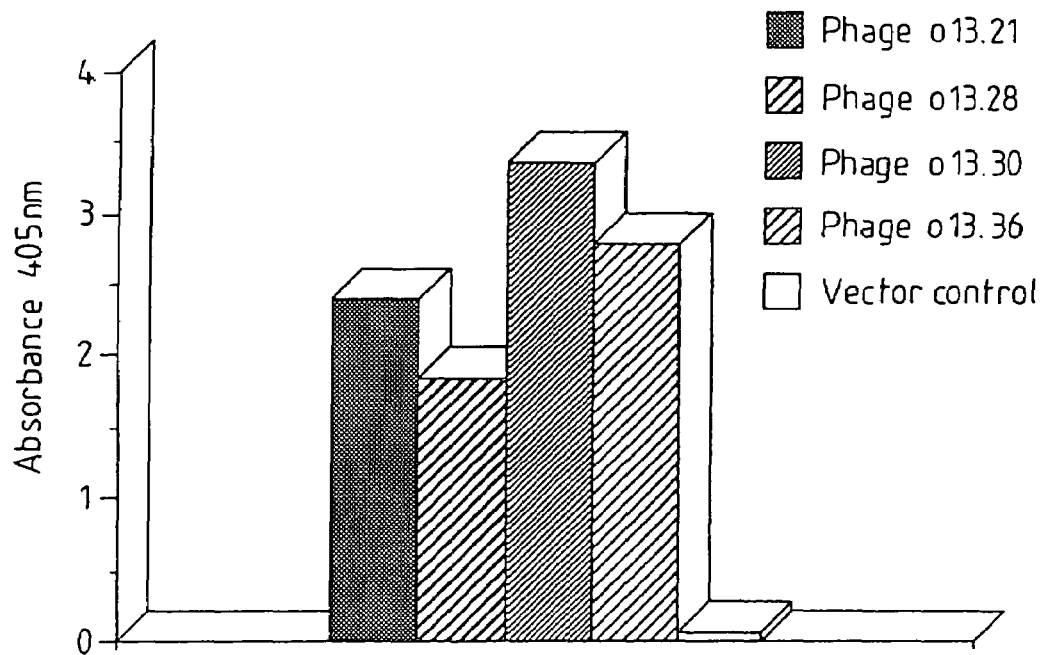
FIG. 32 is a plot showing positive results from an ELISA screen of phage displaying scFv fragments derived from the cell line 013 which express a monoclonal antibody directed against oestriol.
Figure 33:
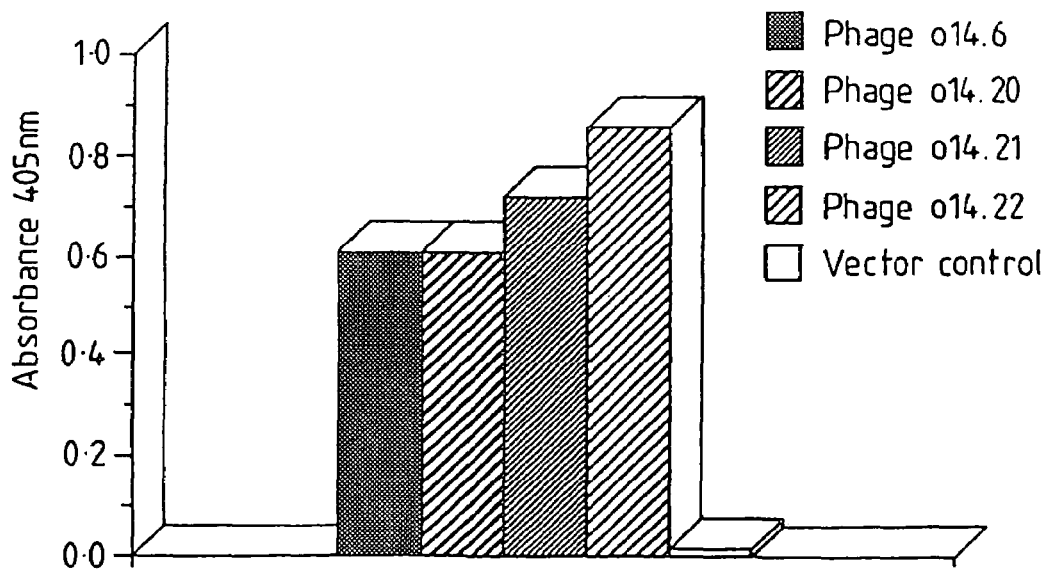
FIG. 33 is a plot showing positive results from an ELISA screen of phage displaying scFv fragments derived from the cell line 014 which express a monoclonal antibody directed against oestriol.

Recombinants expressing functional antibody were detected by incubation with the chromogenic substrate 2'2' axinobis (3-ethyl benzthiazoline sulphonic acid). The results are shown in FIGS. 32 and 33.

Example 30

Kinetic Properties of Alkaline Phosphatase Displayed on the Surface of Bacteriophage fd This example demonstrates that kinetic properties of an enzyme expressed on phage are qualitatively similar to those in solution. Bacteriophage fd displaying alkaline phosphatase fusions of gene 3 with either the native arginine (see example 31) or the mutant residue alanine at position 166 (see example 11) were prepared by PEG precipitation as described in the materials and methods.

The kinetic parameters of alkaline phosphatase expressed on the surface of fd phage were investigated in 1M Tris/HCl, pH8.0 at 20° C. with 1 ml 4-nitrophenyl phosphate as substrate. The reactions were initiated by the addition of 100 μl of a phage-alkaline phosphatase fusion preparation, 50 fold concentrated with respect to the original culture supernatant. The rate of change of absorbance was monitored at 410 nm using a Philips 8730 spectrophotometer and the initial reaction rate calculated using a molar absorbance of 16200 1/mol/cm. For the fdphoAla 166 enzyme but not fdphoArgl 166 a lag phage was seen following this addition, the reaction rate accelerating until a steady state was obtained after approximately 60 to 90 secs. This steady state rate was used for determination of kinetic parameters. No deviation form Michaelis Menten kinetics was apparent for either phage enzyme. Values of $K_m$ and $k_{cat}$ were derived from plots of s/v against s and are shown in Table 6.

Because of the difficulty in establishing the relationship between the number of phage particles an the number of active enzyme dimers formed on the phage $k_{cat}$ values are expressed not as absolute values, but as relative values between the two enzyme forms. Western blots (carried out as in example 31 using antig3p antiserum) of the phage enzyme preparations used in this experiment showed approximately equal intensities for the full length fusion band with the Arg166 and Ala166 enzymes when detected using antibody directed against gene3. In these preparations the intact fusion represents approximately 30% of the detected material. The two preparations were therefore assumed to be expressing approximately the same concentrations of intact fusions.

Table 6 summarises the kinetic data from this experiment and compares it with data from Chaidaroglou, A. et al (Biochemistry 27, 8338-8343 (1988)) obtained with soluble preparations of the wild type and mutant enzyme forms. The same substrate and assay conditions were used in both experiments. Soluble alkaline phosphatase was also tested in parallel in our experiments ($K_m$=8.5 μM; kcat=3480 mol substrate converted mol enzyme$-^1$ min$-^1$).

The effect of mutating arginine at position 166 to alanine is qualitatively similar for the phage enzyme as for the soluble enzyme. $K_m$ is increased about 15 fold and the relative $k_{cat}$ is decreased to 36% of that for wild type. This increased $K_m$ would reflect a reduction in substrate affinity in the phage enzyme on mutation of Arg166, as was proposed for the soluble enzyme (Chaidaroglou et al, 1988 supra), assuming the same kinetic mechanism applies. There are, however, some quantitative differences in the behaviour of $K_m$ of the phage enzyme. The $K_m$ of 73 μM observed for fdphoArg166 compares with a $K_m$ of 12.7 μM for the free enzyme; the $K_m$ for fdphoAla166 is 1070 μM whereas the free mutant enzyme has a $K_m$ of 1620 μM. One can speculate that the higher $K_m$ for fdphoArg 166 and the lower $K_m$ for fdphoAla166, compared to the soluble enzymes result from the 'anchored' alkaline phosphatase fusion molecules interacting to form dimers in a different manner to the enzyme in free solution. The relative values of $k_{cat}$ for the Arg166 and Ala166 forms are however very similar for both the phage enzymes and the soluble enzymes, a reduction occurring on mutation to 35 to 40% of the value for the native enzyme. The rate limiting step, determining $k_{cat}$ for soluble phoArg166 is thought to be dissociation of non-covalently bound phosphate from the enzyme (Hull W. E. et al. Biochemistry 15, 1547-1561 1976). Chaidaroglou et al (1988) supra suggest that, for the soluble enzyme, mutation of Arg166 to alanine alters additional steps, one of which may be hydrolysis of the phosphoenzyme intermediate. The similarity in the reduction in $k_{cat}$ on mutation of Arg166 to alanine for the phage enzymes suggests that the same steps may be altered in a quantitatively similar manner in the mutant phage enzyme as in the mutant soluble enzyme.

Thus, enzymes displayed on phage show qualitatively similar characteristics to soluble enzymes.

Example 31

Demonstration Using Ultrafiltration that Cloned Alkaline Phosphatase Behaves as Part of the Virus Particle The construct fdphoAla166 (derived in example 11) was converted back to the wild type residue (arginine) at position 166 by in vitro mutagenesis (Amersham International) using the printer APARG166:5' TAGCATTTGCGCGAGGT-CACA 3' (SEQ ID NO:51). This construct with the wild type insert was called fdphoArg166.

E. coli TG1 or KS272 cells (cells with a deletion in the endogenous phoA gene, Strauch and Beckwith, 1988 Supra) containing either fd-phoAla166, fdphoArg 166 or fd-CAT2 were grown for 16 hours at 37° C. in 2×TY with 15 µg/ml tetracycline. Concentrated phage were prepared as follows. Phage-enzyme cultures are clarified by centrifugation (15 min at 10,000 rpm, 8×50 ml rotor, sorval RC-5B centrifuge). Phage are precipitated by adding 1/5 volume 20% polyethylene glycol, 2.5M NaCl, leaving for 1 hr at 4° C., and centrifuging (as above). Phage pellets are resuspended in 10 mM Tris-HCl, pH 8.0 to 1/100th of the original volume, and residual bacteria and aggregated phage removed by centrifugation for 10 to 15 minutes in a bench microcentrifuge at 13000 rpm at 4° C.

SDS/Polyacrylamide gel electrophoresis and western blotting were basically as described previously (example 2). Denatured samples consisting of 16 µl of a 50 fold concentrate of phage were separated using a 10% SDS/polyacrylamide gel and detected with polyclonal antiserum raised against either E. coli alkaline phosphatase (Northumbria Biologicals, South Nelson Industrial Estate, Cramlington, Northumberland, NE23 9HL) or against the minor coat protein encoded by gene 3 (from Prof. I. Rasched, Universitat Konstanz, see Stengele et al, 1990) at 1 in 1000 dilution. This was followed by incubation with peroxidase-conjugated goat-anti-rabbit immunoglobulin (Sigma 1 in 5000) and detection with the ECL Western blotting system (Amersham International).

The presence of fusion proteins was confirmed by western blotting of proteins from phage particles derived from fd-phoAla166 (phage-enzyme) or fd-CAT2 (vector phage). Detection with antiserum raised against the gene 3 protein reveals a product of apparent relative molecular mass (Mr) of 63,000 in vector phage (FIG. 34e). Although this is different from the predicted molecular weight based on the amino acid sequence (42,000), the natural product of gene 3 has previously been reported to exhibit reduced mobility during electrophoresis (Stengele et al, 1990).

Figure 34:
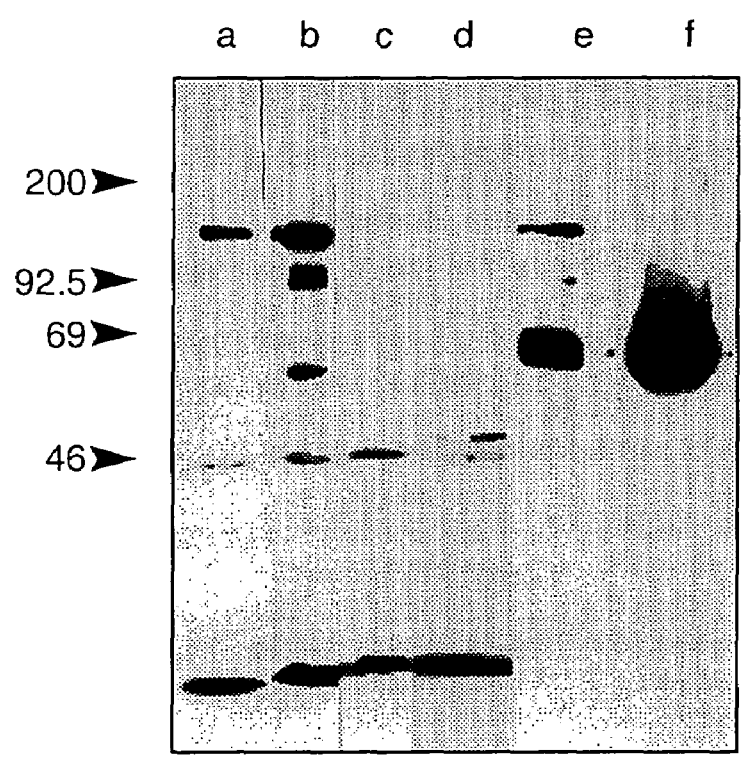
FIG. 34 is a Western Blot showing expression of the alkaline phosphatase-gene 3 fusion. 16 µl of 50 fold concentrate of each phage sample was detected on western blots with either anti-gene 3 antiserum (e-f) or with anti-alkaline phosphatase antiserum (c-f)

In the fd-phoAla166 sample the largest band has an apparent Mr of 115,000, (FIG. 34). Taking into account the aberrant mobility of the gene 3 portion of the fusion, this is approximately the size expected from fusing with an alkaline phosphatase domain of 47 kD. This analysis also reveals that a proportion of the Gene3 reactive material in this phage-enzyme preparation is present at the size of the native gene3 product, suggesting that degradation is occurring. In the preparation shown in FIG. 34, approximately 5-10% of the gene 3 fusions are intact. In more recent preparations and in all the preparations used in this example and example 32, approximately 30-60% of fusions are full length.

The protein of Mr 115,000 is the major protein observed in Western blots of phage-enzyme derived from TG1 cells when probed with antiserum raised against E. coli alkaline phosphatase (anti-BAP), confirming the assignment of this band to intact fusion. Further, when phage enzyme is prepared using KS272 cells, which have a deletion in the endogenous phoA gene (Strauch & Beckwith, 1988, supra.) it is also the major band. There are additional bands at Mr 95000 and 60000 reactive with anti-BAP antiserum which may indicate degradation of the fusion product.

The anti-BAP antiserum also reacts wit material running with the dye front and with a molecule of Mr 45,000 but evidence suggests that this material is not alkaline phosphatase. This pattern is detected in PEG precipitated vector phage samples (FIG. 34c) and is not therefore contributed by protein expressed from the cloned phoA gene. These bands are detected in culture supernatants of cells carrying fd-CAT2 but is not detected in the supernatant of uninfected cells (not shown) and so either represents cross-reactivity with phage encoded material or with a PEG precipitable cellular component leaked from infected cells (Boeke et al, Mol. Gen. Genet. 186, 185-192 1982). Although the fragment of Mr, 45,000 is close to the size of free alkaline phosphatase (47,000), it is present in phage preparations from KS272 cells which have a deletion in the phoA locus. Furthermore its mobility is different from purified alkaline phosphatase and they can be distinguished by electrophoresis (FIG. 34).

Ultrafiltration was used to confirm that the fusion protein behaved as though it were part of a larger structure, as would be expected for an enzyme bound to a phage particle. Phage samples (100 µl of a 50 fold concentrate) were passed through ultrafiltration filters with a nominal molecular weight limit of 300000 daltons (Ultrafree-MC filters, Millipore) by centrifugation for 5 to 15 minutes at 13,000 r.p.m. in an MSE microcentaur microfuge. Retained material was recovered by resuspending in 100 µl of 10 mM Tris, pH 8.0.

Phage-enzyme or free alkaline phosphatase (83 ng) mixed with vector phage were passed through filters with a nominal molecular weight limit of 300,000 daltons (Ultrafree-MC filters, Millipore). FIG. 35A again shows that the band of Mr, 115,000 is the major product reactive with anti-BAP antiserum. This and the other minor products reactive with anti-BAP are present in material retained by the ultrafiltration membrane. Analysis of retained and flow through fractions of phage preparations derived from KS272 demonstrates that different molecular species are being separated by the ultrafiltration membranes. FIG. 35B shows the protein of Mr 115,000 is retained by the filter whereas the putative degradation products of Mr 95,000 and 60,000 found in phage preparations derived from KS272 cells, are not retained.

In mixture of alkaline phosphatase and vector phage FIG. 35B(c-f), free alkaline phosphatase (dimer size of 94,000 daltons) is detected in the flow through as a monomer band with Mr 47,000 on denaturing polyacrylamide gels (FIG. 35B), while the cross reactive molecule found in vector phage preparations (Mr 45,000) is in retained on the filter (FIG. 35B). This suggests that the cross reactive molecule is part of the phage particle and underlines the fact that the ultrafiltration membranes are effecting a separation. Thus the expected fusion band in this phage-enzyme is present in material retained on ultrafiltration membranes demonstrating that it is part of a larger structure as would be expected for viral bound enzyme.

Catalytic activity has been demonstrated on phage particles expressing alkaline phosphatase. Table 7 shows that the wild type alkaline phosphatase gene expressed on phage (fd-phoArg166) has a specific activity (moles of substrate converted per mole of viral particles) of 3,700/min. This is close to the turnover value of 4540/min found for purified alkaline phosphatase by Malamy and Horecker, Biochemistry 3, 1893-1897 1964).

Chaidaroglou et al, 1988 supra have shown that substituting alanine for arginine at the active site (residue 166) leads to a reduction in the rate of catalysis. Preparations of phage displaying alkaline phosphatase with this mutation derived from TG1 and KS272 show reduced specific activities of 380 and 1400 mol substrate converted/mol phage/min respectively. Enzyme activity was measured in the retained and flow-through fractions prepared by ultrafiltration, shown in FIG. 35(A) and FIG. 35(B). The bulk of activity from phage-enzyme was retained on the filters whereas the majority of activity from free enzyme passes through. Therefore, the enzyme activity in these fusions behaved as would be expected for virally associated enzyme (not shown). Little or no catalytic activity is measured in preparations of vector phage from either TG1 or KS272 cells (Table 7), indication that the catalytic activities above are due to phage enzyme and not contamination with bacterial phosphatase. Addition of phage particles to soluble enzyme does not have a significant effect on activity (Table 7).

Therefore, both the catalytic and immunochemical activity of alkaline phosphatase have been demonstrated to be due to enzyme which is part of the phage particle.

Example 32

Affinity Chromatography of Phage Alkaline Phosphatase

Affinity chromatography, using the specific binding properties of enzymes has proved to be a very powerful method for their purification. The purification of phage-enzymes by this approach would enable the genetic material encoding the enzyme to be isolated with the enzyme itself. Thus, mutagenesis of cloned enzymes expressed on the surface of filamentous bacteriophage will lead to a whole population of enzyme variants, from which variants with desired binding properties could be isolated.

Soluble alkaline phosphatase (from calf intestine) has been purified by binding to immobilised arsenate (a competitive inhibitor), and eluting with inorganic phosphate, which is a product (and competitive inhibitor) of the enzyme reaction (Brenna, O. et al, Biochem. J. 151 291-296 1975). The applicants have determined that soluble alkaline phosphatase from *E. coli* is also retained by this matrix (not shown). In this example it is demonstrated that phage displaying *E. coli* alkaline phosphatase binds to arsenate-Sepharose and can be specifically eluted.

Arsenate-Sepharose was prepared by coupling 4-(p-aminophenylazo) phenyl arsonic acid to tyraminyl-Sepharose according to the method of Breena et al, (1975; supra). Affinity chromatography of phage enzyme fdphoArg166 (example 31) was carried out in a disposable chromatography column with a 0.5 ml column volume. Columns were prewashed with 100 volumes of column buffer (100 mM Tris pH 8.4, 1 mM $MgCl_2$, 0.1 mM $ZnCl_2$, 0.1% Tween 20, Brenna et al, 1975, supra.) 1 ml of a 40 fold concentrate of phage-enzyme (in column buffer; prepared as in example 31) was loaded and washed through with 100 volumes of column buffer. Bound phage-enzyme was eluted with 5 mls of column buffer containing 20 mM $NaHPO_4$. The eluate and wash fractions were quantitated by dot blotting onto nitrocellulose and comparing with known amounts of phage-enzyme. The blots were detected using sheep anti-M13 antiserum (gift from M. Hobart), anti-sheep peroxidase (Sigma) and enhanced chemiluminescent substrate (Amersham). A range of exposures were taken.

Table 8 shows the results of affinity chromatography of phage displaying alkaline phosphatase on arsenate-Sepharose. In separate experiments phage particles expressing either mutant (fdphoAla 166; example 11) and or wild type (fdphoArg 166) forms are retained on arsenate-Sepharose and eluted with inorganic phosphate. Approximately 0.5 to 3% of added phage enzyme particles loaded ('input phage') were specifically eluted with phosphate ('output phage') compared to only 0.05% of vector particles. Arsenate is a competitive inhibitor with $K_i$ of 20 μM with respect to 4-nitrophenyl phosphate. Phage particles antibodies have previously been isolated on the basis of interactions with similar affinities (example 23). This association is in within the range of a large number of enzyme-ligand interactions suggesting wide applicability for this approach.

Table 8 also shows that the infectivity of phage particles expressing enzyme is reduced with compared with vector phage particles. This makes titration of infectious particles an inappropriate means of quantitating the number of phage enzyme particles. For this reason the number of phage were measured by dot blotting and phage were detected with anti-M13 antiserum as above.

Whereas, overall recovery of catalytic activity may be an important consideration in enzyme purification, this is not critical with phage-enzymes. Even if only low levels of phage-enzyme bind to and are specifically eluted from affinity columns, this will generate clones which can subsequently be grown up in bulk as phage-enzymes or can be transferred to expression vectors yielding soluble products.

Example 33

PCR Assembly of DNA Encoding Fab Fragments of an Antibody Directed Against Oxazolone Example 25 showed that genes encoding Fab fragments could be subcloned into vectors fdCAT2 and pHEN1 and the protein domains displayed on the surface of phage with retention of binding function. This example shows that the VECH and VKCK domains can be amplified separately and then joined by a linker allowing the expression of the light chain as a geneIII protein fusion and the VHCH fragment as a soluble molecule. A functional Fab fragment is then displayed on phage by association of these domains. The assembly process, described in this example, is required for display of a library of Fab fragments derived from the immune repertoire if both heavy and light chain domains are to be encoded within a single vector.

The VHCH1 and VKCK domains of a construct (example 25; construct II in pUC19) derived from antibody NQ10 12.5 directed against 2-phenyl-5-oxazolone were amplified using PCR. For cloning into the vector fdCAT2 the oligonucleotides VH1BACKAPA (example 25) and HuIgG1-4 CH1FOR (example 40) were used to amplify the VHCH1 domains. For cloning into pHEN1 VH1BACKSFH5 (example 25) replaced VH1BACKAPA for this amplification. For cloning into both vectors the VKCK domains were amplified using VK2BACK (example 25) and CKNOTFOR (example 40). A linker oligonucleotide fragment containing the bacteriophage fd gene 8 terminator and the fd gene 3 promoter was prepared by amplifying the region containing them from the vector fdCAT2 by PCR using the oligonucleotides.

VK-TERM-FOR

5' TGG AGA CTG GGT GAG CTC AAT GTC GGA GTG AGA ATA GAA AGG 3' (SEQ ID NO:52) (overlapping with VK2BACK [example 14])

and

CH1-TERM-BACK
5'AAG CCC AGC AAC ACC AAG GTG GAC AAG AAA GTT GAG CCC AAA TCT AGC TGA TAA ACC GAT ACA ATT AAA GGC 3' (SEQ ID NO:53) (overlapping with HuIgG1-4 CH1-FOR) Assembly of the Fab fragment from the amplified VHCH1 and VKCK domains and the linker prepared as above was as described in example 14E except that the primers VH1BACKAPA (when cloning into fdCAT2) or VH1BACKSFH5 (when cloning into pHEN1) and CKNOTFOR were used for the final reamplification, thereby introducing restriction sites for cloning into fdCAT2 (ApaI1-NotI) or pHEN1 (SfiI-NotI) the assembled Fab fragment is shown in FIG. 34. No assembled product was seen in the absence of linker. An assembled scFv prepared according to example 14 is shown for comparison.

Phage antibodies were prepared as in example 25 and ELISA was performed with oxazolone as antigen according to example 6. Results were as expected for Fab fragments cloned in both fdCAT2 and pHEN1 samples, phage particles bound to oxazolone as detected by a positive ELISA signal.

Example 34

Construction of a Gene III Deficient Helper Phage

To fully realise the potential of the phagemid cloning system, a helper phage lacking gene III is desirable. Rescue of gene III fusions with such a helper phage would result in all the progeny phagemids having a gene III fusion on their capsid, since there would be no competition with the wild type molecule.

Control over the number of fusion molecules contained on each phage will provide particularly useful. For example, a gene III deficient helper phage can be used to rescue low affinity antibodies from a naive repertoire, in which high avidity will be necessary to isolate those phage bearing the correct antibody specificity. The unmutated helper phage can then be used when higher affinity versions are constructed, thereby reducing the avidity component, and permitting selection purely on the basis of affinity. This will prove a surprisingly successful strategy for isolation and affinity maturation of antibodies from naive libraries.

The strategy chosen to construct the helper phage was to partially delete gene III of M13K07 using exonuclease Bal 31. However, phage lacking gene III protein are non-infective so an *E. coli* strain expressing gene III was constructed. Wild type M13 gene III was PCR-amplified with primers gII-IFUFO and gIIIFUBA, exactly as described in example 24. The PCR product was digested with Eco RI and Hind III and inserted into Eco RI and Hind III-cut pUC19 (not a phagemid as it lacks the filamentous phage origin of SS DNA replication) under control of the lac promoter. The plasmid was transformed into *E. coli* TG1, and the resulting strain called TG1/pUC19gIII. This strain provides gIII protein in trans to the helper phage.

There is a single unique Bam HI site in M13KO7, which is approximately in the centre of gIII. Double-stranded M13K07 DNA was prepared by alkaline lysis and caesium chloride centrifugation (Sambrook et al, et supra. 1989); twenty μg of DNA was cut with Bam H1, phenol extracted and ethanol precipitated then resuspended in 50 μl of Bal 31 buffer (600 mM NaCl, 20 mM Tris-HCl pH 8.0, 12 mM CaCl$_2$, 12 mM MgCl$_2$ and 1 mM EDTA) and digested for 4 minutes with 1 unit of Bal 31 (New England BioLabs). This treatment removed approximately 1 Kb of DNA. EGTA was added to 20 mM and the reaction phenol extracted and ethanol precipitated prior to purification of the truncated genome on an agarose gel. The DNA was repaired with klenow enzyme and self-ligated with T4 DNA ligase (New England BioLabs).

Aliquots of the ligation reaction were transformed into competent TG1/pUC19gIII and plated on SOB medium containing ampicillin at 100 g/ml and kanamycin at 50 μg/ml. Colonies were screened for the presence of a deletion by PCR with primers gIIIFUBA and KSJ12 (CGGAATAC-CCAAAAGAACTGG) (SEQ ID NO:54).

KSJ 12 anneals to gene VI which is immediately downstream of gIII in the phage genome, so distinguishing gIII on the helper phage from that resident on the plasmid. Three clones gave truncated PCR products corresponding to deletions of ca. 200, 400 and 800 bp. These clones were called M13K07 gIII Δ Nos 1, 2 and 3 respectively. No clones were isolated from the earlier Bal 31 time points, suggesting that these are in some way lethal to the host cell. Several clones were isolated from later time points, but none of these gave a PCR product, indicating that the deletion reaction had gone too far.

M13K07 gIII Δ No.s 1, 2 and 3 were cultured and the resulting helper phage tested for their ability to rescue an antibody gIII fusion (scFv D1.3) by ELISA, exactly as described in example 18. As shown in FIG. 37, only one clone, M13K07 gIII Δ No3 was found to rescue the antibody well; in fact the signal using this helper was greater than that observed with the parent M13 KO7. M13KO7 gIIIΔ No3 rescued phagemids should have a much higher density of antibody fusions on their surfaces. That this was indeed the case was demonstrated when the phage used in this ELISA were analysed by Western blotting with anti gIII protein antiserum (FIG. 38). This analysis enables estimation of the amount of gIII fusion protein versus free gIII protein present on the phage(mid) particles.

Only a minute fraction of the gIII protein on the M13K07-rescued material is present as an intact fusion (FIGS. 38A-38B). The fusion protein band is induced by IPTG, so is indisputably that synthesised by the phagemid. As expected, even when the lac promoter driving gIII fusion protein synthesis is fully induced (100 μM IPTG), wild type gIII protein, at a lower copy number and driven from a far weaker promoter, predominates. This is in contrast to the pattern generated by the same clone rescued with M13K07 gIIIΔNo3, and the pattern generated by fd CAT2-scFv D1.3. In both of these latter cases, there is no competition with wild-type gIII and the fusion protein band is correspondingly stronger.

It is worthy of note that construction of M13K07 gIII Δ No3 was immensely inefficient: one clone from 20 μg of starting DNA. Moreover, the yield of gIII helper phage from overnight cultures is extremely low ca. $10^6$ cfu/ml compared with ca. $10^{11}$ cfu/ml for the parental phage. Despite this, M13K07 gIII No3 rescues the phagemid as well as the parental phage, as judged by the number of phagemid particles produced after overnight growth. This indicates that trans replication and packaging functions of the helper are intact and suggest that its own replication is defective. Hence it may be that inactivation of gIII is normally toxic to the host cell, and that M13K07 gIII Δ No3 was isolated because of a compensating mutation affecting, for example, replication. Phage fd-tet is unusual in that it tolerates mutations in structural genes that are normally lethal to the host cell, since it has a replication defect that slows down accumulation of toxic phage products; M13K07 gIIIΔ No3 may also have such a defect.

M13K07g IIIΔ No 3 has been deposited at the National Collection of Type Cultures, 61 Colindale Avenue, London, NW9 6HT, UK (Accession No. NCTC 12478). On 28 Jun. 1991, in accordance with the regulations of the Budapest Treaty. It contains a deletion of the M13 genome from bases 1979 to 2768 inclusive (see Van Wezenbeek, P. G. M. F. et al., Gene II p129-148, 1980 for the DNA sequence of the M13 genome).

Example 35

Selection of Bacteriophage Expressing scFv Fragments Directed Against Lysozyme from Mixtures According to Affinity Using a Panning Procedure For isolation of an antibody with a desired high affinity, it is necessary to be able to select an antibody with only a few fold higher affinity than the remainder of the population. This will be particularly important when an antibody with insufficient affinity has been isolated, for example, from a repertoire derived from an immunised animal, and random mutagenesis is used to prepare derivatives with potentially increased affinity. In this example, mixtures of phage expressing antibodies of different affinities directed against hen egg lysozyme were subjected to a panning procedure. It is demonstrated that phage antibodies give the ability to select for an antibody with a $K_d$ of 2 nM against one with a $K_d$ of 13 nM.

The oligonucleotides used in this example are shown in the list below:

Oligonucleotides

```
OLIGONUCLEOTIDES

VHBHD13APA:
5'-CAC AGT GCA CAG GTC CAA CTG      (SEQ ID NO:55)
CAG GAG AGC GGT-3'

VHFHD13:
5'-CGG TGA CGA GGC TGC CTT GAC      (SEQ ID NO:56)
CCC-3'

HD13BLIN:
5'-GGG GTC AGG GCA GCC TCG TCA      (SEQ ID NO:57)
CCG-3'

HD13FLIN3:
5'-TGG GCT CTG GGT CAT CTG GAT      (SEQ ID NO:58)
GTC CGA T-3' T

VKBHD13:
5'- GAC ATC CAG ATG ACC CAG AGC     (SEQ ID NO:59)
CCA-3'

VKFHD13NOT:
5'- GAG TCA TTC TGC GGC CGC ACG     (SEQ ID NO:60)
TTT GAT TTC CAC CTT GGT CCC-3'

MURD13SEQ:
5'-GAG GAG ATT TTC CCT GT-3'        (SEQ ID NO:61)

HUMD13SEQ:
5'-TTG GAG CCT TAC CTG GC-3'        (SEQ ID NO:62)

FDPCRFOR:
5'-TAG CCC CCT TAT TAG CGT TTG      (SEQ ID NO:63)
CCA-3'

FDPCRBAK:
5'-GCG ATG GGT GTT GTC ATT GTC      (SEQ ID NO:64)
GGC-3'.
```

Phage displaying scFv fragments directed against lysozyme were derived from cloned Fab fragments in plasmids. Heavy and light chain variable regions were amplified by the polymerase chain reaction (PCR) from plasmids containing humanized VH-CH1 or VK-CK inserts suitable for production of Fab fragments (gift of J. Foote). The dissociation constant, Kd for different combinations of the two plasmids combined as Fabs, are shown below:

| Heavy Chain Plasmid | Light Chain Plasmid | Kd |
|---|---|---|
| HuH-1 | HuK-3 | 52 nM |
| HuH-1 | HuK-4 | 180 nM |
| HuH-2 | HuK-3 | 13 nM |
| HuH-2 | HuK-4 | (not determined) |

Primary PCR

The primary PCR of the variable regions was performed by combining the following:

36.5 μl Water
5 μl PCR buffer (10×)
2 μl dNTP (5 mM)
2.5 μl Back oligo (10 pmoles/μl) (VHBHD13APA or VKBHD13)
2.5 μl Forward oligo (10 pmoles/μl) (VHFHD13 or VKFHD13NOT)

The reaction is decontaminated by UV irradiation to destroy foreign DNA for 5 minutes, and 1 μl of plasmid DNA added (0.1 μg/μl). The pcr mixture was covered with 2 drops of paraffin oil, and placed on the pcr block at 94° C. for 5 minutes before the addition of 0.5 μl of Taq DNA polymerase under the paraffin. The cycling conditions used were 94° C. 1 min, 40° C. 1 min, 72° C. 1.5 min 17 cycles.

The linker $(Gly_4-Ser)_3$, was amplified from the anti-phOx (2-phenyloxazol-5-one) clone fd-CAT2-scFv NQ11, using the oligos HD13BLIN and HD13FLIN3, with 0.1 μg of plasmid DNA. The PCR cycling used was 94° C. 1 min, 25° C. 1.5 min, for 17 cycles.

Amplified DNA was purified by running the samples on a 2% low melting point agarose gel at 90 mA, excising the appropriate bands and extracting the DNA using the Geneclean II Kit (BIO 101 Inc.) for the VH and VK, or by using Spin-X filter units (Costar) for the linker. A final volume of 10 μl was used to resuspend the extracted DNA.

PCR Assembly

Assembly of the four single chain Fv Humanized D1.3 (scFv HuD1.3) constructs was by the process of 'assembly by overlap extension' example 14.

The following were combined:
34.5 μl Water
5 μl PCR Buffer (10×)
2 μl dNTP (5 mM)
2.5 μl Back oligo (10 pmoles/μl) (VHBHD13APA)
2.5 μl Forward oligo (10 pmoles/μl) (VKFHD13NOT)

Once again, the reaction is decontaminate by UV treatment for 5 minutes before the addition of 1 μl of the primary PCR products; VH-1 or VH-2, VK-3 or VK-4, plus the linker DNA. The reaction was covered with 2 drops of paraffin, and heated at 94° C. for 5 minutes before the addition of 0.5 μl of Taq Polymerase. The PCR cycling conditions used were 94° C. 1 min, 60° C. 1.5 min, 72° C. 2.5 min for 20 cycles.

The aqueous layer under the paraffin was extracted once with phenol, once with phenol: chloroform, once with ether, ethanol precipitated, and resuspended in 36 μl of water. To this was added, 5 μl of 10× Buffer for NotI, 5 μl 1 mg/ml BSA, and 4 µl (40 U) of NotI (New England Biolabs). The restriction was incubated at 37° C. overnight.

The DNA was ethanol precipitated and resuspended in 36 µl of water, and 5 µl 10×NEB Buffer 4, 5 µl 1 mg/ml BSA, and 2 µl (40 U) of ApaLI (New England Biolabs). This was incubated at 37° C. for 5 hours; a further 2 µl of ApaLI was added and the reaction incubated at 37° C. overnight.

The cut DNA was extracted by gel purification on a 1.3% low melting point agarose gel followed by treatment with Geneclean, to yield the insert DNA for cloning.

Vector fd CAT2 (prepared and digested with ApaLI and NotI as in example 20) and the scFv DNA were ligated as in example 20.

Analysis of Clones

Colonies from the ligations were first screened for inserts by PCR screening. The PCR mixture was prepared in bulk by combining 14.8 µL 1×PCR Buffer, 1 µl dNTP (5 mM), 1 µl Back oligo (FDPCRBAK), 1 µl Forward oligo (FDPCR-FOR), and 0.2 µl Taq polymerase per colony screened. 20 µl of this PCR mixture was aliquoted into a 96 well Techne plate. The top of a colony was touched with a toothpick and twirled quickly into the PCR mixture and the colony rescued by placing the toothpick in a Cellwell plate (Nunc) containing 250 µl of 2×TY medium. The PCR mixture is covered with 1 drop of paraffin and the plate placed on the block at 94° C. for 10 minutes before cycling at 94° C. 1 minute, 60° C. 1 minute, 72° C. 2.5 minutes.

The clones thus derived were named as below. The affinity of scFv fragments derived the Fab fragments was not determined but previous results suggests that these are closely related although not necessarily identical (R. E. Bird & B. W. Walker TIBTECH 9 132-137, 1991).

| Construct Name (Kd) | Composition | Affinity of Fab |
| --- | --- | --- |
| TPB1 | VH-HuH2-(Gly$_4$-Ser)$_3$-VK-HuK3 (SEQ ID NO: 269) | 13 nM |
| TPB2 | VH-HuH1-(Gly$_4$-Ser)$_3$-VK-HuK4 (SEQ ID NO: 270) | 180 Nm |
| TPB3 | VH-HuH2-(Gly$_4$-Ser)$_3$-VK-HuK4 (SEQ ID NO: 271) | (Unknown) |
| TPB4 | VH-HuH1-(Gly$_4$-Ser)$_3$-VK-HuK3 (SEQ ID NO: 272). | 52 nM |

Preparation of phage and ELISA was as described in example 6. The clones generated in fd CAT2 were shown to bind lysozyme as expected.

Affinity Selection

Selection of Highest Affinity Binding Phage

Mixing experiments were performed in which fd-CAT2 scFvD1.3 phage (example 19) were mixed with either fd-CAT2 TPB1, fd-CAT2 TPB2, or fd-CAT2 TKPB4, and used in one round of panning.

The general method used for affinity selection by panning is that detailed below. Any deviation from this protocol is described at the relevant point. Panning plates were placed on a rocking platform between manipulations.

Falcon 35 mm Tissue Culture dishes were coated overnight with 1 ml of Lysozyme (various concentrations) dissolved in 50 mM Sodium Hydrogen Carbonate, pH 9.6, and blocked with 2 ml 2% MPBS at room temperature for 2 hours. Phage were prepared in 1 ml 2% MPBS and rocked at room temperature for 2 hours. Plates were washed for 5 minutes with 2 ml of the following solutions; 5 times with PBS, PBS-Tween, 50 mM Tris-HCl, pH 7.5; 500 mM Sodium Chloride, 50 mM Tris-HCl, pH 8.5; 500 mM Sodium Chloride, 50 mM Tris-HCl, pH 9.5; 500 mM Sodium Chloride, 50 mM Sodium Hydrogen Carbonated, pH 9.6; 500 mM Sodium Chloride. Phage were then eluted by adding 1 ml 100 mM Triethylamine and rocking for 5 minutes before removing the eluate which was neutralised with 100 µl 1.0 M Tris-HCl, pH 7.4.

Plates were coated overnight with Lysozyme at the concentration listed below.

Colonies from the single round of panning were probed with either MURDSEQ (for fdCAT2 scFvD1.3) or HUMD13SEQ (for fdCAT2 TPB constructs).

Circles of nitrocellulose (Schleicher & Schuell, BA 85, 0.45 µm) were labelled in pencil and lowered gently onto the colonies derived from the panning experiments and left for one minute. The filters were then pulled off quickly from one edge and placed colony side up on a piece of 3MM paper (Whatman) soaked in Denaturing solution (500 mM Sodium Hydroxide; 1.5 M Sodium Chloride) for 5 minutes. They were then transferred to 3MM soaked in Neutralizing Solution (3.0 M Sodium Chloride; 500 mM Tris-HCl, pH 7.5) for 1 minute, and then to 3 MM soaked in 5×SSC; 250 mM Ammonium Acetate for 1 minute. The filters were then air dried before baking in an 80° C. vacuum oven for 30 minutes.

The oligonucleotide probe was prepared by combining the following:

2 µl oligonucleotide (1 pmoles/µl)
2 µl γ-32P ATP (3000 Ci/mmole) (Amersham International plc)
2 µl 10× Kinase buffer (0.5 M Tris-HCl, pH 7.5; 100 mM Magnesium Chloride;
10 mM DTT)
12 µl Water
2 µl Polynucleotide Kinase (20 Units)

This was incubated at 37° C. for 1 hour.

Hybridization was performed in the Techne HB-1 Hybridiser. The baked filters were pre-hybridized at 37° C. in 40 ml of Hybridization Buffer (10 ml 100 mM Sodium pyrophosphate; 180 ml 5.0 M Sodium chloride; 20 ml 50× Denharts Solution; 90 ml 1.0 M Tris-HCl, pH 7.5; 24 ml 250 mM EDTA; 50 ml 10% NP40; made to 1 litre with water; 60.3 mg rATP; 200 mg yeast RNA (Sigma)), for 15 minutes before the addition of the 20 µl of the kinased oligo. The filters were incubated at 37° C. for at least one hour, and then washed 3 times with 50 ml of 6×SSC at 37° C. for 10 minutes (low stringency wash). Filters were air dried, covered with Saran wrap and exposed overnight with Kodak X-AR film.

Selection of fd-CAT2 scFv D1.3 from fd-CAT2 TPB4

FIG. 39, summarizes the results from panning experiments using a mixture of the high affinity fd-CAT2 scFv D1.3 phage (Kd-2 nM) and the fd-CAT2 TPB4 construct (Kd-52 nM).

At a coating concentration of 3000 µg/ml Lysozyme, little or no enrichment could be obtained. It was however, possible to get enrichment for the scFv D1.3 phage when a lower concentration of Lysozyme was used for coating the plates. The best enrichment value obtained was from 1.5% fd-CAT2 scFv D1.3 in the starting mixture, to 33% fd-CAT2 scFv D1.3 in the eluted faction, on a plate coated overnight with 30 µg/ml Lysozyme.

Selection of fd-CAT2 scFv D1.3 from fd-CAT2 TPB1

Enrichment for the high affinity scFv D1.3 phage over the fd-CAT2 TPB1 phage (Kd-13) nM, could only be shown from experiments where the plates had been coated overnight with low concentrations of Lysozyme, as shown in FIG. 40.

In summary, single chain Fv versions of a series of humanized D1.3 antibodies have been constructed in phage fd-CAT2. By affinity selection of fd-CAT2 phage mixtures, by panning in small petri dishes, it was shown that the high affinity scFv D1.3 phage, could be preferentially selected for against a background of lower affinity scFv HuD1.3 phage.

Example 36

Expression of Catalytically Active Staphylococcal Nuclease on the Surface of Bacteriophage fd Examples 11 and 12 showed that alkaline phosphatase from E. coli can be expressed as a catalytically active enzyme on the surface of bacteriophage fd. Here we show that Staphylococcal nuclease can also be expressed in a catalytically active form suggesting that this methodology may be general.

The gene for the enzyme Staphylococcal nuclease (SNase) was amplified from M13 mp18—SNase (Neuberger, M. S. et al Nature 312 604-608, 1984) by PCR using primers with internal ApaLI (5'-GGAATTCGTGCACAGAGTGCAACT-TCAACTAAAAAATTAC-3')(SEQ ID NO:65) and NotI (5'-GGGATCCGCGGCCGCTTGACCTGAAT-CAGCGTTGTCTTCG-3') (SEQ ID NO:66) restriction sites, cloned into phage vector fd-CAT2 after digestion with ApaLI-NotI restriction enzymes and the nucleotide sequence of the SNase gene and junctions with gene III checked by DNA sequencing. The fd-tet-SNase phage was prepared from the supernatant of infected E. coli TG1 cultures by three rounds of PEG precipitation, and the fusion protein demonstrated by SDS-gel electrophoresis and Western blotting using rabbit anti-g3p antiserum (Prof. I. Rasched, Konstanz) and peroxidase-labelled goat anti-rabbit antibodies (Sigma) (FIG. 41) as described in example 27. As well as the fusion protein band (calculated Mr 59749, but runs at a higher position due to the aberrant g3p behaviour), a smaller proteolytic product is seen.

The fusion protein was shown to be catalytically active by incubation of the fd-tet-SNase phage ($4 \times 10^9$ tetracyclin resistant colonies [TU]) with single stranded DNA (1 μg) for 1 hr at 37° C. in the presence of $Ca^{2+}$, and analysis of the digest by agarose gel electrophoresis (FIG. 42). Nuclease activity was not detected with the parent fd-CAT2 ($2 \times 10^{10}$ TU) phage alone or after three rounds of PEG precipitation of mixtures of fd-CAT2 ($2 \times 10^{10}$ TU) with SNase (0.7 μg). Thus the nuclease activity results from the display of the enzyme on the surface of the phage and not from co-precipitated or soluble SNase set free by degradation of the fusion protein. The nuclease activity of fd-tet-SNase (FIG. 42) lies in the same order of magnitude, ($2 \times 10^8$ TU and assuming three copies of SNase per TU) as an equimolar amount of SNase (0.03 ng or $10^9$ particles), and like the authentic SNase was dependent on $Ca^{2+}$, since incubation with 40 mM $MgCl_2$ and 25 mM EGTA blocked activity (not shown).

Example 37

Display of the Two Aminoterminal Domains of Human CD4 on the Surface of fd Phage The protein CD4, a member of the immunoglobulin superfamily, is a cell surface receptor involved in MHC class II restricted immune recognition. It is also recognised by the protein gp120 derived from the human immunodeficiency virus (AIDS virus). The first two domains (named V1 and V2, residues 1-178) of the surface antigen CD4 were amplified from pUC13-T4 (gift from T. Simon) containing the human cDNA of CD4, by PCR using primers with internal ApaLI (5'-GGA ATT CGT GCA CAG AAG AAA GTG GTG CTG GGC AAA AAA GGG G-3') (SEQ ID NO:67) and NotI (5'-GGG ATC CGC GGC CGC AGC TAG CAC CAC GAT GTC TAT TTT GAA CTC-3') (SEQ ID NO:68) restriction sites. After digestion with these two enzymes, the PCR-product was cloned into fdCAT2, and the complete nucleotide sequence of the CD4-V1V2 DNA and junctions with gene III checked by dideoxy sequencing using oligonucleotides fd-seq1 (5'-GAA TTT TCT GTA TGA GG)(SEQ ID NO:69), CD4-seq1 (5'-GAA GTT TCC TTG GTC CC-3') (SEQ ID NO:70) and CD4-seq2 (5'-ACT ACC AGG GGG GCT CT-3') (SEQ ID NO:71). In the same way, a fd-CD4-V1 version was made, linking residues 1-107 to the N-terminus of gene III, using previously mentioned primers and oligonucleotide 5'-GGG ATC CGC GGC CGC GGT GTC AGA GTT GGC AGT CAA TCC GAA CAC-3' (SEQ ID NO:72) for amplification, PCR conditions and cloning were essentially as described in example 15 except that digestion was with ApaLI and NotI (used according to the manufacturers instructions).

Both fd-CD4-V1 and fd-CD4-V1V2 phages were prepared from the supernatant of infected E. coli TG1 cultures by three rounds of PEG precipitation, thereby concentrating the sample 100-fold for ELISA analysis. The fusion protein was detected in a Western blot (results not shown) with a rabbit anti-gene III antiserum, and revealed bands of the expected size.

Binding of the CD4 moiety to soluble gp120 (recombinant HIV-IIIB gp120 from CHO cells, ADP604, obtained from the Aids Directed Programme, National Institute for Biological Standards and Controls, South Mimms, Potters Bar, UK) was analysed in an ELISA, using 5 μg/ml gp120 for coating (overnight, in PBS). Anti-M13 antiserum was used to detect bound phage; all other conditions were as in Example 9. FIG. 43 shows the ELISA signals of wild-type phage (fd-tet) and both CD4-phages. Both CD4-phages can bind gp120, but fd-CD4-V1V2 binds much stronger to gp120 than fd-CD4-V1. The binding competitors, soluble CD4 (recombinant soluble CD4 from Baculovirus, ADP 608; from the AIDS Directed Programme) (25 μg/ml) or soluble gp120 (20 μg/ml), added together with the 50 μl phage stock sample during the ELISA, decreased the signal to background level. These results indicate that phage binding to gp120 is mediated by the CD4 molecule displayed at its surface, and that binding is stronger when the two aminoterminal domains of CD4 are presented.

Thus, CD4 is a cell surface receptor molecule which is active when displayed on bacteriophage fd. Like the PDGF-BB receptor, the functional display of which is described in examples 15 and 16, CD4 is a member of the immunoglobulin superfamily and this result suggests that this class of molecule may be generally suitable for display on the surface of phage.

Example 38

Generation and Selection of Mutants of an Anti-4-hydroxy-3-nitrophenylacetic acid (NP) Antibody Expressed on Phage Using Mutator Strains It will sometimes be desirable to increase the diversity of a pool of genes cloned in phage, for example a pool of antibody genes, or to produce a large number of variants of a single cloned gene. There are many suitable in vitro mutagenesis methods. However, an attractive method, particularly for making a more diverse population of a library of antibody genes, is to use mutator strains. This has the advantage of generating very large numbers of mutants, essentially limited only by the number of phage that can be handled. The phage display system allows full advantage to be taken of this number to isolate improved or altered clones.

Nucleotide sequences encoding an antibody scFv fragment directed against 4-hydroxy-3-nitrophenylacetic acid (NP), scFvB18, derived as in example 14 from a monoclonal antibody against NP were cloned into fdCAT2 using ApaLI and NotI restriction sites as in example 11 to create fdCAT2scFvB18 or into fdDOGKan (fdCAT2 with its tetracycline resistance gene removed and replaced by a kanamycin resistance gene) using PstI and NotI restriction sites to create fdDOGKanscFvB18 or into the phagemid vector pHEN1 using the restriction sites SfiI and NotI as a fusion protein with gene III to create pHEN1scFvB18.

The following mutator strains (R. M. Schaaper & R. L. Dunn J. Mol. Biol. 262 1627-16270, 1987; R. M. Schaaper Proc. Natl. Acad. Sci. U.S.A. 85 8126-8130 1988) were used:
NR9232: ara, thi, mutD5-zaf13::Tn10, prolac, F'prolac
NR9670: ara, thi, azi, mutT1, leu::Tn10, prolac
NR9292: ara, thi, mutH101, prolac, F'prolac
NR9084: ara, thi, mutT1, azi, prolac, F'prolacI⁻Z⁻ΔM15 M15
NR9046: ara, thi, supE, rif, nalA, metB, argE(am), prolac, F'prolac
were kind gifts of Dr. R. M. Schaaper (Department of Health & Human Services, N1H, PO Box 12233, Research Triangle Park, N.C. 27709)
NR9046mutD5: NR9046 mutD5::Tn10
NR9046mutT1: NR9046 mutT1::Tn10
were constructed by P1 transduction according to standard procedures. Mutator strains were transfected with fdCAT2scFvB18 of fdDOGKanscFvB18 and transfectants selected for antibiotic resistance. Transfectants were grown for 24 h at 37° C. before mutant phage was harvested by PEG precipitation. The mutant phage were selected on a 1 ml NIP (4-hydroxy-3-iodo-5nitrophenylacetic acid)-BSA-Sepharose affinity column (prepared according to the manufacturers instructions) prewashed with 200 ml of PBS and blocked by 20 ml MPBS. Phage were loaded on the column in 10 ml MPBS and unbound material reapplied to ensure complete binding. The column was subsequently washed with 10 ml of MPBS and 500 ml of PBS. Phage bound to the affinity matrix was eluted with 5 column volumes of 0.33 mM NIP-Cap (example 48).

Phage eluate was incubated for 30 min to 1 h with log phase ($2\times10^8$ cells/ml) E. coli mutator strains without antibiotic selection. The infected cells were then diluted 1:100 in 2×TY and grown for 24 h with antibiotic selection (15 μg/ml tetracyclin or 30 μg/ml kanamycin for fdCAT2scFvB18 or fdDOGKanscFvB18 respectively). Phage from this culture was used for another round of affinity selection and mutation.

Binding of phage antibodies was assayed by ELISA as in example 9 except that ELISA plates were coated with NIP-BSA (4-hydroxy-3-iodo-5-nitrophenylacetyl-BSA; 0.4 mg/ml). Culture supernatants were prepared following growth in Cellwells as described in example 21 and 20 μl of culture supernatant was added to each well diluted to 200 μl with MPBS.

Phage samples giving signals in ELISA of more than twice the background were tested ELISA as above for non-specific binding against lysozyme, BSA or Ox-BSA (example 9). Specificity for NIP was further confirmed by an ELISA in which serial dilutions of NIP-CAP were added together with phage antibodies. Addition of increasing concentrations of NIP-CAP reduced the ELISA signal to the background level.

Phage giving positive signals in ELISA were sequenced and 2 different mutants were subcloned into pHEN1 phagemid and transformed into HB2151 for soluble expression and TG1 for phage display (example 27).

For expression of soluble scFv fragments, transformants in E. coli HB2151 were grown at 37° C. in 1 litre 2×TY, 0.2% glucose, 0.1 mg/ml ampicillin to an OD600 of 1 and expression of soluble scFv fragments induced by adding IPTG to 1 mM. Cultures were shaken at 30° C. for 16 h.

Soluble scFvB18 was concentrated from crude bacterial supernatant in a FLOWGEN ultrafiltration unit to a volume of 200 ml.

The concentrate was passed two times over a 2 ml column of NIP-BSA-Sepharose prewashed with 200 ml of PBS. The column was washed with 500 ml of PBS and 200 ml of 0.1M Tris pH7.5, 0.5M NaCl and phage antibodies eluted with 50 mM Citrate buffer pH2.3. The eluate was immediately neutralised with 1 MTris pH8. The eluate was dialysed against two changes of 1 litre PBS, 0.2 mM EDTA, Precipitated protein was removed by centrifugation at 10000 g and protein yield was determined by measuring the absorbance at 280 nm of the supernatant.

After 4 rounds of mutation and selection, isolated clones were screened and in one or two rare examples strongly positive ELISA signals were obtained from phage antibodies derived from the mutation of each of fdCAT2scFvB18 and fdDOGKanscFvB18 in the ELISA. The ELISA conditions were such that the parent phage fdCAT2scFvB18 only generated weak signals. These phage antibodies giving strongly positive ELISA signals were enriched in further rounds by a factor of roughly 2.5 per round. Forty phage antibodies giving strongly positive signals were sequenced and they each displayed single mutations in six different positions in the scFvB18 nucleotide sequences, five of which reside in the light chain. More than 70% of the mutations occurred at positions 724 and 725 changing the first glycine in the J segment of the light chain (framework 4) to serine (in 21 cases) or aspartate (in 3 cases). The mutations found are shown in Table 9. The sequence of scFvB18 is shown in FIGS. 44a through 44b.

The nucleotide sequences encoding the scFv fragments of a framework mutant with the above glycine to serine mutation, as well as a mutant where Tyr in the CDR3 of the light chain had been mutated to aspartate, were amplified by PCR from the phage antibody clones and subcloned into pHEN1 phagemid (essentially as in example 25). This avoids possible problems with geneIII mutations caused by the mutator strains. The same pattern of ELISA signals was seen when the mutants were displayed on phage following rescue of the phagemid with helper phage (as described in example 25) as when the mutants were assayed when expressed from the phage genome as above.

The scFv fragments from scFvB18 and the scFv fragments containing the glycine to serine and tyrosine to aspartate mutations respectively were expressed in solution (following transformation into E. coli HB2151 as in example 27) at 30° C. They showed no differences in the ELISA signals between wild-type B18 and the framework mutant. The signal obtained from the phage antibody with the Tyr mutated to aspartate in CDR3 of scFvB18 was about 10× stronger. Expression yields were found to be comparable as judged by Western blotting using an antiserum raised against g3p (as described above). Affinity measurements were performed using fluorescence quenching as described in example 23. Affinity measurement of affinity purified scFv fragments however showed scFvB18, and the scFvB18 (Gly->Ser) and scFvB18 (Tyr->Asp) mutants all to have a comparable affinity of 20 nM for NIP-CAP.

A Western blot using an anti-geneIII antibody showed the framework mutant had suffered significantly less proteolytic cleavage than scFvB18.

Hence, the use of mutator strains generates a diverse range of mutants in phage antibodies when they are used as hosts for clones for gene III fusions. In this case some of the clones exhibit higher ELISA signals probably due to increased stability to proteolyic attack. The mutator strains can therefore be used to introduce diversity into a clone or population of clones. This diversity should generate clones with desirable characteristics such as a higher affinity or specificity. Such clones may then be selected following display of the proteins on phage.

Example 39

Expression of a Fv Fragment on the Surface of Bacteriophage by Non-Covalent Association of VH and VL Domains This example shows that functional Fv fragments can be expressed on the surface of bacteriophage by non-covalent association of VH and VL domains. One chain is expressed as a gene III fusion and the other as a soluble polypeptide. Thus Fv fragments can be used for all the strategies discussed for Fab fragments including dual combinatorial libraries (example 26).

A useful genetic selection system for stably associated Fv fragments could be established if the expression of Fv fragments as fusion proteins on the phage surface would be possible such that one V domain is fused to the gene III protein and the other V domain is expressed separately in secreted form, allowing it to associate with the V domain on the fusion protein provided the interaction strength is sufficiently high. This idea was tested in a model experiment using the V domains from the anti-hen egg lysozyme antibody D1.3 by fusing the D1.3 VK gene to gene III and separately expressing the D1.3 VH domain.

Experimentally this was achieved as follows: The vector fd-DOG1 was digested with the restriction enzymes PstI and XhoI. From the Fv expression plasmid pSW1-VHD1.3-VKD1.3myc version 3/pUC119 (Ward et al., 1989 supra) a Pst 1/Xho I-digested restriction fragment was isolated that carries the VH domain coding sequence (terminated by 2 stop codons), a spacer region between VH and VK genes including a ribosome-binding site for expression of the VK gene, a pelB leader sequence, and, following in frame, the VK gene. This fragment was cloned into the digested fd-DOG vector to generate the construct fd-tet Fv D1.3. As shown on the map in FIG. 45, the dicistronic VH/VK-gene III operon is transcribed from the gene III promoter; secretion of the VH domain is achieved by the gene III protein leader, secretion of the VK-geneIII fusion protein by the pelB leader sequence. For control purposes a second construct with the name fd-tet Fv D1.3 (AS-Stuffer) was made by a similar route as described above: the VH used in this construct carries an insertion of a 200 bp fragment in the Sty I restriction site at the junction of VH CDR 3/FR4, thus interrupting the VH with several in frame stop codons. It is known from previous work that this insertion sufficiently disrupts the VH structure to abolish binding to the antigen lysozyme when expressed either as a soluble Fv or single-chain Fv fragment or as a single-chain Fv fragment on phage surface. This construct was used as a control. TG1 bacteria carrying either the fd-tet Fv D1.3, fd-tet Fv D1.3 (AS-Stuffer) or as single-chain wild-type control fd-tet scFv D1.3 plasmids were grown in liquid culture (medium 2×TY containing 15 µg/ml tetracycline) for 24 h to produce phage particles in the supernatant. After removal of bacterial cells by centrifugation the phage titer in the supernatants was determined by re-infecting exponentially growing TG1 cells with dilutions of the supernatants and scoring tetracycline-resistants colonies after plating on tetracycline-plates. The infectious phage titers achieved were $1 \times 10^{11}$ tetR transducing units/ml for the single-chain wild-type control fd-tet scFv D1.3 and $2 \times 10^{10}$ tetR transducing units/ml for Fv phage constructs fd-tet Fv D1.3 and fd-tet Fv D1.3 (ΔS-Stuffer).

ELISA of Hen Egg Lysozyme was Performed as in Example 2.

The results are shown in FIG. 46. Phage derived from bacteria carrying and expressing the Fv construct fd-tet Fv D1.3 bind to the immobilised hen egg lysozyme, and when taking the phage titer into account, indeed apparently better than the single-chain Fv bearing phages produced by fd-tet scFv D1.3 carrying bacteria. The specificity of the reaction and the requirement for a functional VH domain is demonstrated by the fd-tet Fv D1.3 (ΔS-Stuffer) control in which disruption of the VH domain and consequently of the Fv fragment association eliminates binding to lysozyme.

As a final control of the expected structure of the VK/geneIII fusion protein a Western Blot was carried out. 20 µl of phage suspensions concentrated 100 fold by two sequential precipitations with PEG were applied to a 10% SDS-PAGE gel, electrophoretically separated and then transferred to a PVDF membrane (Immobilon, Millipore) in a semi-dry Western transfer apparatus (Hoefer). Remaining binding sites on the filter were blocked by 1 h incubation with 3% BSA in PBS, and detection of the gene III protein accomplished by incubation with a 1:1000 diluted rabbit anti-geneIII antiserum for 2 h, several washes in PBS/0.1% Tween 20, incubation with peroxidase-conjugated goat anti-rat immunoglobulin antibodies, washes and development with the chromogenic substrate diaminobenzidine/$CoCl_2$/0.03% $H_2O_2$. The Fv phage fd-tet Fv D1.3 yields a band for the gene III fusion protein (data not shown), that is intermediate in size between the bands obtained for a wild-type gene III protein from fd-DOG1 and the scFv-gene III fusion protein from fd-tet scFv D1.3, thus proving the presence of a single immunoglobulin domain covalently fused to the gene III product in the Fv phage.

In summary, Fv-gene III fusions in which one V domain is fused to the gene III protein and the other V domain associates non-covalently can be presented in functionally active form on the surface of filamentous phage. This opens the possibility to genetically select for stably associated Fv fragments with defined binding specificities from V gene libraries expressed in phages.

Example 40

A PCR Based Technique for One Step Cloning of Human V-Genes as Fab Constructs

This example describes a PCR based technique to "assemble" human Fabs by splicing together the heavy and light chain DNA with a separate piece of 'linker' DNA. A mixture of universal primers is used which should make the technique applicable to all human V-genes.

The general technique for PCR assembly of human V-genes to create a Fab construct is described. The efficiency of this technique was assessed by "assembling", cloning and expressing a human anti rhesus-D (Rh-D) Fab from a IgG-K monoclonal hybridoma. We also demonstrate the potential to rescue human monoclonal antibodies from polyclonal cell populations by assembling, cloning, expressing and isolating an IgG-lambda monoclonal anti-Rh-D Fab from a polyclonal lymphoblastic cell line (LCL).

The overall strategy for the PCR assembly is shown in FIG. 47 and is described in more detail below. For Fab assembly, the VH-CH1 and VK-CK or V lambda-C lambda light chains are amplified from first strand cDNA and gel purified. Heavy and light chain DNA are then combined together with linker DNA and flanking oligonucleotides in a new PCR reaction. This results in a full length Fab construct since the 5' end of the linker DNA is complementary to the 3' end of the CH1 domain and the 3' end of the linker is complementary to the 5' end of the light chain domain. The linker DNA contains terminal residues of the human CH1 domain, the bacterial leader sequence (pelB) for the light chain and the initial residues of the VK or V lambda light chain. Finally, after gel purification, the Fab construct is reamplified with flanking oligonucleotides containing restriction sites for cloning.

Oligonucleotide Primers:

In order to develop the PCR cloning of human V genes it was necessary to design a new range of human specific oligonucleotide primers.

The PCR primers at the 5' end of the VH and VK and Vlambda gene exon (BACK primers) are based on sequence data extracted from the Kabat database, (Kabat, E. A. et al, Sequences of Proteins of Immunological Interest. 4th Edition. US Department of Health and Human Services. 1987) the EMBL database, the literature (Chuchana, P., et al, Eur J. Immunol. 1990. 20:1317) and unpublished data. The sequence of the VH, VK and Vlambda primers are given in table 1. In addition, extended VH primers with SfiI sites at the 5' end were also designed (Table 10) for adding a restriction site after assembly.

Table 10 also shows the 3' primers (FORWARD primers) designed for the PCR based cloning of human V genes. There are two sets of these depending on whether a Fab or scFv is to be produced. For Fab assembly, the forward primer was based at the 3' end of the CH1 domain, CK domain and Clambda domain. In addition, the CK and C2 FORWARD primers were also synthesized as extended versions with NotI sites at their 5' ends.

Primers complementary to the CH1 forward primers and the VkK and V lambda back primers were synthesized to permit generation of linker DNA by PCR amplification of a plasmid template containing the Fab linker (Table 10). To ensure adequate amplification, the primers were extended into the actual linker sequence.

A RNA Preparation

This is essentially the same as described in Example 14, but using material of human origin. In the results given in this example human hybridoma and human polyclonal lymphoblastic cell lines were used.

B cDNA Preparation

Approximately 4 μg of total RNA in 20 ul water was heated at 65° C. for 3 minutes, quenched on ice and added to a 30 ul reaction mixture resulting in a 50 ul reaction mixture containing 140 mM KCl, 50 mM Tris, HCl (pH8.1 @ 42° C.), 8 mM MgCl2, 10 mM DTT, 500 uM deoxythymidine triphosphate 500 uM deoxycytosine triphosphate, 500 uM deoxyadenosine triphosphate and 500 uM deoxyguanosine triphosphate, 80 units of human placental RNAse inhibitor and 10 pmol of the appropriate Forward primer (HuIgG1-4CH1FOR, HuIgMFOR, HuCKFOR, HuCLFOR). Two ul (50 units) of avian myeloblastosis virus (AMV) reverse transcriptase was added, the reaction incubated at 42° C. for 1 hour, heated to 100° C. for 3 minutes, quenched on ice and centrifuged for 5 minutes.

C Primary PCRs

For the primary PCR amplifications, an equimolar mixture of the appropriate family based BACK and FORWARD primers was used. (See specific examples 40a and 40b given later in this example). A 50 ul reaction mixture was prepared containing 5 ul of the supernatant from the cDNA synthesis, 20 pmol total concentration of the FORWARD primers, 250 uM dNTPs, 50 mM KCl, 100 mM Tris. HCl (pH 8.3), 1.5 mM MgCl2, 175 ug/ml BSA and 1 ul (5 units) *Thermus aquaticus* (Taq) DNA polymerase (Cetus, Emeryville, Calif.). The reaction mixture was overlaid with paraffin oil and subjected to 30 cycles of amplification using a Techne thermal cycler. The cycle was 94° C. for 1 minute (denaturation), 57° C. for 1 minute (annealing) and 72° C. for 1 minute (extension). The product was analyzed by running 5 ul on a 2% agarose gel. The remainder was extracted twice with ether, twice with phenol/chloroform, ethanol precipitated and resuspended in 50 ul of H₂O.

D Preparation of Linker

To make the Fab linker DNA, 13 separate PCR reactions were performed using HuIgG1-4CH1FOR and each of the reverse VK or V lambda oligonucleotides. The template was approximately 1 ng of pJM-1Fab D1.3 (FIG. 48) The PCR reaction reagents were as described above and the cycle was 94° C.: 1 min, 45° C.: 1 min and 72° C.: 1 min. The linkers were analyzed on a 4% agarose gel, purified on a 2% agarose gel, eluted from the gel on a Spin-X column and ethanol precipitated.

E Assembly PCRs

For PCR assembly of a human Fab approximately 1ug of a primary heavy chain amplification and 1ug of a primary light chain amplification were mixed with approximately 250 ng of the appropriate linker DNA in a PCR reaction mixture without primers and cycled 7 times (94° C.: 2 min, 72° C.: 2.5 min) to join the fragments. The reaction mixture was then amplified for 25 cycles (94° C.: 1 ml, 68°-72° C.: 1 min, 72° C.: 2.5 min) after the addition of 20 pmol of the appropriate flanking BACK and FORWARD primers.

F Adding Restriction Sites

The assembled products were gel purified and reamplified for 25 cycles (94° C.: 1 min, 55° C.: 1 min, 72° C.: 25 min) with the flanking oligonucleotides containing the appended restriction sites. PCR buffers and NTPs were as described previously.

Specific Examples of PCR Assembly of Human Immunoglobulin Genes a. PCR assembly of a Fab from a human hybridoma: the human monoclonal anti Rh-D cell lines Fog-1 (IgG-k) was derived from EBV transformation of the PBLs of a Rh-D negative blood donor immunized with Rh-D positive blood and has been previously described (Melamed, M. D., et al., J. Immunological Methods. 1987. 104:245) (Hughes-Jones N. C., et al., Biochem. J. 1990. 268:135) (Gorick, B. D. et al., Vox. Sang. 1988. 55:165) Total RNA was prepared from approximately $10^7$ hybridoma cells. First strand cDNA synthesis was performed as described above using the primers HuIgG1-4CH1FOR and HuCKFOR. Primary PCRs were performed for the VH-CH1 using a mixture of the 6 HuVH-BACK primers and HuIgG1-4CG1FOR and for the VK-CK using a mixture of the 6 HuVKBACK primers and HuCK-FOR. A Fab construct was assembled as described above, restricted with SfiI and NotI, gel purified and ligated into pJM-1Fab D1.3 restricted with SfiI and NotI. The ligation mixture was used to transform competent *E. coli* E.M.G. cells. Ninety-six clones were toothpicked into media in microtitre plate wells, grown to mid-log phase at 30° C. and then expression of the Fab was induced by heat shocking at 42° C. for 30 min followed by growing for 4 hours at 37° C. The ninety-six clones were then screened for anti-Rh-D activity as described below.

b. assembly of human Fabs from a polyclonal (LCL): A polyclonal LCL "OG" was derived from EBV transformation of approximately $10^7$ peripheral blood lymphocytes (PBLs) from a Rh-D negative donor immunized with Rh-D positive red blood cells. The cells were plated at a concentration of approximately $10^5$ cells per well. Positive wells were identified by screening the cells harvested and then subcloned once. Typing of the well indicated that an IgG-lambda antibody was being produced. At this stage, total RNA was prepared from approximately $10^6$ cells. First strand cDNA synthesis was performed as described above using the primers HulgG1-4CG1FOR and HuCLFOR. Primary PCRs were performed for the VH-CH1 using a mixture of the 6 HuVHBACK2 primers and HulgG1-4 CG1FOR and for the V lambda-C lambda using a mixture of the 7 HuV BACK primers and HuC FOR. Restriction, cloning and screening proceeded as described. To determine the diversity of the clones, the VH and V lambda genes of 15 clones were PCR amplified, restricted with the frequent cutting restriction enzyme BstN1 and analyzed on a 4% agarose gel (see example 20).

Assay for anti-Rh-D activity and demonstration of specificity: A 5% (vol/vol) suspension of either Rh-D positive (OR2R2) or Rh-D negative (Orr) erythrocytes in phosphate buffered saline (PBS, pH 7.3) were incubated with a papain solution for 10 min at 37° C. The erythrocytes were washed three times in PBS and a 1% (vol/vol) suspension of erythrocytes was made up in PBS supplemented with 1% (vol/vol) of bovine serum albumin (BSA). Fifty ul of a papain treated erythrocyte suspension and 50 ul of phage supernatant were placed in the wells of round bottom microtitre plates and the plates were placed on a Tltertek plate shaker for 2 min. After 15 min incubation at 37° C. 100 ul of PBS/BSA was added to each well. The plates were centrifuged at 200 g for 1 min and the supernatant was discarded. The erythrocytes were resuspended in the remaining PBS/BSA and the Fab fragments were crosslinked by addition of the 9E10 monoclonal antibody (50 ul a 1 ug/ml solution in PBS/BSA) directed against the myc peptide tag (Ward, E. S., et al., Nature 1989. supra). The plates were placed at room temperature (RT) until sedimentation had occurred. Agglutination of erthrocytes caused a diffuse button of erythrocytes and the results were evaluated macroscopically. Specificity was confirmed with a standard prepapainized (as above) panel of 9 erythrocyte suspensions in PBS (all suspensions blood group O, 4 D positive and 5 D negative) known to have homozygous expression of all the clinically relevant erythrocyte blood group alloantigens. The number of copies of the D antigen on the D positive cells varied between 10,000 and 20,000 per erythrocyte depending on the Rh genotype. Briefly, 50 ul phage supernatant in PBS supplemented with 2% (vol/vol) skimmed milk was mixed with 50 ul of a 2% erythrocyte suspension in PBS in glass tubes and incubated for 15 min at 37° C. After one wash with PBS/BSA the erythrocytes were pelleted and resuspended in 50 ul donkey anti-human lambda light chain (Sigma L9527, diluted 1:40 in PBS/BSA). The tubes were centrifuged for 1 min at 200 g and agglutination was read macroscopically using "tip and roll" method.

Results a PCR assembly of a Fab from a human hybridoma: A single band of the correct size was obtained after amplification. Thirty-eight of 96 clones (40%) screened specifically agglutinated Rh-D positive but not Rh-D negative red blood cells. The results demonstrate a high frequency of successful splicing in the assembly process and the potential of this technique for one step cloning of human hybridomas.

b Assembly of human Fabs from a polyclonal lymphoblastic cell line (LCL): Analysis of the diversity of the clones indicated that 3 different heavy chain families and 2 different light chains families were present. Five anti-Rh-D specific clones were identified out of 96 screened. The VH and Vλ chains had identical nucleotide sequences in each clone and were typical of anti-Rh-D V-genes (unpublished results). The results demonstrate the potential of this technique to assemble, clone and isolate human antibody fragments from polyclonal cell populations (see also section on isolation of specific binding activities from an 'unimmunized' human library (examples 42 and 43).

Example 41

Selection of Phage Displaying a Human Fab Fragment Directed Against the Rhesus-D Antigen by Binding to Cells Displaying the Rhesus D Antigen on their Surface A large number of important antigens are integral components of cell surface membranes, i.e. they are cell surface antigens. These include tumor specific antigens and red and white blood cell surface antigens. In many instances, it would be important to isolate antibodies against these antigens. For example, antibodies directed against the rhesus-D (Rh-D) antigen on red blood cells are used both diagnostically and therapeutically. Many of these antigens are difficult to purify and some, like Rh-D, are not biologically active when isolated from the membrane. Thus, it would be useful to be able to affinity purify antibody fragments displayed on the surface of bacteriophage directly on cell surface antigens. To test the feasibility of affinity purification on cell surface antigens, the anti-Rh-D human monoclonal antibody Fog-B was displayed as a Fab fragment on the surface of bacteriophage fd. The displayed Fog-B Fab fragment bound antigen as determined by agglutination assay and could be affinity purified on the basis of its binding on the surface of Rh-D positive red blood cells but not Rh-D negative red blood cells.

Materials and Methods

Construction of a clone encoding an anti-Rh-D Fab fragment in phagemid pHENI and display of the Fab fragment on the surface of bacteriophage fd.

The human hybridoma Fog-B has been previously described (N. C. Hughes-Jones et al Biochem, J. 268 135 (1990). It produces an IgG-1/lambda antibody which binds the Rh-D antigen. RNA was prepared from $10^7$ hybridoma cells using a modified method of Cathala (as described in example 14) and 1st strand cDNA synthesized using specific immunoglobulin heavy and light chain primers (HuVH1FOR [example 40] and HuCλ FOR (5'-GGA ATT CTT ATG AAG ATT CTG TAG GGG CCA C-3') (SEQ ID NO:73)) as described in example 14. The VH gene was subsequently amplified from an aliquot of the 1st strand cDNA using HuVH4aBACK and HuVH1FOR. The Vλ gene was amplified using a Vλ primer specific for Fog-B (VλFog-B: 5'-AAC CAG CCA TGG CC AGT CTG TGT TGA CGC AGC C-3') (SEQ ID NO:74). The PCR conditions were as described in example 40. The PCR products were analyzed by running 5 µl on a 2% agarose gel. The remainder was extracted twice with ether, twice with phenol/chloroform, ethanol precipitated and resuspended in 50 µl of $H_2O$. The amplified VH DNA was digested with Pst1 and BstEII, and the amplified Vλ-Cλ DNA with Ncol and EcoR1. The fragments were purified on a 2% agarose gel, extracted using Geneclean, and sequentially ligated into the soluble expression vector pJM-1 Fab D1.3 (FIG. 48a). Clones containing the correct insert were initially identified by restriction analysis and verified by assay of expressed soluble Fab (see example 23 for induction conditions). The Fog-B Fab cassette was amplified from pJM-1 by PCR using HuVH4BACK-Sfi and Hu Cλ-Not, digested with the appropriate restriction enzymes and ligated into pHEN1. Clones containing the correct insert were identified initially by restriction analysis and subsequently by assay (see example 25 for induction conditions).

Assay for soluble Fog-B Fab fragment and phage displayed Fog-B Fab fragment for anti-Rh-D activity and documentation of specificity.

Assay of the soluble expressed Fab was performed on unconcentrated E. coli supernatant. Assay of Fog-B displayed on the phage surface was performed on phage that had been concentrated 10 fold by PEG precipitation and then resuspended in PBS. the assays for activity and specificity are as described in example.

Cell Surface Affinity Purification of Phage Displaying Fog-B Anti-Rh-D Fab Fragment Purified Fog-B phage was mixed with purified phage Fd-Tet CAT-1 displaying the anti-lysozyme scFv D1.3 (pAbD1.3) in a ratio of approximately 1 Fog-B:50 scFvD1.3. Prepapainized erythrocytes (OR2R2 [Rhesus positive] or Orr [Rhesus negative]) were suspended in PBS supplemented with 2% skimmed milk powder in a concentration of $4 \times 10^7$/ml. One ml of this suspension was mixed with $10^{11}$ phage suspended in 2 ml of PBS supplemented with 2% skimmed milk and incubated for 30 min at room temperature under continuous rotation. The erythrocytes were washed three times with an excess of ice-cold PBS (10 ml per wash) and subsequently pelleted. The phage were eluted from the cells by resuspending in 200 µl of 76 mM citric acid pH 2.8 in PBS for 1 min. The cells were then pelleted by centrifugation for 1 min at 3000 rpm and the supernatant containing the eluted phage was neutralized by adding 200 µl of 240 mM Tris-base, 22 mM Disodium hydrogen phosphate in 1% w/vol albumin. Serial dilutions of the eluate was used to infect TG1 cells. Fog-B Fab phage were selected on ampicillin plates and scFvD1.3 phage on tetracycline plates and the titre of each determined prior to selection, after selection on rhesus-D negative cells and after selection on rhesus-D positive cells.

Results

Fog-B Fab fragment displayed on the surface of the phage derived from the phagemid pHEN clone specifically agglutinated rhesus-D positive but not rhesus D-negative red blood cells. Affinity purification of the Fog-1 Fab phagemid on Rh-D positive red blood cells resulted in an enrichment from 1:50 to 1500:1 (Fog-B Fab:scFvD1.3), whereas purification on Rh-D negative red blood cells demonstrated essentially no enrichment (10 fold).

|  | TITRE Fog-B Fab scFvD1.3 | RATIO Fog-B FAb/scFvD1.3 |
|---|---|---|
| Prior to selection | $1.0 \times 10^8$ $5.0 \times 10^9$ | 1:50 |
| Selection on Rh-D negative cells | $2.0 \times 10^4$ $1.0 \times 10^5$ | 1:5 |
| Selection on Rh-D positive cells | $6.0 \times 10^6$ $4.0 \times 10^3$ | 1500:1 |

Example 42

A PCR Based Technique for One Step Cloning of Human scFv Constructs

Assembly of human scFv is similar to the assembly of mouse scFvs described in example 14. To develop the PCR cloning of human V genes it was necessary to design a new range of human specific oligonucleotide primers (table 10). The use of these primers for the generation of human Fabs is described in example 40. The assembly of human scFvs is essentially the same but requires a set of FORWARD primers complementary to the J segments of the VH, VK and V lambda genes. (For Fabs FORWARD primers complementary to the constant region are used). The J segment specific primers were designed based on the published JH, JK and J lambda sequences (Kabat, E. A. et al, Sequences of Proteins of Immunological Interest. 4th Edition. US Department of Health and Human Services. 1987).

In addition, a different linker is needed for scFvs than for Fabs so for human scFvs a new set of primers was needed to prepare the linker. Primers complementary to the JH forward primers and the VK and V lambda back primers were synthesized to permit generation of linker DNA by PCR amplification of a plasmid template containing the scFv linker (Table 10, FIG. 49). To ensure adequate amplification, the primers were extended into the actual linker sequence. Using these primers to make the scFv linker DNA, 52 separate PCR reactions were performed using each of the 4 reverse JH primers in combination with each of the 13 reverse VK and V lambda oligonucleotides. The template was approximately 1 ng of pSW2scD1.3 (Ward, E. S. 1989 supra) containing the short peptide (Gly4Ser)3 (Huston, J. S. et al., Gene 1989. 77:61)

A Specific Example of PCR Assembly of a Human scFv Library

This example describes the generation of a human library of scFvs made from an unimmunized human:

500 ml of blood, containing approximately $10^8$ B-cells, was obtained from a healthy volunteer blood donor. The white cells were separated on Ficoll and RNA was prepared as described in example 14.

Twenty percent of the RNA, containing the genetic material from approximately $2 \times 10^7$ B-cells, was used for cDNA preparation as described in example 40. Heavy chains originating from IgG and IgM antibodies were kept separate by priming cDNA synthesis with either an IgG specific primer (HuIgG1-4CH1FOR) or an IgM specific primer (HuIgM-FOR). Aliquots of the cDNA was used to generate four separate scFv libraries (IgG-K, IgG-lambda, IgM-K and IgM-lambda) as described in example 40. The resulting libraries were purified on 1.5% agarose, electroeluted and ethanol precipitated. For subsequent cloning, the K and lambda libraries were combined giving separate IgG and IgM libraries.

Cloning of the library: The purified scFv fragments (1-4 ug) were digested with the restriction enzymes NotI and either SfiI or NcoI. After digestion, the fragments were extracted with phenol/chloroform, ethanol precipitated. The digested fragments were ligated into either SfiI-NotI or NcoI-NotI digested, agarose gel electrophoresis purified pHEN1 DNA (6 ug) (see example 24), in a 100 µl ligation mix with 2,000 U T4 DNA ligase (New England Biolabs) overnight at room temperature. The ligation mix was purified by phenol extraction and ethanol precipitated. The ligated DNA was resuspended in 10 µl of water, and 2.5 µl samples were electroporated into *E. coli* TG1 (50 µl). Cells were grown in 1 ml SOC for 1 hr and then plated on 2×TY medium with 100 µg/ml ampicillin and 1% glucose (AMP-GLU), in 243×243 mm dishes (Nunc). After overnight growth colonies were scraped off the plates into 10 ml 2×TY containing AMP-GLU and 15% glycerol for storage at −70° C. as a library stock.

Cloning into SfiI-NotI and NcoI-NotI digested pHEN1 yielded libraries of $10^7$ and $2\times10^7$ clones respectively for the IgM libraries and approximately $5\times10^7$ clones for each of the two IgG libraries.

Example 43

Isolation of Binding Activities from a Library of scFvs from an Unimmunized Human The ability to select binding activities from human antibody libraries displayed on the surface of phage should prove even more important than isolation of binding activities from murine libraries. This is because the standard way of generating antibodies via hybridoma technology has not had the success with human antibodies that has been achieved with mouse. While in some instances it will be possible to make libraries from immunized humans, in many cases, it will not prove possible to immunize due to toxicity or lack of availability of an appropriate immunogen or ethical considerations. Alternatively, binding activities could be isolated from libraries made from individuals with diseases in which therapeutic antibodies are generated by the immune response. However, in many cases, the antibody producing cells will be located in the spleen and not available in the circulating pool of peripheral blood lymphocytes (the most easily accessible material for generating the library). In addition, in diseases associated with immunosuppression, therapeutic antibodies may not be produced.

An alternative approach would be to isolate binding activities from a library made from an unimmunized individual. This approach is based on estimates that a primary repertoire of $10^7$ different antibodies is likely to recognize over 99% of epitopes with an affinity constant of $10^5$ M$^{-1}$ or better. (Pewrelson, A. S. Immunol. Rev, (1989) 110:5). While this may not produce high affinity antibodies, affinity could be boosted by mutation of the V-genes and/or by using the isolated VH domain in a hierarchical approach with a library of light chains (or vice versa). In this section, we demonstrate the feasibility of this approach by isolating specific antigen binding activities against three different antigens from a library of scFvs from an unimmunized human.

Materials and Methods

The generation of the human scFv library used for the isolation of binding activities described in this example is detailed in example 42.

Estimation of diversity of original and selected libraries: Recombinant clones were screened before and after selection by PCR (example 20) with primers LMB3 (which sits 5' of the pelB leader sequence and is identical to the reverse sequencing primer (−40 n) of pUC19) and fd-SEQ1 (see example 37) followed by digestion with the frequent-cutting enzyme BstN1. Analysis of 48 clones from each unselected library indicated that 90% of the clones had inset, and the libraries appeared to be extremely diverse as judged by the BstNI restriction pattern.

Rescue of Phagemid libraries for enrichment experiments: To rescue phagemid particles from the library, 100 ml 2×TY containing AMP-GLU (see example 42) was inoculated with $10^9$ bacteria taken from the library (prepared in example 42) (approx. 10 µl) and grown for 1.5 hr, shaking at 37° C. Cells were spun down (IEC—centrifuge, 4 K, 15 min) and resuspended in 100 ml prewarmed (37° C.) 2×TY−AMP (see example 41) medium, $2\times10^{10}$ pfu of VCS-M13 (Stratagene) particles added and incubated 30 min at 37° C. without shaking. Cells were then transferred to 900 ml 2×TY containing ampicillin (100 µg/ml) and kanamycin (25 µg/ml) (AMP-KAN), and grown overnight, while shaking at 37° C. Phage particles were purified and concentrated by three PEG-precipitations (see materials and methods) and resuspended in PBS to $10^{13}$ TU/ml (ampicillin resistant clones).

Enrichment for phOx:BSA binders by selection on tubes: For enrichment, a 75×12 mm Nunc-immunotube (Maxisorp; Cat. No. 4-44202) was coated with 4 ml phOx:BSA (1 mg/ml; 14 phOx per BSA in 50 mM NaHCO3 pH 9.6 buffer) overnight at room temperature. After washing three times with PBS, the tube was incubated for 2 hr at 37° C. with PBS containing 2% Marvel (2% MPBS) for blocking. Following three PBS washes, phagemid particles ($10^{13}$ TU) in 4 ml of 2% MPBS were added, incubated 30 min at room temperature on a rotating turntable and left for a further 1.5 hours. Tubes were then washed with 20 washes of PBS, 0.1% Tween 20 and 20 washes PBS (each washing step was performed by pouring buffer in and out immediately). Bound phage particles were eluted from the tube by adding 1 ml 100 mM triethylamine pH 11.5 and rotating for 15 min. The eluted material was immediately neutralised by adding 0.5 ml 1.0 M Tris-HCl, pH 7.4 and vortexed. Phage was stored at 4° C.

Eluted phage (in 1.5 ml) was used to infect 8 ml logarithmic growing *E. coli* TG1 cells in 15-ml 2×TY medium, and plated on AMP-GLU plates as above yielding on average $10^7$ phage infected colonies.

For selection of phOx:BSA binders, the rescue-tube enrichment-plating cycle was repeated 4 times, after which phagemid clones were analysed for binding by ELISA.

Enrichment for lysozyme binders by panning and on columns: A petri dish (35×10 mm Falcon 3001 Tissue culture dish) was used for enrichment by panning. During all steps, the plates were rocked on an A600 rocking plate (Raven Scientific). Plates were coated overnight with 1 ml turkey egg white lysozyme (3 mg/ml) in 50 mM sodium hydrogen carbonate (pH 9.6), washed three times with 2 ml PBS, and blocked with 2 ml 2% MPBS at room temperature for 2 hours. After three PBS washes approximately $10^{12}$ TU phage particles in 1 ml 2% MPBS were added per plate, and left rocking for 2 hr at room temperature. Plates were washed for 5 min with 2 ml of the following solutions: 5 times PBS, PBS-Tween (0.02% Tween-20), 50 mM Tris-HCl (pH 7.5)+500 mM NaCl, 50 mM Tris-HCl (pH 8.5)+500 mM NaCl, 500 mM Tris-HCl (pH 9.5)+500 mM NaCl and finally 50 mM sodium hydrogen carbonate pH 9.6 Bound phage particles were then eluted by adding 1 ml 100 mM triethylamine pH 11.5 and rocking for 5 min before neutralising with 1 M Tris-HCl (pH 7.4) (as above). Alternatively, 1 ml turkey egg white lysozyme-Sepharose columns were used for affinity purification (McCafferty, J., et al., Nature 1990. 348: 552) Columns were washed extensively with PBS, blocked with 15 ml 2% MPBS, and phage ($10^{12}$ TU) in 1 ml 2% MPBS loaded. After washing with 50 ml PBS, 10 ml PBS—Tween (PBS+ 0.02% Tween-20), 5 ml of 50 mM Tris-HCl (pH 7.5)+500 mM NaCl, 5 mM Tris-HCl 9pH 8.5)+500 mM NaCl, 5 ml of 50 mM Tris-HCl (pH 9.5)+500 mM NaCl and finally 5 ml of 50 mM sodium hydrogen carbonate pH 9.6. Bound phage was eluted using 1.5 ml 100 mM triethylamine and neutralised with 1 M Tris-HCl (pH 7.4).

For selection of turkey egg white lysozyme binders, the rescue-tube enrichment-plating cycle or rescue-column-plating cycle was repeated 4 times, after which phagemid clones were analysed for binding by ELISA.

Rescue of Individual Phagemid Clones for ELISA:

Clones resulting from reinfected and plated phage particles eluted after 4 rounds of enrichment, were inoculated into 150 µl of 2×TY-AMP-GLU in 96-well plates (cell wells, Nunclon), grown with shaking (250 rpm) overnight at 37° C. A 96-well plate replicator ('plunger') was used to inoculate approximately 4 µl of the overnight cultures on the master plate into 200 µl fresh 2×TY-AMP-GLU. After 1 hr, 50 µl 2×TY-AMP-GLU containing $10^8$ pfu of VCS-M13 was added to each well, and the plate incubated at 37° C. for 45 min, followed by shaking the plate at 37° C. for 1 hr. Glucose was then removed by spinning down the cells (4K, 15 min), and aspirating the supernatant with a drawn out glass pasteur pipet. Cells were resuspended in 200 µl 2×TY-AMP-KAN (Kanamycin 50 ug/ml) and grown 20 hr, shaking 37° C. Unconcentrated supernatant containing phage was taken for analysis by ELISA.

ELISA

Analysis for binding to phOx:BSA, BSA or lysozyme was performed by ELISA (see example 9), with 100 µg/ml phOx: BSA or BSA, or 3 mg/ml turkey egg white lysozyme used for coating. Determination of cross reactivity to unrelated antigens with the isolated clones was also determined by ELISA on plates coated with 100 ug/ml of an irrelevant antigen (keyhole limpet haemocyanin (KLH), ovalbumin, chymotrypsinogen, cytochrome C, thyroglobulin, GAP-DH (glyceraldehyde-3-phosphate dehydrogenase), or trypsin inhibitor).

Characterization of ELISA positive clones: All antigen specific clones isolated were checked for cross reactivity against a panel of irrelevant antigens as described above. The diversity of the clones was determined by PCR screening as described above and at least two clones from each restriction pattern were sequenced by the dideoxy chain termination method.

Results

Isolation and characterization of phOx:BSA binders: After 4 rounds of selection, ELISA-positive clones were isolated for phOx:BSA. All clones originated from the IgM library. Of 96 clones analysed, 43 clones were binding to both phOx: BSA and BSA, with ODs ranging from 0.4 to 1.3 (background 0.125). These clones are designated as BSA binders. The binding to BSA seemed to be specific, since none of the 11 clones analysed gave a signal above background when used in an ELISA with KLH, ovalbumin, chymotrypsinogen, cytochrome C, lysozyme, thyroglobulin, GAP-DH, or trypsin inhibitor. all BSA binding clones had the same BstNI restriction pattern, and 14 clones were completely sequenced. Thirteen of the fourteen clones had the same sequence, the VH was derived from a human VH3 family gene and the VL from a human V lambda 3 family gene (Table 1). The other BSA binder was derived from a human VH4 family gene and a human Vk1 family gene (data not shown).

One clone was isolated which bound to phOx:BSA only (OD 0.3), and bound phage could be completed off completely by adding 0.02 mM 4-ε-amino-caproic acid methylene 2-phenyl-oxazol-5-one (phOx-CAP) as a competitor. Also no binding above background could be detected to the panel of irrelevant proteins described above. The sequence revealed a VH derived from a human VH1 family gene and a VL derived from a human V lambda 1 family gene (Table 11).

Isolation and characterisation of lysozyme binders: After 4 rounds of selection, 50 ELISA-positive clones were isolated for turkey lysozyme. The majority of the clones, greater than 95%, were from the IgM library. The binding to lysozyme seemed to be specific, since none of the clones analysed gave a signal above background when used in an ELISA with KLH, ovalbumin, chymotrypsinogen, cytochrome C, thyroglobulin, GAP-DH, or trypsin inhibitor. The lysozyme binding clones gave 3 different BstNI restriction patterns, and at least 2 clones from each restriction pattern were completely sequenced. The sequences indicated the presence of 4 unique human VH-VL combinations. (Table 11).

Conclusion

The results indicate that antigen binding activities can be isolated from repertoires of scFvs prepared from IgM cDNA from human volunteers that have not been specifically immunized.

Example 44

Rescue of human IgM Library using Helper Phage Lacking Gene 3 (δg3)

This example describes the rescue of gene 3 fusions from a human library using a helper phage with a gene 3 deletion.

100 µl of bacterial stock of the IgM phagemid library prepared as described (example 42), containing $5 \times 10^8$ bacteria, was used to inoculate 100 mls of 2×TY medium containing 100 µg/ml ampicillin, 2% glucose (TY/Amp/Glu). This was grown at 37° C. for 2.5 hours. 10 mls of this culture was added to 90 mls of prewarmed TY/Amp/Glu and infection carried out by adding 10 mls of a 200 fold concentrate of KO7 helper phage lacking gene 3 (M13KO7gIIIΔ No. 3) (example 34) and incubating for 1 hour at 37° C. without shaking. Preparation of M13KO7gIII No. 3 was as described in example 34. After centrifugation at 4,000 r.p.m. for 10 minutes the bacteria were resuspended in 100 mls of 2×TY medium containing 100 µg/ml ampicillin (with no glucose). Titration of the culture at this point revealed that there were $1.9 \times 10^8$ infected bacteria as judged by their ability to grow on plates containing both ampicillin (100 µg/ml) and kanamycin (50 µg/ml). Incubation was continued for 1 hour with shaking before transferring to 2.5 litres of 2×TY medium containing 100 µg/ml ampicillin, 50 µg/ml kanamycin, contained in five 2.5 litre flasks. This culture was incubated for 16 hours and the supernatant prepared by centrifugation. (10-15 minutes at 10,000 r.p.m. in a Sorvall RC5B centrifuge at 4° C.). Phage particles were harvested by adding ⅕th volume of 20% polyethylene glycol, 2.5 M NaCl, standing at 4° C. for 30 minutes and centrifuging as above. The resulting pellet was resuspended in 40 mls of 10 mM Tris, 0.1 mM EDTA pH 7.4 and bacterial debris removed by centrifugation as above. The packaged phagemid preparation was then re-precipitated, collected as above and resuspended in 10 mls of 10 mM Tris, 0.1 mM EDTA pH 7.4. The litre of this preparation was $4.1 \times 10^{13}$ transducing units/ml (ampicillin resistance).

Tubes coated with OX-BSA were prepared as described in example 45 for panning the phagemid library from example 42. The rescued library was also panned against tubes coated with bovine thyroglobulin (Sigma). These were coated at a concentration of 1 mg/ml thyroglobulin in 50 mM NaHCO3 pH9.6 at 37° C., overnight. Tubes were blocked with PBS containing 2% milk powder (PBS/M) and incubated with 1 ml of the rescued phagemid library (the equivalent of 250 mls of culture supernatant) mixed with 3 mls of PBS/M for 3 hours. Washing, elution, neutralisation and infection were as described in example 45.

Results: Panning Against Oxazalone-BSA

The first round of panning against OX-BSA yielded $2.8 \times 10^6$ phage. A large bacterial plate with $1.4 \times 10^6$ colonies derived from this eluate was scraped into 10 mls of 2xxTY, 20% glycerol, shaken for 10 minutes, aliquoted and stored. This was also used to inoculate a fresh culture for rescue with M13KO7gIII No. 3. (Bacteria and rescued phage derived from first round panning against OX-BSA are named OXPAN1. Bacteria or rescued phage derived from second and third round pannings are named OXPAN2 and OXPAN3 respectively) Rescue of phagemid with M13KO7gIII No. 3 after each round of panning was essentially as described above but using 5 ml volumes for the initial cultures in TY/Amp/Glu, using 1 ml of helper phage and transferring to 100-500 mls of 2xTY medium containing 100 µg/ml ampicillin, 50 µg/ml kanamycin. Second and third round panning steps were as described above for the first round, but using 0.8-11.0 mls of 100 fold concentrated phage (the equivalent of 80-100 mls of culture supernatant). The eluate from the second round panning contained $8 \times 10^8$ infectious particles and the eluate from the third round panning contained $3.3 \times 10^9$ infectious particles.

Panning Against Thyroglobulin

The first round panning against thyroglobulin yielded $2.52 \times 10^5$ infectious particles. Half of the eluate was used to generate $1.26 \times 10^5$ bacterial colonies on a large plate. These colonies were scraped into 10 mls of 2xTY, 20% glycerol, shaken for 10 minutes, aliquoted and stored. These bacteria and rescued phage derived from them are termed THYPAN1, and used to inoculate a fresh culture for rescue with M13KO7gIII No. 3 to give a polyclonal rescued phage preparation. Material similarly derived from second and third round pannings are termed THYPAN2 and THYPAN3 respectively. Second and their round pannings with thyroglobulin were as described for second and third round OX-BSA panning. The eluate from the second round panning contained $8 \times 10^7$ transducing units and the eluate from the third round panning contained $6 \times 10^7$ infectious particles.

ELISA Screening of Clones Derived by Panning 40 colonies derived form the third round of panning against thyroglobulin (THYPAN3) were picked into a 96 well plate and grown overnight at 37° C. in 200 µl of TY/Amp/Glu. Similarly 48 colonies from two rounds and 48 colonies from three rounds of panning against OX-BSA were grown (OX-PAN2 and OX-PAN3). Polyclonal phage were prepared at the same time. Next day 5 µl from each culture was transferred to 100 µl of fresh prewarmed TY/Amp/Glu grown for 1.5 hours and M13KO7gIII No. 3 added ($2 \times 10^5$ infectious phage per well in 100 µl of TY/Amp/Glu). These were incubated for 1 hour at 37□C without shaking, centrifuged at 4,000 r.p.m. for 10 minutes, resuspended in 150 µl of 2xTY medium containing 100 µg/ml ampicillin and incubated for a further hour with shaking before adding to 2 mls of medium containing 100 µg/ml ampicillin, 50 µg/ml kanamycin. After overnight growth the cultures were centrifuged at 4,000 r.p.m. for 10 minutes and the supernatants collected. ELISA plates used to screen THYPAN3 clones were coated at 37° C. overnight with 200 µg/ml thyroglobulin in 50 mM NaHCO3 pH9.6. Plates used for OXPAN2 and OXPAN3 were coated at 100 µg/ml OX-BSA in PBS at 37° C. overnight.

120 µl of culture supernatant was mixed with 30 µl of 5xPBS, 10% milk powder and incubated at room temperature for 2 hours at room temperature. ELISAs were carried out as described in example 18.

For thyroglobulin, 18 out of 40 clones were positive (0.3-2.0 O.D. after 30 minutes). (A phage control (vector pCAT3) gave a reading of 0.07 O.D.). In addition, positives were also seen on the polyclonal phage preparations THYPAN1 (0.314 O.D.) and THYPAN2 (0.189 O.D.) compared with phage derived from the original non-panned phagemid library (0.069 O.D.). All polyclonal phage were PEG precipitated and used at a 10 fold concentration.

PCR reactions and BstN1 digests were carried out on the positive clones as described above and six different patterns of DNA fragments were obtained showing that at least six different clones had been isolated.

For OX-BSA after two rounds of panning, 30 of 48 clones were positive by ELISA and after three rounds, 42 of 48 were positive. In a separate experiment, positive signal was obtained from the polyclonal phage preparations OXPAN1 (0.988 OD) and OXPAN2 (1.717 OD) compared with phage derived from the original non-panned phagemid library (0.186 O.D.) after 30 minutes.

Specificity of Clones for Thyroglobulin or OX-BSA

Selected clones (11 anti-thyroglobulin, 5 anti-OX-BSA) representing each of the different BstNI restriction digest patterns were assayed for binding to a panel of irrelevant antigens. ELISA plates were coated with antigen (100 µl/ml in 50 mM NaHCO3, pH 9.6) by overnight incubation at 37° C. The panel of antigens consisted of keyhole limpet haemocyanin, hen egg lysozyme, bovine serum albumin, ovalbumin, cytochrome c, chymotrysinogen, trypsin inhibitor, GAP-D11 (glyceraldehyde-3-phosphate dehydrogenase), bovine thyroglobulin and oxazolone-BSA. Duplicate samples of phage supernatant (80 µl+20 µl 5xPBS, 10% milk powder) were added to each antigen and incubated for 1 hour at room temperature. The ELISA was carried out as described in example 18.

Each of the thyroglobulin specific clones (11 from 11) were positive for thyroglobulin (OD 0.12-0.76) but after 60 minutes showed no binding (OD<0.03) to any of the 9 irrelevant antigens. Similarly of the 50x-BSA specific clones 3 had an OD 0.07-0.52 compared to ODs<0.02 for the irrelevant antigens. None of the 5 clones had any binding to BSA alone.

Thus positive clones can be isolated after only two rounds of panning by rescuing with M13KO7gIII No. 3. In addition there is a greater likelihood with this helper of generating phage particles with more than one intact antibody molecule. This will potentially increase the avidity of phage-antibodies and may enable isolation of clones of weaker affinity.

Example 45

Alteration of Fine Specificity of scFv D1.3 Displayed on Phage by Mutagenesis and Selection on Immobilised Turkey Lysozyme The D1.3 antibody binds hen egg lysozyme (HEL) with an affinity constant of $4.5 \times 10^7 M^{-1}$ whereas it binds turkey egg lysozyme (TEL) with an affinity of $<1 \times 10^5 M^{-1}$. (Harper et al (1987) Molecular Immunology 24 p97-108, Amit et al (1986) Science 233 p747-753).

It has been suggested that this is because the glutamine residue present at position 121 of HEL (gln121) is representated by histidine residue at the same position in TEL. Thus mutagenising the D1.3 antibody residues which interact with gln121 of HEL may facilitate binding to TEL.

According to Amit et al, supra, tyrosine at amino acid position 32, phenylalanine at position 91 and tryptophan at position 92 of the light chain interact with gln121 of HEL. In addition tyrosine at position 101 of the heavy chain also interacts. None of these residues are predicted to be involved in determining the main chain conformation of the antibody variable regions (Chothia and Lesk (1987) Journal of Molecular Biology 196, p901-917).

Mutagenesis of pCAT3SCFvD1.3

The oligonucleotides mutL91,92, was prepared too randomise phenylalanine at position 91 (L91) and tryptophan at position 92 (L92) of the light chain. The oligonucleotides mutL32, was prepared to randomise tyrosine at light chain position 32 (L32) and the oligonucleotides mutH101 was prepared to randomise tyrosine at position 101 of the heavy chain (H101).

```
mutL91, 92:
5' CGT CCG AGG AGT ACT NNN NNN ATG   (SEQ ID NO:75)
TTG ACA GTA ATA 3' mutL32:
5' CTG ATA CCA TGC TAA NNN ATT GTG   (SEQ ID NO:76)
ATT ATT CCC 3' mutH101:
5' CCA GTA GTC AAG CCT NNN ATC TCT   (SEQ ID NO:77)
CTC TCT GGC 3'
```

(N represents a random insertion of equal amounts of A, C, G or T) in vitro mutagenesis of the phagemid vector, pCAT3scFvD1.3 (example 17) with the oligonucleotide mutL91,92 was carried out using an in vitro mutagenesis kit (Amersham). The resultant DNA was transformed by electroporation into TG1 cells using a Bio-Rad electroportor. 78,000 clones were obtained and these were scraped into 15 mls of 2×TY/20% glycerol. This pool was called D1.3L91L92. Single stranded DNA was prepared by rescue with M13K07 as described in Sambrook et al, 1989 supra, and sequenced with the primer FDTSEQ1, using a Sequenase sequencing kit (United States Biochemical Corporation).

This revealed that the DNA had been successfully mutagenised as judged by the presence of bands in all four DNA sequencing tracks at the nucleotide positions encoding L91 and L92. This mutagenised single stranded DNA was subjected to a further round of mutagenesis as above using either mutL32 or mutH101 oligonucleotides. Mutagenesis with mutL32 gave rise to 71,000 clones (pool called D1.3L32) while mutH101 gave 102,000 clones (pool called D1.3H101). These clones were scraped into 15 mls of 2×TY/20% glycerol. Single stranded DNA derived from each pool was sequenced with the oligonucleotides D1.3L40 and LINKSEQ1 respectively, as described above, and shown to be correctly randomised.

```
D1.3L40:                          (SEQ ID NO: 78)
5' CAG GAG CTG AGG AGA TTT TCC 3'

LINKSEQ1:                         (SEQ ID NO: 79)
5' TCC GCC TGA ACC GCC TCC ACC 3'
```

Preparation of Rescued Phage for Affinity Purification 10-20 μl of bacteria derived from each mutagenised pool (plate scrapes) was used to inoculate 5 mls of TY/Glu/Amp. All bacterial growth was at 37° C. After 2-3 hours growth, 1 ml was diluted in 5 mls of prewarmed TY/Glu/Amp and infected by addition of 0.5 mls of a 200 fold concentrate of the M13K07gIII Δ No. 3 preparation described in example 34. After 1 hour of infection the cultures were centrifuged at 4,000 r.p.m. for 10 minutes, resuspended in 2×TY, 100 μg/ml ampicillin, incubated for a further hour, transferred to 500 mls of 2×TY medium containing 100 μg/ml ampicillin, 50 μg/ml kanamycin and grown for 16 hours. The remaining steps of phage preparation were as described in example 44. Phage were finally dissolved in 10 mM Tris, 1 mM EDTA pH7.4 at 1/100th the original culture volume.

Affinity Purification 10 mls of turkey egg lysozyme at a concentration of 10 mg/ml in 0.1M NaHCO3, 0.5M NaCl pH8.3 was mixed with an equal volume of swollen Cyanogen Bromide Activated Sepharose 4B (Pharmacia), covalently linked and washed according to manufacturers instructions. Before use this matrix (TEL-Sepharose) was washed with 100 volumes of PBS followed by 10 volumes of PBSM. The TEL-Sepharose was resuspended in an equal volume of PBSM and 1 ml was added to 1 ml of a 50 fold concentrate of phage in PBSM and incubated on a rotating platform for 30 minutes at room temperature. The actual phage used for this step was prepared by mixing equal volumes of the independent preparations of the three randomised pools (D1.3L9192, D1.3H101 and D1.3L32). After this binding step, the suspensions were loaded onto a disposable polypropylene column (Poly-Prep columns, Bio-Rad) and washed with 200 volumes of PBS containing 0.1% Tween 20. Bound phage were eluted with 1 ml of 100 mM triethylamine and neutralised with 0.5 ml 1M Tris (pH7.4). A dilution series was prepared from the eluate and used to infect TG1 cells and plated out on TY plates containing 100 μg/ml ampicillin, 2% glucose. Plates carrying approximately $10^6$ colonies were scraped into 3 mls of 2×TY, 20% glycerol and stored at −70° C. 10 μl of this was used to initiate a second round culture which was rescued with M13K07gIIIΔ No. 3 as described above (using a final culture volume of 100 mls). Second and third round affinity column purification steps were carried out as described above for the first round.

Analysis by ELISA 40 colonies derived from the third round of column purification on TEL-Sepharose were picked into a 96 well plate and grown overnight at 37° C. in 200μ of TY/Amp/Glu. Phagemid particles were rescued and prepared for ELISA as described in example 18. ELISA plates were coated overnight at 37° C. with hen egg lysozyme (HEL) or turkey egg lysozyme (TEL) at a concentration of 200 μg/ml in 50 mM $NaHCO_3$ pH9.6 ELISAs were carried out as described in example 18.

After 15 minutes incubation in substrate, 13 clones were found to be negative (OD<0.05 on HEL and TEL). In all positives, a signal of 0.1-0.78 was scored on HEL with the exception of one where signal on HEL was 0.078 but signal on TEL (OD 0.169) brought it in to the positive group. The control phagemid preparation had a percentage ratio of signal TEL:HEL of 22%. Clones were deemed to have an unaltered binding if the ratio of TEL:HEL was less than 40%. 9 clones fell into this category. 18 samples were scored as having altered binding with a ratio of signal on TEL:HEL of between 40-200%.

A dilution series was made on 10 clones which were analysed by ELISA in 6 of these clones the profile of binding to HEL was the same as the original clone (pCAT3SCFvD1.3) while the signal with TEL was increased (see FIG. 50*a* clone B1). In the remaining 4 clones, the increased signal with TEL was accompanied by a decrease in signal on HEL (see FIG. 50 clone A4).

Competition with Soluble Antigen

All of the isolated clones retained binding to HEL to varying extents. In order to determine whether a soluble antigen could compete with the immobilised antigen, a parallel experiment was carried out, as above, but with the addition of hen egg lysozyme (1 mg/ml) to TEL-Sepharose before incubating with the phage preparation. This experiment was carried through 3 rounds of column purification and 40 colonies were picked. None of these clones bound HEL or GEL demonstrating that the soluble antigen had been successful in competing out binding to the immobilised antigen.

Example 46

Modification of the Specificity of an Antibody by Replacement of the VLK Domain by a VLK Library Derived from an Unimmunised Mouse When an antibody specificity is isolated it will often be desirable to alter some of its properties particularly its affinity or specificity. This example demonstrates that the specificity of an antibody can be altered by use of a different VL domain derived form a repertoire of such domains. This method using display on phage would be applicable to improvement of existing monoclonal antibodies as well as antibody specificities derived using phage antibodies. This example shows that replacement of the VL domain of scFvD1.3 specific for Hen eggwhite lysozyme (HEL) with a library of VL domains allows selection of scFv fragments with bind also to Turkey eggwhite lysozyme (TEL). More generally this experimental approach shows that specificities of antibodies can be modified by replacement of a variable domain and gives a further example of the hierarchical approach to isolating antibody specificities.

The D1.3 heavy chain was amplified from an existing construct (pSW1-VHD1.3, Ward et al., 1989 supra) by PCR using the primers VH1BACK and VH1FOR, the light chain library was amplified from a cDNA library derived from the spleen of an unimmunised mouse, which was synthesized by using the MJKFONX primers 1, 2, 4, 5 for the first strand as in example 14. The subsequent amplification was performed with the same forward primers and the VK2BACK primer. The PCR assembly of the D1.3 heavy chain with the light chain library was mediated by the signal chain Fv linker as described in example 14.

Cloning the assembled PCR products (scFv sequences) was done after an additional PCR step (pull-through) using a BACK primer providing an ApaLI site and forward primers which contained a Not 1 site as described in example 14. ApaL1/Not 1 digested PCR fragments were cloned into the similarly digested vector fdCAT2 as in example 11. $5 \times 10^5$ transformations were obtained after electroporation of the ligation reaction into MC1061 cells.

Screening of the phage library for TEL binders was performed by panning. Polystyrene Falcon 2058 tubes were coated (16 hrs) with 2 ml of TEL-PBS (3 mg/ml) and blocked for 2 hrs with 4 ml MPBS (PBS containing 2% skimmed milk powder). Phage derived from the library ($5 \times 10^{10}$ transducing unites) in 2 ml of MPBS (2%) were incubated in these tubes for 2 hrs at room temperature. The tubes were washed 3× with PBS, 1× with 50 mM Tris-HCl, pH 7.5, 0.5 M NaCl; 1× with 50 mM Tris-HCl, pH8.5, 0.5 M NaCl, 50 mM Tris-HCl, pH 9.5 M NaCl. Finally phage were eluted with 100 mM triethylamine. Eluted phages were taken to infect TG1 cells, the cells were plated on 2×TY plates containing 15 µg/ml tetracycline and grown for 16 h. The colonies were scraped into 25 ml of 2×Ty medium and the phages were recovered by PEG precipitation. After a second round of selection for TEL binders ELISAs were performed as described (example 2).

Analysis of 100 clones from the library before affinity selection by ELISA on plates coated with TEL showed no binders. In contrast, after two rounds of selection for TEL binding phages about 10% of the phage clones showed positive ELISA signals. ELISA signals were scored positive with values at least two fold higher than the fdCAT2 vector without insert. A more detailed analysis of binding properties of TEL binding phages is shown in FIG. 51.

As shown in FIG. 51, several clones were found which bind equally to TEL and HEL in contrast to the original D1.3 scFv, which binds almost exclusively to HEL. None of the clones bound to BSA. These findings indicate that the specificity of these scFvs was broader in comparison to D1.3, since both lysozymes (HEL and TEL) are recognized, but specificity for lysozyme was retained since other BSA was not recognized. The deduced amino acid sequences (derived by DNA sequencing) of two light chains from clones MF1 and M21, which correspond to clones 3 and 9 in FIG. 51 are shown in FIG. 52.

In the case of isolated antibodies the experimental approach as described in this study may be particularly useful if recognition of a wider range of different but closely related antigens is desired. For example, monoclonal antibodies against viral antigens viral antigens like V3 loop of HIV-1 gp120 are in most cases quite specific for one particular virus isolate because of the variability in this part of the HIV-1 env gene. The modification of such antibodies in the way described in this example may lead to antibodies which cross react with a wider range of HIV-1 isolates, and would therefore be of potentially higher therapeutic or diagnostic value.

A similar approach could be taken in which a light chain variable domain of desired properties is kept fixed and combined with a library of heavy chain variable domains. Some heavy chains, for example VHD1.3 retain binding activity as single domains. This may allow a strategy where VH domains are screened for binding activity when expressed on phage and then binding domains combined with a library of VL domains for selection of suitable light chain partners.

Example 47

Selection of a Phage Antibody Specificity by Binding to an Antigen Attached to Magnetic Beads. Use of a Cleavable Reagent to Allow Elution of Bound Phage Under Mild Conditions When a phage antibody binds to its antigen with high affinity or avidity it may not be possible to elute the phage antibody from an affinity matrix with a molecule related to the antigen. Alternatively, there may be no suitable specific eluting molecule that can be prepared in sufficiently high concentration. In these cases it is necessary to use an elution method which is not specific to the antigen-antibody complex. Unfortunately, some of the non-specific elution methods disrupt phage structure, for instance phage viability is reduced with time at pH12 (Rossomando, E. F. and Zinder, N. D. J. Mol. Biol. 36 387-399 1968). A method was therefore devised which allows elution of bound phage antibodies under mild conditions (reduction of a dithiol group with dithiothreitol) which do not disrupt phage structure.

Target antigen was biotinylated using a cleavable biotinylation reagent. BSA conjugated with 2-phenyl-5-oxazolone (O. Makela et al. supra) was modified using a biotinylation reagent with a cleavable dithiol group (sulphosuccinimidyl 2-(biotinamido) ethyl-1,3-dithiopropionate from Pierce) according to the manufacturers instructions. This biotinylated antigen was bound to streptavidin coated magnetic beads and the complex used to bind phage. Streptavidin coated magnetic beads (Dynal) were precoated with antigen by mixing 650 µg of biotinylated OX-BSA in 1 ml PBS, with 200 µl of beads for at least 1 hour at room temperature. Free antigen was removed by washing in PBS. One fortieth of the complex (equivalent to 5 µl of beads and an input of 17.5 µg of OX-BSA) was added to 0.5 ml of phage in PBSM (PBS containing 2% skimmed milk powder) containing $1.9 \times 10^{10}$ phage particles mixed at the ratios of pAbD1.3 directed against lysozyme (example 2) to pAbNQ11 directed against 2-phenyl-5-oxazolone (example 11) shown in Table 12. After 1 hour of incubation with mixing at room temperature, magnetic beads were recovered using a Dynal MPC-E magnetic desperation device. They were then washed in PBS containing 0.5% Tween 20, (3×10 minutes, 2×1 hour, 2×10 minutes) and phage eluted by 5 minutes incubation in 50 µl PBS containing 10 mM dithiothreitol. The eluate was used to infect TG1 cells and the resulting colonies probed with the oligo NQ11CDR3(5' AAACCAGGCCCCGTAATCATAGCC 3') (SEQ ID NO:80) derived from CDR3 of the NQ11 antibody (This hybridises to pAbNO11 but not pAb D1.3).

A 670 fold enrichment of pAbNQ11 (table 12) was achieved form a background of pAbD1.3 in a single round of purification using the equivalent of 17.5 µg of biotinylated OX-BSA.

This elution procedure is just one example of an elution procedure under mild conditions. A particularly advantageous method would be to introduce a nucleotide sequence encoding amino acids constituting a recognition site for cleavage by a highly specific protease between the foreign gene inserted, in this instance a gene for an antibody fragment, and the sequence of the remainder of gene III. Examples of such highly specific proteases are Factor X and thrombin. After binding of the phage to an affinity matrix and elution to remove non-specific binding phage and weak binding phage, the strongly bound phage would be removed by washing the column with protease under conditions suitable for digestion at the cleavage site. This would cleave the antibody fragment from the phage particle eluting the phage. These phage would be expected to be infective since the only protease site should be the one specifically introduced. Strongly binding phage could then be recovered by infecting e.g. *E. coli* TG1 cells.

Example 48

Use of Cell Selection to Provide an Enriched Pool of Antigen Specific Antibody Genes, Application to Reducing the Complexity of Repertoires of Antibody Fragment Displayed on the Surface of Bacteriophage There are approximately $10^{14}$ different combinations of heavy and light chains derived from the spleen of an immunised mouse. If the random combinatorial approach is used to clone heavy and light chain fragments into a single vector to display scFv, Fv or Fab fragments on phage, it is not a practical proposition to display all $10^{14}$ combinations. One approach, described in this example, to reducing the complexity is to clone genes only from antigen selected cells. (An alternative approach, which copes with the complexity is the dual combinatorial library described in example 26).

The immune system uses the binding of antigen by surface immunoglobulin to select the population of cells that respond to produce specific antibody. This approach of selecting antigen binding cells has been investigated to reduce the number of combinatorial possibilities and so increase the chance of recovering the original combination of heavy and light chains.

The immunological response to the hapten 4-hydroxy-3-nitrophenylacetic acid (NP) has been extensively studied. Since the primary immune response to NP uses only a single light chain the applicants were able to examine the use of the combinatorial method using a fixed light chain and a library of heavy chains to examine the frequencies genes that code for antibodies binding to NIP (4-hydroxy-3-iodo-5-nitrophenylacetic acid). The applicants have thus used this system to investigate the merits of selecting cell populations prior to making combinatorial libraries for display on phage.

Methods 2.1 Hapten Conjugates

Chick gamma globulin (CGG, Sigma, Poole, UK) and Bovine serum albumen (BSA, Boehringer, Mannheim, Germany) were conjugated with NP—O-succinimide or NIP-caproate-O-succinimide (Cambridge Research Biochemicals, Northwich, UK) based on the method described by Brownstone (Brownstone, A., Mitchison, N. A. and Pitt-Rivers, R., Immunology 1966. 10: 465-492). The activated compounds were dissolved in dimethylformamide and added to proteins in 0.2 M sodium hydrogen carbonate. They were mixed with constant agitation for 16 hours at 4° C. and then dialysed against several changes of 0.2 M sodium hydrogen carbonate. They were finally dialysed into phosphate buffered saline (PBS). The conjugates made were $NP_{12}CGG$, $NIP_{10}BSA$. The $NIP_{10}BSA$ derivative was subsequently biotinylated using a biotinylation kit purchased from Amersham (Amersham International, Amersham, UK).

2.2 Animals and Immunisation

Mice of the strain C57BL/6 were immunised by intraperitoneal injection of 100 µg NP-CGG in Complete Freunds Adjuvant at 10 weeks of age.

2.3 Spleen Preparation

Seven days after immunization cells from the spleen were prepared as described by Galfre and Milstein (Galfre, G. and Milstein, C. Methods Enzymol. 1981. 73:3-46). Red cells were lysed with ammonium chloride (Boyle, W. Transplantation 1968.6:71) and when cell selection was performed dead cells were removed by the method described by von Boehmer and Shortman (von Boehmer, H. and Shortman, K, J. Immunol, Methods 1973:1:273). The cells were suspended in phosphage buffered saline (PBS), 1% Bovine serum albumen, 0.01% sodium azide; throughout all cell selection procedures the cells were kept at 4° C. in this medium.

2.4 Cell Solution

Biotinylated NIP-BSA was coupled to streptavidin coupled magnetic beads (Dynabeads M280 Streptavidin, Dynal, Oslo, Norway) by incubating $10^8$ beads with 100 µg of biotinylated protein for 1 hour, with occasional agitation, and then washing five times to remove unbound antigen. The coupled beads were stored at 4° C. in medium until required. For selection of antigen binding cells the cells ($2-4 \times 10^7$/ml) were first incubated for 30 minutes with uncoupled beads, at a bead: cell ratio of 1:1, to examine the degree of non-specific binding. The beads were then separated by placing the tube in a magnetic device (MPC-E Dynal) for 3-5 minutes. The unbound cells were removed and then incubated with NIP-BSA coupled magnetic beads, at a bead:cell ratio of 0.1:1, for 60 minutes, with occasional agitation. The beads and rosetted cells were separated as described above. The beads were then resuspended in 1 ml of medium and the separation repeated; this process was repeated 5-7 times until no unbound cells could be detected when counted on a haemocytometer.

For the depletion of surface immunoglobulin positive cells the cells were incubated with 20 μg biotinylated goat anti-mouse polyvalent immunoglobulin (Sigma, Poole, UK). The cells were then washed twice with medium and added to streptavidivin coupled magnetic beads at a bead to cell ratio of 30:1. After 30 minutes incubation the beads and rosetted cells were separated by applying the magnetic device three times—taking the supernatant each time.

2.4 DNA/cDNA Preparation, PCR Amplification and Cloning

DNA was prepared by a simple proteinase-K digest method that was particularly convenient for small numbers of cells (PCR Protocols: A Guide to Methods and Applications. Ed Innis M. A., Gelfand D. H., Sninsky J. J. and White T. J. Academic Press). RNA preparation and subsequent cDNA synthesis was performed as described by Gherardi et al (Gherardi E., Pannell R. and Milstein C. J. Immunol. Methods, 1990. 126:61-68). PCR and cloning of the heavy chain libraries was performed using the primers and conditions described by Ward et al (Ward, E. S., Güssow, D., Griffiths, A. D., Jones, P. T. and Winter, G., Nature, 1989. 341: 544-546); 40 cycles of PCR amplification were performed. The VH and Fv expression vectors used were adapted from those previously described by Ward et al. They were both subcloned into pUC119 (Veira and Messing see later) and the Fv expression vector was modified to include a germline lambda-1 light chain (obtained as a gift from T. Simon (originally cloned by Siegfried Weiss, Basel Institute of Immunology)). THe vector is shown in FIG. 53.

2.5 Expression and ELISA

For screening single colonies were picked into individual wells of microtitre plates (Bibby) in 200 μl 2×TY/Ampicillin 100 μg/ml/0.1% glucose and then incubated at 37° C. for 5-6 hours with agitation, Isopropyl-β-D-thiogalactopyranoside (IPTG, Sigma, Poole, UK) was then added to a final concentration of 1 mM and the incubation continued for a further 16 hours at 30° C. before harvesting the supernatants. The wells of Falcon ELISA plates (Becton Dickenson, N.J., USA) were coated overnight at room temperature with $NIP_{10}$-BSA (40 μg/ml in PBS) and then blocked with 2% skimmed milk powder in PBS for 2 hours at room temperature. The bacterial supernatants were added and incubated at room temperature for 1 hour and then the plates were washed three times with PBS. Peroxidase conjugated-Goat anti-mouse lambda-chain (Southern Biotechnology, Birmingham, USA) was added and again incubated for 1 hour at room temperature before washing six times with PBS and then developing with 2,2'-Azino-bis (3-ethylbenzthiazoline-6-sulfonic acid) (Sigma, Poole, UK) as the peroxidase substrate. The optical density at 405 nm was measured using a Thermomax microplate reader (Molecular Devices, Menlo Park, USA) after 30 minutes. Western blotting using the C-terminal myc tag as described in example 27.

3.1 Comparison of RNA/DNA and Antigen Selected Cells

The results of antigen selection are shown in Table 13. Less than 1% of cells bind to NIP-BSA coated beads and the non-specific binding is very low. Assessment of the proportion of expressed genes from each VH library using western blotting showed that full length VH domains were expressed in 95% ($^{19}/_{20}$) of all clones when RNA was used as the starting material but only 60% ($^{12}/_{20}$) of clones when DNA (either selected cells or from total spleen) was used as the starting material. This difference probably results from the fact that many re-arranged pseudogenes could be amplified with our primers and it appears that there must be some degree of selection, at the level of transcription, for functional genes.

A variable number of clones from each type of library were screened for the production of Fv fragments that bound to NIP. Initial screening ELISAs were performed and positives taken to include those with an optical density of at least twice the background. The initial positives were retransformed and the binding checked in duplicate; it was confirmed that the binding was specific to NIP and not to BSA. The frequency of confirmed positive NIP binding clones for each starting material are shown in Table 14. Using DNA as the starting material for the PCR amplification is approximately equivalent to sampling the cells present as there is only one functional re-arranged heavy chain gene and at most one re-arranged pseudogene per B-cell. Amplifying from the RNA of an animal of course biases the repertoire to the reacting B-cells and in a recently immunised animal this would be expected to give some bias towards the immunogen. The data in Table 14 clearly shows how powerful this selection is with the number of antigen specific genes being enriched at least 96 fold when RNA made one week after primary immunisation is used as the starting material. The data also show that selection for antigen binding cells also provides an alternative powerful method of selection for the required genetic starting material.

3.2 Comparison of Total Spleen/Surface Immunoglobulin Depleted Spleen

To examine the cellular basis of the selection achieved by using RNA as the starting material we depleted the spleen of surface immunoglobulin positive cells using biotinylated anti-polyvalent immunoglobulin and streptavidin conjugated magnetic beads. Prior FACS analysis had demonstrated that this method removed over 96% of surface immunoglobulin positive cells. RNA was prepared from both surface immunoglobulin depleted and non-depleted factions of a spleen and VH libraries made from each. The ELISA results (Table 14) show that the number of positives is certainly not decreased by this depletion suggesting that the major portion of the selective effect of using RNA may come from surface immunoglobulin negative G-cells (probably plasma cells).

CONCLUSIONS

The applicants have demonstrated the importance of the amplification of specific RNA produced by immunisation to enable binding activity to be obtained with any reasonable frequency from a combinatorial library. The applicants have also demonstrated an alternative strategy which mimics that of the immune system itself. Using a simple method of selecting for antigen binding cells gave comparable enrichment and has the added advantage of using a broader range of genes. At first sight the random combinatorial approach would appear unlikely to produce the original combination of heavy and light chain because of the vast diversity of the immunoglobulin genes. The applicants show here, however, that following immunisation, with a good antigen, 10% of the VH genes from total splenic RNA isolated come from antigen specific cells so the effective size of the repertoire is greatly reduced. This together with the fact that promiscuity of the heavy and light chains occurs (examples 21 and 22) accounts for the fact that combinatorial system does produce antigen binding clones with reasonable frequency. The data also suggests that the bulk of the antigen specific RNA comes from surface immunoglobulin negative cells which are most likely plasma cells.

The data also show that this simple method of antigen selection may be useful in reducing the complexity of the combinatorial library. In this case an enrichment of antigen specific genes of at least 56 fold has been achieved which in the normal case where heavy and light chains are unknown would result in a reduction of the complexity of the combinatorial library by a factor of over 3000. A further advantage of using antigen selected cells (and amplifying from DNA to reduce any bias due to the state of the cell) is that this results in a broader range of antibody genes amplified. It may be that a simple cell selection such as that the applicants have described here in combination with phage selection would be ideal. From this example it can be seen that by combining cell and phage selection methods one could reasonably expect to screen all the combinations of heavy and light chain (approximately $4 \times 10^{10}$) and would thus be able to screen all binding combinations although this would not, at present, be possible from whole spleen (approximately $4 \times 10^{14}$ combinations, assuming 50% B-cells).

TABLE 1

Enrichment of pAb (D1.3) from vector population

| INPUT RATIO[a] pAb:fd-CAT1 | OUTPUT RATIO oligo[b] pAb:total phage | ELISA[c] pAb:total phage | ENRICHMENT[d] |
|---|---|---|---|
| Single Round | | | |
| $1:4 \times 10^3$ | 43/124 | | $1.3 \times 10^3$ |
| $1:4 \times 10^4$ | 2/82 | | $1.0 \times 10^3$ |
| Two Rounds | | | |
| $1:4 \times 10^4$ | 197/372 | | $2.1 \times 10^4$ |
| $1:4 \times 10^5$ | 90/356 | 3/24 | $1.0 \times 10^5$ |
| $1:4 \times 10^6$ | 27/183 | 5/26 | $5.9 \times 10^5$ |
| $1:4 \times 10^7$ | 13/278 | | $1.8 \times 10^6$ |

Footnotes:
[a]Approximately $10^{12}$ phage with the stated ratio of pAb (D1.3):FDTPs/Bs were applied to 1 ml lysozyme-sepharose columns, washed and eluted.
[b]TG1 cells were infected with the eluted specific binding phage and plated onto TY-tet plates. After overnight incubation at 30-37° C., the plates were analysed by hydridisation to the $^{32}$p, labelled oligonucleotide VH1FOR (Ward et al op cit) which is specific to pAb D1.3.
[c]Single colonies from overnight plates were grown, phage purified, and tested for lysozyme binding.
[d]Enrichment was calculated from the oligonucleotide probing data.

TABLE 2

Enrichment of pAb (D1.3) from mixed pAb population

| Input Ratio1 (pAbD1.3:pAbNQ11) | Output Ratio[2] (pAb D1.3:Total phage) | Enrichment |
|---|---|---|
| Single Round | | |
| $1:2.5 \times 10^4$ | 18/460 | $0.98 \times 10^3$ |
| $1:2.5 \times 10^5$ | 3/770 | $0.97 \times 10^3$ |
| $1:2.5 \times 10^6$ | 0/112 | — |
| pAb NQ11 only | 0/460 | — |
| Second Round | | |
| $1:2.5 \times 10^4$ | 119/170 | $1.75 \times 10^4$ |
| $1:2.5 \times 10^5$ | 101/130 | $1.95 \times 10^5$ |
| $1:2.5 \times 10^6$ | 102/204 | $1.26 \times 10^6$ |
| $1:2.5 \times 10^7$ | 0/274 | — |
| $1:2.5 \times 10^8$ | 0/209 | — |
| pAb NQ11 only | 0/170 | — |

Notes
1. $10^{10}$ phage applied to a lysozyme column as in table 1.
2. Plating of cells and probing with oligonucleotide as in table 1, except the oligonucleotide was D1.3CDR3A.

TABLE 3

Enzyme activity of phage-enzyme

| Input | ng of enzyme or No. of phage | Rate (OD/hr) | No. of molecules of Enzyme equivalent ($\times 10^{-11}$) |
|---|---|---|---|
| Pure Enzyme | 335 | 34 | 24.5 |
| Pure Enzyme | 177.5 | 17.4 | 12.25 |
| Pure Enzyme | 88.7 | 8.7 | 6.125 |
| Pure Enzyme | 44.4 | 4.12 | 3.06 |
| Pure Enzyme | 22.2 | 1.8 | 1.5 |
| Pure Enzyme | 11.1 | 0.86 | 0.76 |
| No Enzyme | 0 | 0.005 | 0 |
| fd-phoAla166/TG1 | $1.83 \times 10^{11}$ | 5.82 | 4.2 |
| fd-CAT2/TG1 | $1.0 \times 10^{12}$ | 0.155 | 0.112 |
| fd-phoAla166/KS272 | $7.1 \times 10^{10}$ | 10.32 | 7.35 |
| fd-CAT2/KS272 | $8.2 \times 10^{12}$ | 0.038 | 0.027 |

TABLE 4

Affinity selection of hapten-binding phage.

| | Clones binding to phOx[†] | | | |
|---|---|---|---|---|
| | Pre-column | After first round | After second round | After third round |
| A Random Combinatorial Libraries | | | | |
| phOx-immunised mice | 0/568 (0%) | 48/376 (13%) | 175/188 (93%) | |
| Unimmunised mice | | | 0/388 (0%) | |
| B Hierarchical Libraries | | | | |
| VH-B/Vκ-rep library | 6/190 (3%) | 348/380 (92%) | | |
| VH-rep/Vκ-d library | 0/190 (0%) | 23/380 (7%) | | |

TABLE 4-continued

Affinity selection of hapten-binding phage.

| | Clones binding to phOx[†] | | | |
|---|---|---|---|---|
| | Pre-column | After first round | After second round | After third round |
| | C Fractionation of VH-B/Vκ-d and VH-B/Vκ-b phage[†] | | | |
| Mixture of clones | 88/1896 (4.6%) [44/1740 (2.5%)*] | 55/95 (57.9%) | 1152/1156 (99.7%) | 1296/1299 (99.8%) |

[†]In panel C, numbers refer to VH-B/Vκ-d colonies.
*Numbers after three reinfections and cycles of growth. This control, omitting the column steps, confirms that a spurious growth or infectivity advantage was not responsible for the enrichment for clone VH-B/Vκ-d.

TABLE 5

| | Phage/Phagemid[†] | Helper Phage | Binding to phOx* | Chain(s) displayed[#] | Chain as gene III fusion[#] | Soluble chain(s)[#] |
|---|---|---|---|---|---|---|
| A | fd CAT2 | | non binding | none | | |
| | fd CAT2-I | | binding | scFv | scFv | |
| | fd CAT2-II | | binding | Fab | light chain | heavy chain |
| | pHEN1 | VCSMB | binding | none | | heavy chain |
| | pHEN1 I | VCSMB | non binding | scFv | scFv | |
| | pHEN1 II | VCSMB | binding | Fab | light chain | heavy chain |
| B | pHEN1 I (HB2151) | | binding | | | scFv[§] |
| | pHEN1 II (HB2151) | | binding | | | Fab[§] |
| C | fd CAT2-III | | non binding | heavy chain | heavy chain | |
| | fd CAT2-IV | | binding | light chain | light chain | |
| | pHEN1 III (HB2151) | VCSMB | non binding | light chain | | heavy chain |
| | pHEN1 III (HB2151) | fd-tet-DOG1 | binding | none | light chain | heavy chain |
| | pHEN1 IV (HB2151) | IV | non binding | Fab | | heavy chain light chain |
| | pHEN1 IV (HB2151) | VCSMB | binding | none | heavy chain | light chain |
| | | fd-tet-DOG1 III | binding non binding binding | Fab | | light chain |

Overview of phOx-BSA ELISA results of phage and phagemid constructions.
*Phase were considered to be 'binding' if $OD_{405}$ of sample was at least 10 fold greater than background in ELISA;
[†]E. coli TG1 was used for the growth of the phage unless the use of E. coli HB2151 is specifically indicated;
[#]Information deduced from genetic structure and in accordance with binding data;
[§]Result confirmed experimentally by Western blot (for Fab, see FIG. 29.

TABLE 6

Kinetic parameters of soluble and phage-bound alkaline phosphase. Relative values of $k_{cat}$ and $K_m$ for the soluble enzyme and for the phage enzyme were derived by comparing with the values for wild type enzyme (phoArg166) and the phage-wild type enzyme (fdphoArg166).

| | Soluble enzyme (Data from Chaidaroglu et al 1988) | | Phage enzyme (Data from this study) | |
|---|---|---|---|---|
| | phoArg166 | phoAla166 | phoArg166 | phoAla166 |
| $K_m$ (μM) | 12.7 | 1620 | 73 | 1070 |
| Relative $K_m$ | 1 | 127 | 1 | 14.6 |
| Relative $k_{cat}$ | 1 | 0.397 | 1 | 0.360 |
| Relative $k_{cat}/K_m$ | 1 | 0.0032 | 1 | 0.024 |

TABLE 7

Enzyme Activity of Phage Samples

| SAMPLE (Construct:host) | INPUT PHAGE PARTICLE (pmol) | RATE (pmol substrate converted/min) | SPECIFIC ACTIVITY (mol substrate converted/mol phage/min) |
|---|---|---|---|
| fdphoArg166:TG1 | 2.3 | 8695 | 3700 |
| fdphoAla166:TG1 | 5.6 | 2111 | 380 |
| fdphoAla166:KS272 | 1.8 | 2505 | 1400 |
| fdCAT2:TG1 | 3.3 | <1 | <0.3 |
| fdCAT2:KS272 | 5.6 | 70 | 12 |

TABLE 8

Affinity chromatography of phage-enzymes

| SAMPLE | INFECTIVITY (Percentage of phage particles which are infectious) | INPUT PHAGE PARTICLE ($\times 10^9$) | OUTPUT PHAGE PARTICLE ($\times 10^9$) |
|---|---|---|---|
| fdphoArg166 | 0.37% | 5160 | 30 |
| fdphoAla166 | 0.26% | 3040 | 90 |
| fdCAT2 | 4.75% | 4000 | 2 |

TABLE 9

Mutations in scFvB18 selected by display on phage following growth in mutator strains

| Nucleotide mutation (base position) | Amino acid mutation | Number |
|---|---|---|
| 308 | Ala->Val (VH FR3) | 3 |
| 703 | Tyr->Asp (VL CDR3) | 1 |
| 706 | Ser->Gly (VL CDR3) | 1 |
| 724 | Gly->Ser (VL FR4) | 21 |
| 725 | Gly->Asp (VL FR4) | 3 |
| 734 | Thr->Ile (VL FR4) | 1 |

TABLE 10

Oligonucleotide primers used for PCR of human immunoglobulin genes

| Oligo Name | Sequence | |
|---|---|---|
| Human VH Back Primers | | |
| HuVH1aBACK | 5'-CAG GTG CAG CTG GTG CAG TCT GG-3' | (SEQ ID NO:81) |
| HuVH2aBACK | 5'-CAG GTC AAC TTA AGG GAG TCT GG-3' | (SEQ ID NO:82) |
| HuVH3aBACK | 5'-GAG GTG CAG CTG GTG GAG TCT GG-3' | (SEQ ID NO:83) |
| HuVH4aBACK | 5'-CAG GTG CAG CTG CAG GAG TCG GG-3' | (SEQ ID NO:84) |
| HuVH5aBACK | 5'-GAG GTG CAG CTG TTG CAG TCT GC-3' | (SEQ ID NO:85) |
| HuVH6aBACK | 5'-CAG GTA CAG CTG CAG CAG TCA GG-3' | (SEQ ID NO:86) |
| HuVH1aBACKSfi HuVH2aBACKSfi | 5'-GTC CTC GCA ACT GCG GCC CAG CCG GCC ATG GCC CAG GTG CAG CTG GTG CAG TCT GG-3' | (SEQ ID NO:87) |
| HuVH3aBACKSfi HuVH4aBACKSfi | 5'-GTC CTC GCA ACT GCG GCC CAG CCG GCC ATG GCC CAG GTC AAC TTA AGG GAG TCT GG-3' | (SEQ ID NO:88) |
| HuVH5aBACKSfi HuVH6aBACKSfi | 5'-GTC CTC GCA ACT GCG GCC CAG CCG GCC ATG GCC GAG GTG CAG CTG GTG GAG TCT GG-3' | (SEQ ID NO:89) |
| | 5'-GTC CTC GCA ACT GCG GCC CAG CCG GCC ATG GCC CAG GTG CAG CTG CAG GAG TCG GG-3' | (SEQ ID NO:90) |
| | 5'-GTC CTC GCA ACT GCG GCC CAG CCG GCC ATG GCC CAG GTG CAG CTG TTG CAG TCT GC-3' | (SEQ ID NO:91) |
| | 5'-GTC CTC GCA ACT GCG GCC CAG CCG GCC ATG GCC CAG GTA CAG CTG CAG CAG TCA GG-3' | (SEQ ID NO:92) |
| Human JH Forward Primers | | |
| HuJH1-2FOR | 5'-TGA GGA GAC GGT GAC CAG GGT GCC-3' | (SEQ ID NO:93) |
| HuJH3FOR | 5'-TGA AGA GAC GGT GAC CAT TGT CCC-3' | (SEQ ID NO:94) |
| HuJH4-5FOR | 5'-TGA GGA GAC GGT GAC CAG GGT TCC-3' | (SEQ ID NO:95) |
| HuJH6FOR | 5'-TGA GGA GAC GGT GAC CGT GGT CCC-3' | (SEQ ID NO:96) |
| Human Heavy Chain Constant Region Primers | | |
| HuIgG1-4CH1FOR | 5'-GTC CAC CTT GGT GTT GCT GGG CTT-3' | (SEQ ID NO:97) |
| HuIgMFOR | 5'-TGG AAG AGG CAC GTT CTT TTC TTT-3' | (SEQ ID NO:98) |

TABLE 10-continued

Oligonucleotide primers used for PCR of human immunoglobulin genes

| Oligo Name | Sequence | |
|---|---|---|
| Human Vκ Back Primers | | |
| HuVκ1aBACK | 5'-GAC ATC CAG ATG ACC CAG TCT CC-3' | (SEQ ID NO:99) |
| HuVκ2aBACK | 5'-GAT GTT GTG ATG ACT CAG TCT CC-3' | (SEQ ID NO:100) |
| HuVκ3aBACK | 5'-GAA ATT GTG TTG ACG CAG TCT CC-3' | (SEQ ID NO:101) |
| HuVκ4aBACK | 5'-GAC ATC GTG ATG ACC CAG TCT CC-3' | (SEQ ID NO:102) |
| HuVκ5aBACK | 5'-GAA ACG ACA CTC ACG CAG TCT CC-3' | (SEQ ID NO:103) |
| HuVκ6aBACK | 5'-GAA ATT GTG CTG ACT CAG TCT CC-3' | (SEQ ID NO:104) |
| Human Jκ Forward Primers | | |
| HuJκ1FOR | 5'-ACG TTT GAT TTC CAC CTT GGT CCC-3' | (SEQ ID NO:105) |
| HuJκ2FOR | 5'-ACG TTT GAT CTC CAG CTT GGT CCC-3' | (SEQ ID NO:106) |
| HuJκ3FOR | 5'-ACG TTT GAT ATC CAC TTT GGT CCC-3' | (SEQ ID NO:107) |
| HuJκ4FOR | 5'-ACG TTT GAT CTC CAC CTT GGT CCC-3' | (SEQ ID NO:108) |
| HuJκ5FOR | 5'-ACG TTT AAT CTC CAG TCG TGT CCC-3' | (SEQ ID NO:109) |
| HuJκ1BACKNot HuJκ2BACKNot | 5'-GAG TCA TTC TCG ACT TGC GGC CGC ACG TTT GAT TTC CAC CTT GGT CCC-3' | (SEQ ID NO:110) |
| HuJκ3BACKNot HuJκ4BACKNot | 5'-GAG TCA TTC TCG ACT TGC GGC CGC ACG TTT GAT CTC CAG CTT GGT CCC-3' | (SEQ ID NO:111) |
| HuJκ5BACKNot | 5'-GAG TCA TTC TCG ACT TGC GGC CGC ACG TTT GAT ATC CAC TTT GGT CCC-3' | (SEQ ID NO:112) |
| | 5'-GAG TCA TTC TCG ACT TGC GGC CGC ACG TTT GAT CTC CAC CTT GGT CCC-3' | (SEQ ID NO:113) |
| | 5'-GAG TCA TTC TCG ACT TGC GGC CGC ACG TTT AAT CTC CAG TCG TGT CCC-3' | (SEQ ID NO:114) |
| Human κ Constant Region Primers | | |
| HuCκFOR | 5'-AGA CTC TCC CCT GTT GAA GCT CTT-3' | (SEQ ID NO:115) |
| HuCκFORNot1 HuCκFORNot2 | 5'-GAG TCA TTC TCG ACT TGC GGC CGC TTA TTA AGA CTC TCC CCT GTT GAA GCT CTT-3' | (SEQ ID NO:116) |
| | 5'-GAG TCA TTC TCG ACT TGC GGC CGC AGA CTC TCC CCT GTT GAA GCT CTT-3' | (SEQ ID NO:117) |
| Human λ Back Primers | | |
| HuVλ1BACK | 5'-CAG TCT GTG TTG ACG CAG CCG CC-3' | (SEQ ID NO:118) |
| HuVλ2BACK | 5'-CAG TCT GCC CTG ACT CAG CCT GC-3' | (SEQ ID NO:119) |
| HuVλ3aBACK | 5'-TCC TAT GTG CTG ACT CAG CCA CC-3' | (SEQ ID NO:120) |
| HuVλ3bBACK | 5'-TCT TCT GAG CTG ACT CAG GAC CC-3' | (SEQ ID NO:121) |
| HuVλ4BACK | 5'-CAC GTT ATA CTG ACT CAA CCG CC-3' | (SEQ ID NO:122) |
| HuVλ5BACK | 5'-CAG GCT GTG CTC ACT CAG CCG TC-3' | (SEQ ID NO:123) |
| HuVλ6BACK | 5'-AAT TTT ATG CTG ACT CAG CCC CA-3' | (SEQ ID NO:124) |

TABLE 10-continued

Oligonucleotide primers used for PCR of human immunoglobulin genes

| Oligo Name | Sequence | |
|---|---|---|
| Human λ Forward Primers | | |
| HuJλ1FOR | 5'-ACC TAG GAC GGT GAC CTT GGT CCC-3' | (SEQ ID NO:125) |
| HuJλ2-3FOR | 5'-ACC TAG GAC GGT CAG CTT GGT CCC-3' | (SEQ ID NO:126) |
| HuJλ4-5FOR | 5'-ACC TAA AAC GGT GAG CTG GGT CCC-3' | (SEQ ID NO:127) |
| HuJλFORNOT HuJλ2-3FORNOT | 5'-GAG TCA TTC TCG ACT TGC GGC CGC ACC TAG GAC GGT GAC CTT GGT CCC-3' | (SEQ ID NO:128) |
| HuJλ4-5FORNOT | 5'-GAG TCA TTC TCG ACT TGC GGC CGC ACC TAG GAC GGT CAG CTT GGT CCC-3' | (SEQ ID NO:129) |
| | 5'-GAG TCA TTC TCG ACT TGC GGC CGC ACY TAA AAC GGT GAG CTG GGT CCC-3' | (SEQ ID NO:130) |
| Human λ Constant Region Primers | | |
| HuCλFOR | 5'-TGA AGA TTC TGT AGG GGC CAC TGT CTT-3' | (SEQ ID NO:131) |
| HuCλFORNot1 | 5'-GAG TCA TTC TCG ACT TGC GGC CGC TTA TTA TGA AGA TTC TGT AGG GGC CAC TGT CTT-3' | (SEQ ID NO:132) |
| HuCλFORNot2 | 5'-GAG TCA TTC TCG ACT TGC GGC CGC TGC AGA TTC TGT AGG GGC TGT CTT-3' | (SEQ ID NO:133) |
| Linker oligos Reverse JH for scFv linker | | |
| RHuJH1-2 | 5'-GCA CCC TGG TCA CCG TCT CCT CAG GTG G-3' | (SEQ ID NO:134) |
| RHuJH3 | 5'-GGA CAA TGG TCA CCG TCT CTT CAG GTG G-3' | (SEQ ID NO:135) |
| RHuJH4-5 | 5'-GAA CCC TGG TCA CCG TCT CCT CAG GTG G-3' | (SEQ ID NO:136) |
| RHuJH6 | 5'-GGA CCA CGG TCA CCG TCT CCT CAG GTG C-3' | (SEQ ID NO:137) |
| Reverse IgG1-4CH1 primer for Fab linker | | |
| RhuIgG1-4CH1FOR | 5'-AAG CCC AGC AAC ACC AAG GTG GAC-3' | (SEQ ID NO:138) |
| Reverse Vκ for scFv linker | | |
| RhuVκ1aBACKFv | 5'-GGA GAC TGG GTC ATC TGG ATG TCC GAT CCG CC-3' | (SEQ ID NO:139) |
| RhuVκ2aBACKFv | 5'-GGA GAC TGA GTC ATC ACA ACA TCC GAT CCG CC-3' | (SEQ ID NO:140) |
| RhuVκ3aBACKFv | 5'-GGA GAC TGC GTC AAC ACA ATT TCC GAT CCG CC-3' | (SEQ ID NO:141) |
| RhuVκ4aBACKFv | 5'-GGA GAC TGG GTC ATC ACG ATG TCC GAT CCG CC-3' | (SEQ ID NO:142) |
| RhuVκ5aBACKFv | 5'-GGA GAC TGC GTG AGT GTC GTT CCG ATC CG CC-3' | (SEQ ID NO:143) |
| RhuVκ6aBACKFv | 5'-GGA GAC TGA GTC AGC ACA ATT TCC GAT CCG CC-3' | (SEQ ID NO:144) |
| Reverse Vκ for Fab linker | | |
| RHuVκ1aBACKFab | 5'-GGA GAC TGG GTC ATC TGG ATG TCG GCC ATC GCT GG-3' | (SEQ ID NO:145) |
| RHuVκ2aBACKFab | 5'-GGA GAC TGC GTC ATC ACA ACA TCG GCC ATC GCT GG-3' | (SEQ ID NO:146) |
| RHuVκ3aBACKFab | 5'-GGA GAC TGC GTC AAC ACA ATT TCG GCC ATC GCT GG-3' | (SEQ ID NO:147) |
| RHuVκ4aBACKFab | 5'-GGA GAC TGG GTC ATC ACG ATG TCG GCC ATC GCT GG-3' | (SEQ ID NO:148) |
| RHuVκ5aBACKFab | 5'-GGA GAC TGC GTG AGT GTC GTT CG GCC ATC GCT GG-3' | (SEQ ID NO:149) |
| RHuVκ6aBACKFab | 5'-GGA GAC TGC GTC AGC ACA ATT TCG GCC ATC GCT GG-3' | (SEQ ID NO:150) |

TABLE 10-continued

Oligonucleotide primers used for PCR of human immunoglobulin genes

| Oligo Name | Sequence | |
|---|---|---|
| Reverse Vλ for svFv linker | | |
| RHuVλBACK1Fv | 5'-GGC GGC TGC GTC AAC ACA GAC TGC GAT CCG CCA CCG CCA GAG-3' | (SEQ ID NO:151) |
| RHuVλBACK2Fv | 5'-GCA GGC TGA GTC AGA GCA GAC TGC GAT CCG CCA CCG CCA GAG-3' | (SEQ ID NO:152) |
| RHuVλBACK3aFv | 5'-GGT GGC TGA GTC AGC ACA TAG GAC GAT CCG CCA CCG CCA GAG-3' | (SEQ ID NO:153) |
| RHuVλBACK3bFv | 5'-GGG TCC TGA GTC AGC TCA GAA GAC GAT CCG CCA CCG CCA GAG-3' | (SEQ ID NO:154) |
| RHuVλBACK4Fv | 5'-GGC GGT TGA GTC AGT ATA ACG TGC GAT CCG CCA CCG CCA GAG-3' | (SEQ ID NO:155) |
| RHuVλBACK5Fv | 5'-GAC GGC TGA GTC AGC ACA GAC TGC GAT CCG CCA CCG CCA GAG-3' | (SEQ ID NO:156) |
| RHuVλBACK6Fv | 5'-TGG GGC TGA GTC AGC ATA AAA TTC GAT CCG CCA CCG CCA GAG-3' | (SEQ ID NO:157) |
| Reverse Vλ for Fab linker | | |
| RHuVλBACK1Fab | 5'-GGC GGC TGC GTC AAC ACA GAC TGG GCC ATC GCT GGT TGG GCA-3' | (SEQ ID NO:158) |
| RHuVλBACK2Fab | 5'-GCA GGC TGA GTC AGA GCA GAC TGG GCC ATC GCT GGT TGG GCA-3' | (SEQ ID NO:159) |
| RHuVλBACK3aFab | 5'-GGT GGC TGA GTC AGC ACA TAG GAG GCC ATC GCT GGT TGG GCA-3' | (SEQ ID NO:160) |
| RHuVλBACK3bFab | 5'-GGG TCC TGA GTC AGC TCA GAA GAG GCC ATC GCT GGT TGG GCA-3' | (SEQ ID NO:161) |
| RHuVλBACK4Fab | 5'-GGC GGT TGA GTC AGT ATA ACG TGG GCC ATC GCT GGT TGG GCA-3' | (SEQ ID NO:162) |
| RHuVλBACK5Fab | 5'-GAC GGC TGA GTC AGC ACA GAC TGG GCC ATC GCT GGT TGG GCA-3' | (SEQ ID NO:163) |
| RHuVλBACK6Fab | 5'-TGG GGC TGA GTC AGC ATA AAA TTG GCC ATC GCT GGT TGG GCA-3' | (SEQ ID NO:164) |

TABLE 11

Deduced protein sequences of heavy and light chains selected from unimmunized library

Oxazolone binder

HEAVY CHAIN
VH15.4
QVQLVQSGAEVKKPGASVKVSCKASGYTFT SYGIS WVRQAPGQGLEWMG WISAYNGNTKYAWKLQG RVTMTDTSTSTAYMELRSLRSDDTAVYYCVR LLPKRTATLH (SEQ ID NO:165)
YYIDVWGGT

LIGHT CHAIN
VL15.4
NNYVS WYQHLPGTAPNLLIY DNNKRPS GIPDRPSGSKSGTSATLGITGLQTGDEADYYC GIWDGR (SEQ ID NO:166)

BSA Binders

HEAVY CHAINS
VH3.5
QVQLVQSGGGVVQPGRSLRLSCAAGFTFS SYGMH WVRQAPGKGLEWVA VISYDGSNKYYADSVKG RFTISRDNSKNTLYLQMNSLRAEDTAVYYCAK TGYSSGWGY (SEQ ID NO:167)
FDYWGQGT

LIGHT CHAINS
VL3.5
SSELTQDPAVSVALGQTVRITC QGDSLRSYYAS WYQQKPGQAPVLVIY GKNNRPS GIPDRFSGSSSGNTASLTITGAQAEDEADYYC NSRDSSGNH (SEQ ID NO:168)
VVFGG

Lysozyme binders:

HEAVY CHAINS
VH10.1
SLTCSVSGDSIS SGGYS WIRQPSGKGLEWIG SVHHSGPTYYNPSLKS RVTMSVDTSKNQFSLKLKSVTAADTAMYFCAR EGGSTWRSLYKH (SEQ ID NO:169)
YYMDVWGK

VH14.1
QVQLQESGPGLVKPSETLSLVCTVSGGSLS FSYWG WIRQPPGKGLEWIG YISHRGTDYHSSLQS RVTISADTSKNQFSLKLSSVTAADTAVYYCAR SFSNSFFFGY (SEQ ID NO:170)
WGQGT

VH13.1
QVQLVQSGAEVKKPGQSLMISCQGSGYSFS NYWIG WVRQMPGKGLEWMG IIYPGDSDTRYSPSFQG QVTISADKSISTAYLHWSSLKASDTALYYCAR LVGGTPAY (SEQ ID NO:171)
WGQGT

VH16.1
QVQLVQSGAEVKKPGQSLRISCKGAGYSFS TYWIG WVRQMPGKGLEWMG IIYPDDSDTRYSPSFEG QVTISVDKSITTAYLHWSSLKA (SEQ ID NO:172)

LIGHT CHAINS
VK10.1
EIVLTQSPSSLSASVGDRVTITC RASQSISNYLN WYQQKPGKAPKLLIY AASTLQS GVPSRFSGSGSGTDFTLTINSLQPEDFATYYC QQTIISFP (SEQ ID NO:173)
LTFGGG

VL14.1
SSELTQDPAVSVAFGQTVRITC QGDSLRSSYAS WYQQKPGQAPLLVIY GENSRPS GIPDRFSGSSSGNTASLTITGAQAEDEADYYC NSRDSRGTHL (SEQ ID NO:174)
EVFGG

VL13.1
HVILTQPASVSGSPGQSITISC TGSSRDVGGYNYVS WYQHHPGKAPKLLIS EVTHRPS GVSNRFSGSKSGNTASLTISGLQAEDEADYFC ASYTSSKT (SEQ ID NO:175)
YVFGG

VL16.1
QSALTQPASVSGSPGQSITISC SGSSSDIGRYDYVS WYQHYPDKAPKLLIY EVKHRPS GISHRFSASKSGNTASLTISELQPGDEADYYC ASYT (SEQ ID NO:176)

TABLE 12

Enrichment of pAbNQ11 from pAbD1.3 background by affinity selection using Ox-BSA biotinylated with a cleavable reagent and binding to streptavidin magnetic beads

| Input Ratio[1] (pAbD1.3:pAbNQ11) | Output Ratio[2] (pAb NQ11:Total phage) | Enrichment |
|---|---|---|
| 2235:1 | 61/197 | 690 |
| 22350:1 | 5/202 | 544 |

[1] $1.9 \times 10^{10}$ phage in 0.5 ml mixed for 1 hour with 5 μl streptavidin-magnetic beads precoated with antigen (OX-BSA).
[2] Colonies probed with the oligonucleotide NQ11CDR3

TABLE 13

Results of antigenic cell selection

| | Number of Cells | % of total cells |
|---|---|---|
| Total spleen cells | $4 \times 10^7$ | — |
| Cells bound to uncoated beads | $0.8 \times 10^4$ | 0.02 |
| Cells bound to NIP-BSA coated beads | $22 \times 10^4$ | 0.55 |

TABLE 14

Results of Fv NIP binding ELISAs from selected cell populations:

| Cell Population | Positives | *Degree of Enrichment |
|---|---|---|
| DNA from total spleen | 0/940 | — |
| RNA from total Spleen | 29/282 | >96 |
| DNA from antigen binding cells | 17/282 | >56 |
| Surface Ig Selection | | |
| RNA fromSurface Ig negative fraction | 8/94 | — |
| RNA from total Spleen | 4/94 | — |

*Degree of enrichment compared to total DNA.

---

The invention claimed is:

1. A method for producing a binding molecule specific for a particular target, which method comprises the steps of:

producing a population of filamentous bacteriophage particles displaying at their surface a population of binding molecules each binding molecule comprising a folded functional immunoglobulin domain, said population of filamentous bacteriophage particles having a range of binding specificities, wherein each binding molecule in the population of binding molecules has a binding domain able to bind a target, and wherein each filamentous bacteriophage particle contains a phagemid genome comprising nucleic acid with a nucleotide sequence encoding the binding molecule which is displayed at the particle surface, wherein the only nucleotide sequences derived from filamentous bacteriophage in the phagemid genome are an origin of replication and a nucleotide sequence encoding a mature gene III capsid protein, and wherein a helper phage, or a plasmid expressing complementing phage genes, is used to package said phagemid genome within each filamentous bacteriophage particle;

selecting for a filamentous bacteriophage particle displaying a binding molecule with a desired specificity by contacting the population of filamentous bacteriophage particles with a target so that individual binding molecules displayed on filamentous bacteriophage particles with the desired specificity bind to said target.

2. A method according to claim 1 additionally comprising separating bound filamentous bacteriophage particles from the target.

3. A method according to claim 2 additionally comprising recovering separated filamentous bacteriophage particles displaying a binding molecule with the desired specificity.

4. A method according to claim 3 additionally comprising producing in a recombinant system by expression from nucleic acid derived from said separated particles the binding molecule, or a fragment or derivative thereof with binding specificity for the target, separate from filamentous bacteriophage particles.

5. A method according to claim 4 wherein said derivative comprises an Fc tail.

* * * * *

UNITED STATES PATENT AND TRADEMARK OFFICE
CERTIFICATE OF CORRECTION

PATENT NO. : 7,662,557 B2  Page 1 of 1
APPLICATION NO. : 10/803653
DATED : February 16, 2010
INVENTOR(S) : McCafferty et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 371 days.

Signed and Sealed this

Thirtieth Day of November, 2010

David J. Kappos
*Director of the United States Patent and Trademark Office*

SEQUENCE LISTING

<160> NUMBER OF SEQ ID NOS: 272

<210> SEQ ID NO 1
<211> LENGTH: 5
<212> TYPE: PRT
<213> ORGANISM: Bacteriophage fd

<400> SEQUENCE: 1

Gln Val Gln Leu Gln
1               5

<210> SEQ ID NO 2
<211> LENGTH: 5
<212> TYPE: PRT
<213> ORGANISM: Bacteriophage fd

<400> SEQUENCE: 2

Val Thr Val Ser Ser
1               5

<210> SEQ ID NO 3
<211> LENGTH: 5
<212> TYPE: PRT
<213> ORGANISM: Bacteriophage fd

<400> SEQUENCE: 3

Leu Glu Ile Lys Arg
1               5

<210> SEQ ID NO 4
<211> LENGTH: 75
<212> TYPE: DNA
<213> ORGANISM: Artificial Sequence
<220> FEATURE:

```
<223> OTHER INFORMATION: oligonucleotide for mutagensis

<400> SEQUENCE: 4
actttcaaca gtttctgcgg ccgcccgttt gatctcgagc tcctgcagtt ggacctgtgc      60
actgtgagaa tagaa                                                      75

<210> SEQ ID NO 5
<211> LENGTH: 22
<212> TYPE: DNA
<213> ORGANISM: Artificial Sequence
<220> FEATURE:
<223> OTHER INFORMATION: PCR primer

<400> SEQUENCE: 5
aggtgcagct gcaggagtca gg                                              22

<210> SEQ ID NO 6
<211> LENGTH: 34
<212> TYPE: DNA
<213> ORGANISM: Artificial Sequence
<220> FEATURE:
<223> OTHER INFORMATION: PCR primer

<400> SEQUENCE: 6
ggtgacctcg agtgaagatt tgggctcaac tttc                                 34

<210> SEQ ID NO 7
<211> LENGTH: 27
<212> TYPE: DNA
<213> ORGANISM: Artificial Sequence
<220> FEATURE:
<223> OTHER INFORMATION: PCR primer

<400> SEQUENCE: 7
tgaggacwcw gccgtctact actgtgc                                         27

<210> SEQ ID NO 8
<211> LENGTH: 24
<212> TYPE: DNA
<213> ORGANISM: Artificial Sequence
<220> FEATURE:
<223> OTHER INFORMATION: oligonucleotide probe distinguishing between
      pAb D1.3 and pAB NQ11

<400> SEQUENCE: 8
gtagtcaagc ctataatctc tctc                                            24

<210> SEQ ID NO 9
<211> LENGTH: 51
<212> TYPE: DNA
<213> ORGANISM: Artificial Sequence
<220> FEATURE:
<223> OTHER INFORMATION: PCR primer

<400> SEQUENCE: 9
tattctcaca gtgcacaaac tgttgaacgg acaccagaaa tgcctgttct g              51

<210> SEQ ID NO 10
<211> LENGTH: 39
<212> TYPE: DNA
<213> ORGANISM: Artificial Sequence
<220> FEATURE:
<223> OTHER INFORMATION: PCR primer

<400> SEQUENCE: 10
```
acatgtacat gcggccgctt tcagcccag agcggcttt         39

<210> SEQ ID NO 11
<211> LENGTH: 33
<212> TYPE: DNA
<213> ORGANISM: Artificial Sequence
<220> FEATURE:
<223> OTHER INFORMATION: PCR primer

<400> SEQUENCE: 11
tttaatgagg atccacaggt gcagctgcaa gag         33

<210> SEQ ID NO 12
<211> LENGTH: 30
<212> TYPE: DNA
<213> ORGANISM: Artificial Sequence
<220> FEATURE:
<223> OTHER INFORMATION: PCR primer

<400> SEQUENCE: 12
aacgaatgga tcccgtttga tctcaagctt         30

<210> SEQ ID NO 13
<211> LENGTH: 24
<212> TYPE: DNA
<213> ORGANISM: Artificial Sequence
<220> FEATURE:
<223> OTHER INFORMATION: oligonucleotide for mutagensis - removal of a
      BamH1 site

<400> SEQUENCE: 13
caaacgaatg ggtcctcctc atta         24

<210> SEQ ID NO 14
<211> LENGTH: 26
<212> TYPE: DNA
<213> ORGANISM: Artificial Sequence
<220> FEATURE:
<223> OTHER INFORMATION: oligonucleotide for mutagensis - introduction
      of a BamH1 site

<400> SEQUENCE: 14
ccrccaccct cggatccrcc accctc         26

<210> SEQ ID NO 15
<211> LENGTH: 15
<212> TYPE: PRT
<213> ORGANISM: Artificial Sequence
<220> FEATURE:
<223> OTHER INFORMATION: linker between VH and VLK

<400> SEQUENCE: 15

Gly Gly Gly Gly Ser Gly Gly Gly Gly Ser Gly Gly Gly Gly Ser
1               5                   10                  15

<210> SEQ ID NO 16
<211> LENGTH: 23
<212> TYPE: DNA
<213> ORGANISM: Artificial Sequence
<220> FEATURE:
<223> OTHER INFORMATION: primer for reverse transcription

<400> SEQUENCE: 16
ctggacaggg atccagagtt cca         23

<210> SEQ ID NO 17

```
<211> LENGTH: 23
<212> TYPE: DNA
<213> ORGANISM: Artificial Sequence
<220> FEATURE:
<223> OTHER INFORMATION: primer for reverse transcription

<400> SEQUENCE: 17
ctggacaggg ctccatagtt cca                                              23

<210> SEQ ID NO 18
<211> LENGTH: 32
<212> TYPE: DNA
<213> ORGANISM: Artificial Sequence
<220> FEATURE:
<223> OTHER INFORMATION: PCR primer

<400> SEQUENCE: 18
tgaggagacg gtgaccgtgg tcccttggcc cc                                    32

<210> SEQ ID NO 19
<211> LENGTH: 22
<212> TYPE: DNA
<213> ORGANISM: Artificial Sequence
<220> FEATURE:
<223> OTHER INFORMATION: PCR primer

<400> SEQUENCE: 19
aggtsmarct gcagsagtcw gg                                               22

<210> SEQ ID NO 20
<211> LENGTH: 24
<212> TYPE: DNA
<213> ORGANISM: Artificial Sequence
<220> FEATURE:
<223> OTHER INFORMATION: PCR primer

<400> SEQUENCE: 20
ccgtttgatt tccagcttgg tgcc                                             24

<210> SEQ ID NO 21
<211> LENGTH: 24
<212> TYPE: DNA
<213> ORGANISM: Artificial Sequence
<220> FEATURE:
<223> OTHER INFORMATION: PCR primer

<400> SEQUENCE: 21
ccgttttatt tccagcttgg tccc                                             24

<210> SEQ ID NO 22
<211> LENGTH: 24
<212> TYPE: DNA
<213> ORGANISM: Artificial Sequence
<220> FEATURE:
<223> OTHER INFORMATION: PCR primer

<400> SEQUENCE: 22
ccgttttatt tccaactttg tccc                                             24

<210> SEQ ID NO 23
<211> LENGTH: 24
<212> TYPE: DNA
<213> ORGANISM: Artificial Sequence
<220> FEATURE:
<223> OTHER INFORMATION: PCR primer

<400> SEQUENCE: 23
```

```
ccgtttcagc tccagcttgg tccc                                          24

<210> SEQ ID NO 24
<211> LENGTH: 24
<212> TYPE: DNA
<213> ORGANISM: Artificial Sequence
<220> FEATURE:
<223> OTHER INFORMATION: PCR primer

<400> SEQUENCE: 24
gacattgagc tcacccagtc tcca                                          24

<210> SEQ ID NO 25
<211> LENGTH: 24
<212> TYPE: DNA
<213> ORGANISM: Artificial Sequence
<220> FEATURE:
<223> OTHER INFORMATION: PCR primer

<400> SEQUENCE: 25
tggagactcg gtgagctcaa tgtc                                          24

<210> SEQ ID NO 26
<211> LENGTH: 24
<212> TYPE: DNA
<213> ORGANISM: Artificial Sequence
<220> FEATURE:
<223> OTHER INFORMATION: PCR primer

<400> SEQUENCE: 26
gggaccacgg tcaccgtctc ctca                                          24

<210> SEQ ID NO 27
<211> LENGTH: 38
<212> TYPE: DNA
<213> ORGANISM: Artificial Sequence
<220> FEATURE:
<223> OTHER INFORMATION: PCR primer

<400> SEQUENCE: 27
catgaccaca gtgcacaggt smarctgcag sagtcwgg                           38

<210> SEQ ID NO 28
<211> LENGTH: 42
<212> TYPE: DNA
<213> ORGANISM: Artificial Sequence
<220> FEATURE:
<223> OTHER INFORMATION: PCR primer

<400> SEQUENCE: 28
gagtcattct gcggccgccc gtttgatttc cagcttggtg cc                      42

<210> SEQ ID NO 29
<211> LENGTH: 42
<212> TYPE: DNA
<213> ORGANISM: Artificial Sequence
<220> FEATURE:
<223> OTHER INFORMATION: PCR primer

<400> SEQUENCE: 29
gagtcattct gcggccgccc gttttatttc cagcttggtc cc                      42

<210> SEQ ID NO 30
<211> LENGTH: 42
<212> TYPE: DNA
```

<210> SEQ ID NO 31
<211> LENGTH: 42
<212> TYPE: DNA
<213> ORGANISM: Artificial Sequence
<220> FEATURE:
<223> OTHER INFORMATION: PCR primer

<400> SEQUENCE: 30
gagtcattct gcggccgccc gttttatttc caactttgtc cc            42

<210> SEQ ID NO 31
<211> LENGTH: 42
<212> TYPE: DNA
<213> ORGANISM: Artificial Sequence
<220> FEATURE:
<223> OTHER INFORMATION: PCR primer

<400> SEQUENCE: 31
gagtcattct gcggccgccc gtttcagctc cagcttggtc cc            42

<210> SEQ ID NO 32
<211> LENGTH: 69
<212> TYPE: DNA
<213> ORGANISM: Artificial Sequence
<220> FEATURE:
<223> OTHER INFORMATION: PCR primer

<400> SEQUENCE: 32
cacagtgcac tggtcgtcac accccegggg ccagagcttg tcctcaatgt ctccagcacc    60
ttcgttctg                                                             69

<210> SEQ ID NO 33
<211> LENGTH: 33
<212> TYPE: DNA
<213> ORGANISM: Artificial Sequence
<220> FEATURE:
<223> OTHER INFORMATION: PCR primer

<400> SEQUENCE: 33
gatctcgagc ttaaagggca aggagtgtgg cac                      33

<210> SEQ ID NO 34
<211> LENGTH: 40
<212> TYPE: DNA
<213> ORGANISM: Artificial Sequence
<220> FEATURE:
<223> OTHER INFORMATION: PCR primer

<400> SEQUENCE: 34
tgcgaagctt tggagccttt tttttggag attttcaacg                40

<210> SEQ ID NO 35
<211> LENGTH: 43
<212> TYPE: DNA
<213> ORGANISM: Artificial Sequence
<220> FEATURE:
<223> OTHER INFORMATION: PCR primer

<400> SEQUENCE: 35
cagtgaattc ctattaagac tccttattac gcagtatgtt agc           43

<210> SEQ ID NO 36
<211> LENGTH: 17
<212> TYPE: DNA
<213> ORGANISM: Artificial Sequence
<220> FEATURE:
<223> OTHER INFORMATION: sequencing primer

<400> SEQUENCE: 36
gaattttctg tatgagg                                                              17

<210> SEQ ID NO 37
<211> LENGTH: 5
<212> TYPE: PRT
<213> ORGANISM: Homo sapiens
<220> FEATURE:
<221> NAME/KEY: misc_feature
<222> LOCATION: (2)..(2)
<223> OTHER INFORMATION: X = A, C, D, E, F, G, H, I, K, L, M, N, P, Q,
      R, S, T, V, W or Y
<220> FEATURE:
<221> NAME/KEY: misc_feature
<222> LOCATION: (4)..(5)
<223> OTHER INFORMATION: X = A, C, D, E, F, G, H, I, K, L, M, N, P, Q,
      R, S, T, V, W or Y

<400> SEQUENCE: 37

Asp Xaa Gly Xaa Xaa
1               5

<210> SEQ ID NO 38
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = D or, N
<220> FEATURE:
<221> NAME/KEY: MISC_FEATURE
<222> LOCATION: (2)..(2)
<223> OTHER INFORMATION: X = A, C, D, E, F, G, H, I, K, L, M, N, P, Q,
      R, S, T, V, W or Y
<220> FEATURE:
<221> NAME/KEY: MISC_FEATURE
<222> LOCATION: (4)..(5)
<223> OTHER INFORMATION: X = A, C, D, E, F, G, H, I, K, L, M, N, P, Q,
      R, S, T, V, W or Y

<400> SEQUENCE: 38

Xaa Xaa Gly Xaa Xaa
1               5

<210> SEQ ID NO 39
<211> LENGTH: 45
<212> TYPE: DNA
<213> ORGANISM: Artificial Sequence
<220> FEATURE:
<223> OTHER INFORMATION: PCR primer

<400> SEQUENCE: 39
tcgcggccca gccggccatg gccsaggtsm arctgcagsg tcwgg                               45

<210> SEQ ID NO 40
<211> LENGTH: 20
<212> TYPE: DNA
<213> ORGANISM: Artificial Sequence
<220> FEATURE:
<223> OTHER INFORMATION: oilgonucleotide probe for Vk-b

<400> SEQUENCE: 40
gagcgggtaa ccactgtact                                                           20

<210> SEQ ID NO 41
<211> LENGTH: 20
<212> TYPE: DNA
<213> ORGANISM: Artificial Sequence
<220> FEATURE:

-continued

```
<223> OTHER INFORMATION: oilgonucleotide probe for Vk-d

<400> SEQUENCE: 41
gaatggtata gtactaccct                                              20

<210> SEQ ID NO 42
<211> LENGTH: 43
<212> TYPE: DNA
<213> ORGANISM: Artificial Sequence
<220> FEATURE:
<223> OTHER INFORMATION: PCR primer

<400> SEQUENCE: 42
cagtgaattc ttattaagac tccttattac gcagtatgtt agc                    43

<210> SEQ ID NO 43
<211> LENGTH: 40
<212> TYPE: DNA
<213> ORGANISM: Artificial Sequence
<220> FEATURE:
<223> OTHER INFORMATION: PCR primer

<400> SEQUENCE: 43
tgcgaagctt tggagccttt tttttggag attttcaacg                         40

<210> SEQ ID NO 44
<211> LENGTH: 38
<212> TYPE: DNA
<213> ORGANISM: Artificial Sequence
<220> FEATURE:
<223> OTHER INFORMATION: PCR primer

<400> SEQUENCE: 44
catgaccaca gtgcacaggt smarctgcag sagtcwgg                          38

<210> SEQ ID NO 45
<211> LENGTH: 57
<212> TYPE: DNA
<213> ORGANISM: Artificial Sequence
<220> FEATURE:
<223> OTHER INFORMATION: PCR primer

<400> SEQUENCE: 45
catgccatga ctcgcggccc agccggccat ggccsaggts marctgcags agtcwgg     57

<210> SEQ ID NO 46
<211> LENGTH: 48
<212> TYPE: DNA
<213> ORGANISM: Artificial Sequence
<220> FEATURE:
<223> OTHER INFORMATION: PCR primer

<400> SEQUENCE: 46
ccacgattct gcggccgctg aagatttggg ctcaactttc ttgtcgac               48

<210> SEQ ID NO 47
<211> LENGTH: 48
<212> TYPE: DNA
<213> ORGANISM: Artificial Sequence
<220> FEATURE:
<223> OTHER INFORMATION: PCR primer

<400> SEQUENCE: 47
ccacgattct gcggccgctg actctccgcg gttgaagctc tttgtgac               48
```

```
<210> SEQ ID NO 48
<211> LENGTH: 36
<212> TYPE: DNA
<213> ORGANISM: Artificial Sequence
<220> FEATURE:
<223> OTHER INFORMATION: PCR primer

<400> SEQUENCE: 48
cacagtgcac tcgacattga gctcacccag tctcca                                 36

<210> SEQ ID NO 49
<211> LENGTH: 54
<212> TYPE: DNA
<213> ORGANISM: Artificial Sequence
<220> FEATURE:
<223> OTHER INFORMATION: PCR primer

<400> SEQUENCE: 49
catgaccacg cggcccagcc ggccatggcc gacattgagc tcacccagtc tcca             54

<210> SEQ ID NO 50
<211> LENGTH: 36
<212> TYPE: DNA
<213> ORGANISM: Artificial Sequence
<220> FEATURE:
<223> OTHER INFORMATION: PCR primer

<400> SEQUENCE: 50
ttctgcggcc gcccgtttca gctcgagctt ggtccc                                 36

<210> SEQ ID NO 51
<211> LENGTH: 21
<212> TYPE: DNA
<213> ORGANISM: Artificial Sequence
<220> FEATURE:
<223> OTHER INFORMATION: oligonucleotide for mutagensis - Ala166 to Arg

<400> SEQUENCE: 51
tagcatttgc gcgaggtcac a                                                 21

<210> SEQ ID NO 52
<211> LENGTH: 42
<212> TYPE: DNA
<213> ORGANISM: Artificial Sequence
<220> FEATURE:
<223> OTHER INFORMATION: PCR primer

<400> SEQUENCE: 52
tggagactgg gtgagctcaa tgtcggagtg agaatagaaa gg                          42

<210> SEQ ID NO 53
<211> LENGTH: 72
<212> TYPE: DNA
<213> ORGANISM: Artificial Sequence
<220> FEATURE:
<223> OTHER INFORMATION: PCR primer

<400> SEQUENCE: 53
aagcccagca acaccaaggt ggacaagaaa gttgagccca atctagctg ataaaccgat        60 acaattaaag gc                                                           72

<210> SEQ ID NO 54
<211> LENGTH: 21
<212> TYPE: DNA
<213> ORGANISM: Artificial Sequence
<220> FEATURE:
```

```
<223> OTHER INFORMATION: PCR primer

<400> SEQUENCE: 54
cggaataccc aaaagaactg g                                              21

<210> SEQ ID NO 55
<211> LENGTH: 33
<212> TYPE: DNA
<213> ORGANISM: Artificial Sequence
<220> FEATURE:
<223> OTHER INFORMATION: PCR primer

<400> SEQUENCE: 55
cacagtgcac aggtccaact gcaggagagc ggt                                 33

<210> SEQ ID NO 56
<211> LENGTH: 24
<212> TYPE: DNA
<213> ORGANISM: Artificial Sequence
<220> FEATURE:
<223> OTHER INFORMATION: PCR primer

<400> SEQUENCE: 56
cggtgacgag gctgccttga cccc                                           24

<210> SEQ ID NO 57
<211> LENGTH: 24
<212> TYPE: DNA
<213> ORGANISM: Artificial Sequence
<220> FEATURE:
<223> OTHER INFORMATION: PCR primer

<400> SEQUENCE: 57
ggggtcaggg cagcctcgtc accg                                           24

<210> SEQ ID NO 58
<211> LENGTH: 28
<212> TYPE: DNA
<213> ORGANISM: Artificial Sequence
<220> FEATURE:
<223> OTHER INFORMATION: PCR primer

<400> SEQUENCE: 58
tgggctctgg gtcatctgga tgtccgat                                       28

<210> SEQ ID NO 59
<211> LENGTH: 24
<212> TYPE: DNA
<213> ORGANISM: Artificial Sequence
<220> FEATURE:
<223> OTHER INFORMATION: PCR primer

<400> SEQUENCE: 59
gacatccaga tgacccagag ccca                                           24

<210> SEQ ID NO 60
<211> LENGTH: 42
<212> TYPE: DNA
<213> ORGANISM: Artificial Sequence
<220> FEATURE:
<223> OTHER INFORMATION: PCR primer

<400> SEQUENCE: 60
gagtcattct gcggccgcac gtttgatttc caccttggtc cc                       42
```

```
<210> SEQ ID NO 61
<211> LENGTH: 17
<212> TYPE: DNA
<213> ORGANISM: Artificial Sequence
<220> FEATURE:
<223> OTHER INFORMATION: PCR primer

<400> SEQUENCE: 61
gaggagattt tccctgt                                                      17

<210> SEQ ID NO 62
<211> LENGTH: 17
<212> TYPE: DNA
<213> ORGANISM: Artificial Sequence
<220> FEATURE:
<223> OTHER INFORMATION: PCR primer

<400> SEQUENCE: 62
ttggagcctt acctggc                                                      17

<210> SEQ ID NO 63
<211> LENGTH: 24
<212> TYPE: DNA
<213> ORGANISM: Artificial Sequence
<220> FEATURE:
<223> OTHER INFORMATION: PCR primer

<400> SEQUENCE: 63
tagccccctt attagcgttt gcca                                              24

<210> SEQ ID NO 64
<211> LENGTH: 24
<212> TYPE: DNA
<213> ORGANISM: Artificial Sequence
<220> FEATURE:
<223> OTHER INFORMATION: PCR primer

<400> SEQUENCE: 64
gcgatgggtg ttgtcattgt cggc                                              24

<210> SEQ ID NO 65
<211> LENGTH: 40
<212> TYPE: DNA
<213> ORGANISM: Artificial Sequence
<220> FEATURE:
<223> OTHER INFORMATION: PCR primer

<400> SEQUENCE: 65
ggaattcgtg cacagagtgc aacttcaact aaaaaattac                             40

<210> SEQ ID NO 66
<211> LENGTH: 40
<212> TYPE: DNA
<213> ORGANISM: Artificial Sequence
<220> FEATURE:
<223> OTHER INFORMATION: PCR primer

<400> SEQUENCE: 66
gggatccgcg gccgcttgac ctgaatcagc gttgtcttcg                             40

<210> SEQ ID NO 67
<211> LENGTH: 43
<212> TYPE: DNA
<213> ORGANISM: Artificial Sequence
<220> FEATURE:
<223> OTHER INFORMATION: PCR primer
```

```
<400> SEQUENCE: 67
ggaattcgtg cacagaagaa agtggtgctg ggcaaaaaag ggg                 43

<210> SEQ ID NO 68
<211> LENGTH: 45
<212> TYPE: DNA
<213> ORGANISM: Artificial Sequence
<220> FEATURE:
<223> OTHER INFORMATION: PCR primer

<400> SEQUENCE: 68
gggatccgcg gccgcagcta gcaccacgat gtctattttg aactc              45

<210> SEQ ID NO 69
<211> LENGTH: 17
<212> TYPE: DNA
<213> ORGANISM: Artificial Sequence
<220> FEATURE:
<223> OTHER INFORMATION: sequencing primer

<400> SEQUENCE: 69
gaattttctg tatgagg                                              17

<210> SEQ ID NO 70
<211> LENGTH: 17
<212> TYPE: DNA
<213> ORGANISM: Artificial Sequence
<220> FEATURE:
<223> OTHER INFORMATION: sequencing primer

<400> SEQUENCE: 70
gaagtttcct tggtccc                                              17

<210> SEQ ID NO 71
<211> LENGTH: 17
<212> TYPE: DNA
<213> ORGANISM: Artificial Sequence
<220> FEATURE:
<223> OTHER INFORMATION: sequencing primer

<400> SEQUENCE: 71
actaccaggg gggctct                                              17

<210> SEQ ID NO 72
<211> LENGTH: 45
<212> TYPE: DNA
<213> ORGANISM: Artificial Sequence
<220> FEATURE:
<223> OTHER INFORMATION: PCR primer

<400> SEQUENCE: 72
gggatccgcg gccgcggtgt cagagttggc agtcaatccg aacac              45

<210> SEQ ID NO 73
<211> LENGTH: 31
<212> TYPE: DNA
<213> ORGANISM: Artificial Sequence
<220> FEATURE:
<223> OTHER INFORMATION: primer for reverse transcription

<400> SEQUENCE: 73
ggaattctta tgaagattct gtagggggcca c                            31

<210> SEQ ID NO 74
<211> LENGTH: 33
```

```
<212> TYPE: DNA
<213> ORGANISM: Artificial Sequence
<220> FEATURE:
<223> OTHER INFORMATION: PCR primer

<400> SEQUENCE: 74
aaccagccat ggccagtctg tgttgacgca gcc                                    33

<210> SEQ ID NO 75
<211> LENGTH: 36
<212> TYPE: DNA
<213> ORGANISM: Artificial Sequence
<220> FEATURE:
<223> OTHER INFORMATION: oligonuleotide for mutagenesis - randomization
      of Phe91 and Phe92 of the light chain
<220> FEATURE:
<221> NAME/KEY: misc_feature
<222> LOCATION: (16)..(21)
<223> OTHER INFORMATION: n = a, c, g or t

<400> SEQUENCE: 75
cgtccgagga gtactnnnnn natgttgaca gtaata                                 36

<210> SEQ ID NO 76
<211> LENGTH: 33
<212> TYPE: DNA
<213> ORGANISM: Artificial Sequence
<220> FEATURE:
<223> OTHER INFORMATION: oligonuleotide for mutagenesis - randomization
      of Tyr32 of the light chain
<220> FEATURE:
<221> NAME/KEY: misc_feature
<222> LOCATION: (16)..(18)
<223> OTHER INFORMATION: n = a, c, g or t

<400> SEQUENCE: 76
ctgataccat gctaannnat tgtgattatt ccc                                    33

<210> SEQ ID NO 77
<211> LENGTH: 33
<212> TYPE: DNA
<213> ORGANISM: Artificial Sequence
<220> FEATURE:
<223> OTHER INFORMATION: oligonuleotide for mutagenesis - randomization
      of Tyr101 of the light chain
<220> FEATURE:
<221> NAME/KEY: misc_feature
<222> LOCATION: (16)..(18)
<223> OTHER INFORMATION: n = a, c, g or t

<400> SEQUENCE: 77
ccagtagtca agcctnnnat ctctctctct ggc                                    33

<210> SEQ ID NO 78
<211> LENGTH: 21
<212> TYPE: DNA
<213> ORGANISM: Artificial Sequence
<220> FEATURE:
<223> OTHER INFORMATION: sequencing primer

<400> SEQUENCE: 78
caggagctga ggagattttc c                                                 21

<210> SEQ ID NO 79
<211> LENGTH: 21
<212> TYPE: DNA
<213> ORGANISM: Artificial Sequence
<220> FEATURE:
<223> OTHER INFORMATION: sequencing primer
```

<400> SEQUENCE: 79
tccgcctgaa ccgcctccac c					21

<210> SEQ ID NO 80
<211> LENGTH: 24
<212> TYPE: DNA
<213> ORGANISM: Artificial Sequence
<220> FEATURE:
<223> OTHER INFORMATION: oligonucleotide probe for CD2 of the NQ11
      antibody

<400> SEQUENCE: 80
aaaccaggcc ccgtaatcat agcc				24

<210> SEQ ID NO 81
<211> LENGTH: 23
<212> TYPE: DNA
<213> ORGANISM: Artificial Sequence
<220> FEATURE:
<223> OTHER INFORMATION: PCR Primer

<400> SEQUENCE: 81
caggtgcagc tggtgcagtc tgg				23

<210> SEQ ID NO 82
<211> LENGTH: 23
<212> TYPE: DNA
<213> ORGANISM: Artificial Sequence
<220> FEATURE:
<223> OTHER INFORMATION: PCR Primer

<400> SEQUENCE: 82
caggtcaact taagggagtc tgg				23

<210> SEQ ID NO 83
<211> LENGTH: 23
<212> TYPE: DNA
<213> ORGANISM: Artificial Sequence
<220> FEATURE:
<223> OTHER INFORMATION: PCR Primer

<400> SEQUENCE: 83
gaggtgcagc tggtggagtc tgg				23

<210> SEQ ID NO 84
<211> LENGTH: 23
<212> TYPE: DNA
<213> ORGANISM: Artificial Sequence
<220> FEATURE:
<223> OTHER INFORMATION: PCR Primer

<400> SEQUENCE: 84
caggtgcagc tgcaggagtc ggg				23

<210> SEQ ID NO 85
<211> LENGTH: 23
<212> TYPE: DNA
<213> ORGANISM: Artificial Sequence
<220> FEATURE:
<223> OTHER INFORMATION: PCR Primer

<400> SEQUENCE: 85
gaggtgcagc tgttgcagtc tgc				23

```
<210> SEQ ID NO 86
<211> LENGTH: 23
<212> TYPE: DNA
<213> ORGANISM: Artificial Sequence
<220> FEATURE:
<223> OTHER INFORMATION: PCR Primer

<400> SEQUENCE: 86
caggtacagc tgcagcagtc agg                                      23

<210> SEQ ID NO 87
<211> LENGTH: 56
<212> TYPE: DNA
<213> ORGANISM: Artificial Sequence
<220> FEATURE:
<223> OTHER INFORMATION: PCR Primer

<400> SEQUENCE: 87
gtcctcgcaa ctgcggccca gccggccatg gcccaggtgc agctggtgca gtctgg    56

<210> SEQ ID NO 88
<211> LENGTH: 56
<212> TYPE: DNA
<213> ORGANISM: Artificial Sequence
<220> FEATURE:
<223> OTHER INFORMATION: PCR Primer

<400> SEQUENCE: 88
gtcctcgcaa ctgcggccca gccggccatg gcccaggtca acttaaggga gtctgg    56

<210> SEQ ID NO 89
<211> LENGTH: 56
<212> TYPE: DNA
<213> ORGANISM: Artificial Sequence
<220> FEATURE:
<223> OTHER INFORMATION: PCR Primer

<400> SEQUENCE: 89
gtcctcgcaa ctgcggccca gccggccatg gccgaggtgc agctggtgga gtctgg    56

<210> SEQ ID NO 90
<211> LENGTH: 56
<212> TYPE: DNA
<213> ORGANISM: Artificial Sequence
<220> FEATURE:
<223> OTHER INFORMATION: PCR Primer

<400> SEQUENCE: 90
gtcctcgcaa ctgcggccca gccggccatg gcccaggtgc agctgcagga gtcggg    56

<210> SEQ ID NO 91
<211> LENGTH: 56
<212> TYPE: DNA
<213> ORGANISM: Artificial Sequence
<220> FEATURE:
<223> OTHER INFORMATION: PCR Primer

<400> SEQUENCE: 91
gtcctcgcaa ctgcggccca gccggccatg gcccaggtgc agctgttgca gtctgc    56

<210> SEQ ID NO 92
<211> LENGTH: 56
<212> TYPE: DNA
<213> ORGANISM: Artificial Sequence
<220> FEATURE:
<223> OTHER INFORMATION: PCR Primer
```

```
<400> SEQUENCE: 92
gtcctcgcaa ctgcggccca gccggccatg gcccaggtac agctgcagca gtcagg          56

<210> SEQ ID NO 93
<211> LENGTH: 24
<212> TYPE: DNA
<213> ORGANISM: Artificial Sequence
<220> FEATURE:
<223> OTHER INFORMATION: PCR Primer

<400> SEQUENCE: 93
tgaggagacg gtgaccaggg tgcc                                              24

<210> SEQ ID NO 94
<211> LENGTH: 24
<212> TYPE: DNA
<213> ORGANISM: Artificial Sequence
<220> FEATURE:
<223> OTHER INFORMATION: PCR Primer

<400> SEQUENCE: 94
tgaagagacg gtgaccattg tccc                                              24

<210> SEQ ID NO 95
<211> LENGTH: 24
<212> TYPE: DNA
<213> ORGANISM: Artificial Sequence
<220> FEATURE:
<223> OTHER INFORMATION: PCR Primer

<400> SEQUENCE: 95
tgaggagacg gtgaccaggg ttcc                                              24

<210> SEQ ID NO 96
<211> LENGTH: 24
<212> TYPE: DNA
<213> ORGANISM: Artificial Sequence
<220> FEATURE:
<223> OTHER INFORMATION: PCR Primer

<400> SEQUENCE: 96
tgaggagacg gtgaccgtgg tccc                                              24

<210> SEQ ID NO 97
<211> LENGTH: 24
<212> TYPE: DNA
<213> ORGANISM: Artificial Sequence
<220> FEATURE:
<223> OTHER INFORMATION: PCR Primer

<400> SEQUENCE: 97
gtccaccttg gtgttgctgg gctt                                              24

<210> SEQ ID NO 98
<211> LENGTH: 24
<212> TYPE: DNA
<213> ORGANISM: Artificial Sequence
<220> FEATURE:
<223> OTHER INFORMATION: PCR Primer

<400> SEQUENCE: 98
tggaagaggc acgttctttt cttt                                              24

<210> SEQ ID NO 99
<211> LENGTH: 23
```

```
<212> TYPE: DNA
<213> ORGANISM: Artificial Sequence
<220> FEATURE:
<223> OTHER INFORMATION: PCR Primer

<400> SEQUENCE: 99
gacatccaga tgacccagtc tcc                                              23

<210> SEQ ID NO 100
<211> LENGTH: 23
<212> TYPE: DNA
<213> ORGANISM: Artificial Sequence
<220> FEATURE:
<223> OTHER INFORMATION: PCR Primer

<400> SEQUENCE: 100
gatgttgtga tgactcagtc tcc                                              23

<210> SEQ ID NO 101
<211> LENGTH: 23
<212> TYPE: DNA
<213> ORGANISM: Artificial Sequence
<220> FEATURE:
<223> OTHER INFORMATION: PCR Primer

<400> SEQUENCE: 101
gaaattgtgt tgacgcagtc tcc                                              23

<210> SEQ ID NO 102
<211> LENGTH: 23
<212> TYPE: DNA
<213> ORGANISM: Artificial Sequence
<220> FEATURE:
<223> OTHER INFORMATION: PCR Primer

<400> SEQUENCE: 102
gacatcgtga tgacccagtc tcc                                              23

<210> SEQ ID NO 103
<211> LENGTH: 23
<212> TYPE: DNA
<213> ORGANISM: Artificial Sequence
<220> FEATURE:
<223> OTHER INFORMATION: PCR Primer

<400> SEQUENCE: 103
gaaacgacac tcacgcagtc tcc                                              23

<210> SEQ ID NO 104
<211> LENGTH: 23
<212> TYPE: DNA
<213> ORGANISM: Artificial Sequence
<220> FEATURE:
<223> OTHER INFORMATION: PCR Primer

<400> SEQUENCE: 104
gaaattgtgc tgactcagtc tcc                                              23

<210> SEQ ID NO 105
<211> LENGTH: 24
<212> TYPE: DNA
<213> ORGANISM: Artificial Sequence
<220> FEATURE:
<223> OTHER INFORMATION: PCR Primer

<400> SEQUENCE: 105
```

```
acgtttgatt tccaccttgg tccc                                              24
```

<210> SEQ ID NO 106
<211> LENGTH: 24
<212> TYPE: DNA
<213> ORGANISM: Artificial Sequence
<220> FEATURE:
<223> OTHER INFORMATION: PCR Primer

<400> SEQUENCE: 106

```
acgtttgatc tccagcttgg tccc                                              24
```

<210> SEQ ID NO 107
<211> LENGTH: 24
<212> TYPE: DNA
<213> ORGANISM: Artificial Sequence
<220> FEATURE:
<223> OTHER INFORMATION: PCR Primer

<400> SEQUENCE: 107

```
acgtttgata tccactttgg tccc                                              24
```

<210> SEQ ID NO 108
<211> LENGTH: 24
<212> TYPE: DNA
<213> ORGANISM: Artificial Sequence
<220> FEATURE:
<223> OTHER INFORMATION: PCR Primer

<400> SEQUENCE: 108

```
acgtttgatc tccaccttgg tccc                                              24
```

<210> SEQ ID NO 109
<211> LENGTH: 24
<212> TYPE: DNA
<213> ORGANISM: Artificial Sequence
<220> FEATURE:
<223> OTHER INFORMATION: PCR Primer

<400> SEQUENCE: 109

```
acgtttaatc tccagtcgtg tccc                                              24
```

<210> SEQ ID NO 110
<211> LENGTH: 48
<212> TYPE: DNA
<213> ORGANISM: Artificial Sequence
<220> FEATURE:
<223> OTHER INFORMATION: PCR Primer

<400> SEQUENCE: 110

```
gagtcattct cgacttgcgg ccgcacgttt gatttccacc ttggtccc                    48
```

<210> SEQ ID NO 111
<211> LENGTH: 48
<212> TYPE: DNA
<213> ORGANISM: Artificial Sequence
<220> FEATURE:
<223> OTHER INFORMATION: PCR Primer

<400> SEQUENCE: 111

```
gagtcattct cgacttgcgg ccgcacgttt gatctccagc ttggtccc                    48
```

<210> SEQ ID NO 112
<211> LENGTH: 48
<212> TYPE: DNA
<213> ORGANISM: Artificial Sequence

```
<220> FEATURE:
<223> OTHER INFORMATION: PCR Primer

<400> SEQUENCE: 112
gagtcattct cgacttgcgg ccgcacgttt gatatccact ttggtccc            48

<210> SEQ ID NO 113
<211> LENGTH: 48
<212> TYPE: DNA
<213> ORGANISM: Artificial Sequence
<220> FEATURE:
<223> OTHER INFORMATION: PCR Primer

<400> SEQUENCE: 113
gagtcattct cgacttgcgg ccgcacgttt gatctccacc ttggtccc            48

<210> SEQ ID NO 114
<211> LENGTH: 48
<212> TYPE: DNA
<213> ORGANISM: Artificial Sequence
<220> FEATURE:
<223> OTHER INFORMATION: PCR Primer

<400> SEQUENCE: 114
gagtcattct cgacttgcgg ccgcacgttt aatctccagt cgtgtccc            48

<210> SEQ ID NO 115
<211> LENGTH: 24
<212> TYPE: DNA
<213> ORGANISM: Artificial Sequence
<220> FEATURE:
<223> OTHER INFORMATION: PCR Primer

<400> SEQUENCE: 115
agactctccc ctgttgaagc tctt                                      24

<210> SEQ ID NO 116
<211> LENGTH: 54
<212> TYPE: DNA
<213> ORGANISM: Artificial Sequence
<220> FEATURE:
<223> OTHER INFORMATION: PCR Primer

<400> SEQUENCE: 116
gagtcattct cgacttgcgg ccgcttatta agactctccc ctgttgaagc tctt     54

<210> SEQ ID NO 117
<211> LENGTH: 48
<212> TYPE: DNA
<213> ORGANISM: Artificial Sequence
<220> FEATURE:
<223> OTHER INFORMATION: PCR Primer

<400> SEQUENCE: 117
gagtcattct cgacttgcgg ccgcagactc tcccctgttg aagctctt            48

<210> SEQ ID NO 118
<211> LENGTH: 23
<212> TYPE: DNA
<213> ORGANISM: Artificial Sequence
<220> FEATURE:
<223> OTHER INFORMATION: PCR Primer

<400> SEQUENCE: 118
cagtctgtdt tgacgcagcc gcc                                       23
```

<210> SEQ ID NO 119
<211> LENGTH: 23
<212> TYPE: DNA
<213> ORGANISM: Artificial Sequence
<220> FEATURE:
<223> OTHER INFORMATION: PCR Primer

<400> SEQUENCE: 119
cagtctgccc tgactcagcc tgc                                            23

<210> SEQ ID NO 120
<211> LENGTH: 23
<212> TYPE: DNA
<213> ORGANISM: Artificial Sequence
<220> FEATURE:
<223> OTHER INFORMATION: PCR Primer

<400> SEQUENCE: 120
tcctatgtgc tgactcagcc acc                                            23

<210> SEQ ID NO 121
<211> LENGTH: 23
<212> TYPE: DNA
<213> ORGANISM: Artificial Sequence
<220> FEATURE:
<223> OTHER INFORMATION: PCR Primer

<400> SEQUENCE: 121
tcttctgagc tgactcagga ccc                                            23

<210> SEQ ID NO 122
<211> LENGTH: 23
<212> TYPE: DNA
<213> ORGANISM: Artificial Sequence
<220> FEATURE:
<223> OTHER INFORMATION: PCR Primer

<400> SEQUENCE: 122
cacgttatac tgactcaacc gcc                                            23

<210> SEQ ID NO 123
<211> LENGTH: 23
<212> TYPE: DNA
<213> ORGANISM: Artificial Sequence
<220> FEATURE:
<223> OTHER INFORMATION: PCR Primer

<400> SEQUENCE: 123
caggctgtgc tcactcagcc gtc                                            23

<210> SEQ ID NO 124
<211> LENGTH: 23
<212> TYPE: DNA
<213> ORGANISM: Artificial Sequence
<220> FEATURE:
<223> OTHER INFORMATION: PCR Primer

<400> SEQUENCE: 124
aattttatgc tgactcagcc cca                                            23

<210> SEQ ID NO 125
<211> LENGTH: 24
<212> TYPE: DNA
<213> ORGANISM: Artificial Sequence
<220> FEATURE:
<223> OTHER INFORMATION: PCR Primer

<400> SEQUENCE: 125
acctaggacg gtgaccttgg tccc 24

<210> SEQ ID NO 126
<211> LENGTH: 24
<212> TYPE: DNA
<213> ORGANISM: Artificial Sequence
<220> FEATURE:
<223> OTHER INFORMATION: PCR Primer

<400> SEQUENCE: 126
acctaggacg gtcagcttgg tccc 24

<210> SEQ ID NO 127
<211> LENGTH: 24
<212> TYPE: DNA
<213> ORGANISM: Artificial Sequence
<220> FEATURE:
<223> OTHER INFORMATION: PCR Primer

<400> SEQUENCE: 127
acctaaaacg gtgagctggg tccc 24

<210> SEQ ID NO 128
<211> LENGTH: 48
<212> TYPE: DNA
<213> ORGANISM: Artificial Sequence
<220> FEATURE:
<223> OTHER INFORMATION: PCR Primer

<400> SEQUENCE: 128
gagtcattct cgacttgcgg ccgcacctag gacggtgacc ttggtccc 48

<210> SEQ ID NO 129
<211> LENGTH: 48
<212> TYPE: DNA
<213> ORGANISM: Artificial Sequence
<220> FEATURE:
<223> OTHER INFORMATION: PCR Primer

<400> SEQUENCE: 129
gagtcattct cgacttgcgg ccgcacctag gacggtcagc ttggtccc 48

<210> SEQ ID NO 130
<211> LENGTH: 48
<212> TYPE: DNA
<213> ORGANISM: Artificial Sequence
<220> FEATURE:
<223> OTHER INFORMATION: PCR Primer

<400> SEQUENCE: 130
gagtcattct cgacttgcgg ccgcacytaa aacggtgagc tgggtccc 48

<210> SEQ ID NO 131
<211> LENGTH: 27
<212> TYPE: DNA
<213> ORGANISM: Artificial Sequence
<220> FEATURE:
<223> OTHER INFORMATION: PCR Primer

<400> SEQUENCE: 131
tgaagattct gtaggggcca ctgtctt 27

<210> SEQ ID NO 132

```
<211> LENGTH: 57
<212> TYPE: DNA
<213> ORGANISM: Artificial Sequence
<220> FEATURE:
<223> OTHER INFORMATION: PCR Primer

<400> SEQUENCE: 132
gagtcattct cgacttgcgg ccgcttatta tgaagattct gtaggggcca ctgtctt      57

<210> SEQ ID NO 133
<211> LENGTH: 48
<212> TYPE: DNA
<213> ORGANISM: Artificial Sequence
<220> FEATURE:
<223> OTHER INFORMATION: PCR Primer

<400> SEQUENCE: 133
gagtcattct cgacttgcgg ccgctgcaga ttctgtaggg gctgtctt                48

<210> SEQ ID NO 134
<211> LENGTH: 28
<212> TYPE: DNA
<213> ORGANISM: Artificial Sequence
<220> FEATURE:
<223> OTHER INFORMATION: PCR Primer

<400> SEQUENCE: 134
gcaccctggt caccgtctcc tcaggtgg                                      28

<210> SEQ ID NO 135
<211> LENGTH: 28
<212> TYPE: DNA
<213> ORGANISM: Artificial Sequence
<220> FEATURE:
<223> OTHER INFORMATION: PCR Primer

<400> SEQUENCE: 135
ggacaatggt caccgtctct tcaggtgg                                      28

<210> SEQ ID NO 136
<211> LENGTH: 28
<212> TYPE: DNA
<213> ORGANISM: Artificial Sequence
<220> FEATURE:
<223> OTHER INFORMATION: PCR Primer

<400> SEQUENCE: 136
gaaccctggt caccgtctcc tcaggtgg                                      28

<210> SEQ ID NO 137
<211> LENGTH: 28
<212> TYPE: DNA
<213> ORGANISM: Artificial Sequence
<220> FEATURE:
<223> OTHER INFORMATION: PCR Primer

<400> SEQUENCE: 137
ggaccacggt caccgtctcc tcaggtgc                                      28

<210> SEQ ID NO 138
<211> LENGTH: 24
<212> TYPE: DNA
<213> ORGANISM: Artificial Sequence
<220> FEATURE:
<223> OTHER INFORMATION: PCR Primer

<400> SEQUENCE: 138
```
aagcccagca acaccaaggt ggac                                              24

<210> SEQ ID NO 139
<211> LENGTH: 32
<212> TYPE: DNA
<213> ORGANISM: Artificial Sequence
<220> FEATURE:
<223> OTHER INFORMATION: PCR Primer

<400> SEQUENCE: 139
ggagactggg tcatctggat gtccgatccg cc                                     32

<210> SEQ ID NO 140
<211> LENGTH: 32
<212> TYPE: DNA
<213> ORGANISM: Artificial Sequence
<220> FEATURE:
<223> OTHER INFORMATION: PCR Primer

<400> SEQUENCE: 140
ggagactgag tcatcacaac atccgatccg cc                                     32

<210> SEQ ID NO 141
<211> LENGTH: 32
<212> TYPE: DNA
<213> ORGANISM: Artificial Sequence
<220> FEATURE:
<223> OTHER INFORMATION: PCR Primer

<400> SEQUENCE: 141
ggagactgcg tcaacacaat ttccgatccg cc                                     32

<210> SEQ ID NO 142
<211> LENGTH: 32
<212> TYPE: DNA
<213> ORGANISM: Artificial Sequence
<220> FEATURE:
<223> OTHER INFORMATION: PCR Primer

<400> SEQUENCE: 142
ggagactggg tcatcacgat gtccgatccg cc                                     32

<210> SEQ ID NO 143
<211> LENGTH: 32
<212> TYPE: DNA
<213> ORGANISM: Artificial Sequence
<220> FEATURE:
<223> OTHER INFORMATION: PCR Primer

<400> SEQUENCE: 143
ggagactgcg tgagtgtcgt ttccgatccg cc                                     32

<210> SEQ ID NO 144
<211> LENGTH: 32
<212> TYPE: DNA
<213> ORGANISM: Artificial Sequence
<220> FEATURE:
<223> OTHER INFORMATION: PCR Primer

<400> SEQUENCE: 144
ggagactgag tcagcacaat ttccgatccg cc                                     32

<210> SEQ ID NO 145
<211> LENGTH: 35
<212> TYPE: DNA

-continued

<213> ORGANISM: Artificial Sequence
<220> FEATURE:
<223> OTHER INFORMATION: PCR Primer

<400> SEQUENCE: 145
ggagactggg tcatctggat gtcggccatc gctgg      35

<210> SEQ ID NO 146
<211> LENGTH: 35
<212> TYPE: DNA
<213> ORGANISM: Artificial Sequence
<220> FEATURE:
<223> OTHER INFORMATION: PCR Primer

<400> SEQUENCE: 146
ggagactgcg tcatcacaac atcggccatc gctgg      35

<210> SEQ ID NO 147
<211> LENGTH: 35
<212> TYPE: DNA
<213> ORGANISM: Artificial Sequence
<220> FEATURE:
<223> OTHER INFORMATION: PCR Primer

<400> SEQUENCE: 147
ggagactgcg tcaacacaat ttcggccatc gctgg      35

<210> SEQ ID NO 148
<211> LENGTH: 35
<212> TYPE: DNA
<213> ORGANISM: Artificial Sequence
<220> FEATURE:
<223> OTHER INFORMATION: PCR Primer

<400> SEQUENCE: 148
ggagactggg tcatcacgat gtcggccatc gctgg      35

<210> SEQ ID NO 149
<211> LENGTH: 35
<212> TYPE: DNA
<213> ORGANISM: Artificial Sequence
<220> FEATURE:
<223> OTHER INFORMATION: PCR Primer

<400> SEQUENCE: 149
ggagactgcg tgagtgtcgt ttcggccatc gctgg      35

<210> SEQ ID NO 150
<211> LENGTH: 35
<212> TYPE: DNA
<213> ORGANISM: Artificial Sequence
<220> FEATURE:
<223> OTHER INFORMATION: PCR Primer

<400> SEQUENCE: 150
ggagactgcg tcagcacaat ttcggccatc gctgg      35

<210> SEQ ID NO 151
<211> LENGTH: 42
<212> TYPE: DNA
<213> ORGANISM: Artificial Sequence
<220> FEATURE:
<223> OTHER INFORMATION: PCR Primer

<400> SEQUENCE: 151
ggcggctgcg tcaacacaga ctgcgatccg ccaccgccag ag      42

<210> SEQ ID NO 152
<211> LENGTH: 42
<212> TYPE: DNA
<213> ORGANISM: Artificial Sequence
<220> FEATURE:
<223> OTHER INFORMATION: PCR Primer

<400> SEQUENCE: 152
gcaggctgag tcagagcaga ctgcgatccg ccaccgccag ag             42

<210> SEQ ID NO 153
<211> LENGTH: 42
<212> TYPE: DNA
<213> ORGANISM: Artificial Sequence
<220> FEATURE:
<223> OTHER INFORMATION: PCR Primer

<400> SEQUENCE: 153
ggtggctgag tcagcacata ggacgatccg ccaccgccag ag             42

<210> SEQ ID NO 154
<211> LENGTH: 42
<212> TYPE: DNA
<213> ORGANISM: Artificial Sequence
<220> FEATURE:
<223> OTHER INFORMATION: PCR Primer

<400> SEQUENCE: 154
gggtcctgag tcagctcaga agacgatccg ccaccgccag ag             42

<210> SEQ ID NO 155
<211> LENGTH: 42
<212> TYPE: DNA
<213> ORGANISM: Artificial Sequence
<220> FEATURE:
<223> OTHER INFORMATION: PCR Primer

<400> SEQUENCE: 155
ggcggttgag tcagtataac gtgcgatccg ccaccgccag ag             42

<210> SEQ ID NO 156
<211> LENGTH: 42
<212> TYPE: DNA
<213> ORGANISM: Artificial Sequence
<220> FEATURE:
<223> OTHER INFORMATION: PCR Primer

<400> SEQUENCE: 156
gacggctgag tcagcacaga ctgcgatccg ccaccgccag ag             42

<210> SEQ ID NO 157
<211> LENGTH: 42
<212> TYPE: DNA
<213> ORGANISM: Artificial Sequence
<220> FEATURE:
<223> OTHER INFORMATION: PCR Primer

<400> SEQUENCE: 157
tggggctgag tcagcataaa attcgatccg ccaccgccag ag             42

<210> SEQ ID NO 158
<211> LENGTH: 42
<212> TYPE: DNA
<213> ORGANISM: Artificial Sequence
<220> FEATURE:

-continued

<223> OTHER INFORMATION: PCR Primer

<400> SEQUENCE: 158
ggcggctgcg tcaacacaga ctgggccatc gctggttggg ca     42

<210> SEQ ID NO 159
<211> LENGTH: 42
<212> TYPE: DNA
<213> ORGANISM: Artificial Sequence
<220> FEATURE:
<223> OTHER INFORMATION: PCR Primer

<400> SEQUENCE: 159
gcaggctgag tcagagcaga ctgggccatc gctggttggg ca     42

<210> SEQ ID NO 160
<211> LENGTH: 42
<212> TYPE: DNA
<213> ORGANISM: Artificial Sequence
<220> FEATURE:
<223> OTHER INFORMATION: PCR Primer

<400> SEQUENCE: 160
ggtggctgag tcagcacata ggaggccatc gctggttggg ca     42

<210> SEQ ID NO 161
<211> LENGTH: 42
<212> TYPE: DNA
<213> ORGANISM: Artificial Sequence
<220> FEATURE:
<223> OTHER INFORMATION: PCR Primer

<400> SEQUENCE: 161
gggtcctgag tcagctcaga agaggccatc gctggttggg ca     42

<210> SEQ ID NO 162
<211> LENGTH: 42
<212> TYPE: DNA
<213> ORGANISM: Artificial Sequence
<220> FEATURE:
<223> OTHER INFORMATION: PCR Primer

<400> SEQUENCE: 162
ggcggttgag tcagtataac gtgggccatc gctggttggg ca     42

<210> SEQ ID NO 163
<211> LENGTH: 42
<212> TYPE: DNA
<213> ORGANISM: Artificial Sequence
<220> FEATURE:
<223> OTHER INFORMATION: PCR Primer

<400> SEQUENCE: 163
gacggctgag tcagcacaga ctgggccatc gctggttggg ca     42

<210> SEQ ID NO 164
<211> LENGTH: 42
<212> TYPE: DNA
<213> ORGANISM: Artificial Sequence
<220> FEATURE:
<223> OTHER INFORMATION: PCR Primer

<400> SEQUENCE: 164
tggggctgag tcagcataaa attggccatc gctggttggg ca     42

<210> SEQ ID NO 165
<211> LENGTH: 118
<212> TYPE: PRT
<213> ORGANISM: Homo sapiens

<400> SEQUENCE: 165

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Lys Tyr Ala Gln Lys Ile
    50                  55                  60

Gln Gly Arg Val Thr Met Ile Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Val Arg Leu Leu Pro Lys Arg Thr Ala Thr Leu His Tyr Tyr Ile Asp
                100                 105                 110

Val Trp Gly Lys Gly Thr
            115

<210> SEQ ID NO 166
<211> LENGTH: 65
<212> TYPE: PRT
<213> ORGANISM: Homo sapiens

<400> SEQUENCE: 166

Asn Asn Tyr Val Ser Trp Tyr Gln His Leu Pro Gly Thr Ala Pro Asn
1               5                   10                  15

Leu Leu Ile Tyr Asp Asn Asn Lys Arg Pro Ser Gly Ile Pro Asp Arg
                20                  25                  30

Phe Ser Gly Ser Lys Ser Gly Thr Ser Ala Thr Leu Gly Ile Thr Gly
            35                  40                  45

Leu Gln Thr Gly Asp Glu Ala Asp Tyr Tyr Cys Gly Ile Trp Asp Gly
    50                  55                  60

Arg
65

<210> SEQ ID NO 167
<211> LENGTH: 115
<212> TYPE: PRT
<213> ORGANISM: Homo sapiens

<400> SEQUENCE: 167

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Thr Gly Tyr Ser Ser Gly Trp Gly Tyr Phe Asp Tyr Trp Gly
            100                 105                 110

Gln Gly Thr
        115

<210> SEQ ID NO 168
<211> LENGTH: 101
<212> TYPE: PRT
<213> ORGANISM: Homo sapiens

<400> SEQUENCE: 168

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly
            100

<210> SEQ ID NO 169
<211> LENGTH: 100
<212> TYPE: PRT
<213> ORGANISM: Homo sapiens

<400> SEQUENCE: 169

Ser Leu Thr Cys Ser Val Ser Gly Asp Ser Ile Ser Ser Gly Gly Tyr
1               5                   10                  15

Ser Trp Ile Arg Gln Pro Ser Gly Lys Gly Ile Glu Trp Ile Gly Ser
            20                  25                  30

Val His His Ser Gly Pro Thr Tyr Tyr Asn Pro Ser Leu Lys Ser Arg
        35                  40                  45

Val Thr Met Ser Val Asp Thr Ser Lys Asn Gln Phe Ser Leu Lys Ile
    50                  55                  60

Lys Cys Ser Val Thr Ala Ala Asp Thr Ala Met Tyr Phe Cys Ala Arg
65                  70                  75                  80

Glu Gly Gly Ser Thr Trp Arg Ser Leu Tyr Lys His Tyr Tyr Met Asp
                85                  90                  95

Val Trp Gly Lys
            100

<210> SEQ ID NO 170
<211> LENGTH: 111
<212> TYPE: PRT
<213> ORGANISM: Homo sapiens

<400> SEQUENCE: 170

Gln Val Gln Leu Gln Glu Ser Gly Pro Gly Leu Val Lys Pro Ser Glu
1               5                   10                  15

Thr Leu Ser Leu Val Cys Thr Val Ser Gly Gly Ser Leu Ser Phe Ser
            20                  25                  30
```

Tyr Trp Gly Trp Ile Arg Gln Pro Pro Gly Lys Gly Leu Glu Trp Ile
            35                  40                  45

Gly Tyr Ile Ser His Arg Gly Thr Asp Tyr Asn Ser Ser Leu Gln Ser
    50                  55                  60

Arg Val Thr Ile Ser Ala Asp Thr Ser Lys Asn Gln Phe Ser Leu Lys
65                  70                  75                  80

Leu Ser Ser Val Thr Ala Ala Asp Thr Ala Val Tyr Tyr Cys Ala Arg
                85                  90                  95

Ser Phe Ser Asn Ser Phe Phe Phe Gly Tyr Trp Gly Gln Gly Thr
                100                 105                 110

<210> SEQ ID NO 171
<211> LENGTH: 111
<212> TYPE: PRT
<213> ORGANISM: Homo sapiens

<400> SEQUENCE: 171

Gln Val Gln Leu Val Gln Ser Gly Ala Glu Val Lys Lys Pro Gly Gln
1               5                   10                  15

Ser Leu Met Ile Ser Cys Gln Gly Ser Gly Tyr Ser Phe Ser Asn Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu His Trp Ser Ser Leu Lys Ala Ser Asp Thr Ala Leu Tyr Tyr Cys
                85                  90                  95

Ala Arg Leu Val Gly Gly Thr Pro Ala Tyr Trp Gly Gln Gly Thr
                100                 105                 110

<210> SEQ ID NO 172
<211> LENGTH: 88
<212> TYPE: PRT
<213> ORGANISM: Homo sapiens

<400> SEQUENCE: 172

Gln Val Gln Leu Val Gln Ser Gly Ala Glu Val Lys Lys Pro Gly Gln
1               5                   10                  15

Ser Leu Arg Ile Ser Cys Lys Gly Ala Gly Tyr Ser Phe Ser Thr Tyr
                20                  25                  30

Trp Ile Gly Trp Val Arg Gln Met Pro Gly Lys Gly Leu Glu Trp Met
            35                  40                  45

Gly Ile Ile Tyr Pro Asp Asp Ser Asp Thr Arg Tyr Ser Pro Ser Phe
    50                  55                  60

Glu Gly Gln Val Thr Ile Ser Val Asp Lys Ser Ile Thr Thr Ala Tyr
65                  70                  75                  80

Leu Trp Trp Ser Ser Leu Lys Ala
                85

<210> SEQ ID NO 173
<211> LENGTH: 102
<212> TYPE: PRT
<213> ORGANISM: Homo sapiens

<400> SEQUENCE: 173

Glu Ile Val Leu Thr Gln Ser Pro Ser Ser Leu Ser Ala Ser Val Gly

```
                1               5                   10                  15
Asp Arg Val Thr Ile Thr Cys Arg Ala Ser Gln Ser Ile Ser Asn Tyr
                20                  25                  30

Leu Asn Trp Tyr Gln Gln Lys Pro Gly Lys Ala Pro Lys Leu Leu Ile
                35                  40                  45

Tyr Ala Ala Ser Thr Leu Gln Ser Gly Val Pro Ser Arg Phe Ser Gly
                50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Thr Ile Ile Ser Phe Pro
                85                  90                  95

Leu Thr Phe Gly Gly Gly
                100

<210> SEQ ID NO 174
<211> LENGTH: 102
<212> TYPE: PRT
<213> ORGANISM: Homo sapiens

<400> SEQUENCE: 174

Ser Ser Glu Leu Thr Gln Asp Pro Ala Val Ser Val Ala Phe Gly Gln
1               5                   10                  15

Thr Val Arg Ile Thr Cys Gln Gly Asp Ser Leu Arg Ser Ser Tyr Ala
                20                  25                  30

Ser Trp Tyr Gln Gln Lys Pro Gly Gln Ala Pro Leu Leu Val Ile Tyr
                35                  40                  45

Gly Glu Asn Ser Arg Pro Ser Gly Ile Pro Asp Arg Phe Ser Gly Ser
                50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Arg Gly Thr His
                85                  90                  95

Leu Glu Val Phe Gly Gly
                100

<210> SEQ ID NO 175
<211> LENGTH: 103
<212> TYPE: PRT
<213> ORGANISM: Homo sapiens

<400> SEQUENCE: 175

His Val Ile Leu Thr Gln Pro Ala Ser Val Ser Gly Ser Pro Gly Gln
1               5                   10                  15

Ser Ile Thr Ile Ser Cys Thr Gly Ser Ser Arg Asp Val Gly Gly Tyr
                20                  25                  30

Asn Tyr Val Ser Trp Tyr Gln His His Pro Gly Lys Ala Pro Lys Leu
                35                  40                  45

Leu Ile Ser Glu Val Thr Asn Arg Pro Ser Gly Val Ser Asn Arg Phe
                50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ala Ser Tyr Thr Ser Ser
                85                  90                  95

Lys Thr Tyr Val Phe Gly Gly
                100
```

<210> SEQ ID NO 176
<211> LENGTH: 94
<212> TYPE: PRT
<213> ORGANISM: Homo sapiens

<400> SEQUENCE: 176

```
Gln Ser Ala Leu Thr Gln Pro Ala Ser Val Ser Gly Ser Pro Gly Gln
1               5                   10                  15

Ser Ile Thr Ile Ser Cys Ser Gly Ser Ser Ser Asp Ile Gly Arg Tyr
            20                  25                  30

Asp Tyr Val Ser Trp Tyr Gln His Tyr Pro Asp Lys Ala Pro Lys Leu
        35                  40                  45

Leu Ile Tyr Glu Val Val His Arg Pro Ser Gly Ile Ser His Arg Phe
    50                  55                  60

Ser Ala Ser Lys Ser Gly Asn Thr Ala Ser Leu Thr Ile Ser Glu Leu
65                  70                  75                  80

Gln Pro Gly Asp Glu Ala Asp Tyr Tyr Cys Ala Ser Tyr Thr
                85                  90
```

<210> SEQ ID NO 177
<211> LENGTH: 69
<212> TYPE: DNA
<213> ORGANISM: Artificial Sequence
<220> FEATURE:
<223> OTHER INFORMATION: oligonucleotide for mutagenesis

<400> SEQUENCE: 177
acaactttca acagttgagg agacggtgac cgtaagcttc tgcagttgga cctgagcgga        60
gtgagaata                                                               69

<210> SEQ ID NO 178
<211> LENGTH: 51
<212> TYPE: DNA
<213> ORGANISM: Artificial Sequence
<220> FEATURE:
<223> OTHER INFORMATION: oligonucleotide for mutagenesis

<400> SEQUENCE: 178
acaactttca acagtttccc gtttgatctc gagctcctgc agttggacct g                 51

<210> SEQ ID NO 179
<211> LENGTH: 21
<212> TYPE: DNA
<213> ORGANISM: Artificial Sequence
<220> FEATURE:
<223> OTHER INFORMATION: sequencing primer

<400> SEQUENCE: 179
gtcgtctttc cagacgttag t                                                  21

<210> SEQ ID NO 180
<211> LENGTH: 26
<212> TYPE: DNA
<213> ORGANISM: Bacteriophage fd

<400> SEQUENCE: 180
tctcactccg ctgaaactgt tgaaag                                             26

<210> SEQ ID NO 181
<211> LENGTH: 62
<212> TYPE: DNA
<213> ORGANISM: Artificial Sequence
<220> FEATURE:

<223> OTHER INFORMATION: engineered insertion site for VH

<400> SEQUENCE: 181

```
tctcactccg ctcaggtcca actgcagaag cttacggtca ccgtctcctc aactgttgaa    60
ag                                                                    62
```

<210> SEQ ID NO 182
<211> LENGTH: 59
<212> TYPE: DNA
<213> ORGANISM: Artificial Sequence
<220> FEATURE:
<223> OTHER INFORMATION: engineered insertion site for Fv

<400> SEQUENCE: 182

```
tctcactccg ctcaggtcca actgcaggag ctcgagatca acgggaaac tgttgaaag      59
```

<210> SEQ ID NO 183
<211> LENGTH: 272
<212> TYPE: PRT
<213> ORGANISM: Artificial Sequence
<220> FEATURE:
<223> OTHER INFORMATION: scFv of genetically engineered anti-hen
      egg-white lysozyme (HEL) monoclonal antibody D1.3

<400> SEQUENCE: 183

```
Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Ser Gly Pro Gly
                20                  25                  30

Leu Val Ala Pro Ser Gln Ser Leu Ser Ile Thr Cys Thr Val Ser Gly
            35                  40                  45

Phe Ser Leu Thr Gly Tyr Gly Val Asn Trp Val Arg Gln Pro Pro Gly
        50                  55                  60

Lys Gly Leu Glu Trp Leu Gly Met Ile Trp Gly Asp Gly Asn Thr Asp
65                  70                  75                  80

Tyr Asn Ser Ala Leu Lys Ser Arg Leu Ser Ile Ser Lys Asp Asn Ser
                85                  90                  95

Lys Ser Gln Val Phe Leu Lys Met Asn Ser Leu His Thr Asp Asp Thr
            100                 105                 110

Ala Arg Tyr Tyr Cys Ala Arg Glu Arg Asp Tyr Arg Leu Asp Tyr Trp
        115                 120                 125

Gly Gln Gly Thr Thr Val Thr Val Ser Ser Gly Gly Gly Gly Ser Gly
    130                 135                 140

Gly Gly Gly Ser Gly Gly Gly Ser Asp Ile Glu Leu Thr Gln Ser
145                 150                 155                 160

Pro Ala Ser Leu Ser Ala Ser Val Gly Glu Thr Val Thr Ile Thr Cys
                165                 170                 175

Arg Ala Ser Gly Asn Ile His Asn Tyr Leu Ala Trp Tyr Gln Gln Lys
            180                 185                 190

Gln Gly Lys Ser Pro Gln Leu Leu Val Tyr Tyr Thr Thr Thr Leu Ala
        195                 200                 205

Asp Gly Val Pro Ser Arg Phe Ser Gly Ser Gly Ser Gly Thr Gln Tyr
    210                 215                 220

Ser Leu Lys Ile Asn Ser Leu Gln Pro Glu Asp Phe Gly Ser Tyr Tyr
225                 230                 235                 240

Cys Gln His Phe Trp Ser Thr Pro Arg Thr Phe Gly Gly Gly Thr Lys
                245                 250                 255
```

Leu Glu Ile Lys Arg Glu Gln Lys Leu Ile Ser Glu Glu Asp Leu Asn
            260                 265                 270

<210> SEQ ID NO 184
<211> LENGTH: 889
<212> TYPE: DNA
<213> ORGANISM: Artificial Sequence
<220> FEATURE:
<223> OTHER INFORMATION: nucleotide sequence encoding scFv of
      genetically engineered anti-hen egg-white lysozyme (HEL)
      monoclonal antibody D1.3 and surrounding sequence

<400> SEQUENCE: 184
gcatgcaaat tctatttcaa ggagacagtc ataatgaaat acctattgcc tacggcagcc      60
gctggattgt tattactcgc tgcccaacca gcgatggccc aggtgcagct gcaggagtca     120
ggacctggcc tggtggcgcc ctcacagagc ctgtccatca catgcaccgt ctcaggttc      180 tcattaaccg ctatggtgt aaactgggtt cgccagcctc caggaaaggg tctggagtgg     240
ctgggaatga tttggggtga tggaaacaca gactataatt cagctctcaa atccagactg     300
agcatcagca aggacaactc caagagccaa gttttcttaa aaatgaacag tctgcacact     360
gatgacacag ccaggtacta ctgtgccaga gagagagatt ataggcttga ctactggggc     420
caaggcacca cggtcaccgt ctcctcaggt ggaggcggtt caggcggagg tggctctggc     480
ggtggcggat cggacatcga gctcactcag tctccagcct cccttctctgc gtctgtggga     540 gaaactgtca ccatcacatg tcgagcaagt gggaatattc acaattattt agcatggtat     600
cagcagaaac agggaaaatc tcctcagctc ctggtctatt atacaacaac cttagcagat     660
ggtgtgccat caaggttcag tggcagtgga tcaggaacac aatattctct caagatcaac     720
agcctgcaac tgaagatttt gggagttat tactgtcaac attttggag tactcctcgg     780 acgttcggtg agggaccaa gctcgagatc aaacgggaac aaaaactcat ctcagaagag     840
gatctgaatt aataatgatc aaacggtaat aaggatccag ctcgaattc                 889

<210> SEQ ID NO 185
<211> LENGTH: 20
<212> TYPE: PRT
<213> ORGANISM: Artificial Sequence
<220> FEATURE:
<223> OTHER INFORMATION: amino acids encoded by the nucleotide sequence
      around the cloning site in gene III of fd-CAT2

<400> SEQUENCE: 185

His Ser Ala Gln Val Gln Leu Gln Glu Leu Glu Ile Lys Arg Ala Ala
1               5                   10                  15

Ala Glu Thr Val
            20

<210> SEQ ID NO 186
<211> LENGTH: 60
<212> TYPE: DNA
<213> ORGANISM: Artificial Sequence
<220> FEATURE:
<223> OTHER INFORMATION: nucleotide sequence around the cloning site in
      gene III of fd-CAT2

<400> SEQUENCE: 186
cacagtgcac aggtccaact gcaggagctc gagatcaaac gggcggccgc agaaactgtt      60

<210> SEQ ID NO 187
<211> LENGTH: 241
<212> TYPE: PRT

<213> ORGANISM: Artificial Sequence
<220> FEATURE:
<223> OTHER INFORMATION: VH of Fab D1.3 from genetically engineered
      anti-hen egg-white lysozyme (HEL) monoclonal antibody

<400> SEQUENCE: 187

```
Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Ser Gly Pro Gly
            20                  25                  30

Leu Val Ala Pro Ser Gln Ser Leu Ser Ile Thr Cys Thr Val Ser Gly
        35                  40                  45

Phe Ser Leu Thr Gly Tyr Gly Val Asn Trp Val Arg Gln Pro Pro Gly
    50                  55                  60

Lys Gly Leu Glu Trp Leu Gly Met Ile Trp Gly Asp Gly Asn Thr Asp
65                  70                  75                  80

Tyr Asn Ser Ala Leu Lys Ser Arg Leu Ser Ile Ser Lys Asp Asn Ser
                85                  90                  95

Lys Ser Gln Val Phe Leu Lys Met Asn Ser Leu His Thr Asp Asp Thr
            100                 105                 110

Ala Arg Tyr Tyr Cys Ala Arg Glu Arg Asp Tyr Arg Leu Asp Tyr Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Ser
```

<210> SEQ ID NO 188
<211> LENGTH: 236
<212> TYPE: PRT
<213> ORGANISM: Artificial Sequence
<220> FEATURE:
<223> OTHER INFORMATION: VL of Fab D1.3 from genetically engineered
      anti-hen egg-white lysozyme (HEL) monoclonal antibody

<400> SEQUENCE: 188

```
Met Lys Tyr Leu Leu Pro Thr Ala Ala Ala Gly Leu Leu Leu Leu Ala
1               5                   10                  15

Ala Gln Pro Ala Met Ala Asp Ile Glu Leu Thr Gln Ser Pro Ala Ser
            20                  25                  30

Leu Ser Ala Ser Val Gly Glu Thr Val Thr Ile Thr Cys Arg Ala Ser
        35                  40                  45

Gly Asn Ile His Asn Tyr Leu Ala Trp Tyr Gln Gln Lys Gln Gly Lys
    50                  55                  60

Ser Pro Gln Leu Leu Val Tyr Tyr Thr Thr Thr Leu Ala Asp Gly Val
65                  70                  75                  80
```

```
Pro Ser Arg Phe Ser Gly Ser Gly Ser Gly Thr Gln Tyr Ser Leu Lys
            85                  90                  95

Ile Asn Ser Leu Gln Pro Glu Asp Phe Gly Ser Tyr Tyr Cys Gln His
            100                 105                 110

Phe Trp Ser Thr Pro Arg Thr Phe Gly Gly Gly Thr Lys Leu Glu Ile
            115                 120                 125

Lys Arg Thr Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Ser
225                 230                 235

<210> SEQ ID NO 189
<211> LENGTH: 1526
<212> TYPE: DNA
<213> ORGANISM: Artificial Sequence
<220> FEATURE:
<223> OTHER INFORMATION: nucleotide sequence of Fab D1.3 from
      genetically engineered anti-hen egg-white lysozyme (HEL)
      monoclonal antibody

<400> SEQUENCE: 189
gcatgcaaat tctatttcaa ggagacagtc ataatgaaat acctattgcc tacggcagcc      60
gctggattgt tattactcgc tgcccaacca gcgatggccc aggtgcagct gcaggagtca     120
ggacctggcc tggtggcgcc ctcacagagc ctgtccatca catgcaccgt ctcaggttc      180 tcattaaccg gctatggtgt aaactgggtt cgccagcctc aggaaaggg tctggagtgg     240 ctgggaatga tttgggggtga tggaaacaca gactataatt cagctctcaa atccagactg    300
agcatcagca aggacaactc caagagccaa gttttcttaa aaatgaacag tctgcacact    360
gatgacacag ccaggtacta ctgtgccaga gagagagatt ataggcttga ctactggggc    420
caaggcacca cggtcaccgt ctcctcagcc tccaccaagg gcccatcggt cttcccctg     480 gcaccctcct ccaagagcac ctctgggggc acagcggccc tgggctgcct ggtcaaggac    540
tacttccccg aaccggtgac ggtgtcgtgg aactcaggcg ccctgaccag cggcgtgcac    600 accttccgg ctgtcctaca gtcctcagga ctctactccc tcagcagcgt ggtgaccgtg    660
ccctccagca gcttgggcac ccagacctac atctgcaacg tgaatcacaa gcccagcaac    720
accaaggtcg acaagaaagt tgagcccaaa tcttcataat aacccgggag cttgcatgca    780
aattctattt caaggagaca gtcataatga aatacctatt gcctacggca gccgctggat    840
tgttattact cgctgcccaa ccagcgatgg ccgacatcga gctcacccag tctccagcct    900
ccctttctgc gtctgtggga gaaactgtca ccatcacatg tcgagcaagt gggaatattc    960
acaattattt agcatggtat cagcagaaac agggaaaatc tcctcagctc ctggtctatt   1020
atacaacaac cttagcagat ggtgtgccat caaggttcag tggcagtgga tcaggaacac   1080
```

-continued

```
aatattctct caagatcaac agcctgcagc ctgaagattt tgggagttat tactgtcaac    1140 attttggag tactcctcgg acgttcggtg gaggcaccaa gctcgagatc aaacggactg    1200
tggctgcacc atctgtcttc atcttcccgc catctgatga gcagttgaaa tctggaactg    1260
cctctgttgt gtgcctgctg aataacttct atcccagaga ggccaaagta cagtggaagg    1320
tggataacgc cctccaatcg ggtaactccc aggagagtgt cacagagcag gacagcaagg    1380
acagcaccta cagcctcagc agcaccctga cgctgagcaa agcagactac gagaaacaca    1440
aagtctacgc ctgcgaagtc acccatcagg gcctgagctc gcccgtcaca aagagcttca    1500
accgcggaga gtcatagtaa gaattc                                         1526
```

<210> SEQ ID NO 190
<211> LENGTH: 249
<212> TYPE: PRT
<213> ORGANISM: Artificial Sequence
<220> FEATURE:
<223> OTHER INFORMATION: scFv form of the anti-oxazalone antibody NQ11

<400> SEQUENCE: 190

```
Gln Val Gln Leu Gln Glu Ser Gly Gly Gly Leu Val Gln Pro Gly Gly
1               5                   10                  15

Ser Leu Arg Leu Ser Cys Ala Thr Ser Gly Phe Thr Phe Ser Asn Tyr
            20                  25                  30

Tyr Met Gly Trp Val Arg Gln Pro Gly Lys Ala Leu Glu Trp Leu
        35                  40                  45

Gly Ser Val Arg Asn Lys Val Asn Gly Tyr Thr Thr Glu Tyr Ser Ala
    50                  55                  60

Ser Val Lys Gly Arg Phe Thr Ile Ser Arg Asp Asn Phe Gln Ser Ile
65                  70                  75                  80

Leu Tyr Leu Gln Ile Asn Thr Leu Arg Thr Glu Asp Ser Ala Thr Tyr
                85                  90                  95

Tyr Cys Ala Arg Gly Tyr Asp Tyr Gly Ala Trp Phe Ala Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Asp Ile Glu Leu Thr Gln Thr Pro
    130                 135                 140

Leu Ser Leu Pro Val Ser Leu Gly Asp Gln Ala Ser Ile Ser Cys Arg
145                 150                 155                 160

Ser Ser Gln Ser Ile Val His Ser Asn Gly Asn Thr Tyr Leu Glu Trp
                165                 170                 175

Tyr Leu Gln Lys Pro Gly Gln Ser Pro Lys Leu Leu Ile Tyr Lys Val
            180                 185                 190

Ser Asn Arg Phe Ser Gly Val Pro Asp Arg Phe Ser Gly Ser Gly Ser
        195                 200                 205

Gly Thr Asp Phe Thr Leu Lys Ile Ser Arg Val Glu Ala Glu Asp Leu
    210                 215                 220

Gly Val Tyr Tyr Cys Phe Gln Gly Ser His Val Pro Tyr Thr Phe Gly
225                 230                 235                 240

Gly Gly Thr Lys Leu Glu Ile Lys Arg
                245
```

<210> SEQ ID NO 191
<211> LENGTH: 747
<212> TYPE: DNA
<213> ORGANISM: Artificial Sequence

```
<220> FEATURE:
<223> OTHER INFORMATION: nucleotide sequence encoding scFv form of the
      anti-oxazalone antibody NQ11

<400> SEQUENCE: 191
caggtgcagc tgcaggagtc aggaggaggc ttggtacagc ctgggggttc tctgagactc      60
tcctgtgcaa cttctgggtt caccttcagt aattactaca tgggctgggt ccgccagcct     120
ccaggaaagg cacttgagtg gttgggttct gttagaaaca agttaatgg ttacacaaca      180 gagtacagtg catctgtgaa ggggcggttc accatctcca gagataattt ccaaagcatc     240
ctctatcttc aaataaacac cctgagaact gaggacagtg ccacttatta ctgtgcaaga     300
ggctatgatt acggggcctg gtttgcttac tggggccaag gaccctggt caccgtctcc      360 tcaggtggag gcggttcagg cggaggtggc tctggcggtg gcggatcgga catcgagctc     420
acccaaactc cactctccct gcctgtcagt cttggagatc aagcctccat ctcttgcaga     480
tctagtcaga gcattgtaca tagtaatgga aacacctatt tagaatggta cctgcagaaa     540
ccaggccagt ctccaaagct cctgatctac aaagtttcca accgattttc tggggtccca    600
gacaggttca gtggcagtgg atcggggaca gatttcacac tcaagatcag cagagtggag    660
gctgaggatc tgggagttta ttactgcttt caaggttcac atgttccgta cacgttcgga    720
ggggggacca agctcgagat caaacgg                                         747

<210> SEQ ID NO 192
<211> LENGTH: 8
<212> TYPE: PRT
<213> ORGANISM: Artificial Sequence
<220> FEATURE:
<223> OTHER INFORMATION: amino terminus of phoAla 166

<400> SEQUENCE: 192

Arg Thr Pro Glu Met Pro Val Leu
1               5

<210> SEQ ID NO 193
<211> LENGTH: 48
<212> TYPE: DNA
<213> ORGANISM: Artificial Sequence
<220> FEATURE:
<223> OTHER INFORMATION: 5' insertion site of phoAla 166 in frame to
      geneIII

<400> SEQUENCE: 193
tctcacagtg cacaaactgt tgaacggaca ccagaaatgc ctgttctg                   48

<210> SEQ ID NO 194
<211> LENGTH: 7
<212> TYPE: PRT
<213> ORGANISM: Artificial Sequence
<220> FEATURE:
<223> OTHER INFORMATION: carboxy terminus of phoAla 166

<400> SEQUENCE: 194

Lys Ala Ala Leu Gly Leu Lys
1               5

<210> SEQ ID NO 195
<211> LENGTH: 45
<212> TYPE: DNA
<213> ORGANISM: Artificial Sequence
<220> FEATURE:
<223> OTHER INFORMATION: 3' insertion site of phoAla 166 in frame to
      geneIII
```

```
<400> SEQUENCE: 195
aaagccgctc tggggctgaa agcggccgca gaaactgttg aaagt                45

<210> SEQ ID NO 196
<211> LENGTH: 6
<212> TYPE: PRT
<213> ORGANISM: Artificial Sequence
<220> FEATURE:
<223> OTHER INFORMATION: amino terminus of scFv PCR product

<400> SEQUENCE: 196

Gln Val Gln Leu Gln Glu
1               5

<210> SEQ ID NO 197
<211> LENGTH: 6
<212> TYPE: PRT
<213> ORGANISM: Artificial Sequence
<220> FEATURE:
<223> OTHER INFORMATION: carboxy terminus of scFv PCR product

<400> SEQUENCE: 197

Lys Leu Glu Ile Lys Arg
1               5

<210> SEQ ID NO 198
<211> LENGTH: 33
<212> TYPE: DNA
<213> ORGANISM: Artificial Sequence
<220> FEATURE:
<223> OTHER INFORMATION: 5' end of scFv PCR product

<400> SEQUENCE: 198
tttaatgagg atccacaggt gcagctgcaa gag                              33

<210> SEQ ID NO 199
<211> LENGTH: 27
<212> TYPE: DNA
<213> ORGANISM: Artificial Sequence
<220> FEATURE:
<223> OTHER INFORMATION: 3' end of scFv PCR product

<400> SEQUENCE: 199
aagcttgaga tcaaacggga tccattc                                     27

<210> SEQ ID NO 200
<211> LENGTH: 15
<212> TYPE: DNA
<213> ORGANISM: Artificial Sequence
<220> FEATURE:
<223> OTHER INFORMATION: site in geneIII for introduction of BamHI site
      via olgio G3 Bamlink

<400> SEQUENCE: 200
gagggtggtg gctct                                                  15

<210> SEQ ID NO 201
<211> LENGTH: 15
<212> TYPE: DNA
<213> ORGANISM: Artificial Sequence
<220> FEATURE:
<223> OTHER INFORMATION: site in geneIII for introduction of BamHI site
      via olgio G3 Bamlink

<400> SEQUENCE: 201
```
gagggtggcg gctct 15

<210> SEQ ID NO 202
<211> LENGTH: 15
<212> TYPE: DNA
<213> ORGANISM: Artificial Sequence
<220> FEATURE:
<223> OTHER INFORMATION: site in geneIII for introduction of BamHI site
via olgio G3 Bamlink

<400> SEQUENCE: 202
gagggtggcg gctct 15

<210> SEQ ID NO 203
<211> LENGTH: 15
<212> TYPE: DNA
<213> ORGANISM: Artificial Sequence
<220> FEATURE:
<223> OTHER INFORMATION: site in geneIII for introduction of BamHI site
via olgio G3 Bamlink

<400> SEQUENCE: 203
gagggtggcg gcact 15

<210> SEQ ID NO 204
<211> LENGTH: 15
<212> TYPE: DNA
<213> ORGANISM: Artificial Sequence
<220> FEATURE:
<223> OTHER INFORMATION: site in geneIII for introduction of BamHI site
via olgio G3 Bamlink

<400> SEQUENCE: 204
gagggcggcg gctct 15

<210> SEQ ID NO 205
<211> LENGTH: 15
<212> TYPE: DNA
<213> ORGANISM: Artificial Sequence
<220> FEATURE:
<223> OTHER INFORMATION: site in geneIII for introduction of BamHI site
via olgio G3 Bamlink

<400> SEQUENCE: 205
gagggtggtg gttct 15

<210> SEQ ID NO 206
<211> LENGTH: 15
<212> TYPE: DNA
<213> ORGANISM: Artificial Sequence
<220> FEATURE:
<223> OTHER INFORMATION: site in geneIII for introduction of BamHI site
via olgio G3 Bamlink

<400> SEQUENCE: 206
gagggcggcg gctct 15

<210> SEQ ID NO 207
<211> LENGTH: 15
<212> TYPE: DNA
<213> ORGANISM: Artificial Sequence
<220> FEATURE:
<223> OTHER INFORMATION: site in geneIII for introduction of BamHI site
via olgio G3 Bamlink

<400> SEQUENCE: 207
gagggcggcg gctct 15

<210> SEQ ID NO 208
<211> LENGTH: 15
<212> TYPE: DNA
<213> ORGANISM: Artificial Sequence
<220> FEATURE:
<223> OTHER INFORMATION: site in geneIII for introduction of BamHI site
      via olgio G3 Bamlink

<400> SEQUENCE: 208
gagggcggcg gttct                                                  15

<210> SEQ ID NO 209
<211> LENGTH: 15
<212> TYPE: DNA
<213> ORGANISM: Artificial Sequence
<220> FEATURE:
<223> OTHER INFORMATION: site in geneIII for introduction of BamHI site
      via olgio G3 Bamlink

<400> SEQUENCE: 209
gagggcggcg gctct                                                  15

<210> SEQ ID NO 210
<211> LENGTH: 15
<212> TYPE: DNA
<213> ORGANISM: Artificial Sequence
<220> FEATURE:
<223> OTHER INFORMATION: site in geneIII for introduction of BamHI site
      via olgio G3 Bamlink

<400> SEQUENCE: 210
gagggcggcg gttct                                                  15

<210> SEQ ID NO 211
<211> LENGTH: 15
<212> TYPE: DNA
<213> ORGANISM: Artificial Sequence
<220> FEATURE:
<223> OTHER INFORMATION: site in geneIII for introduction of BamHI site
      via olgio G3 Bamlink

<400> SEQUENCE: 211
gagggcggcg gctct                                                  15

<210> SEQ ID NO 212
<211> LENGTH: 15
<212> TYPE: DNA
<213> ORGANISM: Artificial Sequence
<220> FEATURE:
<223> OTHER INFORMATION: site in geneIII for introduction of BamHI site
      via olgio G3 Bamlink

<400> SEQUENCE: 212
gagggtggcg gatcc                                                  15

<210> SEQ ID NO 213
<211> LENGTH: 11
<212> TYPE: DNA
<213> ORGANISM: Artificial Sequence
<220> FEATURE:
<223> OTHER INFORMATION: site in geneIII for introduction of BamHI site
      via olgio G3 Bamlink

<400> SEQUENCE: 213
gagggtggcg g                                                      11

```
<210> SEQ ID NO 214
<211> LENGTH: 114
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 214
```

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Asn Arg Tyr Gly Ala Tyr Trp Gly Gln Gly Thr Thr Val Thr Val
            100                 105                 110

Ser Ser

```
<210> SEQ ID NO 215
<211> LENGTH: 114
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 215
```

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Arg Asp
            20                  25                  30

Trp Met His Trp Leu Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Tyr Gly Leu Tyr Trp Gly Gln Gly Thr Thr Val Thr Val
            100                 105                 110

Ser Ser

```
<210> SEQ ID NO 216
<211> LENGTH: 115
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 216
```

-continued

```
Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Asp Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Ile Tyr Arg Ser Phe Pro Tyr Trp Gly Gln Gly Thr Thr Val Thr
            100                 105                 110

Val Ser Ser
        115
```

<210> SEQ ID NO 217
<211> LENGTH: 116
<212> TYPE: PRT
<213> ORGANISM: Artificial Sequence
<220> FEATURE:
<223> OTHER INFORMATION: VH of scFv from mouse immunized with
    2-phenyl-5-oxazolone

<400> SEQUENCE: 217

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile Asn Pro Tyr Asn Gly Asp Thr Phe Tyr Asn Gln Lys Phe
    50                  55                  60

Lys Asp Lys Ala Thr Leu Thr Val Asp Lys Ser Ser Ser Thr Ala His
65                  70                  75                  80

Met Glu Leu Leu Ser Leu Thr Ser Glu Asp Ser Ala Val Tyr Tyr Cys
                85                  90                  95

Val Gly Ile Thr Thr Arg Phe Ala Tyr Trp Gly Gln Gly Thr Thr Val
            100                 105                 110

Thr Val Ser Ser
        115
```

<210> SEQ ID NO 218
<211> LENGTH: 113
<212> TYPE: PRT
<213> ORGANISM: Artificial Sequence
<220> FEATURE:
<223> OTHER INFORMATION: VH of scFv from mouse immunized with
    2-phenyl-5-oxazolone

<400> SEQUENCE: 218

```
Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45
```

-continued

Gly Val Ile Trp Ala Gly Gly Ser Thr Asn Tyr Asn Ser Ala Leu Met
            50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Thr Ala Met Tyr Tyr Cys Ala
                85                  90                  95

Arg Asp Arg Gly Asp Tyr Trp Gly Gln Gly Thr Thr Val Thr Val Ser
            100                 105                 110

Ser

<210> SEQ ID NO 219
<211> LENGTH: 114
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 219

Gln Val Lys Leu Gln Gln Ser Gly Pro Glu Leu Ala Lys Pro Gly Ala
1               5                   10                  15

Ser Val Lys Met Ser Cys Lys Ala Ser Gly Tyr Thr Phe Thr Ser Tyr
                20                  25                  30

Leu Met His Trp Val Lys Gln Arg Pro Gly Gln Gly Leu Lys Trp Ile
            35                  40                  45

Gly Tyr Ile Asn Pro Ser Thr Gly Tyr Thr Glu Tyr Asn Gln Lys Phe
        50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Asp Tyr Gly Tyr Tyr Trp Gly Gln Gly Thr Thr Val Thr Val
            100                 105                 110

Ser Ser

<210> SEQ ID NO 220
<211> LENGTH: 114
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 220

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Arg Tyr
                20                  25                  30

Leu Met His Trp Val Lys Gln Arg Pro Gly Gln Gly Leu Glu Trp Ile
            35                  40                  45

Gly Tyr Ile Asn Pro Ser Thr Gly Tyr Thr Glu Tyr Asn Gln Lys Phe
        50                  55                  60

Lys Asp Glu Ala Thr Leu Thr Ala Asp Lys Ser Ser Asn Thr Ala Tyr
 65                  70                  75                  80

Met Gln Leu Ser Ser Leu Thr Ser Glu Asp Ser Ala Val Tyr Tyr Cys
                85                  90                  95

Ala Arg Asp Tyr Gly Tyr Tyr Trp Gly Gln Gly Thr Thr Val Thr Val
            100                 105                 110

Ser Ser

<210> SEQ ID NO 221
<211> LENGTH: 114
<212> TYPE: PRT
<213> ORGANISM: Artificial Sequence
<220> FEATURE:
<223> OTHER INFORMATION: VH of scFv from mouse immunized with
    2-phenyl-5-oxazolone

<400> SEQUENCE: 221

Gln Val Gln Leu Gln Gln Ser Gly Pro Glu Leu His Lys Pro Gly Ala
1               5                   10                  15

Ser Val Lys Ile Ser Cys Lys Ala Ser Gly Tyr Ser Phe Ser Arg Asn
            20                  25                  30

Tyr Met His Trp Val Lys Gln Ser His Gly Lys Ser Leu Glu Trp Ile
        35                  40                  45

Gly Tyr Ile Ala Pro Phe Asn Gly Gly Thr Thr Tyr Asn Gln Lys Phe
    50                  55                  60

Lys Asp Lys Ala Thr Leu Thr Val Asp Arg Ser Ser Thr Ala Tyr
65                  70                  75                  80

Met His Leu Ser Ser Leu Thr Ser Glu Asp Ser Ala Val Tyr Tyr Cys
                85                  90                  95

Ala Thr Asp Tyr Gly Arg Asp Trp Gly Gln Gly Thr Thr Val Thr Val
            100                 105                 110

Ser Ser

<210> SEQ ID NO 222
<211> LENGTH: 114
<212> TYPE: PRT
<213> ORGANISM: Artificial Sequence
<220> FEATURE:
<223> OTHER INFORMATION: VH of scFv from mouse immunized with
    2-phenyl-5-oxazolone

<400> SEQUENCE: 222

Gln Val Lys Leu Gln Gln Ser Gly Pro Glu Leu Ala Arg Pro Gly Val
1               5                   10                  15

Ser Val Lys Met Ser Cys Lys Ala Ser Gly Tyr Thr Phe Thr Ser Tyr
            20                  25                  30

Ala Met His Trp Val Lys Gln Ser Gln Ser Lys Ser Leu Glu Trp Ile
        35                  40                  45

Gly Val Ile Ser Thr Tyr Asn Gly Asn Thr Asn Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Asp Tyr Gly Asp Tyr Trp Gly Gln Gly Thr Thr Val Thr Val
            100                 105                 110

Ser Ser

<210> SEQ ID NO 223
<211> LENGTH: 114
<212> TYPE: PRT
<213> ORGANISM: Artificial Sequence
<220> FEATURE:
<223> OTHER INFORMATION: VH of scFv from mouse immunized with
    2-phenyl-5-oxazolone

<400> SEQUENCE: 223

```
Gln Val Lys Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Arg Gly Ala Tyr Trp Gly Gln Gly Thr Thr Val Thr Val
            100                 105                 110

Ser Ser
```

<210> SEQ ID NO 224
<211> LENGTH: 114
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 224

```
Gln Val Lys Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Arg Asp
            20                  25                  30

Trp Met His Trp Val Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Tyr Gly Leu Tyr Trp Gly Gln Gly Thr Thr Val Thr Val
            100                 105                 110

Ser Ser
```

<210> SEQ ID NO 225
<211> LENGTH: 114
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 225

```
Gln Val Gln Leu Gln Gln Ser Gly Leu Glu Leu Ala Lys Pro Gly Ala
1               5                   10                  15

Ser Val Lys Met Ser Cys Lys Ala Ser Gly Tyr Thr Phe Thr Asn Tyr
            20                  25                  30

Leu Met His Trp Val Lys Gln Arg Pro Gly Gln Gly Leu Glu Trp Ile
        35                  40                  45
```

Gly Tyr Ile Asn Pro Ser Thr Gly Tyr Thr Glu Tyr Asn Gln Lys Phe
            50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asp Tyr Gly Tyr Tyr Trp Gly Gln Gly Thr Thr Val Thr Val
            100                 105                 110

Ser Ser

<210> SEQ ID NO 226
<211> LENGTH: 114
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 226

Gln Val Lys Leu Gln Gln Ser Gly Ala Glu Leu Ala Lys Pro Gly Ala
 1               5                  10                  15

Ser Val Lys Met Ser Cys Lys Ala Ser Gly Tyr Thr Phe Thr Asn Tyr
                 20                  25                  30

Trp Met His Trp Val Lys Gln Arg Pro Gly Gln Gly Leu Glu Trp Ile
             35                  40                  45

Gly Tyr Ile Asn Pro Ser Thr Gly Tyr Thr Glu Tyr Asn Gln Lys Phe
            50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Asp Asp Ser Ala Val Tyr Tyr Cys
                 85                  90                  95

Ala Arg Asp Tyr Gly Tyr Phe Trp Gly Gln Gly Thr Thr Val Thr Val
            100                 105                 110

Ser Ser

<210> SEQ ID NO 227
<211> LENGTH: 114
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 227

Gln Val Gln Leu Gln Gln Ser Gly Ala Glu Leu Val Lys Pro Gly Ala
 1               5                  10                  15

Ser Val Lys Leu Ser Cys Lys Thr Ser Gly Tyr Thr Phe Thr Ser Tyr
                 20                  25                  30

Thr Met His Trp Val Lys Gln Arg Pro Gly Gln Gly Leu Glu Trp Ile
             35                  40                  45

Gly Tyr Ile Asn Pro Ser Ser Gly Tyr Thr Asn Tyr Asn Gln Lys Phe
            50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asp Tyr Gly Tyr Tyr Trp Gly Gln Gly Thr Thr Val Thr Val

-continued

```
                100                 105                 110
Ser Ser

<210> SEQ ID NO 228
<211> LENGTH: 114
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 228

Gln Val Gln Leu Gln Gln Ser Gly Ala Glu Leu Ala Lys Pro Gly Ala
1               5                   10                  15

Ser Val Lys Met Ser Cys Glu Ala Ser Gly Tyr Thr Phe Thr Ser His
            20                  25                  30

Leu Met His Trp Val Lys Gln Arg Pro Gly Gln Gly Leu Glu Trp Ile
        35                  40                  45

Gly Tyr Ile Asn Pro Arg Thr Gly Tyr Thr Glu Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Tyr Gly Ala Tyr Trp Gly Gln Gly Thr Thr Val Thr Val
            100                 105                 110

Ser Ser

<210> SEQ ID NO 229
<211> LENGTH: 114
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 229

Gln Val Lys Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Tyr Gly Tyr Tyr Trp Gly Gln Gly Thr Thr Val Thr Val
            100                 105                 110

Ser Ser

<210> SEQ ID NO 230
<211> LENGTH: 114
<212> TYPE: PRT
<213> ORGANISM: Artificial Sequence
<220> FEATURE:
<223> OTHER INFORMATION: VH of scFv from mouse immunized with
```

2-phenyl-5-oxazolone

<400> SEQUENCE: 230

Gln Val Lys Leu Gln Gln Ser Gly Ala Glu Leu Ala Lys Pro Gly Ala
1               5                   10                  15

Ser Val Lys Met Ser Cys Lys Ala Thr Gly Tyr Thr Phe Thr Ser Tyr
            20                  25                  30

Leu Met His Trp Val Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Tyr Gly Tyr Tyr Trp Gly Gln Gly Thr Thr Val Thr Val
            100                 105                 110

Ser Ser

<210> SEQ ID NO 231
<211> LENGTH: 114
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 231

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Arg Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Tyr Gly Ile Tyr Trp Gly Gln Gly Thr Thr Val Thr Val
            100                 105                 110

Ser Ser

<210> SEQ ID NO 232
<211> LENGTH: 114
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 232

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Thr Phe
            20                  25                  30

Leu Met His Trp Leu Lys Gln Arg Pro Gly Gln Gly Leu Glu Trp Ile

-continued

```
                35                  40                  45
Gly Tyr Ile Asn Pro Ser Thr Gly Tyr Thr Glu Tyr Asn Gln Lys Phe
             50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asp Tyr Gly Tyr Tyr Trp Gly Gln Gly Thr Val Thr Val
                100                 105                 110

Ser Ser

<210> SEQ ID NO 233
<211> LENGTH: 114
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 233

Gln Val Lys Leu Gln Gln Ser Gly Ala Glu Leu Ala Arg Pro Gly Ala
 1               5                  10                  15

Ser Val Lys Met Ser Cys Lys Ala Ser Gly Tyr Thr Phe Thr Ser Tyr
                 20                  25                  30

Thr Met His Trp Val Lys Gln Arg Pro Gly Gln Gly Leu Gly Trp Ile
             35                  40                  45

Gly Tyr Ile Asn Pro Ser Ser Gly Tyr Thr Asn Tyr Asn Gln Lys Phe
             50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asp Tyr Gly Tyr Tyr Trp Gly Gln Gly Thr Val Thr Val
                100                 105                 110

Ser Ser

<210> SEQ ID NO 234
<211> LENGTH: 114
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 234

Gln Val Lys Leu Gln Gln Ser Gly Ala Glu Leu Ala Lys Pro Gly Ala
 1               5                  10                  15

Ser Val Lys Met Ser Cys Lys Ala Ser Gly Tyr Thr Phe Thr Ser Tyr
                 20                  25                  30

Thr Met His Trp Val Lys Gln Arg Pro Gly Gln Gly Leu Glu Trp Ile
             35                  40                  45

Gly Tyr Ile Asn Pro Thr Thr Gly Tyr Thr Glu Tyr Asn Gln Lys Phe
             50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95
```

Ala Arg Asp Tyr Gly Tyr Tyr Trp Gly Gln Gly Thr Thr Val Thr Val
            100                 105                 110

Ser Ser

<210> SEQ ID NO 235
<211> LENGTH: 114
<212> TYPE: PRT
<213> ORGANISM: Artificial Sequence
<220> FEATURE:
<223> OTHER INFORMATION: VH of scFv from mouse immunized with
      2-phenyl-5-oxazolone

<400> SEQUENCE: 235

Gln Val Lys Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Arg Asp
            20                  25                  30

Trp Met His Trp Leu Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Tyr Gly Tyr Tyr Trp Gly Gln Gly Thr Thr Val Thr Val
            100                 105                 110

Ser Ser

<210> SEQ ID NO 236
<211> LENGTH: 109
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 236

Asp Ile Glu Leu Thr Gln Ser Pro Ser Ser Leu Ala Ser Leu Gly
1               5                   10                  15

Glu Arg Val Ser Leu Thr Cys Arg Ala Ser Gln Glu Ile Ser Ser Gly
            20                  25                  30

Tyr Leu Ser Trp Leu Gln Gln Lys Pro Asp Gly Ser Ile Lys Arg Leu
        35                  40                  45

Ile Tyr Ala Ala Ser Thr Leu Glu Ser Gly Val Pro Lys Arg Phe Ser
    50                  55                  60

Gly Ser Arg Ser Gly Ser Asp Tyr Ser Leu Thr Ile Ser Ser Leu Glu
65                  70                  75                  80

Ser Glu Asp Phe Ala Asp Tyr Tyr Cys Leu Gln Tyr Ala Ser Tyr Pro
                85                  90                  95

Thr Phe Gly Ala Gly Thr Lys Leu Glu Ile Lys Arg Ala
            100                 105

<210> SEQ ID NO 237
<211> LENGTH: 110
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 237

Asp Ile Glu Leu Thr Gln Ser Pro Ala Ile Met Ser Ala Ser Pro Gly
1               5                   10                  15

Glu Lys Val Thr Met Thr Cys Arg Ala Ser Ser Val Ser Ser Ser
            20                  25                  30

Tyr Leu His Trp Tyr Gln Gln Lys Pro Gly Ala Ser Pro Lys Val Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Ile Lys Arg Ala
            100                 105                 110

<210> SEQ ID NO 238
<211> LENGTH: 110
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 238

Asp Ile Glu Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Thr Ile Pro
                85                  90                  95

Leu Thr Phe Gly Ala Gly Thr Lys Leu Glu Ile Lys Arg Ala
            100                 105                 110

<210> SEQ ID NO 239
<211> LENGTH: 110
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 239

Asp Ile Glu Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Asn
            20                  25                  30

Tyr Leu His Trp Phe Gln Gln Lys Pro Gly Phe Ser Pro Lys Leu Leu
        35                  40                  45

Ile Ser Arg Thr Ser Asn Leu Ala Ser Gly Val Pro Ala Arg Phe Ser
    50                  55                  60

```
Gly Ser Gly Ser Gly Thr Ser Tyr Ser Leu Thr Ile Gly Thr Met Glu
 65                  70                  75                  80

Ala Glu Asp Val Ala Thr Tyr Tyr Cys Gln Gln Gly Ser Thr Ile Pro
                 85                  90                  95

Phe Thr Phe Gly Ser Gly Thr Lys Leu Glu Ile Lys Arg Ala
            100                 105                 110

<210> SEQ ID NO 240
<211> LENGTH: 108
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 240

Asp Ile Glu Leu Thr Gln Ser Pro Ala Ile Met Ser Ala Ser Pro Gly
  1               5                  10                  15

Glu Lys Val Thr Ile Thr Cys Ser Ala Ser Ser Val Asn Tyr Met
                 20                  25                  30

His Trp Phe Gln Gln Lys Pro Gly Thr Ser Pro Lys Leu Trp Ile Tyr
             35                  40                  45

Arg Thr Ser Asn Leu Ala Ser Gly Val Pro Thr Arg Phe Ser Gly Ser
 50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Ser Ser Tyr Pro Pro Thr
                 85                  90                  95

Phe Gly Ser Gly Thr Lys Leu Glu Ile Lys Arg Ala
            100                 105

<210> SEQ ID NO 241
<211> LENGTH: 108
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 241

Asp Ile Glu Leu Thr Gln Ser Pro Ala Ile Met Ser Ala Phe Pro Gly
  1               5                  10                  15

Glu Lys Val Thr Met Thr Cys Ser Ala Ser Ser Val Ser Tyr Met
                 20                  25                  30

His Trp Tyr Gln Gln Lys Ser Gly Thr Ser Pro Lys Arg Trp Ile Tyr
             35                  40                  45

Asp Thr Ser Lys Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Phe Ser Ser Asn Pro Leu Thr
                 85                  90                  95

Phe Gly Ala Gly Thr Lys Leu Glu Leu Lys Arg Ala
            100                 105

<210> SEQ ID NO 242
<211> LENGTH: 108
<212> TYPE: PRT
<213> ORGANISM: Artificial Sequence
<220> FEATURE:
```

<223> OTHER INFORMATION: VL of scFv from mouse immunized with
      2-phenyl-5-oxazolone

<400> SEQUENCE: 242

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Ile Asn Tyr Met
            20                  25                  30

His Trp Tyr Gln Gln Lys Pro Gly Ala Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Pro Trp Thr
                85                  90                  95

Phe Gly Gly Gly Thr Lys Leu Glu Ile Lys Arg Ala
            100                 105

<210> SEQ ID NO 243
<211> LENGTH: 108
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 243

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asn Pro Leu Thr
                85                  90                  95

Phe Gly Ala Gly Thr Lys Leu Glu Ile Lys Arg Ala
            100                 105

<210> SEQ ID NO 244
<211> LENGTH: 108
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 244

Asp Ile Glu Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Ile
            20                  25                  30

His Trp Pro Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser

```
                50                  55                  60
Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Tyr His Ser Tyr Pro Leu Thr
                 85                  90                  95

Phe Gly Ala Gly Thr Lys Leu Glu Ile Lys Arg Ala
                100                 105

<210> SEQ ID NO 245
<211> LENGTH: 110
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 245

Asp Ile Glu Leu Thr Gln Ser Pro Thr Thr Met Ala Ala Ser Pro Gly
 1               5                  10                  15

Glu Lys Ile Thr Ile Thr Cys Ser Ala Ser Ser Ser Ile Ser Ser Asn
                20                  25                  30

Tyr Leu His Trp Phe Gln Gln Lys Pro Gly Phe Ser Pro Lys Leu Leu
             35                  40                  45

Ile Tyr Arg Thr Ser Asn Leu Ala Ser Gly Val Pro Ala Arg Phe Ser
 50                  55                  60

Gly Ser Gly Ser Gly Thr Ser Tyr Ser Leu Thr Ile Gly Thr Met Glu
 65                  70                  75                  80

Ala Glu Asp Val Ala Thr Tyr Tyr Cys Gln Gln Gly Ser Ser Ile Pro
                 85                  90                  95

Leu Thr Phe Gly Gly Gly Thr Lys Leu Glu Ile Lys Arg Ala
                100                 105                 110

<210> SEQ ID NO 246
<211> LENGTH: 110
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 246

Asp Ile Glu Leu Thr Gln Ser Pro Thr Thr Met Ala Ala Ser Pro Gly
 1               5                  10                  15

Glu Met Ile Thr Ile Thr Cys Ser Ala Ser Ser Ser Ile Ser Ser Asn
                20                  25                  30

Tyr Leu His Trp Tyr Gln Gln Lys Pro Gly Phe Ser Pro Lys Leu Leu
             35                  40                  45

Ile Tyr Arg Thr Ser Asn Leu Ala Ser Gly Val Pro Ala Arg Phe Ser
 50                  55                  60

Gly Ser Gly Ser Gly Thr Ser Tyr Ser Leu Thr Ile Gly Ala Met Glu
 65                  70                  75                  80

Ala Glu Asp Val Ala Thr Tyr Tyr Cys Gln Gln Gly Ser Ser Ile Pro
                 85                  90                  95

Tyr Thr Phe Gly Ala Gly Thr Lys Leu Glu Ile Lys Arg Ala
                100                 105                 110

<210> SEQ ID NO 247
<211> LENGTH: 110
<212> TYPE: PRT
```

<213> ORGANISM: Artificial Sequence
<220> FEATURE:
<223> OTHER INFORMATION: VL of scFv from mouse immunized with
      2-phenyl-5-oxazolone

<400> SEQUENCE: 247

Asp Ile Glu Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Ile Pro
                85                  90                  95

Tyr Thr Phe Gly Gly Gly Thr Lys Leu Glu Ile Lys Arg Ala
            100                 105                 110

<210> SEQ ID NO 248
<211> LENGTH: 110
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 248

Asp Ile Glu Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Asn
            20                  25                  30

His Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Gly Ile Pro
                85                  90                  95

Tyr Thr Phe Gly Gly Gly Thr Lys Leu Glu Ile Lys Arg Ala
            100                 105                 110

<210> SEQ ID NO 249
<211> LENGTH: 110
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 249

Asp Ile Glu Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
        35                  40                  45

```
Ile Tyr Arg Thr Ser Asn Leu Ala Ser Gly Val Pro Ala Arg Phe Ser
         50                  55                  60

Gly Ser Gly Ser Gly Thr Ser Tyr Ser Leu Thr Ile Gly Thr Met Glu
 65                  70                  75                  80

Ala Glu Asp Val Ala Thr Tyr Tyr Cys Gln Gln Gly Ser Ser Ile Pro
                 85                  90                  95

Phe Thr Phe Gly Gly Gly Thr Lys Leu Glu Ile Lys Arg Ala
            100                 105                 110

<210> SEQ ID NO 250
<211> LENGTH: 110
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 250

Asp Ile Glu Leu Thr Gln Ser Pro Ala Ile Met Ser Ala Ser Pro Gly
1               5                   10                  15

Glu Lys Ile Thr Ile Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
         35                  40                  45

Ile Tyr Arg Thr Ser Asn Leu Ala Ser Gly Val Pro Ala Arg Phe Ser
         50                  55                  60

Gly Ser Gly Ser Gly Thr Ser Tyr Ser Leu Thr Ile Gly Thr Met Glu
 65                  70                  75                  80

Ala Glu Asp Val Ala Thr Tyr Tyr Cys Gln Gln Gly Ser Ser Ile Pro
                 85                  90                  95

Tyr Thr Phe Gly Gly Gly Thr Lys Leu Glu Ile Lys Arg Ala
            100                 105                 110

<210> SEQ ID NO 251
<211> LENGTH: 108
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 251

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
         35                  40                  45

Asp Thr Ser Lys Leu Ala Ser Gly Val Pro Ala Arg Phe Ser Gly Ser
         50                  55                  60

Gly Ser Gly Thr Ser Tyr Ser Leu Thr Ile Ser Ser Met Glu Ala Glu
 65                  70                  75                  80

Asp Val Ala Thr Tyr Tyr Cys Gln Gln Trp Ser Ser Asn Pro Leu Thr
                 85                  90                  95

Phe Gly Ala Gly Thr Lys Leu Glu Ile Lys Arg Ala
            100                 105

<210> SEQ ID NO 252
```

<211> LENGTH: 108
<212> TYPE: PRT
<213> ORGANISM: Artificial Sequence
<220> FEATURE:
<223> OTHER INFORMATION: VL of scFv from mouse immunized with
    2-phenyl-5-oxazolone

<400> SEQUENCE: 252

Asp Ile Glu Leu Thr Gln Ser Pro Ala Ile Met Ser Ala Ser Pro Gly
1               5                   10                  15

Glu Lys Val Thr Leu Thr Cys Ser Ala Ser Ser Ser Val Arg Tyr Val
            20                  25                  30

Asn Trp Phe Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Ala
            100                 105

<210> SEQ ID NO 253
<211> LENGTH: 108
<212> TYPE: PRT
<213> ORGANISM: Artificial Sequence
<220> FEATURE:
<223> OTHER INFORMATION: VL of scFv from mouse immunized with
    2-phenyl-5-oxazolone

<400> SEQUENCE: 253

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Ala Leu Thr
                85                  90                  95

Phe Gly Ala Gly Thr Lys Leu Glu Ile Lys Arg Ala
            100                 105

<210> SEQ ID NO 254
<211> LENGTH: 110
<212> TYPE: PRT
<213> ORGANISM: Artificial Sequence
<220> FEATURE:
<223> OTHER INFORMATION: VL of scFv from mouse immunized with
    2-phenyl-5-oxazolone

<400> SEQUENCE: 254

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Thr Ser Asn
            20                  25                  30

```
Tyr Leu Asn Trp Tyr Gln Gln Lys Ser Gly Ala Ser Pro Lys Leu Trp
        35                  40                  45

Val Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Val Glu
 65                  70                  75                  80

Ala Glu Asp Ala Ala Thr Tyr Tyr Cys Gln Gln Tyr Ser Gly Tyr Pro
                 85                  90                  95

Leu Thr Phe Gly Ala Gly Thr Lys Leu Glu Ile Lys Arg Ala
                100                 105                 110

<210> SEQ ID NO 255
<211> LENGTH: 110
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 255

Asp Ile Glu Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Ser Asn
                20                  25                  30

Tyr Leu Asn Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Arg Met Glu
 65                  70                  75                  80

Ala Glu Asp Ala Ala Thr Tyr Tyr Cys Gln Gln Arg Ser Ser Tyr Pro
                 85                  90                  95

Leu Thr Phe Gly Ala Gly Thr Lys Leu Glu Ile Lys Arg Ala
                100                 105                 110

<210> SEQ ID NO 256
<211> LENGTH: 110
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 256

Asp Ile Glu Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Ser Asn
                20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Val Glu
 65                  70                  75                  80

Ala Glu Asp Ala Ala Thr Tyr Tyr Cys Gln Gln Tyr Ser Gly Tyr Pro
                 85                  90                  95

Leu Thr Phe Gly Ala Gly Thr Lys Leu Glu Ile Lys Arg Ala
                100                 105                 110
```

-continued

```
<210> SEQ ID NO 257
<211> LENGTH: 110
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 257

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Val Ser Ser Asn
            20                  25                  30

Tyr Leu His Trp Phe Gln Gln Lys Ser Gly Ala Ser Pro Lys Leu Trp
        35                  40                  45

Ile Tyr Ser Thr Ser Asn Leu Pro Ser Gly Val Pro Ala Arg Phe Ser
    50                  55                  60

Gly Ser Gly Ser Gly Thr Ser Tyr Ser Leu Thr Ile Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Gly Gly Thr Lys Leu Glu Ile Lys Arg Ala
                100                 105                 110

<210> SEQ ID NO 258
<211> LENGTH: 110
<212> TYPE: PRT
<213> ORGANISM: Artificial Sequence
<220> FEATURE:
<223> OTHER INFORMATION: VL of scFv from mouse immunized with
      2-phenyl-5-oxazolone

<400> SEQUENCE: 258

Asp Ile Glu Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Ile Pro
                85                  90                  95

Leu Thr Phe Gly Ala Gly Thr Lys Leu Glu Ile Lys Arg Ala
                100                 105                 110

<210> SEQ ID NO 259
<211> LENGTH: 41
<212> TYPE: PRT
<213> ORGANISM: Artificial Sequence
<220> FEATURE:
<223> OTHER INFORMATION: residues encoded by insertion site and
      surrounding sequence in pHEN1

<400> SEQUENCE: 259

Leu Leu Ala Ala Gln Pro Ala Met Ala Gln Val Gln Leu Gln Val Asp
1               5                   10                  15

Leu Glu Ile Lys Arg Ala Ala Ala Glu Gln Lys Leu Ile Ser Glu Glu
```

20                  25                  30

Asp Leu Asn Gly Ala Ala Thr Val Glu
        35                  40

<210> SEQ ID NO 260
<211> LENGTH: 126
<212> TYPE: DNA
<213> ORGANISM: Artificial Sequence
<220> FEATURE:
<223> OTHER INFORMATION: insertion site and surrounding sequence in
      pHEN1

<400> SEQUENCE: 260
ttactcgcgg cccagccggc catggcccag gtgcagctgc aggtcgacct cgagatcaaa      60
cgggcggccg cagaacaaaa actcatctca gaagaggatc tgaatggggc cgcatagact    120
gttgaa                                                                126

<210> SEQ ID NO 261
<211> LENGTH: 734
<212> TYPE: PRT
<213> ORGANISM: Artificial Sequence
<220> FEATURE:
<223> OTHER INFORMATION: scFvB18

<400> SEQUENCE: 261

Pro His Glu Thr Tyr Arg Ser Glu Arg His Ile Ser Ser Glu Arg Ala
1               5                   10                  15

Leu Ala Gly Leu Asn Val Ala Leu Gly Leu Asn Leu Glu Gly Leu Asn
            20                  25                  30

Gly Leu Asn Ser Glu Arg Gly Leu Tyr Ala Leu Ala Gly Leu Leu Glu
        35                  40                  45

Val Ala Leu Leu Tyr Ser Pro Arg Gly Leu Tyr Ala Leu Ala Ser Glu
    50                  55                  60

Arg Val Ala Leu Leu Tyr Ser Leu Glu Ser Glu Arg Cys Tyr Ser Leu
65                  70                  75                  80

Tyr Ser Ala Leu Ala Ser Glu Arg Gly Leu Tyr Thr Tyr Arg Thr His
                85                  90                  95

Arg Pro His Glu Thr His Arg Ser Glu Arg Thr Tyr Arg Thr Arg Pro
            100                 105                 110

Met Glu Thr His Ile Ser Thr Arg Pro Val Ala Leu Leu Tyr Ser Gly
        115                 120                 125

Leu Asn Ala Arg Gly Pro Arg Gly Leu Tyr Ala Arg Gly Gly Leu Tyr
    130                 135                 140

Leu Glu Gly Leu Thr Arg Pro Ile Leu Glu Gly Leu Tyr Ala Arg Gly
145                 150                 155                 160

Ile Leu Glu Ala Ser Pro Pro Arg Ala Ser Asn Ser Glu Arg Gly Leu
                165                 170                 175

Tyr Gly Leu Tyr Thr His Arg Leu Tyr Ser Thr Tyr Arg Ala Ser Asn
            180                 185                 190

Gly Leu Leu Tyr Ser Pro His Glu Leu Tyr Ser Ser Glu Arg Leu Tyr
        195                 200                 205

Ser Ala Leu Ala Thr His Arg Leu Glu Thr His Arg Val Ala Leu Ala
    210                 215                 220

Ser Pro Leu Tyr Ser Pro Arg Ser Glu Arg Ser Glu Arg Thr His Arg
225                 230                 235                 240

Ala Leu Ala Thr Tyr Arg Met Glu Thr Gly Leu Asn Leu Glu Ser Glu
                245                 250                 255

-continued

```
Arg Ser Glu Arg Leu Glu Thr His Arg Ser Glu Arg Gly Leu Ala Ser
            260                 265                 270

Pro Ser Glu Arg Ala Leu Ala Val Ala Leu Thr Tyr Arg Thr Tyr Arg
        275                 280                 285

Cys Tyr Ser Ala Leu Ala Ala Arg Gly Thr Tyr Arg Ala Ser Pro Thr
    290                 295                 300

Tyr Arg Gly Leu Tyr Ser Glu Arg Ser Glu Arg Thr Tyr Arg Thr Tyr
305                 310                 315                 320

Arg Pro His Glu Ala Ser Pro Thr Tyr Arg Thr Arg Pro Gly Leu Tyr
                325                 330                 335

Gly Leu Asn Gly Leu Tyr Thr His Arg Thr His Arg Val Ala Leu Thr
            340                 345                 350

His Arg Val Ala Leu Ser Glu Arg Ser Glu Arg Gly Leu Tyr Gly Leu
        355                 360                 365

Tyr Gly Leu Tyr Gly Leu Tyr Ser Glu Arg Gly Leu Tyr Gly Leu Tyr
    370                 375                 380

Gly Leu Tyr Gly Leu Tyr Ser Glu Arg Gly Leu Tyr Gly Leu Tyr Gly
385                 390                 395                 400

Leu Tyr Gly Leu Tyr Ser Glu Arg Gly Leu Asn Ala Leu Ala Val Ala
                405                 410                 415

Leu Gly Leu Tyr Thr His Arg Gly Leu Asn Gly Leu Ser Glu Arg Ala
            420                 425                 430

Leu Ala Leu Glu Thr His Arg Thr His Arg Ser Glu Arg Pro Arg Gly
        435                 440                 445

Leu Tyr Gly Leu Thr His Arg Val Ala Leu Thr His Arg Leu Glu Thr
    450                 455                 460

His Arg Cys Tyr Ser Ala Arg Gly Ser Glu Arg Ser Glu Arg Thr His
465                 470                 475                 480

Arg Gly Leu Tyr Ala Leu Ala Val Ala Leu Thr His Arg Thr His Arg
                485                 490                 495

Ser Glu Arg Ala Ser Asn Thr Tyr Arg Ala Leu Ala Ala Ser Asn Thr
            500                 505                 510

Arg Pro Val Ala Leu Gly Leu Asn Gly Leu Leu Tyr Ser Pro Arg Ala
        515                 520                 525

Ser Pro His Ile Ser Leu Glu Pro His Glu Thr His Arg Gly Leu Tyr
    530                 535                 540

Leu Glu Ile Leu Glu Gly Leu Tyr Gly Leu Tyr Thr His Arg Ala Ser
545                 550                 555                 560

Asn Ala Ser Asn Ala Arg Gly Ala Leu Ala Pro Arg Gly Leu Tyr Val
                565                 570                 575

Ala Leu Pro Arg Ala Leu Ala Ala Arg Gly Pro His Glu Ser Glu Arg
            580                 585                 590

Gly Leu Tyr Ser Glu Arg Leu Glu Ile Leu Glu Gly Leu Tyr Ala Ser
        595                 600                 605

Pro Leu Tyr Ser Ala Leu Ala Ala Leu Ala Leu Glu Thr His Arg Ile
    610                 615                 620

Leu Glu Thr His Arg Gly Leu Tyr Ala Leu Ala Gly Leu Asn Thr His
625                 630                 635                 640

Arg Gly Leu Ala Ser Pro Gly Leu Ala Leu Ala Ile Leu Glu Thr Tyr
                645                 650                 655

Arg Pro His Glu Cys Tyr Ser Ala Leu Ala Leu Glu Thr Arg Pro Thr
            660                 665                 670
```

```
Tyr Arg Ser Glu Arg Ala Ser Asn His Ile Ser Thr Arg Pro Val Ala
        675                 680                 685

Leu Pro His Glu Gly Leu Tyr Gly Leu Tyr Gly Leu Tyr Thr His Arg
        690                 695                 700

Leu Tyr Ser Leu Glu Thr His Arg Val Ala Leu Leu Glu Gly Leu Ile
705                 710                 715                 720

Leu Glu Leu Tyr Ser Ala Arg Gly Ala Leu Ala Ala Leu Ala
                725                 730
```

<210> SEQ ID NO 262
<211> LENGTH: 770
<212> TYPE: DNA
<213> ORGANISM: Artificial Sequence
<220> FEATURE:
<223> OTHER INFORMATION: scFvB18

<400> SEQUENCE: 262

```
ttctattctc acagtgcaca ggtccagctg cagcagtctg ggctgagct  tgtgaagcct      60
ggggcttcag tgaagctgtc ctgcaaggct tctggctaca ccttcaccag ctactggatg     120
cactgggtga agcagaggcc tggacgaggc cttgagtgga ttggaaggat tgatcctaat     180
agtggtggta ctaagtacaa tgagaagttc aagagcaagg ccacactgac tgtagacaaa     240
ccctccagca cagcctacat gcagctcagc agcctgacat ctgaggactc tgcggtctat     300
tattgtgcaa gatacgacta cggtagtagc tactactttg actactgggg ccaagggacc     360
acggtcaccg tctcctcagg tggaggcggt tcaggcggag gtggctctgg cggtggcgga     420
tcccaggctg ttgggacaca ggaatctgca ctcaccacat cacctggtga acagtcaca     480
ctcacttgtc gctcaagtac tggggctgtt acaactagta actatgccaa ctgggtccaa     540
gaaaaaccag atcatttatt cactggtcta ataggtggta ccaacaaccg agctccaggt     600
gttcctgcca gattctcagg ctccctgatt ggagacaagg ctgccctcac catcacaggg     660
gcacagactg aggatgaggc aatatatttc tgtgctctat ggtacagcaa ccattgggtg     720
ttcggtggag gaaccaaact gactgtcctc gagatcaaac gggcggccgc              770
```

<210> SEQ ID NO 263
<211> LENGTH: 35
<212> TYPE: PRT
<213> ORGANISM: Artificial Sequence
<220> FEATURE:
<223> OTHER INFORMATION: carboxy terminus of Hman CH1 and hinge from
      pJM1-Fab D1.3

<400> SEQUENCE: 263

```
Lys Pro Ser Asn Thr Lys Val Asp Lys Lys Val Glu Pro Lys Ser Ser
1               5                   10                  15

Thr Lys Thr His Thr Ser Gly Gly Glu Gln Lys Leu Ile Ser Glu Glu
            20                  25                  30

Asp Leu Asn
        35
```

<210> SEQ ID NO 264
<211> LENGTH: 30
<212> TYPE: PRT
<213> ORGANISM: Artificial Sequence
<220> FEATURE:
<223> OTHER INFORMATION: pelB leader and amino terminus of VK from
      pJM1-Fab D1.3

<400> SEQUENCE: 264

Met Lys Tyr Leu Leu Pro Thr Ala Ala Ala Gly Leu Leu Pro Ala
1               5                   10                  15

Ala Gln Pro Ala Met Ala Asp Ile Glu Phe Thr Gln Ser Pro
            20                  25                  30

<210> SEQ ID NO 265
<211> LENGTH: 241
<212> TYPE: DNA
<213> ORGANISM: Artificial Sequence
<220> FEATURE:
<223> OTHER INFORMATION: linker region of pJM1-Fab D1.3

<400> SEQUENCE: 265
aaccccagca acaccaaggt cgacaagaaa gttgagccca atcttcaac taagacgcac      60 acatcaggag gtgaacagaa gctcatctca gaagaggatc tgaattaata agggagcttg    120
catgcaaatt ctatttcaag gagacagtca taatgaaata cctattgcct acggcagccg    180
ctggattgtt attacctgct gcccaaccag cgatggccga catcgagttc acccagtctc    240
c                                                                    241

<210> SEQ ID NO 266
<211> LENGTH: 108
<212> TYPE: PRT
<213> ORGANISM: Artificial Sequence
<220> FEATURE:
<223> OTHER INFORMATION: light chain of D1.3

<400> SEQUENCE: 266

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Tyr Thr Thr Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
                85                  90                  95

Thr Phe Gly Gly Gly Thr Lys Leu Glu Ile Lys Arg
            100                 105

<210> SEQ ID NO 267
<211> LENGTH: 108
<212> TYPE: PRT
<213> ORGANISM: Artificial Sequence
<220> FEATURE:
<223> OTHER INFORMATION: light chain from clone M1F

<400> SEQUENCE: 267

Asp Ile Glu Leu Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Trp
                85                  90                  95

Thr Phe Gly Gly Gly Thr Lys Leu Glu Leu Lys Arg
            100                 105

<210> SEQ ID NO 268
<211> LENGTH: 109
<212> TYPE: PRT
<213> ORGANISM: Artificial Sequence
<220> FEATURE:
<223> OTHER INFORMATION: light chain from M21

<400> SEQUENCE: 268

Asp Ile Glu Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
                20                  25                  30

Asn Leu His Trp Tyr Gln Gln Lys Ser Glu Thr Ser Pro Lys Pro Trp
            35                  40                  45

Ile Tyr Gly Thr Ser Asn Leu Ala Ser Gly Val Pro Val Arg Phe Ser
        50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Leu Thr Phe Gly Ala Gly Thr Lys Leu Glu Ile Lys Arg
            100                 105

<210> SEQ ID NO 269
<211> LENGTH: 15
<212> TYPE: PRT
<213> ORGANISM: Artificial Sequence
<220> FEATURE:
<223> OTHER INFORMATION: linker between VH-HuH2 and VK-HuK3

<400> SEQUENCE: 269

Gly Gly Gly Gly Ser Gly Gly Gly Gly Ser Gly Gly Gly Gly Ser
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: linker between VH-HuH1 and VK-HuK4

<400> SEQUENCE: 270

Gly Gly Gly Gly Ser Gly Gly Gly Gly Ser Gly Gly Gly Gly Ser
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: linker between VH-HuH2 and VK-HuK4

<400> SEQUENCE: 271

Gly Gly Gly Gly Ser Gly Gly Gly Gly Ser Gly Gly Gly Gly Ser
1               5                   10                  15

```
<210> SEQ ID NO 272
<211> LENGTH: 15
<212> TYPE: PRT
<213> ORGANISM: Artificial Sequence
<220> FEATURE:
<223> OTHER INFORMATION: linker between VH-HuH1 and VK-HuK3

<400> SEQUENCE: 272

Gly Gly Gly Gly Ser Gly Gly Gly Gly Ser Gly Gly Gly Gly Ser
1               5                   10                  15
```